US009403801B2

(12) United States Patent
Xi et al.

(10) Patent No.: US 9,403,801 B2
(45) Date of Patent: Aug. 2, 2016

(54) SUBSTITUTED HETEROARYL COMPOUNDS AND METHODS OF USE

(71) Applicants: Calitor Sciences, LLC, Newbury Park, CA (US); Sunshine Lake Pharma Co., Ltd., Dongguan, Guangdong (CN)

(72) Inventors: Ning Xi, Newbury Park, CA (US); Minxiong Li, Guangdong (CN); Haiyang Hu, Guangdong (CN); Weilong Dai, Guangdong (CN)

(73) Assignees: CALITOR SCIENCES, LLC, Newbury Park, CA (US); SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 14/670,421

(22) Filed: Mar. 27, 2015

(65) Prior Publication Data

US 2015/0274704 A1  Oct. 1, 2015

Related U.S. Application Data

(60) Provisional application No. 61/971,552, filed on Mar. 28, 2014.

(51) Int. Cl.
*A61K 31/506* (2006.01)
*C07D 403/14* (2006.01)
*A61K 31/527* (2006.01)
*C07D 401/14* (2006.01)
*A61K 45/06* (2006.01)
*C07D 493/04* (2006.01)
*C07D 403/12* (2006.01)

(52) U.S. Cl.
CPC ............ *C07D 403/14* (2013.01); *A61K 31/506* (2013.01); *A61K 31/527* (2013.01); *A61K 45/06* (2013.01); *C07D 401/14* (2013.01); *C07D 493/04* (2013.01); *C07D 403/12* (2013.01)

(58) Field of Classification Search
CPC ... C07D 403/12; C07D 403/14; A61K 31/506
See application file for complete search history.

(56) References Cited

U.S. PATENT DOCUMENTS

| 6,656,939 | B2 | 12/2003 | Bebbington et al. |
| 7,173,028 | B2 | 2/2007 | Dahmann et al. |
| 7,427,681 | B2 | 9/2008 | Bebbington et al. |
| 7,557,210 | B2 | 7/2009 | Singh et al. |
| 7,582,648 | B2 | 9/2009 | Singh et al. |
| 7,754,714 | B2 | 7/2010 | Li et al. |
| 7,863,286 | B2 | 1/2011 | Argade et al. |
| 7,868,013 | B2 | 1/2011 | Li et al. |
| 7,947,698 | B2 | 5/2011 | Atuegbu et al. |
| 8,039,479 | B2 | 10/2011 | Michellys et al. |
| 8,063,058 | B2 | 11/2011 | Jia et al. |
| 8,097,630 | B2 | 1/2012 | Singh et al. |
| 8,138,339 | B2 | 3/2012 | Bauer et al. |
| 8,211,929 | B2 | 7/2012 | Chen et al. |
| 8,258,144 | B2 | 9/2012 | Song et al. |
| 8,263,632 | B2 | 9/2012 | Iwama et al. |
| 8,304,422 | B2 | 11/2012 | Atuegbu et al. |
| 8,334,297 | B2 | 12/2012 | Li et al. |
| 8,377,924 | B2 | 2/2013 | Singh et al. |
| 8,426,408 | B2 | 4/2013 | Curtin et al. |
| 8,450,335 | B2 | 5/2013 | Singh et al. |
| 8,563,559 | B2 | 10/2013 | Singh et al. |
| 8,697,694 | B2 | 4/2014 | Arasappan et al. |
| 8,710,223 | B2 | 4/2014 | Holland et al. |
| 2003/0022885 | A1 | 1/2003 | Bebbington et al. |
| 2005/0014753 | A1 | 1/2005 | Ding et al. |
| 2007/0293522 | A1 | 12/2007 | Singh et al. |
| 2009/0281073 | A1 | 11/2009 | Bhattacharya et al. |
| 2010/0130486 | A1 | 5/2010 | Singh et al. |
| 2011/0028405 | A1 | 2/2011 | Harrison et al. |
| 2011/0130415 | A1 | 6/2011 | Singh et al. |
| 2012/0094999 | A1 | 4/2012 | Gray et al. |
| 2013/0210810 | A1 | 8/2013 | Singh et al. |
| 2013/0331374 | A1 | 12/2013 | Singh et al. |
| 2014/0275055 | A1 | 9/2014 | Singh et al. |
| 2014/0329842 | A1 | 11/2014 | Holland et al. |
| 2015/0005281 | A1 | 1/2015 | Hobson et al. |
| 2015/0025095 | A1 | 1/2015 | Dekhtyar et al. |
| 2015/0274705 | A1* | 10/2015 | Xi ................. C07D 493/04 514/171 |
| 2015/0274747 | A1* | 10/2015 | Xi ................. C07D 493/04 514/171 |

FOREIGN PATENT DOCUMENTS

| CN | 104262328 A | 1/2015 | |
| WO | 03030909 A1 | 4/2003 | |
| WO | WO 2010144468 A1 * | 12/2010 | ........... C07D 403/12 |
| WO | 2014040555 A1 | 3/2014 | |
| WO | 2014058685 A1 | 4/2014 | |
| WO | 2014081718 A1 | 5/2014 | |

OTHER PUBLICATIONS

Chemotherapy of Neoplastic Diseases in, Goodman & Gilman's: The Pharmacological Basis of Therapeutics 853-908 (L.L. Brunton et al., eds., 11th ed., 2008).*
H. Hrebabecky et al., 74 Collection of Czechoslovak Chemical Communications, 469-485 (2009).*
S. Sasaki et al., 126 Journal of the American Chemical Society, 516-528 (2004).*
L. Pickering et al., 15 Nucleosides & Nucleotides, 1751-1769 (1996).*
ISR of the corresponding PCT application, Jun. 25, 2015.
Written Opinion of the corresponding PCT application, Jun. 25, 2015.
Eng. translation of the abstract of CN104262328.
Curtin et al., Pyrazole diaminopyrimidines as dual inhibitors of KDR and Aurora B kinases, Bioorganic & Medicinal Chemistry Letters, 2012, vol. 22, Issue 14, p. 4750-4755.

* cited by examiner

*Primary Examiner* — Alexander R Pagano
(74) *Attorney, Agent, or Firm* — Kam W. Law; Squire Patton Boggs (US) LLP

(57) ABSTRACT

The present invention provides novel heteroaryl compounds, pharmaceutical acceptable salts and formulations thereof useful in preventing, treating or lessening the severity of a protein kinase-mediated disease. The invention also provides pharmaceutically acceptable compositions comprising such compounds and methods of using the compositions in the treatment of protein kinase-mediated disease.

27 Claims, No Drawings

SUBSTITUTED HETEROARYL COMPOUNDS AND METHODS OF USE

CROSS-REFERENCE TO RELATED APPLICATION

This application claims the benefit of U.S. Provisional Application Ser. No. 61/971,552, filed on Mar. 28, 2014, which is hereby incorporated by reference in its entirety.

FIELD OF THE INVENTION

The present invention provides novel substituted aminopyrimidine compounds, and salts thereof, which are useful in the treatment of proliferative disease, autoimmune disease, allergic disease, inflammatory disease, transplantation rejection, and other diseases, in mammals. In particular, this invention relates to compounds that modulate the activity of JAK kinases, FLT3 kinase, and Aurora kinase resulting in the modulation of inter- and/or intra-cellular signaling. This invention also relates to a method of using such compounds in the treatment of proliferative disease, autoimmune disease, allergic disease, inflammatory disease, transplantation rejection, and other diseases in mammals, especially humans, and to pharmaceutical compositions containing such compounds.

BACKGROUND OF THE INVENTION

Protein kinases constitute a large family of structurally related enzymes that are responsible for the control of a variety of signal transduction processes within the cell. Protein kinases, containing a similar 250-300 amino acid catalytic domain, catalyze the phosphorylation of target protein substrates. It is reported that many diseases are associated with abnormal cellular responses triggered by protein kinase-mediated events. These diseases include benign and malignant proliferation disorders, diseases resulting from inappropriate activation of the immune system, allograft rejection, graft vs host disease, autoimmune diseases, inflammatory diseases, bone diseases, metabolic diseases, neurological and neurodegenerative diseases, cancer, cardiovascular diseases, allergies and asthma, Alzheimer's disease and hormone-related diseases. Accordingly, there has been a substantial effort in medicinal chemistry to find protein kinase inhibitors that are effective as therapeutic agents.

The kinases may be categorized into families by the substrates in the phosphorylate (e.g., protein-tyrosine, protein-serine/threonine, lipids, etc.). Tyrosine phosphorylation is a central event in the regulation of a variety of biological processes such as cell proliferation, migration, differentiation and survival. Several families of receptor and non-receptor tyrosine kinases control these events by catalyzing the transfer of phosphate from ATP to a tyrosine residue of specific cell protein targets. Sequence motifs have been identified that generally correspond to each of these kinase families (Hanks et al., *FASEB J.*, 1995, 9, 576-596; Knighton et al., *Science*, 1991, 253, 407-414; Garcia-Bustos et al., *EMBO J.*, 1994, 13:2352-2361). Some non-limiting examples of the protein kinase include abl, Aurora, Akt, bcr-abl, Blk, Brk, Btk, c-kit, c-Met, c-src, c-fms, CDK1, CDK2, CDK3, CDK4, CDK5, CDK6, CDK7, CDK8, CDK9, CDK0, cRafl, CSF1 R, CSK, EGFR, ErbB2, ErbB3, ErbB4, Erk, Fak, fes, Flt-3, FGFR1, FGFR2, FGFR3, FGFR4, FGFR5, Fgr, Flt-1, Fps, Frk, Fyn, Hck, IGF-1 R, INS-R, JAK, KDR, Lck, Lyn, MEK, p38, PDGFR, PIK, PKC, PYK2, ros, Tie, Tie-2, TRK, Yes, and Zap70.

Aurora kinase family is a collection of highly related serine/threonine kinase that are key regulators of mitosis, essential for accurate and equal segtion of genomic material from parent to daught cells. Members of the Aurora kinase family include three related kinases known as Aurora-A, Aurora-B, and Aurora-C (also known as Aurora-1, Aurora-2, and Aurora-3). Despite significant sequence homology, the localization and functions of these kinases are largely distinct from one another (Richard D. Carvajal, et al. *Clin Cancer Res.*, 2006, 12(23): 6869-6875; Daruka Mahadevan, et al., *Expert Opin. Drug Discov.*, 2007 2(7): 1011-1026).

Aurora-A is ubiquitously expressed and regulates cell cycle events occurring from late S phase through M phase, including centrosome maturation (Berdnik D, et al., *Curr Biol.*, 2002, 12: 640-647), mitotic entry (Hirota T, et al., *Cell*, 2003, 114:585-598; Dutertre S, et al., *J Cell Sci.*, 2004, 117: 2523-2531), centrosome separation (Marumoto T. et al. *J Biol. Chem.*, 2003, 278:51786-51795), bipolar-spindle assembly (Kufer T A, et al. *J Cell Biol.*, 2002; 158:617-623; Eyers P A, et al., *Curr Biol.*, 2003; 13:691-697), chromosome alignment on the metaphase plate (Marumoto T, et al. *J Biol Chem.*, 2003, 278:51786-51795; Kunitoku N, et al., *Dev Cell.*, 2003, 5: 853-864), cytokinesis (Marumoto T, et al., *J Biol. Chem.*, 2003, 278:51786-51795), and mitotic exit. Aurora-A protein levels and kinase activity both increase from late G2 through M phase, with peak activity in prometaphase. Once activated, Aurora-A mediates its multiple functions by interacting with various substrates including centrosomin, transforming acidic coiled-coil protein, cdc25b, Eg5, and centromere protein A.

Aurora-B is a chromosomal passenger protein critical for accurate chromosomal segregation, cytokinesis (Hauf S., et al. *J Cell Biol.*, 2003, 161:281-94; Ditchfield C, et al., *J Cell Biol.*, 2003, 161:267-80; Giet R, et al., *J Cell Biol.*, 2001, 152:669-682; Goto H, et al., *J Biol. Chem.*, 2003, 278:8526-8530), protein localization to the centromere and kinetochore, correct microtubule-kinetochore attachments (Murata-Hori M, et al., *Curr. Biol.*, 2002, 12:894-899), and regulation of the mitotic checkpoint. Aurora-B localizes first to the chromosomes during prophase and then to the inner centromere region between sister chromatids during prometaphase and metaphase (Zeitlin S G, et al. *J Cell. Biol.*, 2001, 155:1147-1157). Aurora-B participates in the establishment of chromosomal biorientation, a condition where sister kinetochores are linked to opposite poles of the bipolar spindle via amphitelic attachments. Errors in this process, manifesting as a merotelic attachment state (one kinetochore attached to microtubules from both poles) or a syntelic attachment state (both sister kinetochores attached to microtubules from the same pole), lead to chromosomal instability and aneuploidy if not corrected before the onset of anaphase. The primary role of Aurora-B at this point of mitosis is to repair incorrect microtubule-kinetochore attachments (Hauf S, et al., *J Cell Biol.*, 2003, 161:281-294; Ditchfield C, et al., *J Cell Biol.*, 2003, 161:267-280; Lan W, et al. *Curr Biol.*, 2004, 14:273-286). Without Aurora-B activity, the mitotic checkpoint is compromised, resulting in increased numbers of aneuploid cells, genetic instability, and tumorigenesis (Weaver B A, et al., *Cancer Cell.*, 2005, 8:7-12).

Aurora-A overexpression is a necessary feature of Aurora-A-induced tumorigenesis. In cells with Aurora-A overexpression, mitosis is characterized by the presence of multiple centrosomes and multipolar spindles (Meraldi P et al., *EMBO J.*, 2002, 21:483-492). Despite the resulting aberrant microtubule-kinetochore attachments, cells abrogate the mitotic checkpoint and progress from metaphase to anaphase, resulting in numerous chromosomal separation defects. These cells fail to undergo cytokinesis, and, with additional cell cycles, polyploidy and progressive chromosomal instability develop (Anand S, et al., *Cancer Cell,* 2003, 3:51-62).

The evidence linking Aurora overexpression and malignancy proliferation disorders, such as colon, breast, lung, pancrease, prostate, bladder, head, neck, cervix, and ovarian cancers, liver, gastric and pancreatic tumors, has stimulated interest in developing Aurora inhibitors for cancer therapy. In normal cells, Aurora-A inhibition results in delayed, but not blocked, mitotic entry, centrosome separation defects resulting in unipolar mitotic spindles, and failure of cytokinesis (Marumoto T, et al., *J Biol Chem.,* 2003, 278:51786-51795). Encouraging antitumor effects with Aurora-A inhibition were shown in three human pancreatic cancer cell lines (Panc-1, MIA PaCa-2, and SU.86.86), with growth suppression in cell culture and near-total abrogation of tumorigenicity in mouse xenografts (Hata T, et al., *Cancer Res.,* 2005, 65:2899-2905).

Aurora-B inhibition results in abnormal kinetochore-microtubule attachments, failure to achieve chromosomal biorientation, and failure of cytokinesis (Goto H, et al. *J Biol Chem.* 2003, 278:8526-30; Severson $AF_1$ et al. *Curr Biol.,* 2000, 10:1162-1171). Recurrent cycles of aberrant mitosis without cytokinesis result in massive polyploidy and, ultimately, to apoptosis (Hauf S, et al., *J Cell Biol.,* 2003, 161: 281-294; Ditchfield C, et al., *J Cell Biol.,* 2003, 161:267-80; Giet R, et al., *J Cell Biol.,* 2001, 152:669-682; Murata-Hori M, *Curr. Biol.,* 2002, 12:894-899; Kallio M J, et al., *Curr Biol.,* 2002, 12:900-905).

Inhibition of Aurora-A or Aurora-B activity in tumor cells results in impaired chromosome alignment, abrogation of the mitotic checkpoint, polyploidy, and subsequent cell death. These in vitro effects are greater in transformed cells than in either non-transformed or non-dividing cells (Ditchfield C, et al. *J Cell Biol.,* 2003, 161:267-280). Thus, targeting Aurora may achieve in vivo selectivity for cancer. Although toxicity to rapidly dividing cell of the hematopoietic and gastrointestinal system is expected, the activity and clinical tolerability shown in xenograft models indicates the presence of a reasonable therapeutic index. Given the preclinical antitumor activity and potential for tumor selectivity, several Aurora kinase inhibitors have been developed.

FLT3 (Flt3, FMS-related tyrosine kinase 3), also known as FLK-2 (fetal liver kinase 2) and STK-1 (human stem cell kinase 1), belongs to a member of the class III receptor tyrosine kinase (RTK-III) family that include KIT, PDGFR, FMS and FLT (Stirewalt D L, et al., *Nat. Rev. Cancer,* 2003, 3:650-665; Rosnet O, et al., *Genomics* 1991, 9:380-385; Yarden Y, et al., *Nature,* 1986, 323: 226-232; Stanley E R, et. al., *J. Cell. Biochem,* 1983, 21:151-159; Yarden Y, et al., *EMBO J.,* 1987, 6:3341-3351). FLT3 is a membrane-spanning protein and composed of four domains; an extracellular ligand-binding domains consisting of five immunoglobin-like structures, a transmembrane (TM) domain, a juxtamembrane (JM) domain and a cytoplasmic C-Terminal tyrosine kinase (TK) domain. (Agnes F, et al., *Gene,* 1994, 145:283-288, Scheijen B, et al., *Oncogene,* 2002, 21:3314-3333).

The ligand for FLT3 (FLT3 or FL) was cloned in 1993 and shown to be a Type I transmembrane protein expressed in cells of the hematopoietic bone marrow microenvironment, including bone marrow fibroblasts and other cells (Lyman S D, et al. Cell 1993, 75:1157-1167). Both the membrane-bound and soluable forms can activate the tyrosine kinase activity of the receptor and stimulate growth of progenitor cells in the marrow and blood. Binding of ligand to receptor induces dimerisation of the receptor and activation of the kinase domains; which then autophosphorylate and catalyse phosphorylation of substrate proteins of various signal transduction pathways such as signal transducer and activator of transcription 5 (STAT5), RAS/mitogen-activated protein kinase (RAS/MAPK), phosphoinositide 3-kinase (PI3K), src homologous and collagen gene (SHC), SH2-containing inositol-5-phosphatase (SHIP), and cytoplasmic tyrosine phosphatase with 2 Src-homology 2 (SH2) domains (SHP2), which play important roles in cellular proliferation, differentiation, and survival (Dosil M, et al. *Mol Cell Biol.,* 1993, 13:6572-6585. Zhang S, *Biochem Biophys Res Commun.,* 1999, 254:440-445). In addition to hemotopoietic cells, FLT3 gene is also expressed in placenta, gonads and brain (Maroc N, et al. *Oncogene,* 1993, 8: 909-918) and also plays an important role in the immune response (deLapeyriere O, et al., *Leukemia,* 1995, 9:1212-1218).

FLT3 has also been implicated in hematopoietic disorders which are pre-malignant disorders including myeloproliferative disorders, such as thrombocythemia, essential thrombocytosis (ET), myelofibrosis (MF), chronic idiopathic myelofibrosis (IMF), and polycythemia vera (PV), pre-malignant myelodysplastic syndromes. Hematological malignancies include leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL). FLT3 is overexpressed at the levels in 70-100% of cases of acute myeloid leukemias (AML), and in a high percentage of T-acute lymphocytic leukemia (ALL) cases (Griffin J D, et al., Haematol J. 2004, 5: 188-190). It is also overexpressed in a smaller subset of chronic myeloid leukemia (CML) in blast crisis. Studies have shown that the leukemic cells of B lineage ALL and AML frequently co-express FL, setting up autocrine or paracrine signaling loops that result in the constitutive activation of FLT3 (Zheng R, et. al., *Blood.,* 2004, 103: 267-274). A high level of the FLT3 ligand is found in the serum of patients with Langerhans cell histocytosis and systemic lupus erythematosus, which further implicates FLT3 signaling in the dysregulation of dendritic cell progenitors in those autoimmune diseases (Rolland et al., *J. Immunol.,* 2005, 174:3067-3071).

Evidence is rapidly accumulating that many types of leukemias and myeloproliferative syndromes have mutation in tyrosine kinases. FLT3 mutations are one of the most frequent somatic alterations in AML, occurring in approximately ⅓ of patients. There are two types of activating mutations in FLT3 described in patients with leukemia. These include a spectrum of internal tandem duplications (ITD) occurring within the auto-inhibitory juxtamembrane domain (Nakao M, et al., *Leukemia,* 1996, 10:1911-1918; Thiede C, et al., *Blood,* 2002, 99:4326-4335), and activation loop mutations that include Asp835Tyr (D835Y), Asp835Val (D835V), Asp835His (D835H), Asp835Glu (D835E), Asp835Ala (D835A), Asp835Asn (D835N), Asp835 deletion and Ile836 deletion (Yamamoto $Y_1$ et al., Blood 2001: 97:2434-2439; Abu-Duhier F M, et al., *Br. J. Haematol.,* 2001, 113:983-988). Internal tandem duplication (ITD) mutations within the JM domain contribute to about 17-34% of FLT3 activating mutations in AML. FLT3-ITD has also been detected at low frequency in myelodysplastic syndrome (MDS) (Yokota S, et al., *Leukemia,* 1997, 11:1605-1609; Horiike S, et al., *Leukemia,* 1997, 11:1442-1446). The ITDs are always in-frame, and are limited to the JM domain. However, they vary in length and position from patient to patient. These repeat sequences may serve to disrupt the autoinhibitory activity of the JM domain resulting in the constitutive activation of FLT3. Both FLT3-ITD and FLT3-Asp835 mutations are associated with FLT3 autophosphorylation and phosphorylation of downstream targets (Mizuki M, et al. *Blood,* 2000, 96:3907-3914; Mizuki M, et al. *Blood,* 2003, 101:3164-3173; Hayakawa F, et al., *Oncogene,* 2000, 19: 624-631).

Inhibitors of FLT3 are presently being studied and have reached clinical trials as monotherapy in relapsed or refractory AML patients, some or all of whom had FLT3 mutations. Collectively, these data suggest that FLT3 is an attractive therapeutic target for the development of kinase inhibitors for AML and other associated diseases.

Janus kinase (JAK) is a family of intracellular, non-receptor tyrosine kinases that transduce cytokine-mediated signals via the JAK-STAT pathway. The JAK family plays a role in the cytokine-dependent regulation of proliferation and function of cells involved in immune response. Cytokines bind to their receptors, causing receptor dimerization, and this enables JAKs to phosphorylate each other as well as specific tyrosine motifs within the cytokine receptors. STATs that recognize these phosphotyrosine motifs are recruited to the receptor, and are then themselves activated by a JAK-dependent tyrosine phosphorylation event. Upon activation, STATs dissociate from the receptors, dimerize, and translocate to the nucleus to bind to specific DNA sites and alter transcription.

Currently, there are four known mammalian JAK family members: JAK1 (Janus kinase-1), JAK2 (Janus kinase-2), JAK3 (Janus kinase, leukocyte; JAKL; L-JAK and Janus kinase-3) and TYK2 (protein-tyrosine kinase 2). While JAK1, JAK2 and TYK2 are ubiquitously expressed, JAK3 is reported to be preferentially expressed in natural killer (NK) cells and not resting T cells ("Biology and significance of the JAK/STAT signaling pathways." Growth Factors, April 2012; 30(2): 88).

JAK1 is essential for signaling for certain type I and type II cytokines. It interacts with the common gamma chain (γc) of type I cytokine receptors to elicit signals from the IL-2 receptor family, the IL-4 receptor family, the gp130 receptor family. It is also important for transducing a signal by type I (IFN-α/β) and type II (IFN-γ) interferons, and members of the IL-10 family via type II cytokine receptors. Genetic and biochemical studies have shown that JAK1 is functionally and physically associated with the type I interferon (e g., IFNalpha), type II interferon (e.g., IFNgamma), IL-2 and IL-6 cytokine receptor complexes. Furthermore, characterization of tissues derived from JAK1 knockout mice demonstrated critical roles for this kinase in the IFN, IL-IO, IL-2/IL-4, and IL-6 pathways.

Expression of JAK1 in cancer cells enables individual cells to contract, potentially allowing them to escape their tumor and metastasize to other parts of the body. Elevated levels of cytokines which signal through JAK1 have been implicated in a number of immune and inflammatory diseases. JAK1 or JAK family kinase inhibitors may be useful for modulating or treating in such diseases. (Kisseleva et al., 2002, *Gene* 285: 1-24; Levy et al., 2005, *Nat. Rev. Mol. Cell Biol.* 3:651-662). A humanized monoclonal antibody targeting the IL-6 pathway (Tocilizumab) was approved by the European Commission for the treatment of moderate-to-severe rheumatoid arthritis (Scheinecker et al., 2009, *Nat. Rev. Drug Discov.* 8:273-274).

JAK2 is implicated in signaling by members of the type II cytokine receptor family (e.g. interferon receptors), the GM-CSF receptor family, the gp130 receptor family. JAK2 signaling is activated downstream from the prolactin receptor. Studies have identified a high prevalence of an acquired activating JAK2 mutation (JAK2V617F) in myleoproliferative disorders such as polycythemia vera, essential thrombocythemia and idiopathic myelofibrosis, etc. The mutant JAK2 protein is able to activate downstream signaling in the absence of cytokine stimulation, resulting in autonomous growth and/or hypersensitivity to cytokines and is believed to play a role in driving these diseases. Additional mutations or translocations resulting dysregulated JAK2 function have been described in other malignancies (Ihle J. N. and Gilliland D. G., *Curr. Opin. Genet. Dev.,* 2007, 17:8; Sayyah J. and Sayeski P. P., *Curr. Oncol. Rep.,* 2009, 11: 117). Inhibitors of JAK2 have been described to be useful in myeloproliferative diseases (Santos et al, *Blood,* 2010, 115:1131; Barosi G. and Rosti V., *Curr. Opin. Hematol,* 2009, 16:129, Atallah E. and Versotvsek S., *Exp. Rev. Anticancer Ther.* 2009, 9:663).

JAK3 associates exclusively with the gamma common cytokine receptor chain, which is present in the IL-2, IL-4, IL-7, IL-9, IL-15 and IL-21 cytokine receptor complexes. JAK3 is predominantly expressed in immune cells and transduces a signal in response to its activation via tyrosine phosphorylation by interleukin receptors. Since JAK3 expression is restricted mostly to hematopoietic cells, its role in cytokine signaling is thought to be more restricted than other JAKs. Mutations of JAK3 result in severe combined immunodeficiency (SCID). (O'Shea et al., 2002, *Cell,* 109 (suppl.): S121-S131). Based on its role in regulating lymphocytes, JAK3 and JAK3-mediated pathways have been targeted for immunosuppressive indications (e.g., transplantation rejection and rheumatoid arthritis) (Baslund et al., 2005, *Arthritis & Rheumatism* 52:2686-2692; Changelian et al., 2003, *Science* 302: 875-878).

TYK2 is implicated in IFN-α, IL-6, IL-10 and IL-12 signaling. Biochemical studies and gene-targeted mice uncovered the crucial role of TYK2 in immunity. Tyk2-deficient mice are viable and fertile but display multiple immunological defects, most prominently high sensitivity to infections and defective tumor surveillance. In contrast, inhibition of TYK2 results in increased resistance against allergic, autoimmune and inflammatory diseases. Particularly, targeting Tyk2 appears to be a promising strategy for the treatment of IL-12-, IL-23- or Type 1 IFN-mediated diseases. These include but are not limited to rheumatoid arthritis, multiple sclerosis, lupus, psoriasis, psoriatic arthritis, inflammatory bowel disease, uveitis, sarcoidosis, and tumors (Shaw, M. et al, *Proc. Natl. Acad. Sci. USA,* 2003, 100, 11594-11599; Ortmann, R. A., and Shevach, E. M. *Clin. Immunol,* 2001, 98, 109-118; Watford et al, *Immunol. Rev.,* 2004, 202: 139). ["Janus Kinase (JAK) Inhibitors in Rheumatoid Arthritis." *Current Rheumatology Reviews,* 2011, 7, 306-312].

A fully human monoclonal antibody targeting the shared p40 subunit of the IL-12 and 11-23 cytokines (Ustekinumab) was recently approved by the European Commission for the treatment of moderate-to-severe plaque psoriasis (Krueger et al., 2007, *N. Engl. J. Med.* 356:580-92; Reich et al., 2009, *Nat. Rev. Drug Discov.* 8:355-356). In addition, an antibody targeting the IL-12 and IL-23 pathways underwent clinical trials for treating Crohn's Disease (Mannon et al., 2004, N. Engl. *J. Med.* 351: 2069-79).

When dysregulated, JAK-mediated responses can positively or negatively affect cells leading to over-activation and malignancy or immune and hematopoietic deficiencies, respectively, and suggests the utility for use of inhibitors of JAK kinases. The JAK/STAT signaling pathway is involved in a variety of hyperproliferative and cancer-related processes including cell-cycle progression, apoptosis, angiogenesis, invasion, metastasis and evasion of the immune system (Haura et al., *Nature Clinical Practice Oncology,* 2005, 2(6), 315-324; Verna et al., *Cancer and Metastasis Reviews,* 2003, 22, 423-434). In addition, the JAK/STAT signaling pathway is important in the genesis and differentiation of hematopoietic cells and regulating both pro- and anti-inflammatory and immune responses (O'Sullivan et al., *Molecular Immunology* 2007, 44:2497).

Therefore, the JAK/STAT pathway, and in particular all four members of the JAK family, are believed to play a role in the pathogenesis of the asthmatic response, chronic obstructive pulmonary disease, bronchitis, and other related inflammatory diseases of the lower respiratory tract. The JAK/STAT pathway has also been implicated to play a role in inflammatory diseases/conditions of the eye including, but not limited to, iritis, uveitis, scleritis, conjunctivitis, as well as chronic allergic responses. Since cytokines utilize different patterns of JAK kinases (O'Sullivan et al., *Mol. Immunol*, 2007, 44:2497; Murray J., *Immunol*, 2007, 178:2623), there may be utility for antagonists of JAK kinases with differing intra-family selectivity profiles in diseases associated with particular cytokines or in diseases associated with mutations or polymorphisms in the JAK/STAT pathways.

Rheumatoid arthritis (RA) is an autoimmune disease characterized by chronic joint inflammation. Patients with rheumatoid arthritis treated with JAK inhibitor showed that inhibition of JAK1 and JAK3 blocks signalling by multiple cytokines that are important for lymphocyte function, including interleukin-2 (IL-2), IL-4, IL-7, IL-9, IL-15 and IL-21. [Fleischmann, R. et al. "Placebo-controlled trial of tofacitinib monotherapy in rheumatoid arthritis." *N. Engl. J. Med.* 367, 495-507 (2012)]. It was conjectured that small-molecule inhibitors that directly inactivate specific JAK isoforms would also reduce not only the clinical symptoms of RA, but also suppress the upregulation of many of the proinflammatory cytokines that are critical in driving RA disease progression. ["Inhibitors of JAK for the treatment of rheumatoid arthritis: rationale and clinical data." *Clin. Invest*. (2012) 2(1), 39-47]

Persistent activation of STAT3 or STAT5 has been demonstrated in a wide spectrum of solid human tumors including breast, pancreatic, prostate, ovarian and hepatic carcinomas, as well as in the majority of hematopoietic tumors including lymphomas and leukemias. In this context, inactivation of JAK/STAT signaling in many hematopoietic tumors resulted in inhibition of cell proliferation and/or induction of apoptosis. Although STAT3 in tumor cells can be activated by various kinases, JAK2 has been shown to be the most important upstream activator mediating STAT3 activation in human tumor cell lines derived from various solid tumors [Mohamad Bassam Sonbol, Belal Firwana, Ahmad Zarzour, Mohammad Morad, Vishal Rana and Ramon V. Tiu "Comprehensive review of JAK inhibitors in myeloproliferative neoplasms." *Therapeutic Advances in Hematology* 2013, 4(1), 15-35; Hedvat M, Huszar D, Herrmann A, Gozgit J M, Schroeder A, Sheehy A, et al. "The JAK2 inhibitor AZD1480 potently blocks Stat3 signaling and oncogenesis in solid tumors." *Cancer Cell* 2009; 16(6):487-97.]. Therefore, inhibition of JAK kinases may have a beneficial role in the therapeutic treatment of these diseases.

Clearly, protein kinase inhibitors have gathered attention as a new drug category for both immunosuppression and antiinflammatory drug, and for cancer drug. Thus, new or improved agents which inhibit protein kinases such as Aurora inhibitors, FLT3 inhibitors and Janus kinases inhibitors are continually needed that act as immunosuppressive agents for organ transplants, and antitumor agents, as well as agents for the prevention and treatment of autoimmune diseases (e.g., multiple sclerosis, psoriasis, rheumatoid arthritis, asthma, type I diabetes, inflammatory bowel disease, Crohn's disease, polycythemia vera, essential thrombocythemia, myelofibrosis, autoimmune thyroid disorders, Alzheimer's disease), diseases involving a hyperactive inflammatory response (e.g., eczema), allergies, chronic obstructive pulmonary disease, bronchitis, cancer (e.g., prostate, acute myelogenous leukemia, chronic myelogenous leukemia, acute lymphocytic leukemia, leukemia, multiple myeloma), and some immune reactions (e.g., skin rash or contact dermatitis or diarrhea) caused by other therapeutics, to name a few. The compounds, compositions and methods described herein are directed toward these needs and other ends.

SUMMARY OF THE INVENTION

The invention provides compounds that inhibit, regulate, and/or modulate one or more protein kinases such as JAK, FLT3 and Aurora kinase activities, and are useful for treating proliferative diseases, autoimmune diseases, allergic diseases, inflammatory diseases, transplantation rejections, and their co-morbidities. This invention also provides methods of making the compound, methods of using such compounds in the treatment of said diseases in mammals, especially in humans, and pharmaceutical compositions containing these compounds. The compounds or the pharmaceutical composition disclosed herein have better prospects for clinical application. Compared with the similar compounds, the compounds disclosed herein have a better pharmacological activity, pharmacokinetic properties, physical and chemical properties and/or lesser toxicity. In particular, the compounds of the present invention display potent inhibitory activities against target kinases, and optimized selectivity and exhibited good absorption and high bioavailability in vivo pharmacokinetic experiments. In addition, the compounds or the pharmaceutical composition disclosed herein have good membrane permeability and solubility.

Specifically, in one aspect, provided herein is a compound having Formula (I):

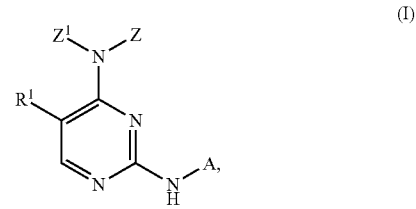

or a stereoisomer, a tautomer, an N-oxide, a solvate, a metabolite, a pharmaceutically acceptable salt or a prodrug thereof, wherein each of Z, $Z^1$, A and $R^1$ is as defined herein.

In one embodiment, Z is $C_7$-$C_{12}$ spiro bicycloalkyl, $C_7$-$C_{12}$ fused bicycloalkyl, 7-12 membered spiro heterobicyclyl or 7-12 membered fused heterobicycloalkyl, wherein Z is optionally substituted by 1, 2, 3, 4 or 5 $R^2$ groups;

$Z^1$ is H, $C_1$-$C_{12}$ alkyl, $C_3$-$C_{12}$ cycloalkyl or 3-12 membered heterocyclyl, wherein $Z^1$ is optionally substituted by 1, 2, 3, 4 or 5 $R^3$ groups;

A is pyrazolyl or imidazolyl, wherein A is optionally substituted by 1, 2, 3, 4 or 5 $R^4$ groups;

$R^1$ is H, F, Cl, Br, I, $NO_2$, $N_3$, CN, $C_1$-$C_{12}$ alkyl, $C_1$-$C_{12}$ haloalkyl, $C_1$-$C_{12}$ alkoxyl, $C_2$-$C_{12}$ alkenyl, $C_2$-$C_{12}$ alkynyl, $C_3$-$C_{12}$ cycloalkyl, 3-12 membered heterocyclyl, $C_6$-$C_{12}$ aryl, 5-12 membered heteroaryl, —$(CR^6R^7)_n$—$OR^c$, —$(CR^6R^7)_n$—$NR^aR^b$, —$C(\!=\!O)R^5$, —$OC(\!=\!O)R^5$, —$O(CR^6R^7)_n$—$R^5$, —$N(R^c)C(\!=\!O)R^5$, —$(CR^6R^7)_nC(\!=\!O)OR^c$, —$(CR^6R^7)_nC(\!=\!O)NR^aR^b$, —$C(\!=\!NR^c)NR^aR^b$, —$N(R^c)C$ $(=O)NR^aR^b$, $-N(R^c)S(=O)_mR^5$ or $-S(=O)_2NR^aR^b$, wherein $R^1$ is optionally substituted by 1, 2, 3, 4 or 5 $R^8$ groups;

each $R^2$ is independently H, F, Cl, Br, I, $NO_2$, $N_3$, CN, OH, $NH_2$, $-C(=O)CH_2CN$, $C_1-C_{12}$ alkyl, $C_1-C_{12}$ haloalkyl, $C_1-C_{12}$ alkoxy, $C_2-C_{12}$ alkenyl, $C_2-C_{12}$ alkynyl, $C_3-C_{12}$ cycloalkyl, $C_6-C_{12}$ aryl, 3-12 membered heterocyclyl, 5-12 membered heteroaryl, $-(CR^6R^7)_n-OR^c$, $-(CR^6R^7)_n-NR^aR^b$, $-C(=O)R^5$, $-S(=O)_2R^5$, $-OC(=O)R^5$, $-O(CR^6R^7)_n-R^5$, $-O(CR^6R^7)_n-OR^c$, $-N(R^c)C(=O)R^5$, $-(CR^6R^7)_nC(=O)OR^c$, $-(CR^6R^7)_nC(=O)NR^aR^b$, $-C(=NR^c)NR^aR^b$, $-N(R^c)C(=O)NR^aR^b$, $-N(R^c)S(=O)_mR^5$ or $-S(=O)_2NR^aR^b$, or two adjacent $R^2$ taken together with the atoms to which they are attached form a $C_3-C_{12}$ cycloalkyl or 3-12 membered heterocycloalkyl group, wherein each of the above substituents is optionally independently substituted by 1, 2, 3, 4 or 5 $R^8$ groups;

each $R^3$ and $R^4$ is independently H, F, Cl, Br, I, $NO_2$, $N_3$, CN, $C_1-C_{12}$ alkyl, $C_2-C_{12}$ alkenyl, $C_2-C_{12}$ alkynyl, $C_3-C_{12}$ cycloalkyl, $-(C_1-C_4$ alkylene$)-(C_3-C_{12}$ cycloalkyl$)$, $C_6-C_{12}$ aryl, 3-12 membered heterocyclyl, $-(C_1-C_4$ alkylene$)-($3-12 membered heterocyclyl$)$, 5-12 membered heteroaryl, $-(CR^6R^7)_n-OR^c$, $-(CR^6R^7)_n-NR^aR^b$, $-C(=O)R^5$, $-OC(=O)R^5$, $-O(CR^6R^7)_n-R^5$, $-N(R^c)C(=O)R^5$, $-(CR^6R^7)_nC(=O)OR^c$, $-(CR^6R^7)_nC(=O)NR^aR^b$, $-C(=NR^c)NR^aR^b$, $-N(R^c)C(=O)NR^aR^b$, $-N(R^c)S(=O)_mR^5$ or $-S(=O)_2NR^aR^b$, wherein each $R^3$ and $R^4$ is optionally independently substituted by 1, 2, 3, 4 or 5 $R^8$ groups;

each $R^5$ is independently H, $C_1-C_{12}$ alkyl, $C_1-C_{12}$ haloalkyl, $C_2-C_{12}$ alkenyl, $C_2-C_{12}$ alkynyl, $C_3-C_{12}$ cycloalkyl, $C_6-C_{12}$ aryl, 3-12 membered heterocyclyl or 5-12 membered heteroaryl, wherein each $R^5$ is optionally independently substituted by 1, 2, 3, 4 or 5 $R^8$ groups;

each $R^6$ and $R^7$ is independently H, F, Cl, Br, I, $NO_2$, $N_3$, CN, $C_1-C_{12}$ alkyl, $C_2-C_{12}$ alkenyl, $C_2-C_{12}$ alkynyl, $C_3-C_{12}$ cycloalkyl, $C_6-C_{12}$ aryl, 3-12 membered heterocyclyl or 5-12 membered heteroaryl, or $R^6$ and $R^7$ taken together with the carbon atom to which they are attached form a $C_3-C_{12}$ cycloalkyl, $C_6-C_{12}$ aryl, 3-12 membered heterocyclyl or 5-12 membered heteroaryl group, wherein each of the above substituents is optionally independently substituted by 1, 2, 3, 4 or 5 $R^8$ groups;

each $R^8$ is independently F, Cl, Br, I, CN, $NO_2$, $N_3$, $C_1-C_{12}$ alkyl, $C_2-C_{12}$ alkenyl, $C_2-C_{12}$ alkynyl, $C_3-C_{12}$ cycloalkyl, $C_6-C_{12}$ aryl, 3-12 membered heterocyclyl, 5-12 membered heteroaryl, $NH_2$, $-NH(C_1-C_{12}$ alkyl$)$, $-NH(CH_2)_n-(C_3-C_{12}$ cycloalkyl$)$, $-NH(CH_2)_n-(C_6-C_{12}$ aryl$)$, $-NH(CH_2)_n-($3-12 membered heterocyclyl$)$, $-NH(CH_2)_n-($5-12 membered heteroaryl$)$, $-N(C_1-C_{12}$ alkyl$)_2$, $-N[(CH_2)_n-(C_3-C_{12}$ cycloalkyl$)]_2$, $-N[(CH_2)_n-(C_6-C_{12}$ aryl$)]_2$, $-N[(CH_2)_n-($3-12 membered heterocyclyl$)]_2$, $-N[(CH_2)_n-($5-12 membered heteroaryl$)]_2$, OH, $-O(C_1-C_{12}$ alkyl$)$, $-O(CH_2)_n-(C_3-C_{12}$cycloalkyl$)$, $-O(CH_2)_n-(C_6-C_{12}$ aryl$)$, $-O(CH_2)_n-($3-12 membered heterocyclyl$)$ or $-O(CH_2)_n-($5-12 membered heteroaryl$)$;

each $R^a$, $R^b$ and $R^c$ is independently H, $C_1-C_6$ alkyl, $C_2-C_6$ alkenyl, $C_2-C_6$ alkynyl, $C_3-C_6$ cycloalkyl, $-(C_1-C_4$ alkylene$)-(C_3-C_6$ cycloalkyl$)$, 3-6 membered heterocyclyl, $-(C_1-C_4$ alkylene$)-($3-6 membered heterocyclyl$)$, $C_6-C_{10}$ aryl, $-(C_1-C_4$ alkylene$)-(C_6-C_{10}$ aryl$)$, 5-10 membered heteroaryl or $-(C_1-C_4$ alkylene$)-($5-10 membered heteroaryl$)$, or $R^a$ and $R^b$ taken together with the nitrogen atom to which they are attached form a 3-8 membered heterocyclyl group, wherein each of the above substituents is optionally independently substituted by 1, 2, 3 or 4 substitutents independently selected from F, Cl, Br, CN, $N_3$, OH, $NH_2$, $C_1-C_6$ alkyl, $C_1-C_6$ haloalkyl, $C_1-C_6$ alkoxy and $C_1-C_6$ alkylamino;

each m is independently 1 or 2; and each n is independently 0, 1, 2, 3 or 4.

In another embodiment, Z is $C_8-C_{11}$ spiro bicycloalkyl, $C_8-C_{10}$ fused bicycloalkyl, 8-11 membered spiro heterobicyclyl or 8-10 membered fused heterobicycloalkyl, wherein Z is optionally substituted by 1, 2, 3 or 4 $R^2$ groups.

In one embodiment, $Z^1$ is H, $C_1-C_6$ alkyl, $C_3-C_6$ cycloalkyl or 3-6 membered heterocyclyl, wherein $Z^1$ is optionally substituted by 1, 2 or 3 $R^3$ groups.

In another embodiment, $R^1$ is H, F, Cl, CN, $N_3$, $C_1-C_6$ alkyl, $C_2-C_6$ alkenyl, $C_2-C_6$ alkynyl, $C_1-C_6$ haloalkyl, $C_1-C_6$ alkoxyl, $C_3-C_6$ cycloalkyl, 3-6 membered heterocyclyl, $-(CR^6R^7)_n-OR^c$, $-(CR^6R^7)_n-NR^aR^b$, $-C(=O)R^5$, $-(CR^6R^7)_nC(=O)NR^aR^b$ or $-S(=O)_2NR^aR^b$, wherein $R^1$ is optionally substituted by 1, 2 or 3 $R^8$ groups.

In one embodiment, each $R^2$ is independently H, F, Cl, CN, $N_3$, $NO_2$, OH, $NH_2$, $-C(=O)CH_2CN$, $C_1-C_6$ alkyl, $C_2-C_6$ alkenyl, $C_2-C_6$ alkynyl, $C_1-C_6$ haloalkyl, $C_1-C_6$ alkoxy, $C_3-C_6$ cycloalkyl, phenyl, 3-6 membered heterocyclyl, 5-6 membered heteroaryl, $-(CR^6R^7)_n-OR^c$, $-(CR^6R^7)_n-NR^aR^b$, $-C(=O)R^5$, $-S(=O)_2R^5$, $-O(CR^6R^7)_n-R^5$, $-O(CR^6R^7)_n-OR^c$, $-N(R^c)C(=O)R^5$, $-(CR^6R^7)_nC(=O)NR^aR^b$, $-N(R^c)C(=O)NR^aR^b$, $-N(R^c)S(=O)_mR^5$ or $-S(=O)_2NR^aR^b$, or two adjacent $R^2$ taken together with the atoms to which they are attached form a $C_3-C_6$ cycloalkyl, or 3-6 membered heterocycloalkyl group, wherein each of the above substituents is optionally independently substituted by 1, 2 or 3 $R^8$ groups.

In another embodiment, each $R^3$ and $R^4$ is independently H, F, Cl, Br, I, $NO_2$, $N_3$, CN, $C_1-C_6$ alkyl, $C_2-C_6$ alkenyl, $C_2-C_6$ alkynyl, $C_3-C_6$ cycloalkyl, $-(C_1-C_2$ alkylene$)-(C_3-C_6$ cycloalkyl$)$, phenyl, 3-6 membered heterocyclyl, $-(C_1-C_2$ alkylene$)-($3-6 membered heterocyclyl$)$, 5-6 membered heteroaryl, $-(CR^6R^7)_n-OR^c$, $-(CR^6R^7)_n-NR^aR^b$, $-C(=O)R^5$, $-OC(=O)R^5$, $-O(CR^6R^7)_n-R^5$, $-N(R^c)C(=O)R^5$, $-(CR^6R^7)_nC(=O)OR^c$, $-(CR^6R^7)_nC(=O)NR^aR^b$, $-N(R^c)S(=O)_mR^5$ or $-S(=O)_2NR^aR^b$, wherein each $R^3$ and $R^4$ is optionally independently substituted by 1, 2 or 3 $R^8$ groups.

In one embodiment, each $R^5$ is independently H $C_1-C_6$ alkyl, $C_1-C_6$ haloalkyl, $C_2-C_6$ alkenyl, $C_2-C_6$ alkynyl, $C_3-C_6$ cycloalkyl, phenyl, 3-6 membered heterocyclyl or 5-6 membered heteroaryl, wherein each $R^5$ is optionally independently substituted by 1, 2 or 3 $R^8$ groups.

In another embodiment, each $R^6$ and $R^7$ is independently H, F, Cl, Br, I, CN, $N_3$, $NO_2$, $C_1-C_6$ alkyl, $C_2-C_6$ alkenyl, $C_2-C_6$ alkynyl, $C_3-C_6$ cycloalkyl, phenyl, 3-6 membered heterocyclyl or 5-6 membered heteroaryl, or $R^6$ and $R^7$ taken together with the carbon atom to which they are attached form a $C_3-C_6$ cycloalkyl, phenyl, 3-6 membered heterocyclyl or 5-6 membered heteroaryl group, wherein each of the above substituents is optionally independently substituted by 1, 2 or 3 $R^8$ groups.

In one embodiment, each $R^8$ is independently F, Cl, CN, $N_3$, $C_1-C_6$ alkyl, $C_2-C_6$ alkenyl, $C_2-C_6$ alkynyl, $C_3-C_6$ cycloalkyl, phenyl, 3-6 membered heterocyclyl, 5-6 membered heteroaryl, $NH_2$, $-NH(C_1-C_6$ alkyl$)$, $-NH(CH_2)_n-(C_3-C_6$ cycloalkyl$)$, $-NH(CH_2)_n$-phenyl, $-NH(CH_2)_n-$(3-6 membered heterocyclyl), $-NH(CH_2)_n-$(5-6 membered heteroaryl), $-N(C_1-C_4$ alkyl$)_2$, $-N[(CH_2)_n-(C_3-C_6$ cycloalkyl$)]_2$, $-N[(CH_2)_n$-phenyl$]_2$, $-N[(CH_2)_n$-(3-6 membered heterocyclyl)]$_2$, —N[(CH$_2$)$_n$-(5-6 membered heteroaryl)]$_2$, OH, —O(C$_1$-C$_6$ alkyl), —O(CH$_2$)$_n$—(C$_3$-C$_6$ cycloalkyl), —O(CH$_2$)$_n$-phenyl, —O(CH$_2$)$_n$-(3-6 membered heterocyclyl) or —O(CH$_2$)$_n$-(5-6 membered heteroaryl).

In another embodiment, each R$^a$, R$^b$ and R$^c$ is independently H, C$_1$-C$_4$ alkyl, C$_2$-C$_4$ alkenyl, C$_2$-C$_4$ alkynyl, C$_3$-C$_6$ cycloalkyl, —(C$_1$-C$_2$ alkylene)-(C$_3$-C$_6$ cycloalkyl), 3-6 membered heterocyclyl, —(C$_1$-C$_2$ alkylene)-(3-6 membered heterocyclyl), phenyl, —(C$_1$-C$_2$ alkylene)-phenyl, 5-6 membered heteroaryl or —(C$_1$-C$_2$ alkylene)-(5-6 membered heteroaryl), or R$^a$ and R$^b$ taken together with the nitrogen atom to which they are attached form a 3-6 membered heterocyclyl group, wherein each of the above substituents is optionally independently substituted by 1, 2 or 3 substitutents independently selected from F, Cl, CN, N$_3$, OH, NH$_2$, C$_1$-C$_4$ alkyl, C$_1$-C$_4$ haloalkyl, C$_1$-C$_4$ alkoxy and C$_1$-C$_4$ alkylamino.

In one embodiment, Z is:

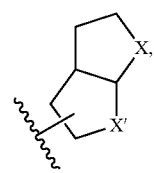
(Z-1)

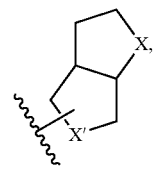
(Z-2)

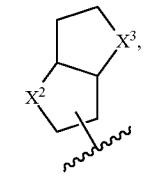
(Z-3)

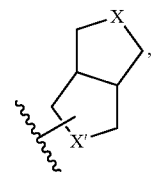
(Z-4)

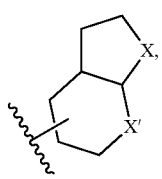
(Z-5)

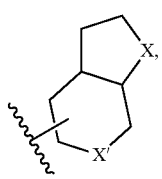
(Z-6)

-continued

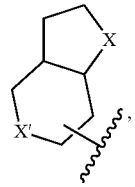
(Z-7)

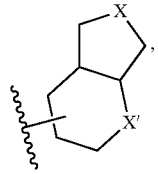
(Z-8)

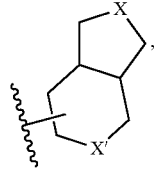
(Z-9)

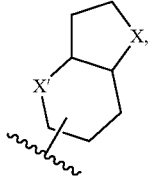
(Z-10)

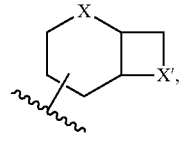
(Z-11)

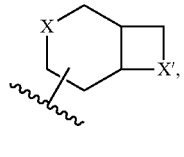
(Z-12)

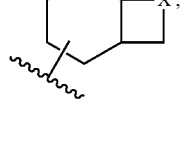
(Z-13)

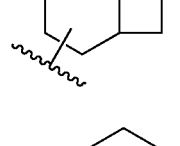
(Z-14)

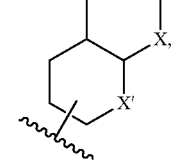
(Z-15)

-continued
(Z-16)
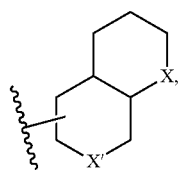
(Z-17)
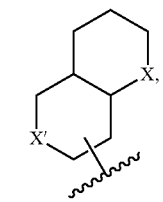
(Z-18)
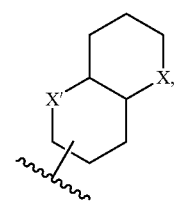
(Z-19)
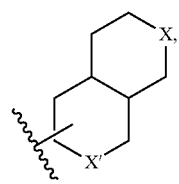
(Z-20)
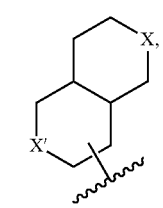
(Z-21)
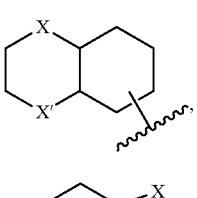
(Z-22)
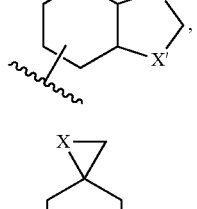
(Z-23)
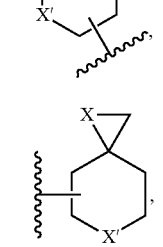
(Z-24)
-continued
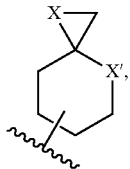
(Z-26)
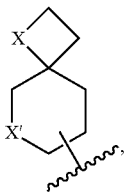
(Z-27)
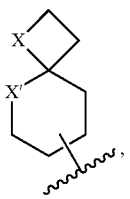
(Z-28)
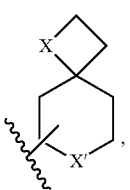
(Z-29)
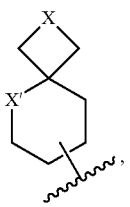
(Z-30)
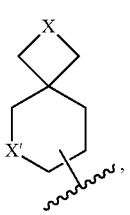
(Z-31)
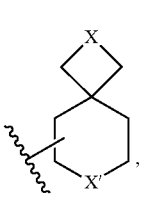
(Z-32)
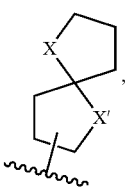

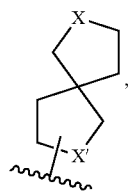 (Z-33)
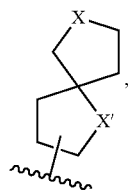 (Z-34)
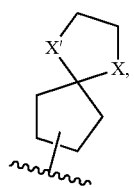 (Z-35)
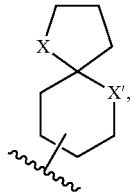 (Z-36)
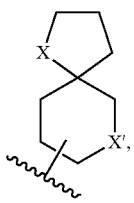 (Z-37)
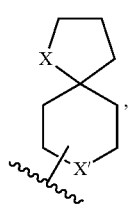 (Z-38)
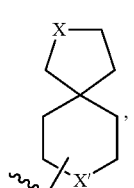 (Z-39)
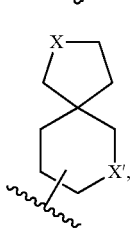 (Z-40)
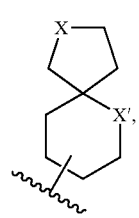 (Z-41)
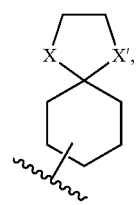 (Z-42)
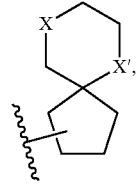 (Z-43)
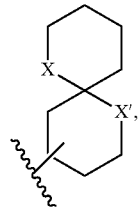 (Z-44)
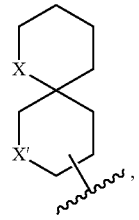 (Z-45)
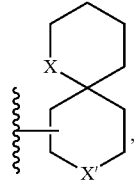 (Z-46)
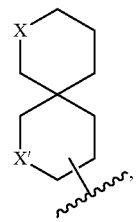 (Z-47)

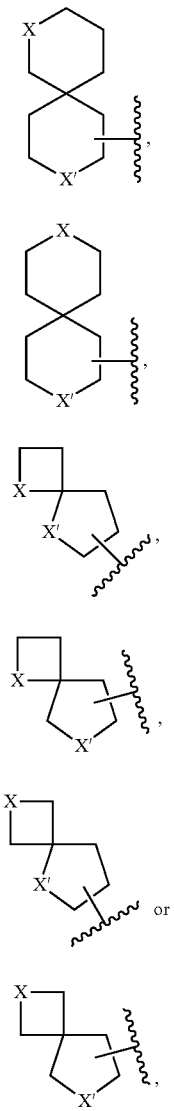

(Z-48)

(Z-49)

(Z-51)

(Z-52)

(Z-53)

(Z-54)

or a stereoisomer thereof, wherein each X, X', X² and X³ is independently CH₂, NH or O, with the proviso that when X² is O, X³ is not O; and wherein Z is optionally substituted by 1, 2 or 3 R² groups.

In another embodiment, A is:

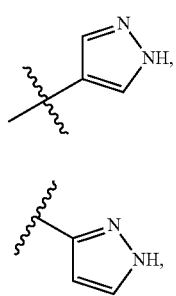

(L)

(M)

(N)

(O)

(P) or (Q)

wherein A is optionally substituted by 1, 2 or 3 $R^4$ groups.

In one embodiment, $Z^1$ is H, methyl, ethyl, n-propyl, isopropyl or cyclopropyl.

In another embodiment, $R^1$ is H, F, Cl, CN, $N_3$, $C_1$-$C_4$ alkyl, $C_2$-$C_4$ alkenyl, $C_2$-$C_4$ alkynyl, $C_1$-$C_4$ haloalkyl, $C_1$-$C_4$ alkoxyl, $C_3$-$C_6$ cycloalkyl, 3-6 membered heterocyclyl, —$(CR^6R^7)_n$—$OR^c$, —$(CR^6R^7)_n$—$NR^aR^b$, —$C(=O)R^5$, —$(CR^6R^7)_nC(=O)NR^aR^b$ or —$S(=O)_2NR^aR^b$, wherein $R^1$ is optionally substituted by 1, 2 or 3 $R^8$ groups.

In one embodiment, each $R^2$ is independently H, F, Cl, CN, $N_3$, $NO_2$, OH, $NH_2$, —$C(=O)CH_2CN$, $C_1$-$C_4$ alkyl, $C_2$-$C_4$ alkenyl, $C_2$-$C_4$ alkynyl, $C_1$-$C_4$ haloalkyl, $C_1$-$C_4$ alkoxy, $C_3$-$C_6$ cycloalkyl, phenyl, 3-6 membered heterocyclyl, 5-6 membered heteroaryl, —$(CR^6R^7)_n$—$OR^c$, —$(CR^6R^7)_n$—$NR^aR^b$, —$C(=O)R^5$, —$S(=O)_2R^5$, —$O(CR^6R^7)_n$—$R^5$, —$O(CR^6R^7)_n$—$OR^c$, —$N(R^c)C(=O)R^5$, —$(CR^6R^7)_nC(=O)NR^aR^b$, —$N(R^c)S(=O)_mR^5$ or —$S(=O)_2NR^aR^b$, wherein each $R^2$ is optionally independently substituted by 1, 2 or 3 $R^8$ groups.

In still another embodiment, each $R^5$ is independently H, $C_1$-$C_4$ alkyl, $C_1$-$C_4$ haloalkyl, $C_2$-$C_4$ alkenyl, $C_2$-$C_4$ alkynyl, $C_3$-$C_6$ cycloalkyl, phenyl, 3-6 membered heterocyclyl or 5-6 membered heteroaryl, wherein each $R^5$ is optionally independently substituted by 1, 2 or 3 $R^8$ groups.

In another aspect, provided herein is a pharmaceutical composition comprising the compound disclosed herein, and a pharmaceutically acceptable excipient, carrier, adjuvant, vehicle or a combination thereof.

In one embodiment, the pharmaceutical composition disclosed herein further comprising a therapeutic agent selected from the group consisting of chemotherapeutic agents, antiproliferative agents, phosphodiesterase 4 (PDE4) inhibitors, $β_2$-adrenoreceptor agonists, corticosteroids, non-steroidal GR agonists, anticholinergic agents, antihistamine, anti-inflammatory agents, immunosuppressants, immunomodulators, agents for treating atherosclerosis, agents for treating pulmonary fibrosis and combinations thereof.

In another aspect, provided herein is a method of preventing, treating or lessening the severity of a protein kinase-mediated disease in a patient by administering to the patient with the compound disclosed herein or the pharmaceutical composition disclosed herein.

In one embodiment, the protein kinase-mediated disease is JAK-, FLT3- or Aurora-mediated disease.

In another embodiment, the protein kinase-mediated disease is a proliferative disease, an autoimmune disease, an allergic disease, an inflammatory disease or a transplantation rejection.

In another embodiment, the protein kinase-mediated disease is cancer, polycythemia vera, essential thrombocytosis, myelofibrosis, chronic myelogenous leukemia (CML), acute myeloid leukemia (AML), acute lymphocytic leukemia (ALL), chronic obstruction pulmonary disease (COPD), asthma, systemic lupus erythematosis, cutaneous lupus erythematosis, lupus nephritis, dermatomyositis, Sjogren's syndrome, psoriasis, type I diabetes mellitus, allergic airway disease, sinusitis, eczema, hives, food allergies, allergies to insect venom, inflammatory bowel syndrome, Chron's disease, rheumatoid arthritis, juvenile arthritis, psoriatic arthritis, organ transplant rejection, tissue transplant rejection or cell transplant rejection.

In another aspect, provided herein is the compound or the pharmaceutical composition disclosed herein for use in preventing, treating or lessening the severity of a protein kinase-mediated disease in a patient.

In another aspect, provided herein is the use of the compound or the pharmaceutical composition disclosed herein in the manufacture of a medicament for treating cancer, polycythemia vera, essential thrombocytosis, myelofibrosis, chronic myelogenous leukemia (CML), acute myeloid leukemia (AML), acute lymphocytic leukemia (ALL), chronic obstruction pulmonary disease (COPD), asthma, systemic and cutaneous lupus erythematosis, lupus nephritis, dermatomyositis, Sjogren's syndrome, psoriasis, type I diabetes mellitus, allergic airway disease, sinusitis, eczema, hives, food allergies, allergies to insect venom, inflammatory bowel syndrome, Crohn's disease, rheumatoid arthritis, juvenile arthritis, psoriatic arthritis, organ transplant rejection, tissue transplant rejection or cell transplant rejection.

In another aspect, provided herein is a method of modulating the activity of a protein kinase with the compound or the pharmaceutical composition disclosed herein.

In one embodiment, the protein kinase is JAK kinase, FLT3 kinase, Aurora kinase or a combination thereof.

In another aspect, provided herein is the compound or the pharmaceutical composition disclosed herein for use in modulating the activity of a protein kinase.

In still another aspect, provided herein is use of the compound or the pharmaceutical composition disclosed herein in the manufacture of a medicament for modulating the activity of a protein kinase.

In another aspect, provided herein are methods for preparation, separation and purification of the compounds represented by Formula (I).

Biological test results indicate that the compounds provided herein can be used as preferable inhibitors of protein kinases.

Any embodiment disclosed herein can be combined with other embodiments as long as they are not contradictory to one another, even though the embodiments are described under different aspects of the invention. In addition, any technical feature in one embodiment can be applied to the corresponding technical feature in other embodiment as long as they are not contradictory to one another, even though the embodiments are described under different aspects of the invention.

The foregoing merely summarizes certain aspects of the invention and is not intended to be limiting in nature. These aspects and other aspects and embodiments are described more fully below.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety.

As used herein, the following definitions shall apply unless otherwise indicated. For purposes of this invention, the chemical elements are identified in accordance with the Periodic Table of the Elements, CAS version, and the Handbook of Chemistry and Physics, $75^{th}$ Ed. 1994. Additionally, general principles of organic chemistry are described in Sorrell et al., "Organic Chemistry", University Science Books, Sausalito: 1999, and Smith et al., "March's Advanced Organic Chemistry", John Wiley & Sons, New York: 2007, all of which are incorporated by reference in their entireties.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of example, "a component" means one or more components, and thus, possibly, more than one component is contemplated and may be employed or used in an implementation of the described embodiments.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, "patient" refers to a human (including adults and children) or other animal. In one embodiment, "patient" refers to a human.

The term "comprising" is meant to be open ended, including the indicated component but not excluding other elements.

"Stereoisomers" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc.

"Chiral" refers to molecules which have the property of non-superimposability of the mirror image partner, while the term "achiral" refers to molecules which are superimposable on their mirror image partner.

"Enantiomers" refer to two stereoisomers of a compound which are non-superimposable mirror images of one another.

"Diastereomer" refers to a stereoisomer with two or more centers of chirality and whose molecules are not mirror images of one another. Diastereomers have different physical properties, e.g. melting points, boiling points, spectral properties or biological activities. Mixture of diastereomers may separate under high resolution analytical procedures such as electrophoresis and chromatography such as HPLC.

Stereochemical definitions and conventions used herein generally follow Parker et al., McGraw-Hill Dictionary of Chemical Terms (1984) McGraw-Hill Book Company, New York and Eliel et al., "Stereochemistry of Organic Compounds", John Wiley & Sons, Inc., New York, 1994.

Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur where there has been no stereoselection or stereospecificity in a chemical reaction or process.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any resulting mixtures of stereoisomers can be separated on the basis of the physicochemical differences of the constituents, into the pure or substantially pure geometric isomers, enantiomers, diastereomers, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, Racemates and Resolutions (Wiley Interscience, New York, 1981); *Principles of Asymmetric Synthesis* ($2^{nd}$ Ed. Robert et al., Elsevier, Oxford, UK, 2012); Eliel et al., Stereochemistry of Carbon Compounds (McGraw-Hill, NY, 1962); and Wilen et al., Tables of Resolving Agents and Optical Resolutions p. 268 (E. L. Eliel, Ed., Univ. of Notre Dame Press, Notre Dame, Ind., 1972). Chiral Separation Techniques: A Practical Approach (Subramanian, G. Ed., Wiley-VCH Verlag GmbH & Co. KGaA, Weinheim, Germany, 2007).

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. Unless otherwise stated, all tautomeric forms of the compounds disclosed herein are within the scope of the invention.

As described herein, compounds disclosed herein may optionally be substituted with one or more substituents, such as those illustrated below, or as exemplified by particular classes, subclasses, and species of the invention. It will be appreciated that the phrase "optionally substituted" is used interchangeably with the phrase "substituted or unsubstituted". In general, the term "substituted" refers to the replacement of one or more hydrogen radicals in a given structure with the radical of a specified substituent. The term "optional" or "optionally" means that the subsequently described event or circumstance may but need not occur, and that the description includes instances where the event or circumstance occurs and instances in which it does not. Unless otherwise indicated, an optionally substituted group may have a substituent at each substitutable position of the group. When more than one position in a given structure can be substituted with more than one substituent selected from a specified group, the substituent may be either the same or different at each position.

Some non-limiting examples of the substituents include D, F, Cl, Br, I, CN, $N_3$, —CN, —$NO_2$, —OH, —SH, —$NH_2$, —C(=O)$CH_2$CN, —$(CR^6R^7)_n$—$OR^c$, —$(CR^6R^7)_n$—$NR^aR^b$, —C(=O)$R^5$, —S(=O)$_2R^5$, —OC(=O)$R^5$, —O$(CR^6R^7)_n$—$R^5$, —O$(CR^6R^7)_n$—OR, —N($R^c$)C(=O)$R^5$, —$(CR^6R^7)_nC$(=O)$OR^c$, —$(CR^6R^7)_nC$(=O)$NR^aR^b$, —C(=$NR^c$)$NR^aR^b$, —N($R^c$)C(=O)$NR^aR^b$, —N($R^c$)S(=O)$_mR^5$, —S(=O)$_2NR^aR^b$, alkyl, haloalkyl, alkenyl, alkynyl, alkoxyl, alkylthiolyl, alkylamino, cycloalkyl, heterocyclyl, aryl and heteroaryl, and the like, wherein each $R^5$, $R^6$, $R^7$, $R^a$, $R^b$, $R^c$, m and n carry the definitions described herein.

At various places in the present specification, substituents of compounds disclosed herein are disclosed in groups or in ranges. It is specifically intended that the invention include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" refers to a saturated linear or branched-chain monovalent hydrocarbon radical of 1 to 20 carbon atoms, wherein the alkyl radical may be optionally substituted independently with one or more substituents described below. Unless otherwise specified, the alkyl group contains 1-20 carbon atoms. In one embodiment, the alkyl group contains 1-12 carbon atoms. In another embodiment, the alkyl group contains 1-6 carbon atoms. In still another embodiment, the alkyl group contains 1-4 carbon atoms. In yet another embodiment, the alkyl group contains 1-3 carbon atoms. The alkyl radical may be optionally substituted independently with one or more substituents described herein.

Some non-limiting examples of the alkyl group include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkylene" refers to a saturated divalent hydrocarbon group derived from a straight or branched chain saturated hydrocarbon by the removal of two hydrogen atoms. Unless otherwise specified, the alkylene group contains 1-12 carbon atoms. In one embodiment, the alkylene group contains 1-6 carbon atoms. In another embodiment, the alkylene group contains 1-4 carbon atoms. In still another embodiment, the alkylene group contains 1-3 carbon atoms. In yet another embodiment, the alkylene group contains 1-2 carbon atoms. The alkylene group is exemplified by methylene (—$CH_2$—), ethylidene (—$CH_2CH_2$—), isopropylidene (—$CH(CH_3)CH_2$—), and the like.

The term "alkenyl" refers to a linear or branched-chain monovalent hydrocarbon radical of 2 to 12 carbon atoms with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. In one embodiment, the alkenyl group contains 2-8 carbon atoms. In another embodiment, the alkenyl group contains 2-6 carbon atoms. In still another embodiment, the alkenyl group contains 2-4 carbon atoms. Some non-limiting examples of the alkenyl group include ethylenyl or vinyl (—CH=$CH_2$), allyl (—$CH_2$CH=$CH_2$), and the like. The alkenyl radical may be optionally substituted independently with one or more substituents described herein.

The term "alkynyl" refers to a linear or branched-chain monovalent hydrocarbon radical of 2 to 12 carbon atoms with at least one site of unsaturation, i.e., a carbon-carbon, sp triple bond, wherein the alkynyl radical may be optionally substituted independently with one or more substituents described herein. In one embodiment, the alkynyl group contains 2-8 carbon atoms. In another embodiment, the alkynyl group contains 2-6 carbon atoms. In still another embodiment, the alkynyl group contains 2-4 carbon atoms. Some non-limiting examples of the alkynyl group include ethynyl (—C≡CH), propargyl (—$CH_2$C≡CH), propynyl (—C≡C—$CH_3$), and the like.

The term "alkoxy" refers to an alkyl group, as previously defined, attached to the principal carbon atom through an oxygen atom. Unless otherwise specified, the alkoxy group contains 1-12 carbon atoms. In one embodiment, the alkoxy group contains 1-6 carbon atoms. In another embodiment, the alkoxy group contains 1-4 carbon atoms. In still another embodiment, the alkoxy group contains 1-3 carbon atoms. The alkoxy radical may be optionally substituted independently with one or more substituents described herein.

Some non-limiting examples of alkoxy groups include methoxy (MeO, —$OCH_3$), ethoxy (EtO, —$OCH_2CH_3$), 1-propoxy (n-PrO, n-propoxy, —$OCH_2CH_2CH_3$), 2-propoxy (i-PrO, i-propoxy, —$OCH(CH_3)_2$), 1-butoxy (n-BuO, n-butoxy, —$OCH_2CH_2CH_2CH_3$), 2-methyl-1-propoxy (i-BuO, i-butoxy, —$OCH_2CH(CH_3)_2$), 2-butoxy (s-BuO, s-butoxy, —$OCH(CH_3)CH_2CH_3$), 2-methyl-2-propoxy (t-BuO, t-butoxy, —$OC(CH_3)_3$), 1-pentoxy (n-pentoxy, —$OCH_2CH_2CH_2CH_2CH_3$), 2-pentoxy (—$OCH(CH_3)CH_2CH_2CH_3$), 3-pentoxy (—$OCH(CH_2CH_3)_2$), 2-methyl-2-butoxy (—$OC(CH_3)_2CH_2CH_3$), 3-methyl-2-butoxy (—$OCH(CH_3)CH(CH_3)_2$), 3-methyl-1-butoxy (—$OCH_2CH_2CH(CH_3)_2$), 2-methyl-1-butoxy (—$OCH_2CH(CH_3)CH_2CH_3$), and the like.

The term "haloalkyl", "haloalkenyl" or "haloalkoxy" refers to alkyl, alkenyl, or alkoxy, as the case may be, substituted with one or more halogen atoms. Some non-limiting examples of haloalkyl and haloalkoxy are include trifluoromethyl (—$CF_3$), trifluoromethoxy (—$OCF_3$) and the like.

The term "carbocycle", "carbocyclyl" or "carbocyclic ring" refers to a monovalent or multivalent non-aromatic, saturated or partially unsaturated ring having 3 to 12 carbon atoms as a monocyclic, bicyclic or tricyclic ring system. The carbobicyclyl refers to a spiro carbobicyclyl, a fused carbobicyclyl or a bridged carbobicyclyl. Some non-limiting examples of carbocyclyl groups include cycloalkyl, cycloalkenyl, and cycloalkynyl. Further non-limiting examples of carbocyclyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, and the like.

The term "cycloalkyl" refers to a monovalent or multivalent saturated ring having 3 to 12 carbon atoms as a monocyclic, bicyclic, or tricyclic ring system. In one embodiment, the cycloalkyl contains 3-12 carbon atoms. In another embodiment, the cycloalkyl contains 3-8 carbon atoms. In another embodiment, the cycloalkyl contains 3-6 carbon atoms. In still another embodiment, cycloalkyl may be a $C_7$-$C_{12}$ bicycloalkyl which refers to $C_7$-$C_{12}$ spiro, $C_7$-$C_{12}$ fused bicycloalkyl and $C_7$-$C_{12}$ bridged bicycloalkyl. In yet another embodiment, cycloalkyl may be a $C_8$-$C_{11}$ bicycloalkyl which refers to $C_8$-$C_{11}$ spiro, $C_8$-$C_{11}$ fused bicycloalkyl and $C_8$-$C_{11}$ bridged bicycloalkyl. The cycloalkyl radical may be optionally substituted independently with one or more substituents described herein.

The term "heterocycle", "heterocyclyl", or "heterocyclic ring" as used interchangeably herein refers to a monovalent or multivalent, saturated or partially unsaturated, non-aromatic monocyclic, bicyclic or tricyclic ring containing 3-12 ring atoms of which at least one ring atom is selected from nitrogen, sulfur and oxygen, and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms may be optionally oxidized to form N-oxides. The heterocyclyl contains saturated heterocyclyl (i.e. heterocycloalkyl) and partially unsaturated heterocyclyl. Some non-limiting examples of heterocyclyl include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, thioxanyl, dithianyl, homopiperazinyl, homopiperidinyl, oxepanyl, thiepanyl, oxazepinyl (e.g. 1,4-oxazepinyl, 1,2-oxazepinyl), diazepinyl (e.g. 1,4-diazepinyl, 1,2-diazepinyl), dioxpinyl (e.g. 1,4-dioxpinyl, 1,2-dioxpinyl), thiazepinyl (e.g. 1,4-thiazepinyl, 1,2-thiazepinyl), 2-oxa-5-azabicyclo[2.2.1]hept-5-yl, 2-azaspiro[4.4]nonanyl, 1,6-dioxaspiro[4.4]nonanyl, 2-azaspiro[4.5]decanyl, 8-azaspiro[4.5]decanyl, 7-azaspiro[4.5]decanyl, 3-azaspiro[5.5]undecanyl, 2-azaspiro[5.5]undecanyl, octahydro-1H-isoindolyl, octahydrocyclopenta[c]pyrrolyl, indolinyl, 1,2,3,4-tetrahydroisoquinolinyl, 1,3-benzodioxolyl, hexahydrofuro[3,2-b]furanyl, decahydroisoquinolinyl, and the like. Some non-limiting examples of heterocyclyl wherein —CH$_2$— group is replaced by —C(=O)— moiety are 2-oxopyrrolidinyl, oxo-1,3-thiazolidinyl, 2-piperidinonyl and 3,5-dioxopiperidinyl. Some non-limiting examples of heterocyclyl wherein the ring sulfur atom is oxidized are sulfolanyl, 1,1-dioxotetrahydrothiophenyl, 1,1-dioxothiomorpholinyl, 1,1-dioxotetrahydro-2H-thiopyranyl. The heterocyclyl group may be optionally substituted with one or more substituents described herein.

In one embodiment, heterocyclyl may be a 3-8 membered heterocyclyl, which refers to a monovalent or multivalent, saturated or partially unsaturated, monocyclic ring containing 3-8 ring atoms, of which at least one ring atom is selected from nitrogen, sulfur and oxygen, and of which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms may be optionally oxidized to form N-oxides. Some non-limiting examples of 3-8 membered heterocyclyl include azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, thioxanyl, dithianyl, homopiperazinyl, homopiperidinyl, oxepanyl, thiepanyl, oxazepinyl, diazepinyl, thiazepinyl, and the like. Some non-limiting examples of heterocyclyl wherein —CH$_2$— group is replaced by —C(=O)— moiety are 2-oxopyrrolidinyl, oxo-1,3-thiazolidinyl, 2-piperidinonyl and 3,5-dioxopiperidinyl. Some non-limiting examples of heterocyclyl wherein the ring sulfur atom is oxidized are sulfolanyl, 1,1-dioxo-thiomorpholinyl, and the like. The 3-8 membered heterocyclyl group may be optionally substituted with one or more substituents described herein.

In another embodiment, heterocyclyl may be a 3-6 membered heterocyclyl, which refers to a monovalent or multivalent, saturated or partially unsaturated, non-aromatic monocyclic ring containing 3-6 ring atoms, of which at least one ring atom is selected from nitrogen, sulfur and oxygen, and of which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms may be optionally oxidized to form N-oxides. Some non-limiting examples of 3-6 membered heterocyclyl include azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, thioxanyl and dithianyl. The 3-6 membered heterocyclyl group may be optionally substituted with one or more substituents described herein.

In another embodiment, heterocyclyl refers to a 7-12 membered heterocyclyl, which refers to a monovalent or multivalent, saturated or partially unsaturated spiro, fused or bridged heterobicyclyl ring containing 7-12 ring atoms, of which at least one ring atom is selected from nitrogen, sulfur and oxygen, and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms may be optionally oxidized to form N-oxides. Some non-limiting examples of 7-12 membered heterocyclyl include indolinyl, 1,2,3,4-tetrahydroisoquinolinyl, 1,3-benzodioxolyl, 2-oxa-5-azabicyclo[2.2.1]hept-5-yl, 2-azaspiro[4.4]nonanyl (e.g. 2-azaspiro[4.4]nonane-4-yl, 2-azaspiro[4.4]nonane-2-yl), 1,6-dioxaspiro[4.4]nonanyl (e.g. 1,6-dioxaspiro[4.4]nonan-9-yl, 1,6-dioxaspiro[4.4]nonane-4-yl), 2-azaspiro[4.5]decanyl (e.g. 2-azaspiro[4.5]decane-8-yl, 2-azaspiro[4.5]decane-2-yl), 7-azaspiro[4.5]decanyl (e.g. 7-azaspiro[4.5]decane-8-yl, 7-azaspiro[4.5]decane-2-yl), 3-azaspiro[5.5]undecanyl (e.g. 3-azaspiro[5.5]undecane-3-yl, 3-azaspiro[5.5]undecane-9-yl), 2-azaspiro[5.5]undecanyl, 8-azaspiro[4.5]decanyl, decahydroisoquinolinyl, octahydro-1H-isoindolyl (e.g. octahydro-1H-isoindole-5-yl, octahydro-1H-isoindole-7-yl), octahydrocyclopenta[c]pyrrolyl (e.g. octahydrocyclopenta[c]pyrrole-5-yl, octahydrocyclopenta[c]pyrrole-2-yl), hexahydrofuro[3,2-b]furanyl (e.g. hexahydrofuro[3,2-b]furan-2-yl, hexahydrofuro[3,2-b]furan-3-yl), and the like. The 7-12 membered heterocyclyl group may be optionally substituted with one or more substituents described herein.

In still one embodiment, heterocyclyl refers to a 7-12 membered spiro heterobicyclyl, which refers to a monovalent or multivalent, saturated or partially unsaturated, non-aromatic, spiro heterobicyclyl ring containing 7-12 ring atoms, of which at least one ring atom is selected from nitrogen, sulfur and oxygen, and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms may be optionally oxidized to form N-oxides. The 7-12 membered spiro heterobicyclyl contains 7-12 membered saturated spiro heterobicyclyl (i.e. 7-12 membered spiro heterobicycloalkyl) and 7-12 membered partially unsaturated spiro heterobicyclyl. Some non-limiting examples of 7-12 membered spiro heterobicyclyl include 2-azaspiro[4.4]nonanyl (e.g. 2-azaspiro[4.4]nonane-4-yl, 2-azaspiro[4.4]nonane-2-yl), 1,6-dioxaspiro[4.4]nonanyl (e.g. 1,6-dioxaspiro[4.4]nonan-9-yl, 1,6-dioxaspiro[4.4]nonane-4-yl), 2-azaspiro[4.5]decanyl (e.g. 2-azaspiro[4.5]decane-8-yl, 2-azaspiro[4.5]decane-2-yl), 7-azaspiro[4.5]decanyl (e.g. 7-azaspiro[4.5]decane-8-yl, 7-azaspiro[4.5]decane-2-yl), 3-azaspiro[5.5]undecanyl (e.g. 3-azaspiro[5.5]undecane-3-yl, 3-azaspiro[5.5]undecane-9-yl), 2-azaspiro[5.5]undecanyl, 8-azaspiro[4.5]decanyl, and the like. The 7-12 membered spiro heterobicyclyl group may be optionally substituted with one or more substituents described herein.

In still another embodiment, heterocyclyl refers to a 8-11 membered spiro heterobicyclyl, which refers to a amonovalent or multivalent, saturated or partially unsaturated, non-aromatic, spiro heterobicyclyl ring containing 8-11 ring atoms, of which at least one ring atom is selected from nitrogen, sulfur and oxygen, and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms may be optionally oxidized to form N-oxides. The 8-11 membered spiro heterobicyclyl contains 8-11 membered saturated spiro heterobicyclyl (i.e. 8-11 membered spiro heterobicycloalkyl) and 8-11 membered partially unsaturated spiro heterobicyclyl. Some non-limiting examples of 8-11 membered spiro heterobicyclyl include 2-azaspiro[4.4]nonanyl (e.g. 2-azaspiro[4.4]nonane-4-yl, 2-azaspiro[4.4]nonane-2-yl), 1,6-dioxaspiro[4.4]nonanyl (e.g. 1,6-dioxaspiro[4.4]nonan-9-yl, 1,6-dioxaspiro[4.4]nonane-4-yl), 2-azaspiro[4.5]decanyl (e.g. 2-azaspiro[4.5]decane-8-yl, 2-azaspiro[4.5]decane-2-yl), 7-azaspiro[4.5]decanyl (e.g. 7-azaspiro[4.5]decane-8-yl, 7-azaspiro[4.5]decane-2-yl), 3-azaspiro[5.5]undecanyl (e.g. 3-azaspiro[5.5]undecane-3-yl, 3-azaspiro[5.5]undecane-9-yl), 2-azaspiro[5.5]undecanyl, 8-azaspiro[4.5]decanyl, and the like. The 8-11 membered spiro heterobicyclyl group may be optionally substituted with one or more substituents described herein.

In yet another embodiment, heterocyclyl refers to a 7-12 membered fused heterobicyclyl, which refers to a amonovalent or multivalent, saturated or partially unsaturated, non-aromatic fused heterobicyclyl ring containing 7-12 ring atoms, of which at least one ring atom is selected from nitrogen, sulfur and oxygen, and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms may be optionally oxidized to form N-oxides. The 7-12 membered fused heterobicyclyl contains 7-12 membered saturated fused heterobicyclyl (i.e. 7-12 membered fused heterobicycloalkyl) and 7-12 membered partially unsaturated fused heterobicyclyl. Some non-limiting examples of 7-12 membered fused heterobicyclyl include octahydrocyclopenta[c]pyrrolyl, octahydro-1H-isoindolyl, indolinyl, 1,2,3,4-tetrahydroisoquinolinyl, 1,3-benzodioxolyl, hexahydrofuro[3,2-b]furanyl, hexahydrofuro[2,3-b]furanyl, decahydroisoquinolinyl, and the like. The 7-12 membered fused heterobicyclyl group may be optionally substituted with one or more substituents described herein.

The terms "fused bicyclic ring", "fused cyclic", "fused bicyclyl" and "fused cyclyl" are used interchangeably refer to a monovalent or multivalent saturated or partially unsaturated, but not aromatic bicyclic ring system, and such that two rings share one common bond. Such a system may contain isolated or conjugated unsaturation, but not aromatic or heteroaromatic rings in its core structure (but may have aromatic substitution thereon).

The terms "spirocyclyl", "spirocyclic", "spiro bicyclyl" and "spiro bicyclic" are used interchangeably and refer to a monovalent or multivalent, saturated or partially unsaturated, ring system wherein a ring originating from a particular annular carbon of another ring. For example, as depicted below in Structure a, a saturated ring system (ring B and B') is termed as "fused bicyclyl", whereas ring A and ring B share an atom between the two saturated ring system, which terms as a "spirocyclyl" or "spiro bicyclyl". Each ring in the fused bicyclyl or the spiro bicyclyl can be either a carbocyclyl or a heterocyclyl, and each ring is optionally substituted independently with one or more substituents described herein.

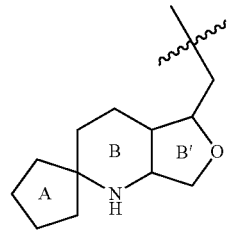

Structure a

The term "heterocycloalkyl" refers to a monovalent or multivalent saturated ring having 3 to 12 ring atoms as a monocyclic, bicyclic, or tricyclic ring system in which at least one ring atom is selected from nitrogen, sulfur and oxygen and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms may be optionally oxidized to form N-oxides. Some non-limiting examples of heterocycloalkyl include azetidinyl, oxetanyl, thietanyl, pyrrolidinyl, pyrazolidinyl, imidazolidinyl, tetrahydrothienyl, tetrahydrofuranyl, piperidinyl, piperazinyl, morpholinyl, dioxanyl, dithianyl, dithiolanyl, isoxazolidinyl, isothiazolidinyl, 1,2-oxazinanyl, 1,2-thiazinanyl, hexahydropyridazinyl, homopiperazinyl, homopiperidinyl, oxepanyl, thiepanyl, oxazepinyl (e.g. 1,4-oxazepinyl, 1,2-oxazepinyl), diazepinyl (e.g. 1,4-diazepinyl, 1,2-diazepinyl), dioxpinyl (e.g. 1,4-dioxpinyl, 1,2-dioxpinyl), thiazepinyl (e.g. 1,4-thiazepinyl, 1,2-thiazepinyl), 2-azaspiro[4.4]nonanyl, 1,6-dioxaspiro[4.4]nonanyl, 2-azaspiro[4.5]decanyl, 8-azaspiro[4.5]decanyl, 7-azaspiro[4.5]decanyl, 3-azaspiro[5.5]undecanyl, 2-azaspiro[5.5]undecanyl, 2-octahydro-1H-isoindolyl, octahydrocyclopenta[c]pyrrolyl, hexahydrofuro[3,2-b]furanyl, decahydroisoquinolinyl, hexahydrofuro[2,3-b]furanyl, and the like. The heterocycloalkyl group may be optionally substituted with one or more substituents described herein.

In one embodiment, heterocycloalkyl refers to a 7-12 membered heterocycloalkyl, which refers to a monovalent or multivalent saturated spiro, fused or bridged heterobicycloalkyl, containing 7-12 ring atoms, of which at least one ring atom is selected from nitrogen, sulfur and oxygen and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms may be optionally oxidized to form N-oxides. The 7-12 membered heterocycloalkyl group may be optionally substituted with one or more substituents described herein.

In one embodiment, heterocycloalkyl refers to a 3-6 membered heterocycloalkyl, which refers to a monovalent or multivalent saturated heterocyclyl ring containing 3-6 ring atoms, of which at least one ring atom is selected from nitrogen, sulfur and oxygen and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms may be optionally oxidized to form N-oxides. Some non-limiting examples of 3-6 membered heterocycloalkyl include azetidinyl, oxetanyl, thietanyl, pyrrolidinyl, pyrazolidinyl, imidazolidinyl, piperidinyl, piperazinyl, morpholinyl, dioxanyl, dithianyl, dithiolanyl, isoxazolidinyl, isothiazolidinyl, and hexahydropyridazinyl. The 3-6 membered heterocycloalkyl group may be optionally substituted with one or more substituents described herein.

In another embodiment, heterocycloalkyl refers to a 7-12 membered spiro heterobicycloalkyl, which refers to a monovalent or multivalent saturated spiro heterobicycloalkyl ring containing 7-12 ring atoms, of which at least one ring atom is selected from nitrogen, sulfur and oxygen. Unless otherwise specified, the 7-12 membered spiro heterobicycloalkyl may be carbon or nitrogen linked, and of which a —CH$_2$— group can optionally be replaced by a —C(=O)— group. Ring sulfur atoms may be optionally oxidized to form S-oxides. Ring nitrogen atoms may be optionally oxidized to form N-oxides. Some non-limiting examples of 7-12 membered spiro heterobicycloalkyl include 2-azaspiro[4.4]nonanyl, 1,6-dioxaspiro[4.4]nonanyl, 2-azaspiro[4.5]decanyl, 8-azaspiro[4.5]decanyl, 7-azaspiro[4.5]decanyl, 3-azaspiro[5.5]undecanyl, 2-azaspiro[5.5]undecanyl, and the like. The 7-12 membered spiro heterobicycloalkyl group may be optionally substituted with one or more substituents described herein.

In another embodiment, heterocycloalkyl refers to a 7-12 membered fused heterobicycloalkyl, which refers to a monovalent or multivalent saturated fused heterobicycloalkyl ring containing 7-12 ring atoms, of which at least one ring atom is selected from nitrogen, sulfur and oxygen. Unless otherwise specified, the 7-12 membered fused heterobicycloalkyl may be carbon or nitrogen linked, and of which a —CH$_2$— group can optionally be replaced by a —C(=O)— group. Ring sulfur atoms may be optionally oxidized to form S-oxides. Ring nitrogen atoms may be optionally oxidized to form N-oxides. Some non-limiting examples of 7-12 membered fused heterobicycloalkyl include octahydro-1H-isoindolyl (e.g. octahydro-1H-isoindole-5-yl, octahydro-1H-isoindole-7-yl), octahydrocyclopenta[c]pyrrolyl (e.g. octahydrocyclopenta[c]pyrrole-5-yl, octahydrocyclopenta[c]pyrrole-2-yl), hexahydrofuro[3,2-b]furanyl (e.g. hexahydrofuro[3,2-b]furan-2-yl, hexahydrofuro[3,2-b]furan-3-yl), decahydroisoquinolinyl, hexahydrofuro[2,3-b]furanyl, and the like. The 7-12 membered fused heterocybicloalkyl group may be optionally substituted with one or more substituents described herein.

In another embodiment, heterocycloalkyl refers to a 8-10 membered fused heterobicycloalkyl, which refers to a monovalent or multivalent saturated fused heterobicycloalkyl ring containing 8-10 ring atoms, of which at least one ring atom is selected from nitrogen, sulfur and oxygen. Unless otherwise specified, the 8-10 membered fused heterobicycloalkyl may be carbon or nitrogen linked, and of which a —CH$_2$— group can optionally be replaced by a —C(=O)— group. Ring sulfur atoms may be optionally oxidized to form S-oxides. Ring nitrogen atoms may be optionally oxidized to form N-oxides. Some non-limiting examples of 8-10 membered fused heterobicycloalkyl include octahydro-1H-isoindolyl (e.g. octahydro-1H-isoindole-5-yl, octahydro-1H-isoindole-7-yl), octahydrocyclopenta[c]pyrrolyl (e.g. octahydrocyclopenta[c]pyrrole-5-yl, octahydrocyclopenta[c]pyrrole-2-yl), hexahydrofuro[3,2-b]furanyl (e.g. hexahydrofuro[3,2-b]furan-2-yl, hexahydrofuro[3,2-b]furan-3-yl), decahydroisoquinolinyl, hexahydrofuro[2,3-b]furanyl, and the like. The 8-10 membered fused heterocybicloalkyl group may be optionally substituted with one or more substituents described herein.

The term "n membered" where n is an integer typically describes the number of ring-forming atoms in a moiety where the number of ring-forming atoms is n. For example, piperidinyl is an example of a 6 membered heterocycloalkyl and 1,2,3,4-tetrahydronaphthalenyl is an example of a 10 membered carbocyclyl group.

The term "unsaturated" refers to a moiety having one or more units of unsaturation.

The term "heteroatom" refers to one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or NR (as in N-substituted pyrrolidinyl).

The term "halogen" refers to Fluoro (F), Chloro (Cl), Bromo (Br), or Iodo (I).

The term "azido" or "N$_3$" refers to an azide moiety. This radical may be attached, for example, to a methyl group to form azidomethane (methyl azide, MeN$_3$); or attached to a phenyl group to form phenyl azide (PhN$_3$).

The term "aryl" refers to monocyclic, bicyclic, and tricyclic carbocyclic ring systems having a total of 6 to 14 ring members, preferably, 6 to 12 ring members, and more preferably 6 to 10 ring members, wherein at least one ring in the system is aromatic, wherein each ring in the system contains 3 to 7 ring members and that has one or more points of attachment to the rest of the molecule. The term "aryl" may be used interchangeably with the term "aryl ring" or "aromatic ring". Some non-limiting examples of the aryl group would include phenyl, naphthyl, and anthracenyl. The aryl radical is optionally substituted independently with one or more substituents described herein.

The term "heteroaryl" or "heteroaromatic ring" refers to monocyclic, bicyclic, and tricyclic ring systems having a total of 5 to 12 ring members, preferably, 5 to 10 ring members, and more preferably 5 to 6 ring members, wherein at least one ring in the system is aromatic, at least one aromatic ring in the system contains one or more heteroatoms, wherein each ring in the system contains 5 to 7 ring members and that has one or more points of attachment to the rest of the molecule. The term "heteroaryl" may be used interchangeably with the term "heteroaryl ring" or the term "heteroaromatic ring". In one embodiment, heteroaryl refers to a 5-12 membered heteroaryl comprises 1, 2, 3 or 4 heteroatoms independently selected from O, S and N. In another embodiment, heteroaryl refers to a 5-10 membered heteroaryl comprises 1, 2, 3 or 4 heteroatoms independently selected from O, S and N. In another embodiment, heteroaryl refers to a 5-6 membered heteroaryl comprises 1, 2, 3 or 4 heteroatoms independently selected from O, S and N. The heteroaryl radical is optionally independently substituted with one or more substituents described herein.

Some non-limiting examples of the heteroaryl group include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, pyridonyl, 2-pyrimidinyl, 4-pyrimidinyl, 5-pyrimidinyl, pyrimidonyl, pyrimidinedionyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl or 4-isoquinolinyl), imidazo[1,2-a]pyridyl, pyrazolo[1,5-a]pyridyl, pyrazolo[4,3-c]pyridinyl, pyrazolo[3,4-b]pyridinyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl and [1,2,4]triazolo[1,5-a]pyridyl.

The term "azolyl" refers to a 5-membered or 9-membered heteroaryl ring system containing at least one nitrogen atom. Some non-limiting examples of the azolyl include pyrazolyl, imidazolyl, oxazolyl, isoxazolyl, oxadiazolyl, thiazolyl, isothiazolyl, thiadiazolyl, diazolyl, triazolyl, indazolyl, pyrazolo[3,4-b]pyridinyl, pyrazolo[4,3-c]pyridinyl,1H-imidazo[4,5-b]pyridinyl and 1H-benzo[d]imidazolyl, and the like.

The term "carboxy" or "carboxyl", whether used alone or with other terms, such as "carboxyalkyl", refers to —CO$_2$H. The term "carbonyl", whether used alone or with other terms, such as "aminocarbonyl", denotes —(C=O)—.

The term "alkylamino" embraces "N-alkylamino" and "N,N-dialkylamino" where amino groups are independently substituted with one alkyl radical or with two alkyl radicals, respectively. In one embodiment alkylamino are "lower alkylamino" radicals having one or two alkyl radicals of one to six carbon atoms, attached to a nitrogen atom. In another embodiment alkylamino are alkylamino radicals having one or two alkyl radicals of one to four carbon atoms, attached to a nitrogen atom. Some non-limiting examples of alkylamino include N-methylamino, N-ethylamino, N,N-dimethylamino, N,N-diethylamino, and the like.

The term "arylamino" refers to amino groups, which have been substituted with one or two aryl radicals, such as N-phenylamino. The arylamino radicals may be further substituted on the aryl ring portion of the radical.

The term "aminoalkyl" refers to linear or branched alkyl radicals having one to about ten carbon atoms any one of which may be substituted with one or more amino radicals. More preferred aminoalkyl radicals are "lower aminoalkyl" radicals having 1-6 carbon atoms and one or more amino radicals. Examples of such radicals include aminomethyl, aminoethyl, aminopropyl, aminobutyl and aminohexyl.

As described herein, a bond drawn from a substituent to the center of one ring within a ring system (as shown below) represents substitution of the substituent at any substitutable position on the ring system. For example, as depicted below, Figure b represents possible substitution in any of the positions on the ring C and ring D shown in Figure c~Structure g.

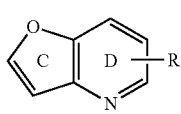

Structure b

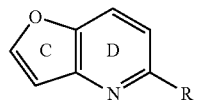

Structure c

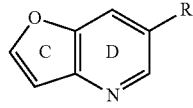

Structure d

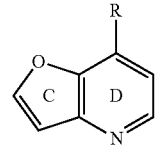

Structure e

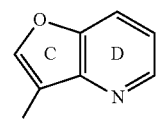

Structure f

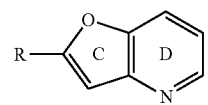

Structure g

As described herein, a connecting bond drawn from the center of one ring within a ring system (as shown in Structure h, wherein each X and X' is independently CH$_2$, NH or O) represents connection of the connecting bond attached to the rest of the molecule at any substitutable position on the ring system. For example, Structure h represents possible connection attached to the rest of the molecule in any of the position on ring E and ring F.

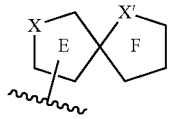

Structure h

As described herein, two connecting bonds drawn from the center of one ring within a ring system (as shown in Structure i) represents connection of the connecting bonds attached to the rest of the molecule at any two substitutable positions on the ring system. For example, Structure i represents possible connection attached to the rest of the molecule in any two of the positions on ring G.

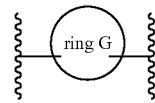

Structure i

The term "protecting group" or "PG" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxy-methyl, 2-(p-toluenesulfonyl)-ethyl, 2-(p-nitrophenylsulfenyl)-ethyl, 2-(diphenylphosphino)-ethyl, nitroethyl and the like. For a general description of protecting groups and their use, see T. W. Greene, Protective Groups in Organic Synthesis, John Wiley & Sons, New York, 1991; and P. J. Kocienski, Protecting Groups, Thieme, Stuttgart, 2005.

The term "prodrug" as used herein, represents a compound that is transformed in vivo into a compound of Formula (I). Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound disclosed herein that contains an OH group may be acylated at this position in its prodrug form. Other prodrug forms include phosphates, such as, for example those phosphates resulting from the phosphonation of an OH group on the parent compound. A thorough discussion of prodrugs is provided in Higuchi et al., Pro-drugs as Novel Delivery Systems, Vol. 14, A.C.S. Symposium Series; Roche et al., Bioreversible Carriers in Drug Design, American Pharmaceutical Association and Pergamon Press, 1987; Rautio et al., Prodrugs: Design and Clinical Applications, Nat. Rev. Drug Discovery, 2008, 7, 255-270, and Hecker et al., Prodrugs of Phosphates and Phosphonates, J. Med. Chem., 2008, 51, 2328-2345, all of which are incorporated herein by reference.

A "metabolite" refers to a product produced through metabolism in the body of a specified compound or salt thereof. The metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof.

A "pharmaceutically acceptable salt" refers to organic or inorganic salts of a compound disclosed herein. The pharmaceutically acceptable salts are well known in the art. For example, Berge et al., describe pharmaceutically acceptable salts in detail in J. Pharm. Sci., 1977, 66, 1-19, which is incorporated herein by reference. Some non-limiting examples of the pharmaceutically acceptable salt include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid.

Other examples of the pharmaceutically acceptable salt include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Pharmaceutically acceptable salts derived from appropriate bases include alkali metal, alkaline earth metal, ammonium and $N^+(C_1$-$C_4$ alkyl$)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further examples of the pharmaceutically acceptable salt include, when appropriate, nontoxic ammonium, quaternary ammonium, and amine cations formed using counterions such as halide, hydroxide, carboxylate, sulfate, phosphate, nitrate, $C_1$-$C_8$ sulfonate and aryl sulfonate.

A "solvate" refers to an association or complex of one or more solvent molecules and a compound disclosed herein. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

"Inflammatory disorder/disease" as used herein can refer to any disease, disorder, or syndrome in which an excessive or unregulated inflammatory response leads to excessive inflammatory symptoms, host tissue damage, or loss of tissue function. "Inflammatory disorder/disease" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (i.e. sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to treatment with the compounds disclosed herein encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

"Autoimmune disease" as used herein refers to any group of disorders in which tissue injury is associated with humoral or cell-mediated responses to the body's own constituents.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Description of Compounds of the Invention

In the present invention, novel compounds which are inhibitors of protein kinase activity, in particular JAK kinase, FLT3 kinase and Aurora kinase activity, are disclosed. Compounds which are protein kinase inhibitors may be useful in the treatment of diseases associated with inappropriate protein kinase activity, in particular inappropriate JAK, FLT3 and Aurora kinase activity, for example in the treatment and prevention of diseases mediated by JAK kinase, FLT3 kinase and Aurora kinase involved signalling pathways. Such diseases include proliferative disease, autoimmune disease, allergic disease, inflammatory disease, transplantation rejection, and their co-morbidities. In particular, a compound of the present invention may be useful in the treatment of diseases such as cancer, polycythemia vera, essential thrombocytosis, myelofibrosis, chronic myelogenous leukemia (CML), acute myeloid leukemia (AML), acute lymphocytic leukemia (ALL), chronic obstruction pulmonary disease (COPD), asthma, systemic and cutaneous lupus erythematosis, lupus nephritis, dermatomyositis, Sjogren's syndrome, psoriasis, type I diabetes mellitus, allergic airway disease, sinusitis, eczema, hives, food allergies, allergies to insect venom, inflammatory bowel syndrome, Crohn's disease, rheumatoid arthritis, juvenile arthritis, psoriatic arthritis, organ transplant rejection, tissue transplant rejection, cell transplant rejection, to name a few.

In one embodiment, the compounds disclosed herein may show potent inhibitory activities against one or more protein kinases.

In one aspect, provided herein is a compound having Formula (I):

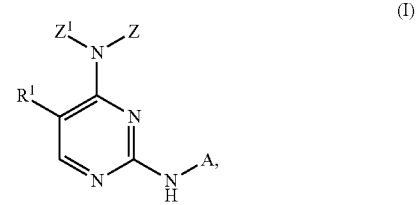

or a stereoisomer, a tautomer, an N-oxide, a solvate, a metabolite, a pharmaceutically acceptable salt or a prodrug thereof, wherein each of Z, $Z^1$, A and $R^1$ is as defined herein.

In one embodiment, Z is $C_7$-$C_{12}$ spiro bicycloalkyl, $C_7$-$C_{12}$ fused bicycloalkyl, 7-12 membered spiro heterobicyclyl or 7-12 membered fused heterobicycloalkyl, wherein Z is optionally substituted by 1, 2, 3, 4 or 5 $R^2$ groups;

$Z^1$ is H, $C_1$-$C_{12}$ alkyl, $C_3$-$C_{12}$ cycloalkyl or 3-12 membered heterocyclyl, wherein $Z^1$, except when $Z^1$ is H, is optionally substituted by 1, 2, 3, 4 or 5 $R^3$ groups;

A is pyrazolyl or imidazolyl, wherein A is optionally substituted by 1, 2, 3, 4 or 5 $R^4$ groups;

$R^1$ is H, F, Cl, Br, I, $NO_2$, $N_3$, CN, $C_1$-$C_{12}$ alkyl, $C_1$-$C_{12}$ haloalkyl, $C_1$-$C_{12}$ alkoxyl, $C_2$-$C_{12}$ alkenyl, $C_2$-$C_{12}$ alkynyl, $C_3$-$C_{12}$ cycloalkyl, 3-12 membered heterocyclyl, $C_6$-$C_{12}$ aryl, 5-12 membered heteroaryl, —$(CR^6R^7)_n$—$OR^c$, —$(CR^6R^7)_n$—$NR^aR^b$, —C(=O)$R^5$, —OC(=O)$R^5$, —O$(CR^6R^7)_n$—$R^5$, —N($R^c$)C(=O)$R^5$, —$(CR^6R^7)_n$C(=O)$OR^c$, —$(CR^6R^7)_n$C(=O)$NR^aR^b$, —C(=N$R^c$)$NR^aR^b$, —N($R^c$)C(=O)$NR^aR^b$, —N($R^c$)S(=O)$_m$$R^5$ or —S(=O)$_2$$NR^aR^b$, wherein when $R^1$ is not H, F, Cl, Br, I, $NO_2$, $N_3$ or CN, $R^1$ is optionally substituted by 1, 2, 3, 4 or 5 $R^8$ groups;

each $R^2$ is independently H, F, Cl, Br, I, $NO_2$, $N_3$, CN, OH, $NH_2$, —C(=O)$CH_2$CN, $C_1$-$C_{12}$ alkyl, $C_1$-$C_{12}$ haloalkyl, $C_1$-$C_{12}$ alkoxy, $C_2$-$C_{12}$ alkenyl, $C_2$-$C_{12}$ alkynyl, $C_3$-$C_{12}$ cycloalkyl, $C_6$-$C_{12}$ aryl, 3-12 membered heterocyclyl, 5-12 membered heteroaryl, —$(CR^6R^7)_n$—$OR^c$, —$(CR^6R^7)_n$—$NR^aR^b$, —C(=O)$R^5$, —S(=O)$_2$$R^5$, —OC(=O)$R^5$, —O$(CR^6R^7)_n$—$R^5$, —O$(CR^6R^7)_n$—OR, —N($R^c$)C(=O)$R^5$, —$(CR^6R^7)_n$C(=O)$OR$, —$(CR^6R^7)_n$C(=O)$NR^aR^b$, —C(=N$R^c$)$NR^aR^b$, —N($R^c$)C(=O)$NR^aR^b$, —N($R^c$)S(=O)$_m$$R^5$ or —S(=O)$_2$$NR^aR^b$, or two adjacent $R^2$ taken together with the atoms to which they are attached form a $C_3$-$C_{12}$ cycloalkyl or 3-12 membered heterocycloalkyl group, wherein each of the above substituents, except H, F, Cl, Br, I, $NO_2$, $N_3$ and CN, is optionally independently substituted by 1, 2, 3, 4 or 5 $R^8$ groups;

each $R^3$ and $R^4$ is independently H, F, Cl, Br, I, $NO_2$, $N_3$, CN, $C_1$-$C_{12}$ alkyl, $C_2$-$C_{12}$ alkenyl, $C_2$-$C_{12}$ alkynyl, $C_3$-$C_{12}$ cycloalkyl, —($C_1$-$C_4$ alkylene)-($C_3$-$C_{12}$ cycloalkyl), $C_6$-$C_{12}$ aryl, 3-12 membered heterocyclyl, —($C_1$-$C_4$ alkylene)-(3-12 membered heterocyclyl), 5-12 membered heteroaryl, —(CR$^6$R$^7$)$_n$—OR$^c$, —(CR$^6$R$^7$)$_n$—NR$^a$R$^b$, —C(=O)R$^5$, —OC(=O)R$^5$, —O(CR$^6$R$^7$)$_n$—R$^5$, —N(R$^c$)C(=O)R$^5$, —(CR$^6$R$^7$)$_n$C(=O)OR$^c$, —(CR$^6$R$^7$)$_n$C(=O)NR$^a$R$^b$, —C(=NR$^c$)NR$^a$R$^b$, —N(R$^c$)C(=O)NR$^a$R$^b$, —N(R$^c$)S(=O)$_m$R$^5$ or —S(=O)$_2$NR$^a$R$^b$, wherein when R$^3$ or R$^4$ is not H, F, Cl, Br, I, NO$_2$, N$_3$ or CN, R$^3$ or R$^4$ respectively is optionally substituted by 1, 2, 3, 4 or 5 R$^8$ groups;

each R$^5$ is independently H, C$_1$-C$_{12}$ alkyl, C$_1$-C$_{12}$ haloalkyl, C$_2$-C$_{12}$ alkenyl, C$_2$-C$_{12}$ alkynyl, C$_3$-C$_{12}$ cycloalkyl, C$_6$-C$_{12}$ aryl, 3-12 membered heterocyclyl or 5-12 membered heteroaryl, wherein each R$^5$, except when R$^5$ is H, is optionally independently substituted by 1, 2, 3, 4 or 5 R$^8$ groups;

each R$^6$ and R$^7$ is independently H, F, Cl, Br, I, NO$_2$, N$_3$, CN, C$_1$-C$_{12}$ alkyl, C$_2$-C$_{12}$ alkenyl, C$_2$-C$_{12}$ alkynyl, C$_3$-C$_{12}$ cycloalkyl, C$_6$-C$_{12}$ aryl, 3-12 membered heterocyclyl or 5-12 membered heteroaryl, or R$^6$ and R$^7$ taken together with the carbon atom to which they are attached form a C$_3$-C$_{12}$ cycloalkyl, C$_6$-C$_{12}$ aryl, 3-12 membered heterocyclyl or 5-12 membered heteroaryl group, wherein each of the above substituents, except H, F, Cl, Br, I, NO$_2$, N$_3$ and CN, is optionally independently substituted by 1, 2, 3, 4 or 5 R$^8$ groups;

each R$^8$ is independently F, Cl, Br, I, CN, NO$_2$, N$_3$, C$_1$-C$_{12}$ alkyl, C$_2$-C$_{12}$ alkenyl, C$_2$-C$_{12}$ alkynyl, C$_3$-C$_{12}$ cycloalkyl, C$_6$-C$_{12}$ aryl, 3-12 membered heterocyclyl, 5-12 membered heteroaryl, NH$_2$, —NH(C$_1$-C$_{12}$ alkyl), —NH(CH$_2$)$_n$—(C$_3$-C$_{12}$ cycloalkyl), —NH(CH$_2$)$_n$—(C$_6$-C$_{12}$ aryl), —NH(CH$_2$)$_n$—(3-12 membered heterocyclyl), —NH(CH$_2$)$_n$-(5-12 membered heteroaryl), —N(C$_1$-C$_{12}$ alkyl)$_2$, —N[(CH$_2$)$_n$—(C$_3$-C$_{12}$ cycloalkyl)]$_2$, —N[(CH$_2$)$_n$—(C$_6$-C$_{12}$ aryl)]$_2$, —N[(CH$_2$)$_n$-(3-12 membered heterocyclyl)]$_2$, —N[(CH$_2$)$_n$-(5-12 membered heteroaryl)]$_2$, OH, —O(C$_1$-C$_{12}$ alkyl), —O(CH$_2$)$_n$—(C$_3$-C$_{12}$cycloalkyl), —O(CH$_2$)$_n$—(C$_6$-C$_{12}$ aryl), —O(CH$_2$)$_n$-(3-12 membered heterocyclyl) or —O(CH$_2$)$_n$-(5-12 membered heteroaryl);

each R$^a$, R$^b$ and R$^c$ is independently H, C$_1$-C$_6$ alkyl, C$_2$-C$_6$ alkenyl, C$_2$-C$_6$ alkynyl, C$_3$-C$_6$ cycloalkyl, —(C$_1$-C$_4$ alkylene)-(C$_3$-C$_6$ cycloalkyl), 3-6 membered heterocyclyl, —(C$_1$-C$_4$ alkylene)-(3-6 membered heterocyclyl), C$_6$-C$_{10}$ aryl, —(C$_1$-C$_4$ alkylene)-(C$_6$-C$_{10}$ aryl), 5-10 membered heteroaryl or —(C$_1$-C$_4$ alkylene)-(5-10 membered heteroaryl), or R$^a$ and R$^b$ taken together with the nitrogen atom to which they are attached form a 3-8 membered heterocyclyl group, wherein each of the above substituents, except H, is optionally independently substituted by 1, 2, 3 or 4 substitutents independently selected from F, Cl, Br, CN, N$_3$, OH, NH$_2$, C$_1$-C$_6$ alkyl, C$_1$-C$_6$ haloalkyl, C$_1$-C$_6$ alkoxy and C$_1$-C$_6$ alkylamino;

each m is independently 1 or 2; and each n is independently 0, 1, 2, 3 or 4.

In another embodiment, Z is C$_8$-C$_{11}$ spiro bicycloalkyl, C$_8$-C$_{10}$ fused bicycloalkyl, 8-11 membered spiro heterobicyclyl or 8-10 membered fused heterobicycloalkyl, wherein Z is optionally substituted by 1, 2, 3 or 4 R$^2$ groups.

In one embodiment, Z$^1$ is H, C$_1$-C$_6$ alkyl, C$_3$-C$_6$ cycloalkyl or 3-6 membered heterocyclyl, wherein Z$^1$, except when Z$^1$ is H, is optionally substituted by 1, 2 or 3 R$^3$ groups.

In another embodiment, R$^1$ is H, F, Cl, CN, N$_3$, C$_1$-C$_6$ alkyl, C$_2$-C$_6$ alkenyl, C$_2$-C$_6$ alkynyl, C$_1$-C$_6$ haloalkyl, C$_1$-C$_6$ alkoxyl, C$_3$-C$_6$ cycloalkyl, 3-6 membered heterocyclyl, —(CR$^6$R$^7$)$_n$—OR$^c$, —(CR$^6$R$^7$)$_n$—NR$^a$R$^b$, —C(=O)R$^5$, —(CR$^6$R$^7$)$_n$C(=O)NR$^a$R$^b$ or —S(=O)$_2$NR$^a$R$^b$, wherein when R$^1$ is not H, F, Cl, CN or N$_3$, R$^1$ is optionally substituted by 1, 2 or 3 R$^8$ groups.

In one embodiment, each R$^2$ is independently H, F, Cl, CN, N$_3$, NO$_2$, OH, NH$_2$, —C(=O)CH$_2$CN, C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_3$-C$_6$ cycloalkyl, phenyl, 3-6 membered heterocyclyl, 5-6 membered heteroaryl, —(CR$^6$R$^7$)$_n$—OR$^c$, —(CR$^6$R$^7$)$_n$—NR$^a$R$^b$, —C(=O)R$^5$, —S(=O)$_2$R$^5$, —O(CR$^6$R$^7$)$_n$—R$^5$, —O(CR$^6$R$^7$)$_n$—OR$^c$, —N(R$^c$)C(=O)R$^5$, —(CR$^6$R$^7$)$_n$C(=O)NR$^a$R$^b$, —N(R$^c$)C(=O)NR$^a$R$^b$, —N(R$^c$)S(=O)$_m$R$^5$ or —S(=O)$_2$NR$^a$R$^b$, or two adjacent R$^2$ taken together with the atoms to which they are attached form a C$_3$-C$_6$ cycloalkyl, or 3-6 membered heterocycloalkyl group, wherein each of the above substituents, except H, F, Cl, CN, N$_3$ and NO$_2$, is optionally independently substituted by 1, 2 or 3 R$^8$ groups.

In another embodiment, each R$^3$ and R$^4$ is independently H, F, Cl, Br, I, NO$_2$, N$_3$, CN, C$_1$-C$_6$ alkyl, C$_2$-C$_6$ alkenyl, C$_2$-C$_6$ alkynyl, C$_3$-C$_6$ cycloalkyl, —(C$_1$-C$_2$ alkylene)-(C$_3$-C$_6$ cycloalkyl), phenyl, 3-6 membered heterocyclyl, —(C$_1$-C$_2$ alkylene)-(3-6 membered heterocyclyl), 5-6 membered heteroaryl, —(CR$^6$R$^7$)$_n$—OR$^c$, —(CR$^6$R$^7$)$_n$—NR$^a$R$^b$, —C(=O)R$^5$, —OC(=O)R$^5$, —O(CR$^6$R$^7$)$_n$—R$^5$, —N(R$^c$)C(=O)R$^5$, —(CR$^6$R$^7$)$_n$C(=O)OR$^c$, —(CR$^6$R$^7$)$_n$C(=O)NR$^a$R$^b$, —N(R$^c$)S(=O)$_m$R$^5$ or —S(=O)$_2$NR$^a$R$^b$, wherein when R$^3$ or R$^4$ is not H, F, Cl, Br, I, NO$_2$, N$_3$ or CN, R$^3$ or R$^4$ respectively is optionally substituted by 1, 2 or 3 R$^8$ groups.

In one embodiment, each R$^5$ is independently H, C$_1$-C$_6$ alkyl, C$_1$-C$_6$ haloalkyl, C$_2$-C$_6$ alkenyl, C$_2$-C$_6$ alkynyl, C$_3$-C$_6$ cycloalkyl, phenyl, 3-6 membered heterocyclyl or 5-6 membered heteroaryl, wherein each R$^5$, except when R$^5$ is H, is optionally independently substituted by 1, 2 or 3 R$^8$ groups.

In another embodiment, each R$^6$ and R$^7$ is independently H, F, Cl, Br, I, CN, N$_3$, NO$_2$, C$_1$-C$_6$ alkyl, C$_2$-C$_6$ alkenyl, C$_2$-C$_6$ alkynyl, C$_3$-C$_6$ cycloalkyl, phenyl, 3-6 membered heterocyclyl or 5-6 membered heteroaryl, or R$^6$ and R$^7$ taken together with the carbon atom to which they are attached form a C$_3$-C$_6$ cycloalkyl, phenyl, 3-6 membered heterocyclyl or 5-6 membered heteroaryl group, wherein each of the above substituents, except H, F, Cl, Br, I, CN, N$_3$ and NO$_2$, is optionally independently substituted by 1, 2 or 3 R$^8$ groups.

In one embodiment, each R$^8$ is independently F, Cl, CN, N$_3$, C$_1$-C$_6$ alkyl, C$_2$-C$_6$ alkenyl, C$_2$-C$_6$ alkynyl, C$_3$-C$_6$ cycloalkyl, phenyl, 3-6 membered heterocyclyl, 5-6 membered heteroaryl, NH$_2$, —NH(C$_1$-C$_6$ alkyl), —NH(CH$_2$)$_n$—(C$_3$-C$_6$ cycloalkyl), —NH(CH$_2$)$_n$-phenyl, —NH(CH$_2$)$_n$-(3-6 membered heterocyclyl), —NH(CH$_2$)$_n$-(5-6 membered heteroaryl), —N(C$_1$-C$_4$ alkyl)$_2$, —N[(CH$_2$)$_n$—(C$_3$-C$_6$cycloalkyl)]$_2$, —N[(CH$_2$)$_n$-phenyl]$_2$, —N[(CH$_2$)$_n$-(3-6 membered heterocyclyl)]$_2$, —N[(CH$_2$)$_n$-(5-6 membered heteroaryl)]$_2$, OH, —O(C$_1$-C$_6$ alkyl), —O(CH$_2$)$_n$—(C$_3$-C$_6$ cycloalkyl), —O(CH$_2$)$_n$-phenyl, —O(CH$_2$)$_n$-(3-6 membered heterocyclyl) or —O(CH$_2$)$_n$-(5-6 membered heteroaryl).

In another embodiment, each R$^a$, R$^b$ and R$^c$ is independently H, C$_1$-C$_4$ alkyl, C$_2$-C$_4$ alkenyl, C$_2$-C$_4$ alkynyl, C$_3$-C$_6$ cycloalkyl, —(C$_1$-C$_2$ alkylene)-(C$_3$-C$_6$ cycloalkyl), 3-6 membered heterocyclyl, —(C$_1$-C$_2$ alkylene)-(3-6 membered heterocyclyl), phenyl, —(C$_1$-C$_2$ alkylene)-phenyl, 5-6 membered heteroaryl or —(C$_1$-C$_2$ alkylene)-(5-6 membered heteroaryl), or R$^a$ and R$^b$ taken together with the nitrogen atom to which they are attached form a 3-6 membered heterocyclyl group, wherein each of the above substituents, except H, is optionally independently substituted by 1, 2 or 3 substitutents independently selected from F, Cl, CN, N$_3$, OH, NH$_2$, C$_1$-C$_4$ alkyl, C$_1$-C$_4$ haloalkyl, C$_1$-C$_4$ alkoxy and C$_1$-C$_4$ alkylamino.

In one embodiment, Z is:
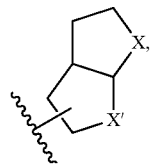 (Z-1)
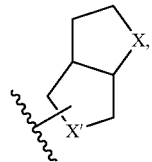 (Z-2)
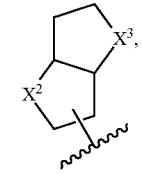 (Z-3)
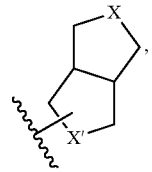 (Z-4)
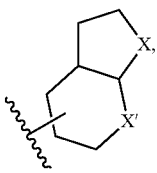 (Z-5)
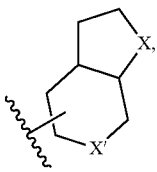 (Z-6)
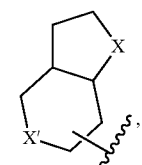 (Z-7)
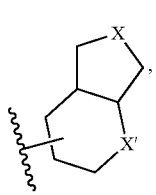 (Z-8)
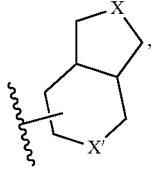 (Z-9)
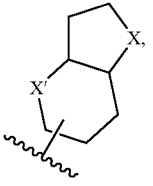 (Z-10)
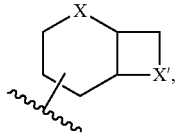 (Z-11)
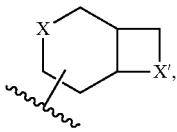 (Z-12)
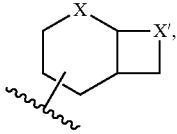 (Z-13)
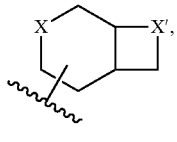 (Z-14)
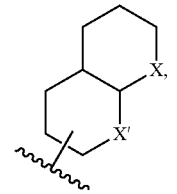 (Z-15)
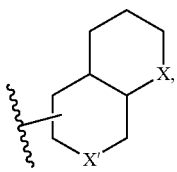 (Z-16)
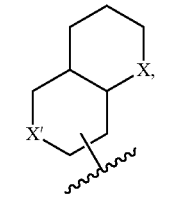 (Z-17)

-continued
(Z-18)
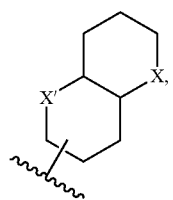
(Z-19)
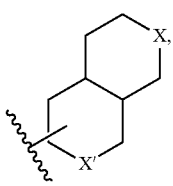
(Z-20)
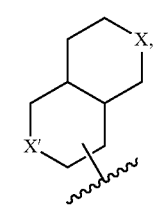
(Z-21)
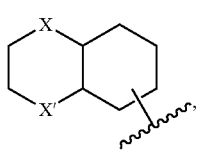
(Z-22)
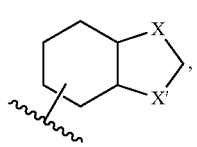
(Z-23)
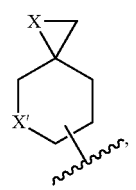
(Z-24)
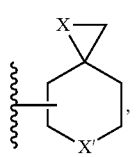
(Z-25)
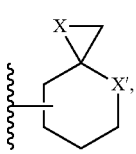
(Z-26)
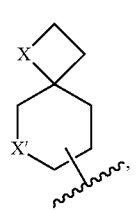
-continued
(Z-27)
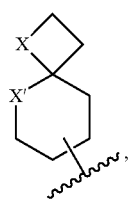
(Z-28)
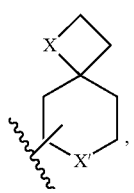
(Z-29)
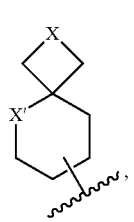
(Z-30)
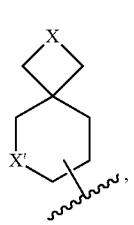
(Z-31)
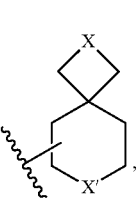
(Z-32)
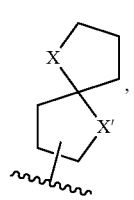
(Z-33)
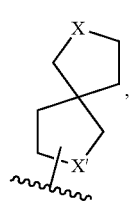
(Z-34)
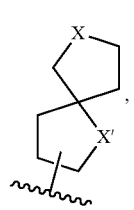

(Z-35) 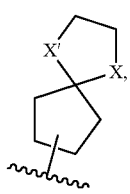
(Z-36) 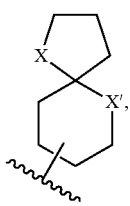
(Z-37) 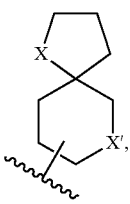
(Z-38) 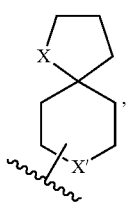
(Z-39) 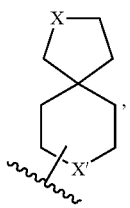
(Z-40) 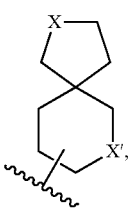
(Z-41) 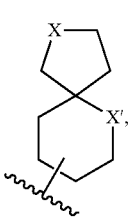
(Z-42) 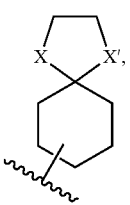
(Z-43) 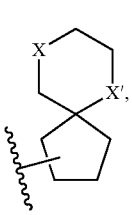
(Z-44) 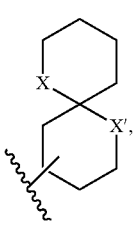
(Z-45) 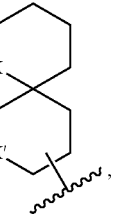
(Z-46) 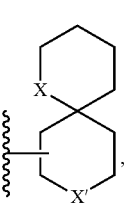
(Z-47) 
(Z-48) 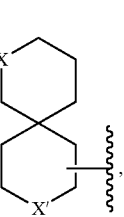

-continued (Z-49)
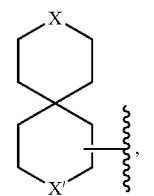

(Z-51)
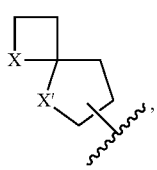

(Z-52)
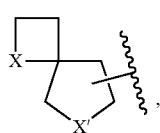

(Z-53)
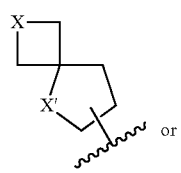

(Z-54)
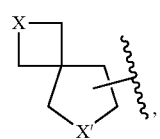 or or a stereoisomer thereof, wherein each X, X', X² and X³ is independently CH₂, NH or O, with the proviso that when X² is O, X³ is not O; and wherein Z is optionally substituted by 1, 2 or 3 R² groups.

In another embodiment, A is:

(L)
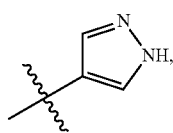

(M)
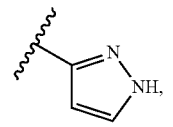

(N)
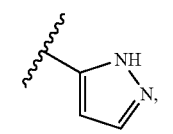

(O)
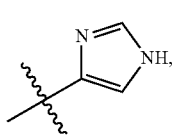

-continued (P)
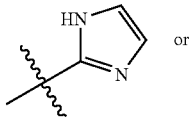 or (Q)
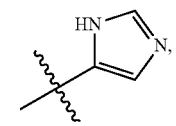

wherein A is optionally substituted by 1, 2 or 3 R⁴ groups.

In one embodiment, Z¹ is H, methyl, ethyl, n-propyl, iso-propyl or cyclopropyl.

In another embodiment, R¹ is H, F, Cl, CN, N₃, C₁-C₄ alkyl, C₂-C₄ alkenyl, C₂-C₄ alkynyl, C₁-C₄ haloalkyl, C₁-C₄ alkoxyl, C₃-C₆ cycloalkyl, 3-6 membered heterocyclyl, —(CR⁶R⁷)ₙ—ORᶜ, —(CR⁶R⁷)ₙ—NRᵃRᵇ, —C(=O)R⁵, —(CR⁶R⁷)ₙC(=O)NRᵃRᵇ or —S(=O)₂NRᵃRᵇ, wherein R¹, except when R¹ is H, F, Cl, CN or N₃, is optionally substituted by 1, 2 or 3 R⁸ groups.

In one embodiment, each R² is independently H, F, Cl, CN, N₃, NO₂, OH, NH₂, —C(=O)CH₂CN, C₁-C₄ alkyl, C₂-C₄ alkenyl, C₂-C₄ alkynyl, C₁-C₄ haloalkyl, C₁-C₄ alkoxy, C₃-C₆ cycloalkyl, phenyl, 3-6 membered heterocyclyl, 5-6 membered heteroaryl, —(CR⁶R⁷)ₙ—ORᶜ, —(CR⁶R⁷)ₙ—NRᵃRᵇ, —C(=O)R⁵, —S(=O)₂R⁵, —O(CR⁶R⁷)ₙ—R⁵, —O(CR⁶R⁷)ₙ—OR, —N(Rᶜ)C(=O)R⁵, —(CR⁶R⁷)ₙC(=O)NRᵃRᵇ, —N(Rᶜ)S(=O)ₘR⁵ or —S(=O)₂NRᵃRᵇ, wherein each R², except when R² is H, F, Cl, CN, N₃ or NO₂, is optionally independently substituted by 1, 2 or 3 R⁸ groups.

In still another embodiment, each R⁵ is independently H, C₁-C₄ alkyl, C₁-C₄ haloalkyl, C₂-C₄ alkenyl, C₂-C₄ alkynyl, C₃-C₆ cycloalkyl, phenyl, 3-6 membered heterocyclyl or 5-6 membered heteroaryl, wherein each R⁵, except when R⁵ is H, is optionally independently substituted by 1, 2 or 3 R⁸ groups.

In yet another embodiment, some non-limiting examples of the compound disclosed herein, and their stereoisomer, tautomer, N-oxide, solvate, pharmaceutically acceptable salts and solvates thereof, are shown in the following:

TABLE 1

(1)
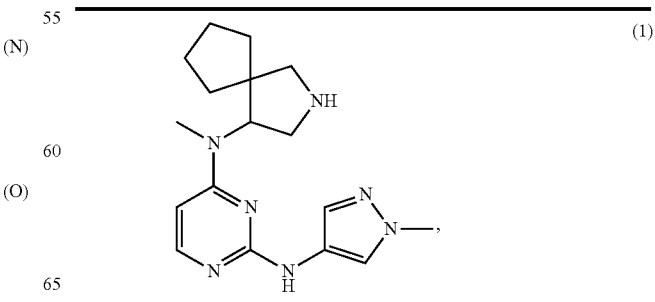

TABLE 1-continued
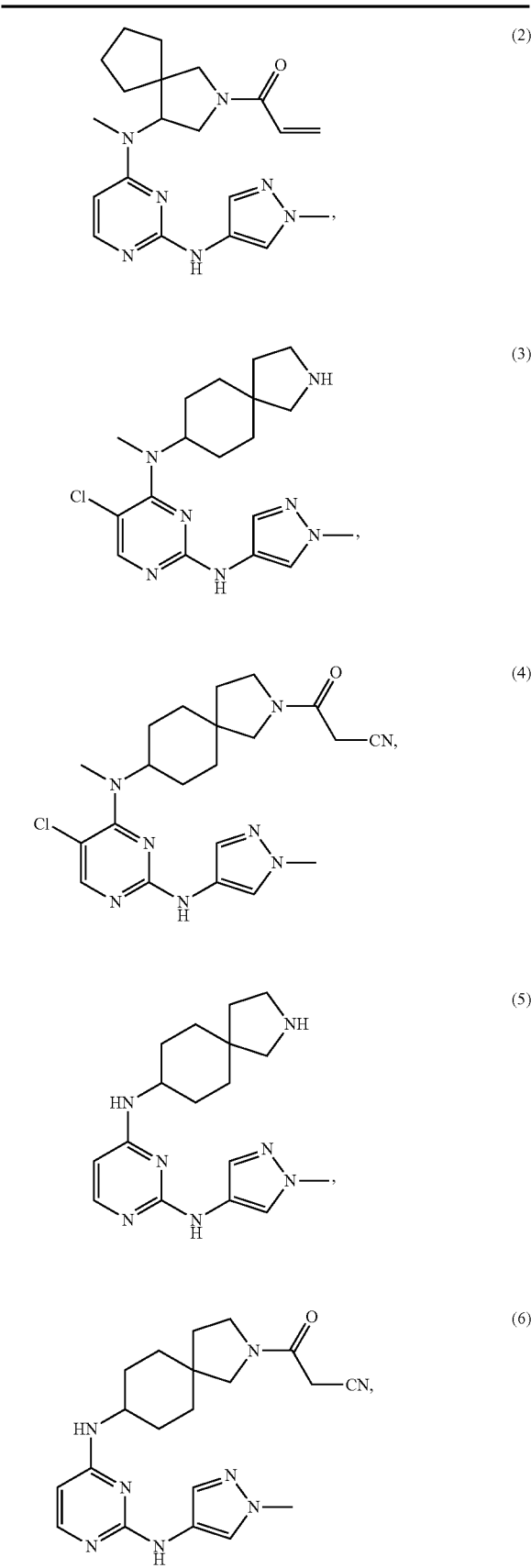
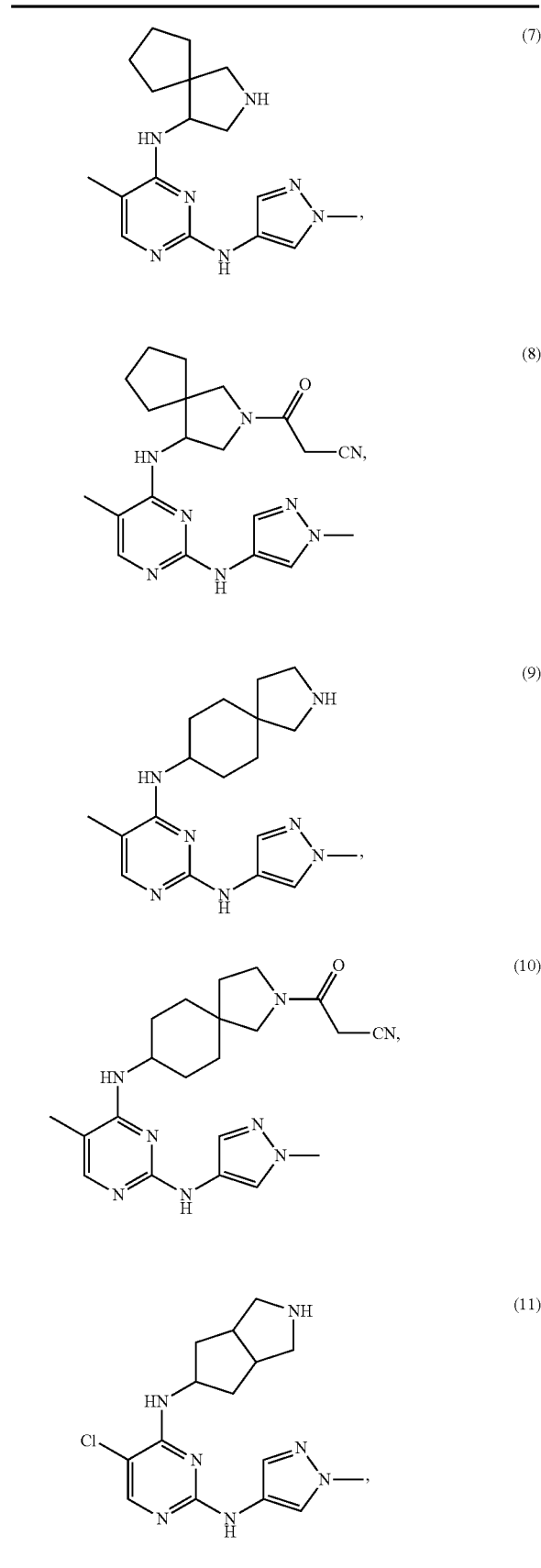

TABLE 1-continued
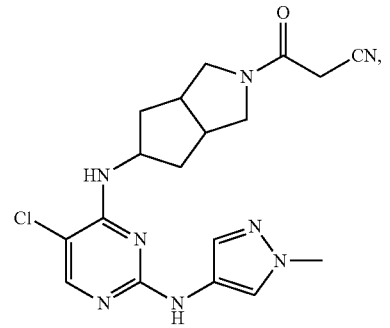 [SMILES: Cn1cc(Nc2ncc(Cl)c(NC3CC4CN(C(=O)CC#N)CC4C3)n2)cn1] (12)
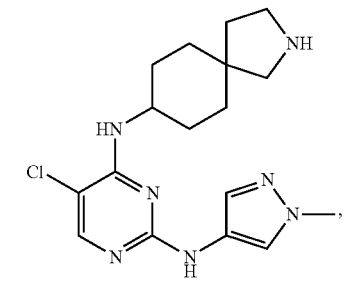 [SMILES: Cn1cc(Nc2ncc(Cl)c(NC3CCC4(CCNC4)CC3)n2)cn1] (13)
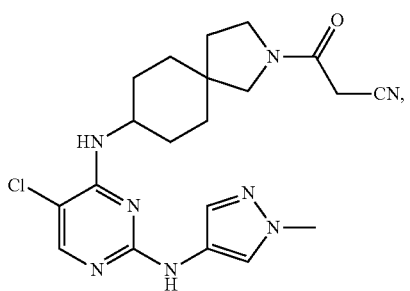 [SMILES: Cn1cc(Nc2ncc(Cl)c(NC3CCC4(CC3)CCN(C(=O)CC#N)C4)n2)cn1] (14)
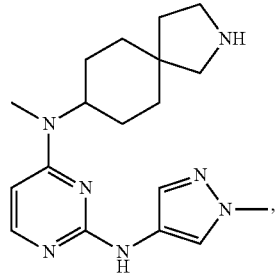 [SMILES: CN(c1ccnc(Nc2cnn(C)c2)n1)C1CCC2(CCNC2)CC1] (15)
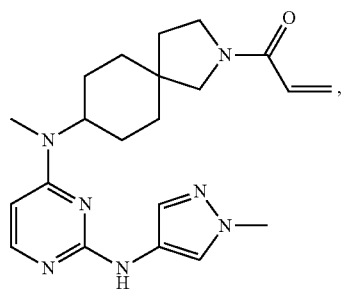 [SMILES: C=CC(=O)N1CCC2(CCC(N(C)c3ccnc(Nc4cnn(C)c4)n3)CC2)C1] (16)
TABLE 1-continued
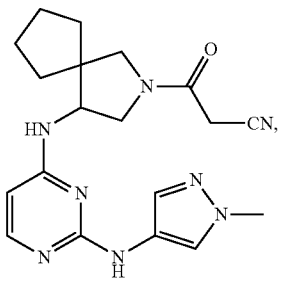 [SMILES: Cn1cc(Nc2nccc(NC3CN(C(=O)CC#N)CC34CCCC4)n2)cn1] (17)
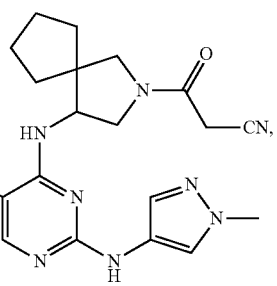 (18)
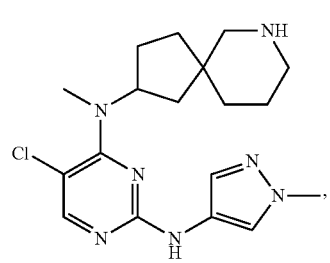 [SMILES: CN(c1nc(Nc2cnn(C)c2)ncc1Cl)C1CCC2(CCCNC2)C1] (19)
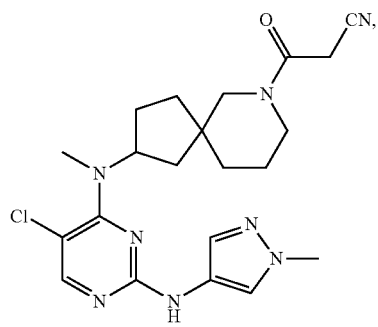 [SMILES: CN(c1nc(Nc2cnn(C)c2)ncc1Cl)C1CCC2(CCCN(C(=O)CC#N)C2)C1] (20)
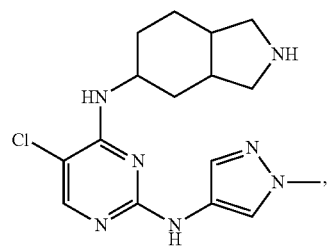 [SMILES: Cn1cc(Nc2ncc(Cl)c(NC3CCC4CNCC4C3)n2)cn1] (21)
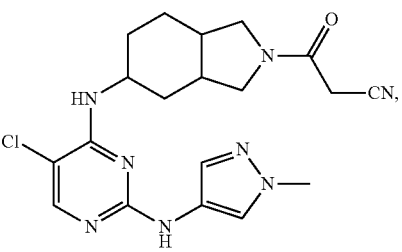 [SMILES: Cn1cc(Nc2ncc(Cl)c(NC3CCC4CN(C(=O)CC#N)CC4C3)n2)cn1] (22)

TABLE 1-continued
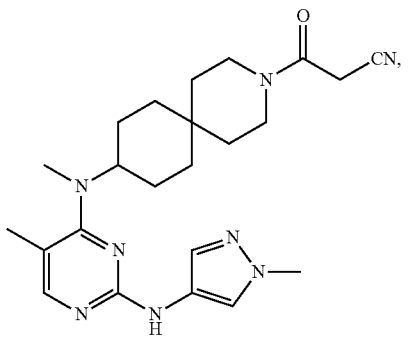 [SMILES: Cc1cnc(Nc2cnn(C)c2)nc1N(C)C1CCC2(CC1)CCN(C(=O)CC#N)CC2] (23)
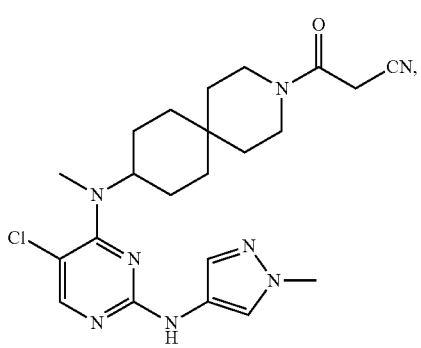 [SMILES: CN(c1nc(Nc2cnn(C)c2)ncc1Cl)C1CCC2(CC1)CCN(C(=O)CC#N)CC2] (24)
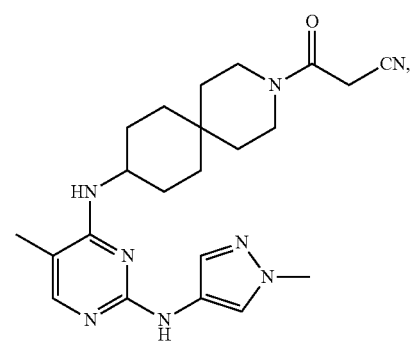 [SMILES: Cc1cnc(Nc2cnn(C)c2)nc1NC1CCC2(CC1)CCN(C(=O)CC#N)CC2] (25)
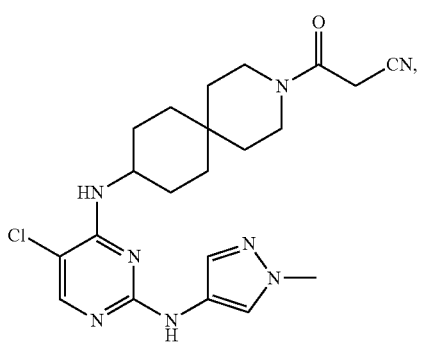 [SMILES: Cn1cc(Nc2ncc(Cl)c(NC3CCC4(CC3)CCN(C(=O)CC#N)CC4)n2)cn1] (26)
TABLE 1-continued
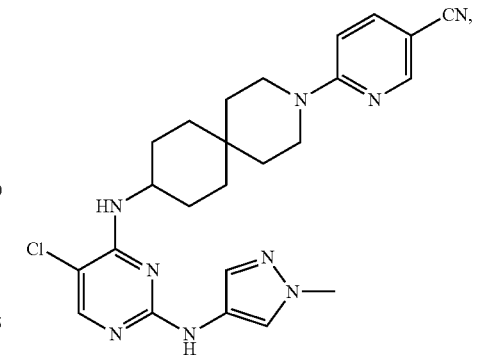 (27)
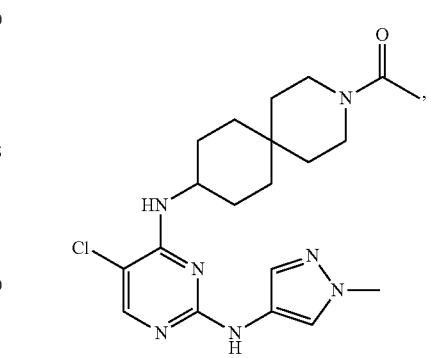 (28)
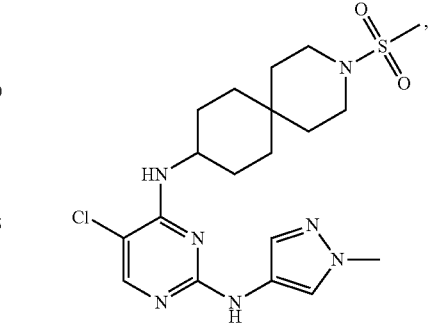 (29)
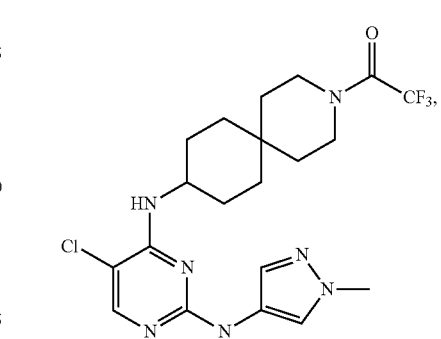 (30)

TABLE 1-continued
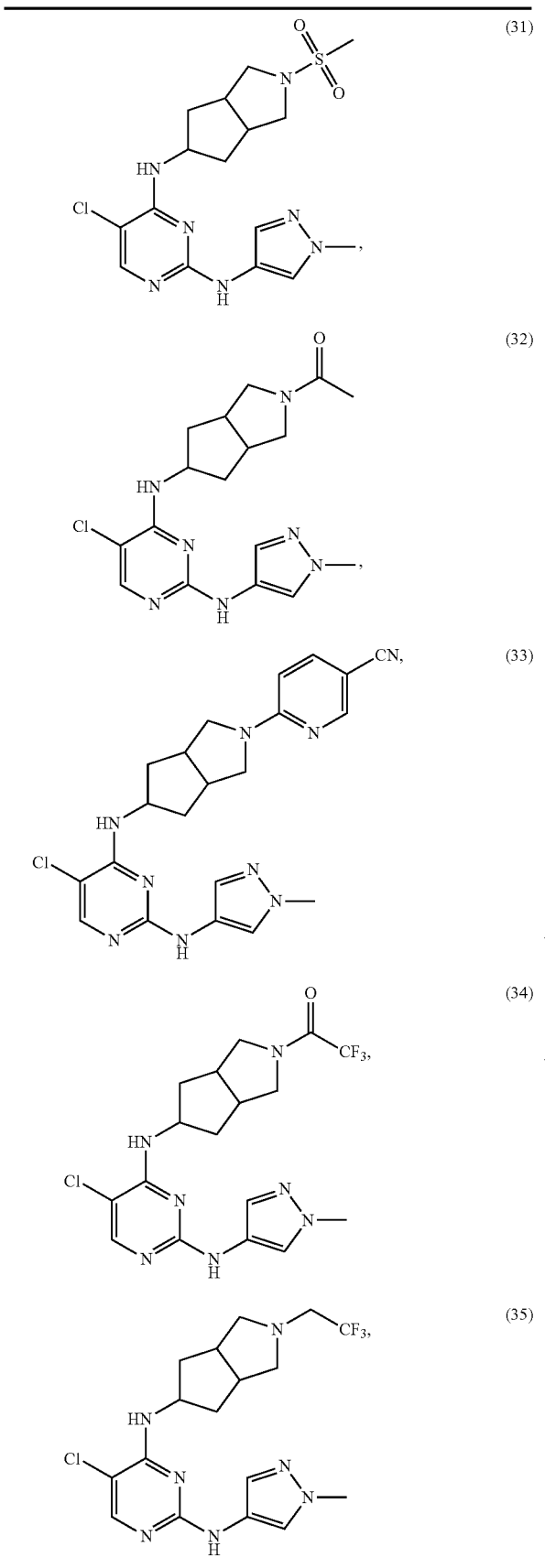
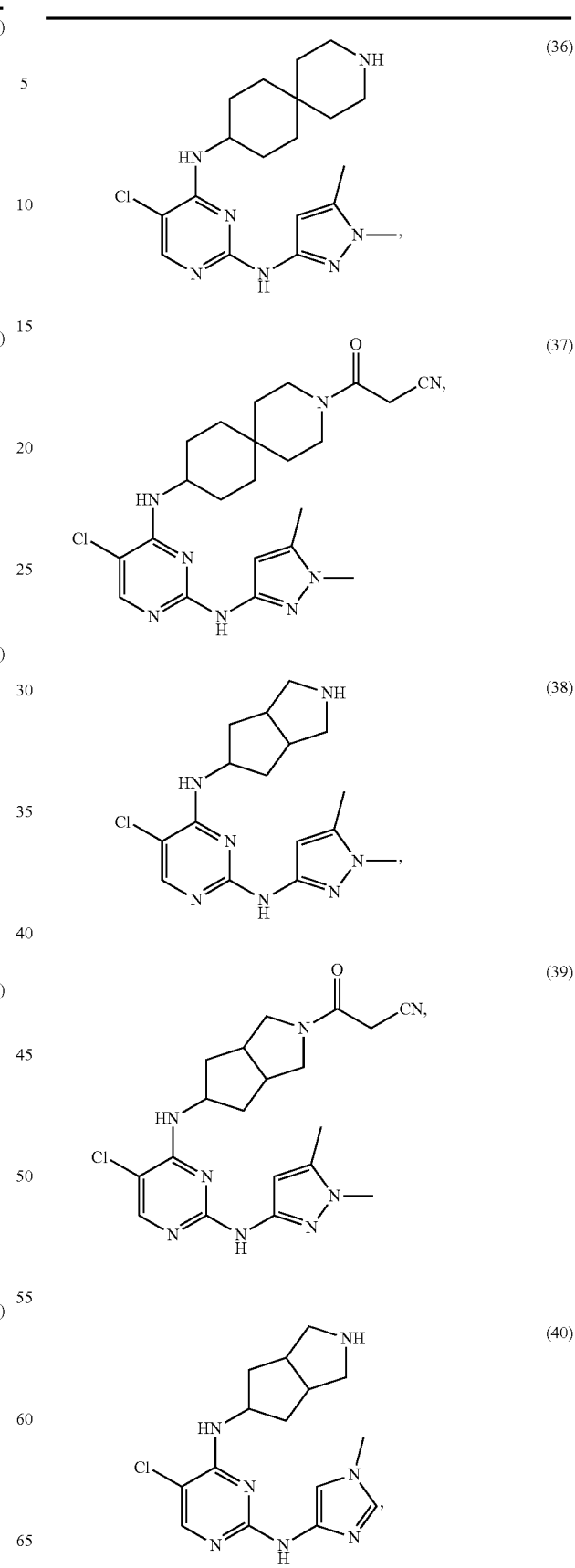

TABLE 1-continued
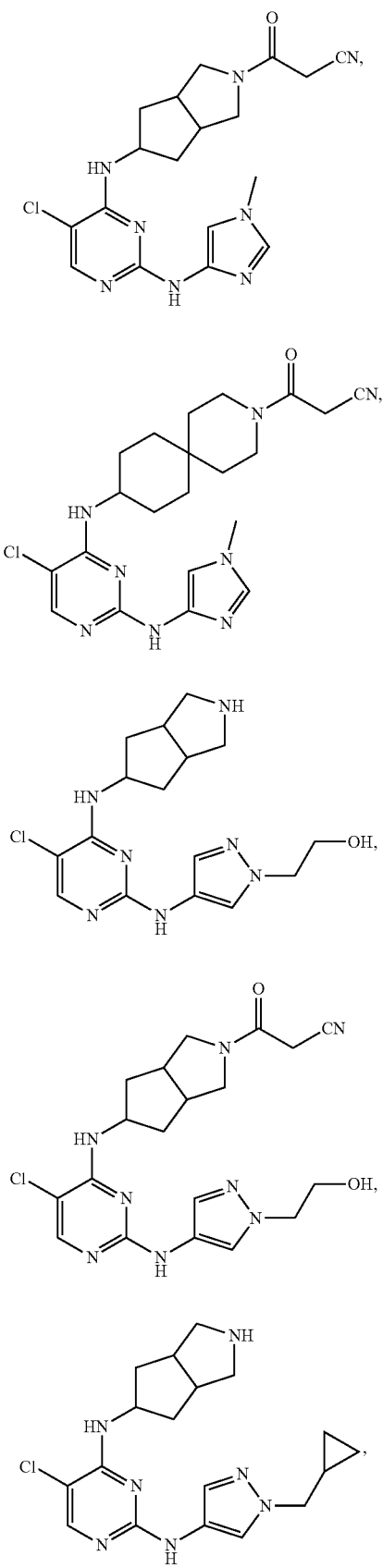
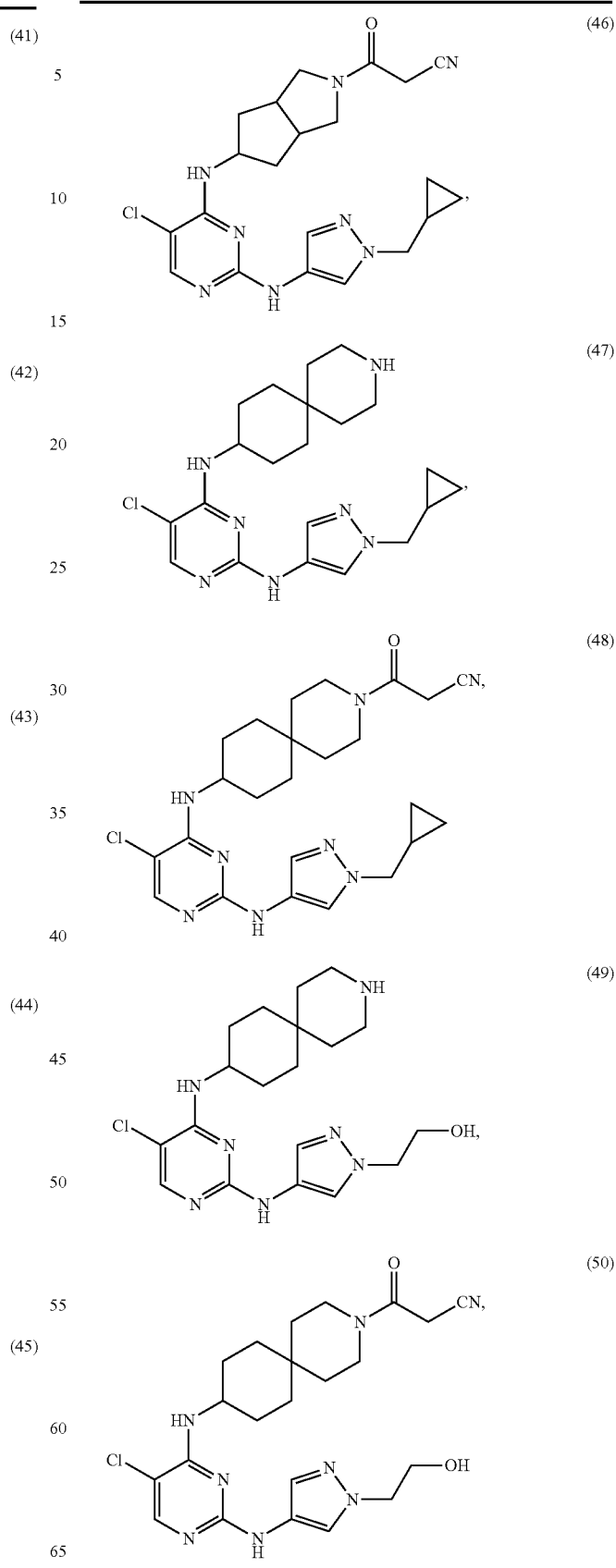

TABLE 1-continued
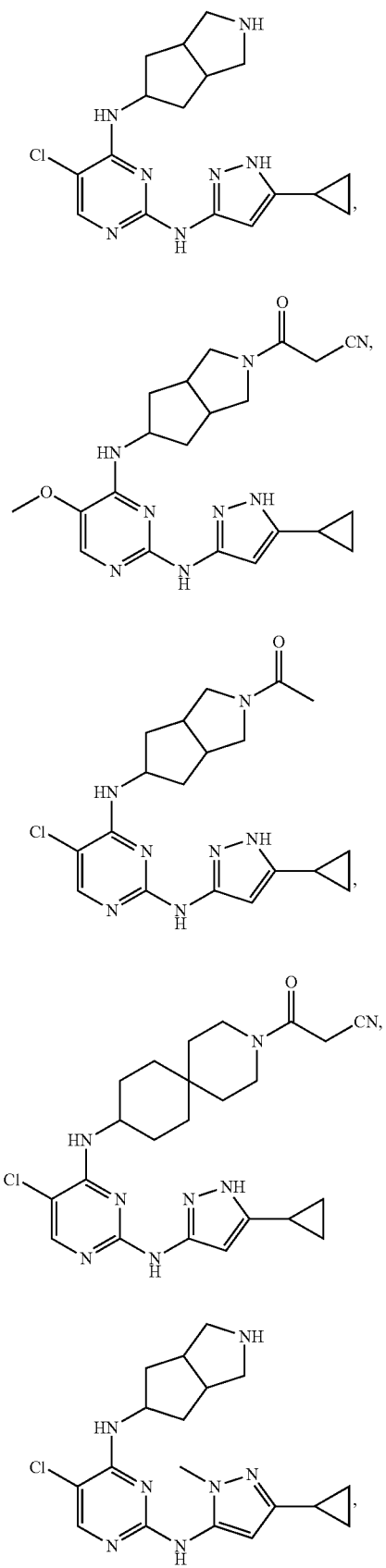
TABLE 1-continued
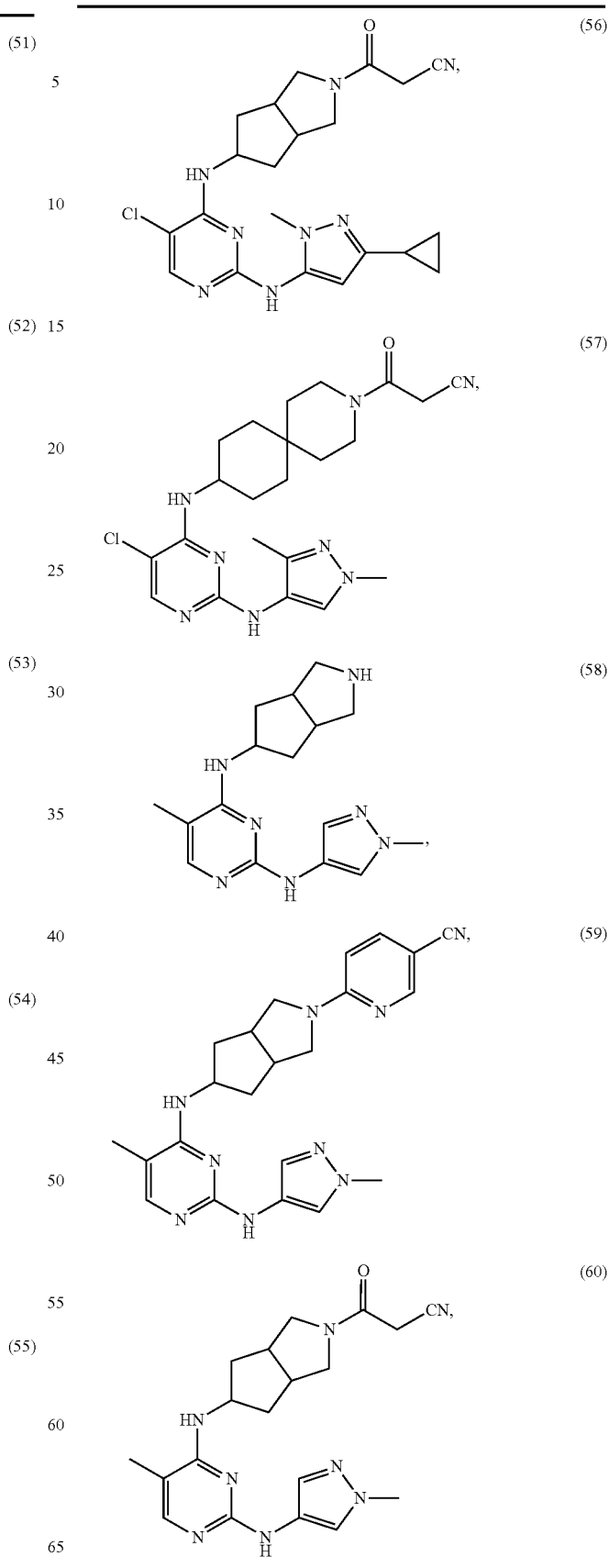

TABLE 1-continued

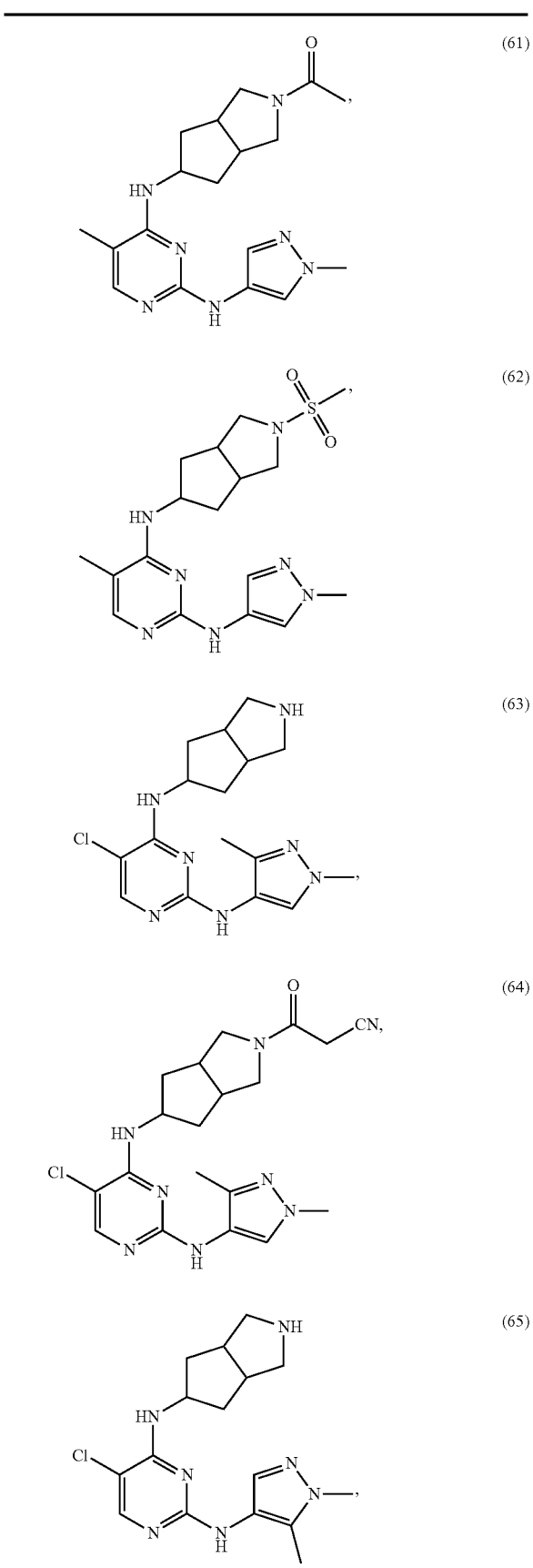

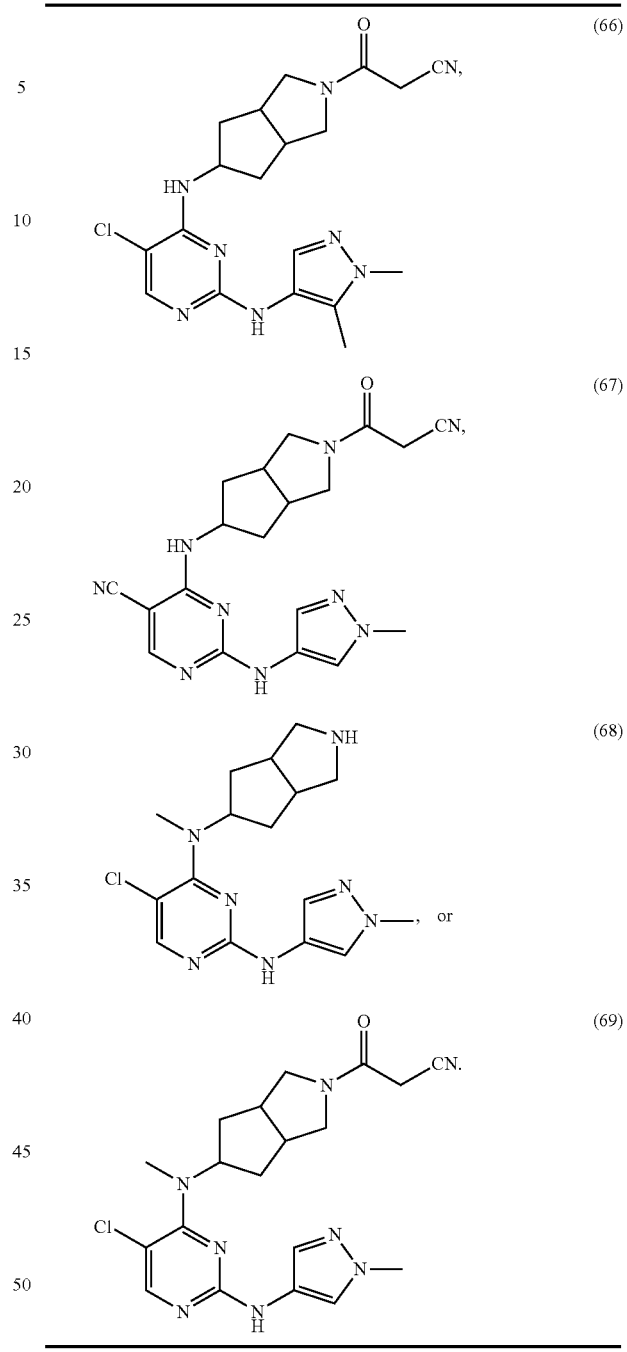

Unless otherwise stated, all stereoisomers, tautomers, solvates, metabolites, salts, and pharmaceutically acceptable prodrugs of the compounds of Formula (I) are within the scope of the invention.

The compounds disclosed herein may contain asymmetric or chiral centers, and therefore exist in different stereoisomeric forms. It is intended that all stereoisomeric forms of compounds of Formula (I), including but not limited to, diastereomers, enantiomers, atropisomers, conformers (rotamers) and geometric (cis/trans) isomers as well as mixtures thereof such as racemic mixtures, form part of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of Formula (I) may exist in different tautomeric forms, and all such forms are embraced within the scope of the invention, as defined by the claims.

The compounds of Formula (I) can be in the form of salts. In one embodiment, the salts are pharmaceutically acceptable salts. The phrase "pharmaceutically acceptable" indicates that the substance or composition must be compatible chemically and/or toxicologically, with the other ingredients comprising a formulation, and/or the mammal being treated therewith. In another embodiment, the salts are not necessarily pharmaceutically acceptable salts, and which may be useful as intermediates for preparing and/or purifying compounds of Formula (I) and/or for separating enantiomers of compounds of Formula (I).

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, subsalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds disclosed herein, including their salts, can also be obtained in the form of their hydrates, or include other solvents such as ethanol, DMSO, and the like, used for their crystallization. The compounds of the present invention may inherently or by design form solvates with pharmaceutically acceptable solvents (including water); therefore, it is intended that the invention embrace both solvated and unsolvated forms.

Any formula given herein is also intended to represent isotopically unenriched forms as well as isotopically enriched forms of the compounds. Isotopically enriched compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H (deuterium, D), $^3$H, $^{11}$C, $^{13}$C, $^{14}$C, $^{15}$N, $^{17}$O, $^{18}$O, $^{18}$F, $^{31}$P, $^{32}$P, $^{35}$S, $^{36}$Cl, $^{125}$I, respectively.

In another aspect, the compounds of the invention include isotopically enriched compounds as defined herein, for example those into which radioactive isotopes, such as $^3$H, $^{14}$C and $^{18}$F, or those into which non-radioactive isotopes, such as $^2$H and $^{13}$C are present. Such isotopically enriched compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F-enriched compound may be particularly desirable for PET or SPECT studies. Isotopically-enriched compounds of Formula (I) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of Formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. $D_2O$, acetone-$d_6$, DMSO-$d_6$.

In another aspect, provided herein are intermediates for preparing the compounds disclosed herein.

In another aspect, provided herein are methods of preparing, methods of separating, and methods of purifying the compounds disclosed herein.

In another aspect, provided herein is a pharmaceutical composition comprising a therapeutically effective amount of the compound disclosed herein, and a pharmaceutically acceptable excipient, carrier, adjuvant, vehicle or a combination thereof. In some embodiments, the composition is a liquid, solid, semi-solid, gel, or an aerosol form.

In another aspect, provided herein is a method of treating a disease or disorder modulated by one or more protein kinases such as JAK kinase, FLT3 kinase and Aurora kinase, comprising administering to a mammal in need of such treatment an effective amount of a compound or a pharmaceutical composition disclosed herein. In one embodiment, the disease or disorder is selected from proliferative disease, autoimmune disease, allergic disease, inflammatory disease or transplantation rejection.

In another aspect, provided herein is the compound or the pharmaceutical composition disclosed herein for use in the treatment of disease or disorder selected from proliferative disease, autoimmune disease, allergic disease, inflammatory disease or transplantation rejection.

In another aspect, provided herein is the use of the compound or the pharmaceutical composition disclosed herein in the manufacture of a medicament for the treatment of disease or disorder selected from proliferative disease, autoimmune disease, allergic disease, inflammatory disease or transplantation rejection.

In still another aspect, provided herein is use of the compound or the pharmaceutical composition disclosed herein in the manufacture of a medicament for modulating the activity of protein kinase.

Pharmaceutical Composition, Formulations and Administration of the Compounds of the Invention The present invention provides a pharmaceutical composition that include a compound disclosed herein, or a compound listed in Table 1; and a pharmaceutically acceptable excipient, carrier, adjuvant, vehicle or a combination thereof. The amount of compound in the pharmaceutical composition disclosed herein is such that is effective to detectably inhibit a protein kinase in a biological sample or in a patient.

It will also be appreciated that certain compounds disclosed herein can exist in free form for treatment, or where appropriate, as a pharmaceutically acceptable derivative thereof. Some non-limiting examples of pharmaceutically acceptable derivative include pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

The pharmaceutical compositions disclosed herein may be prepared and packaged in bulk form wherein a safe and effective amount of the compound disclosed herein can be extracted and then given to the patient such as with powders or syrups. Alternatively, the pharmaceutical compositions disclosed herein may be prepared and packaged in unit dosage form wherein each physically discrete unit contains the compound disclosed herein. When prepared in unit dosage form, the pharmaceutical compositions of the invention typically may contain, for example, from 0.5 mg to 1 g, or from 1 mg to 700 mg, or from 5 mg to 100 mg of the compound disclosed herein.

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound disclosed herein when administered to a patient and interactions which would result in pharmaceutical compositions that are not pharmaceutically acceptable are avoided. In addition, each excipient must be pharmaceutically-acceptable, e.g., of sufficiently high purity.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds disclosed herein once administered to the patient from one organ, or portion of the body, to another organ, or portion of the body. Certain pharmaceutically acceptable excipients may be chosen for their ability to enhance patient compliance.

Suitable pharmaceutically acceptable excipients comprise the following types of excipients: diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds disclosed herein, such as by producing any undesirable biological effect or otherwise interacting in a deleterious manner with any other component(s) of the pharmaceutically acceptable composition, its use is contemplated to be within the scope of this invention.

The pharmaceutical compositions disclosed herein are prepared using techniques and methods known to those skilled in the art. Some of the methods commonly used in the art are described in Remington's Pharmaceutical Sciences (Mack Publishing Company).

Accordingly, in another aspect the invention is directed to process for the preparation of a pharmaceutical composition comprising the compound disclosed herein and a pharmaceutically acceptable excipient, carrier, adjuvant, vehicle or a combination thereof, which comprises mixing the ingredients. A pharmaceutical composition comprising the compound disclosed herein may be prepared by, for example, admixture at ambient temperature and atmospheric pressure.

The compounds disclosed herein will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, granula, and cachets; (2) parenteral administration such as sterile solutions, suspensions, and freeze drying powder; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

In one embodiment, the compounds disclosed herein will be formulated for oral administration. In another embodiment, the compounds disclosed herein will be formulated for inhaled administration. In a further embodiment, the compounds disclosed herein will be formulated for intranasal administration. In another embodiment, the compounds disclosed herein will be formulated for transdermal administration. In a further embodiment, the compounds disclosed herein will be formulated for topical administration.

The pharmaceutical compositions provided herein can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable nonaqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

Where appropriate, dosage unit formulations for oral administration can be microencapsulated. The composition can also be prepared to prolong or sustain the release as for example by coating or embedding particulate material in polymers, wax or the like.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The compounds disclosed herein may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds disclosed herein may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The pharmaceutical compositions provided herein can be formulated as immediate or modified release dosage forms, including delayed-, sustained-, pulsed-, controlled-, targeted-, and programmed-release forms.

The pharmaceutical compositions provided herein can be co-formulated with other active ingredients which do not impair the desired therapeutic action, or with substances that supplement the desired action.

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including $\alpha$-cyclodextrin, $\beta$-cyclodextrin, hydroxypropyl-$\beta$-cyclodextrin, sulfobutylether-$\beta$-cyclodextrin, and sulfobutylether 7-$\beta$-cyclodextrin (CAPTISOL®, CyDex, Lenexa, Kans.).

The pharmaceutical compositions provided herein can be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein can be formulated as immediate or modified release dosage forms, including delayed-, sustained-, pulsed-, controlled-, targeted-, and programmed-release forms.

The pharmaceutical compositions can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

In another aspect, The pharmaceutical compositions disclosed herein can be formulated in any dosage forms that are adapted for administration to a patient by inhalation, for example as a dry powder, an aerosol, a suspension, or a solution composition. In one embodiment, the pharmaceutical compositions disclosed herein can be formulated in a dosage form adapted for administration to a patient by inhalation as a dry powder. In a further embodiment, the pharmaceutical compositions disclosed herein can be formulated in a dosage form adapted for administration to a patient by inhalation via a nebulizer. Dry powder compositions for delivery to the lung by inhalation typically comprise the compounds disclosed herein as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (eg micronised) compound can be defined by a $D_{50}$ value of about 1 to about 10 microns (for example as measured using laser diffraction).

Aerosols may be formed by suspending or dissolving the compound disclosed herein in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising the compound disclosed herein will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils. Ointments, creams and gels, may, for example, be formulated with an aqueous or oily base with the addition of suitable thickening and/or gelling agent and/or solvents. Such bases may thus, for example, include water and/or oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilizing agents, suspending agents or preservatives.

Topical preparations may be administered by one or more applications per day to the affected area; over skin areas occlusive dressings may advantageously be used. Continuous or prolonged delivery may be achieved by an adhesive reservoir system.

For treatments of the eye or other external tissues, for example mouth and skin, the compositions may be applied as a topical ointment or cream. When formulated in an ointment, the compound disclosed herein may be employed with either a paraffinic or a water-miscible ointment base. Alternatively, the compound disclosed herein may be formulated in a cream with an oil-in-water cream base or a water-in-oil base.

Use of the Compounds and Compositions of the Invention

The present invention provides a method of using a compound disclosed herein, or a pharmaceutical composition comprising the compound disclosed herein for the treatment, prevention, or amelioration of a disease or disorder that is mediated or otherwise affected via one or more protein kinases activity, such as JAK kinase (including JAK1, JAK2, JAK3 or TYK2 kinase), FLT3 kinase, and Aurora kinase (including Aurora-A, Aurora-B and Aurora C) activity or one or more symptoms of diseases or disorders that are mediated or otherwise affected via one or more protein kinases activity, such as JAK kinase (including JAK1, JAK2, JAK3 or TYK2 kinase), FLT3 kinase and Aurora kinase (including Aurora-A, Aurora-B and Aurora C kinase) activity.

FLT3 kinase can be wild type and/or mutant form of FLT3 kinase.

JAK kinase can be wild type and/or mutant form of JAK1, JAK2, JAK3 or TYK2 kinase.

In one embodiment, provided herein is a method of using a compound disclosed herein or a pharmaceutical composition comprising a compound disclosed herein for the treatment, prevention, or amelioration of a disease or disorder that is mediated or otherwise affected via inappropriate JAK1 kinase activity or one or more symptoms of diseases or disorders that are mediated or otherwise affected via inappropriate JAK1 kinase activity. In another embodiment, a disease, a disorder or one or more symptoms of diseases or disorders is related to the inappropriate activity of JAK2 kinase. In yet another embodiment, a disease, a disorder or one or more symptoms of diseases or disorders is related to the inappropriate activity of JAK3 kinase.

In one embodiment, provided herein is a method of using a compound disclosed herein or a pharmaceutical composition comprising a compound disclosed herein for the treatment, prevention, or amelioration of a disease or disorder that is mediated or otherwise affected via inappropriate FLT3 kinase activity or one or more symptoms of diseases or disorders that are mediated or otherwise affected via inappropriate FLT3 kinase activity.

In one embodiment, provided herein is a method of using a compound disclosed herein or a pharmaceutical composition comprising a compound disclosed herein for the treatment, prevention, or amelioration of a disease or disorder that is mediated or otherwise affected via inappropriate Aurora-A kinase activity or one or more symptoms of diseases or disorders that are mediated or otherwise affected via inappropriate Aurora-A kinase activity. In another embodiment, a disease, a disorder or one or more symptoms of diseases or disorders is related to the inappropriate activity of Aurora-B kinase. In yet another embodiment, a disease, a disorder or one or more symptoms of diseases or disorders is related to the inappropriate activity of Aurora C kinase.

"Inappropriate JAK kinase activity" refers to any JAK kinase activity that deviates from the normal JAK kinase activity expected in a particular patient. Inappropriate JAK kinase may take the form of, for instance, an abnormal increase in activity, or an aberration in the timing and or control of JAK kinase activity. Such inappropriate activity may result then, for example, from overexpression or mutation of the protein kinase leading to inappropriate or uncontrolled activation. Accordingly, in another aspect the invention is directed to methods of treating such diseases and disorders.

Consistent with the description above, such diseases or disorders include without limitation: myeloproliferative disorders such as polycythemia vera (PCV), essential thrombocythemia and idiopathic myelofibrosis (IMF); leukemia such as myeloid leukemia including chronic myeloid leukemia (CML), imatinib-resistant forms of CML, acute myeloid leukemia (AML), and a subtype of AML, acute megakaryoblastic leukemia (AMKL); lymphoproliferative diseases such as acute lymphocytic leukemia (ALL) and myeloma; cancer including head and neck cancer, prostate cancer, breast cancer, ovarian cancer, melanoma, lung cancer, brain tumor, pancreatic cancer and renal carcinoma; and allergic or inflammatory diseases or disorders related to immune dysfunction, immunodeficiency, immunomodulation, autoimmune diseases, transplantation rejection, graft-versus-host disease, wound healing, kidney disease, multiple sclerosis, thyroiditis, type 1 diabetes, sarcoidosis, psoriasis, allergic rhinitis, inflammatory bowel disease including Crohn's disease and ulcerative colitis (UC), systemic lupus erythematosus (SLE), arthritis, osteoarthritis, rheumatoid arthritis, osteoporosis, asthma and chronic obstructive pulmonary disease (COPD) and dry eye syndrome (or keratoconjunctivitis sicca (KCS)).

In one aspect, provided herein is the compound or the pharmaceutical composition disclosed herein for preventing and/or treating proliferative disease, autoimmune disease, allergic disease, inflammatory disease or transplantation rejection in mammals including humans.

In yet another aspect, provided herein is a method of treating a mammal having, or at risk of having a disease or disclosed herein, said method comprising administering an effective condition-treating or condition-preventing amount of one or more of the pharmaceutical compositions or the compounds disclosed herein. In a particular aspect, provided here is a method of treating a mammal having, or at risk of having proliferative disease, autoimmune disease, allergic disease, inflammatory disease or transplantation rejection.

In additional method of treatment aspects, provided herein is a method of treatment and/or prophylaxis of a mammal susceptible to or afflicted with a proliferative disease, said methods comprising administering an effective condition-treating or condition-preventing amount of one or more of the pharmaceutical compositions or compounds disclosed herein. In a specific embodiment, the proliferative disease is selected from cancer (e.g. solid tumors such as uterine leiomyosarcoma or prostate cancer), polycythemia vera, essential thrombocytosis, myelofibrosis, leukemia (e.g. AML, CML, ALL or CLL), and multiple myeloma.

In another aspect, provided herein is the compound or the pharmaceutical composition disclosed herein for use in the treatment, and/or prophylaxis of a proliferative disease. In a specific embodiment, the proliferative disease is selected from cancer (e.g. solid tumors such as uterine leiomyosarcoma or prostate cancer), polycythemia vera, essential thrombocytosis, myelofibrosis, leukemia (e.g. AML, CML, ALL or CLL), and multiple myeloma.

In yet another aspect, provided herein is the use of the compound or the pharmaceutical composition disclosed herein for use in the manufacture of a medicament for the treatment, and/or prophylaxis of a proliferative disease. In a specific embodiment, the proliferative disease is selected from cancer (e.g. solid tumors such as uterine leiomyosarcoma or prostate cancer), polycythemia vera, essential thrombocytosis, myelofibrosis, leukemia (e.g. AML, CML, ALL or CLL), and multiple myeloma.

In another aspect, provided herein is a method of treatment and/or prophylaxis of a mammal susceptible to or afflicted with an autoimmune disease. The methods comprise administering an effective condition-treating or condition-preventing amount of one or more of the pharmaceutical compositions or compounds disclosed herein. In a specific embodiment, the autoimmune disease is selected from COPD, asthma, systemic and cutaneous lupus erythematosis, lupus nephritis, dermatomyositis, Sjogren's syndrome, psoriasis and type I diabetes mellitus.

In another aspect, provided herein is the compound or the pharmaceutical composition disclosed herein for use in the treatment, and/or prophylaxis of an autoimmune disease. In a specific embodiment, the autoimmune disease is selected from COPD, asthma, systemic and cutaneous lupus erythematosis, lupus nephritis, dermatomyositis, Sjogren's syndrome, psoriasis and type I diabetes mellitus.

In yet another aspect, provided here is the use of the compound or the pharmaceutical composition disclosed herein in the manufacture of a medicament for the treatment, and/or prophylaxis of an autoimmune disease. In a specific embodiment, the autoimmune disease is selected from COPD, asthma, systemic and cutaneous lupus erythematosis, lupus nephritis, dermatomyositis, Sjogren's syndrome, psoriasis and type I diabetes mellitus.

In a method of treatment aspects, provided herein are methods of treatment and/or prophylaxis of a mammal susceptible to or afflicted with an allergic disease. The methods comprising administering an effective condition-treating or condition-preventing amount of one or more of the pharmaceutical compositions or the compounds disclosed herein. In a specific embodiment, the allergic disease is selected from allergic airway disease, sinusitis, eczema and hives, food allergies and allergies to insect venom.

In another aspect, provided herein is the compound or the pharmaceutical composition disclosed herein for use in the treatment, and/or prophylaxis of an allergic disease. In a specific embodiment, the allergic disease is selected from allergic airway disease, sinusitis, eczema and hives, food allergies and allergies to insect venom.

In yet another aspect, provided herein is the use of the compound or the pharmaceutical composition disclosed herein in the manufacture of a medicament for the treatment, or prophylaxis of an allergic disease. In a specific embodiment, the allergic disease is selected from allergic airway disease, sinusitis, eczema and hives, food allergies and allergies to insect venom.

In another aspect, provided herein are methods of treatment and/or prophylaxis of a mammal susceptible to or afflicted with an inflammatory disease. The methods comprise administering an effective condition-treating or condition-preventing amount of one or more of the pharmaceutical compositions or the compounds disclosed herein. In a specific embodiment, the inflammatory disease is selected from inflammatory bowel syndrome, Crohn's disease, rheumatoid arthritis, juvenile arthritis and psoriatic arthritis.

In another aspect, provided herein is the compound or the pharmaceutical composition disclosed herein for use in the treatment, and/or prophylaxis of an inflammatory disease. In a specific embodiment, the inflammatory disease is selected from inflammatory bowel syndrome, Crohn's disease, rheumatoid arthritis, juvenile arthritis and psoriatic arthritis.

In yet another aspect, provided herein is the use of the compound or the pharmaceutical composition disclosed herein in the manufacture of a medicament for the treatment, and/or prophylaxis of an inflammatory disease. In a specific embodiment, the inflammatory disease is selected from inflammatory bowel syndrome, Crohn's disease, rheumatoid arthritis, juvenile arthritis and psoriatic arthritis.

In another aspect, provided herein are methods of treatment and/or prophylaxis of a mammal susceptible to or afflicted with transplantation rejection. The methods comprising administering an effective condition-treating or condition-preventing amount of one or more of the pharmaceutical compositions or the compound of the invention herein described. In a specific embodiment, the transplantation rejection is organ transplant rejection, tissue transplant rejection and cell transplant rejection.

In another aspect, provided herein is the compound or the pharmaceutical composition disclosed herein for use in the treatment, and/or prophylaxis of transplantation rejection. In a specific embodiment, the transplantation rejection is organ transplant rejection, tissue transplant rejection and cell transplant rejection.

In yet another aspect, provided herein is the use of the compound or the pharmaceutical composition disclosed herein for use in the manufacture of a medicament for the treatment and/or prophylaxis of transplantation rejection. In a specific embodiment, the transplantation rejection is organ transplant rejection, tissue transplant rejection and cell transplant rejection.

The present invention provides the compound or the pharmaceutical composition disclosed herein for use as a pharmaceutical especially in the treatment and/or prophylaxis of the aforementioned diseases or disorders. Also provided herein is the use of the compound or the pharmaceutical composition disclosed herein in the manufacture of a medicament for the treatment and/or prophylaxis of one of the aforementioned diseases or disorders.

A particular regimen of the present method comprises the administration to a subject suffering from a disease involving inflammation, of an effective amount of a compound disclosed herein for a period of time sufficient to reduce the level of inflammation in the subject, and preferably terminate the processes responsible for said inflammation. A special embodiment of the method comprises administering of an effective amount of a compound disclosed herein to a subject patient suffering from or susceptible to the development of rheumatoid arthritis, for a period of time sufficient to reduce or prevent, respectively, inflammation in the joints of said patient, and preferably terminate, the processes responsible for said inflammation.

A further particular regimen of the present method comprises the administration to a subject suffering from a disease involving proliferative disease, of an effective amount of a compound disclosed herein for a period of time sufficient to reduce the level of proliferative disease in the subject, and preferably terminate the processes responsible for said proliferative disease. A particular embodiment of the method comprises administering of an effective amount of a compound disclosed herein to a subject patient suffering from or susceptible to the development of cancer, for a period of time sufficient to reduce or prevent, respectively, solid tumor of said patient, and preferably terminate, the processes responsible for said solid.

Combination Therapy

A compound disclosed herein can be administered as the sole active agent or it can be administered in combination with other therapeutic agents, including other compounds that demonstrate the same or a similar therapeutic activity and that are determined to be safe and efficacious for such combined administration.

In one aspect, provided herein is a method of treating, preventing, or ameliorating a disease or disorder comprising administering a safe and effective amount of a combination comprising the compound disclosed herein together with one or more therapeutically active agents. In one embodiment, the combinations comprising one or two other therapeutic agents.

Example of other therapeutic agents may include without limitation anti-cancer agents, including chemotherapeutic agents and antiproliferative agents; anti-inflammatory agents and immunomodulatory agents or immunosuppressive agents.

In another aspect, provided herein is a product comprising a compound disclosed herein and at least one other therapeutic agent as a combined preparation for simultaneous, separate or sequential use in therapy. In one embodiment, the therapy is the treatment of a disease or disorder mediated by the activity of one or more protein kianses, such as JAK kinase, FLT3 kinase and Aurora kinase. Products provided as a combined preparation include a composition comprising the compound disclosed herein and the other therapeutic agent(s) together in the same pharmaceutical composition, or the compound disclosed herein and the other therapeutic agent(s) in separate form, e.g. in the form of a kit.

In another aspect, provided herein is a pharmaceutical composition comprising a compound disclosed herein and another therapeutic agent(s). In one embodiment, the pharmaceutical composition may comprise a pharmaceutically acceptable excipient, carrier, adjuvant or vehicle as described above.

In another aspect, the invention provides a kit comprising two or more separate pharmaceutical compositions, at least one of which contains a compound disclosed herein. In one embodiment, the kit comprises means for separately retaining said compositions, such as a container, divided bottle, or divided foil packet. An example of such a kit is a blister pack, as typically used for the packaging of tablets, capsules and the like.

The invention also provides the use of a compound disclosed herein for treating a disease or condition mediated by the activity of one or more protein kinases, such as JAK kinase, FLT3 kinase, and Aurora kinase, wherein the patient has previously (e.g. within 24 hours) been treated with another therapeutic agent. The invention also provides the use of another therapeutic agent for treating a disease or condition mediated by the activity of one or more protein kinase, such as JAK kinase, FLT3 kinase and Aurora kinase, wherein the patient has previously (e.g. within 24 hours) been treated with a compound disclosed herein.

The compounds disclosed herein may be administered as the sole active ingredient or in conjunction with, e.g. as an adjuvant to, other drugs e.g. immunosuppressive or immunomodulating agents or other anti-inflammatory agents, e.g. for the treatment or prevention of alio- or xenograft acute or chronic rejection or inflammatory or autoimmune disorders, or a chemotherapeutic agent, e.g a malignant cell anti-proliferative agent. For example, the compounds disclosed herein may be used in combination with a calcineurin inhibitor, e.g. cyclosporin A or FK 506; a mTOR inhibitor, e.g. rapamycin, 40-O-(2-hydroxyethyl)-rapamycin, CCI779, ABT578, AP23573, TAFA-93, biolimus-7 or biolimus-9; an ascomycin having immuno-suppressive properties, e.g. ABT-281, ASM981, etc.; corticosteroids; cyclophosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or antihistamines; or antitussives, or a bronchodilatory agent; or an angiotensin receptor blockers; or an anti-infectious agent.

Where the compounds disclosed herein are administered in conjunction with other immunosuppressive/immunomodulatory, anti-inflammatory, chemotherapeutic or anti-infectious therapy, dosages of the co-administered immunosuppressant, immunomodulatory, anti-inflammatory, chemotherapeutic or anti-infectious compound will of course vary depending on the type of co-drug employed, e.g. whether it is a steroid or a calcineurin inhibitor, on the specific drug employed, on the condition being treated and so forth.

In one aspect, provided herein is a combination comprising a compound disclosed herein together with a $\beta_2$-adrenoreceptor agonist. Examples of $\beta_2$-adrenoreceptor agonists include salmeterol, salbutamol, formoterol, salmefamol, fenoterol, carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment, long-acting $\beta_2$-adrenoreceptor agonists, for example, compounds which provide effective bronchodilation for about 12 h or longer, are preferred.

The $\beta_2$-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

In another aspect, provided herein is a combination comprising a compound disclosed herein together with corticosteroids. Suitable corticosteroids refer to those oral and inhaled corticosteroids and their pro-drugs which have anti-inflammatory activity. Examples include methyl prednisolone, prednisolone, dexamethasone, fluticasone propionate, 6α, 9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α, 9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α, 9α-difluoro-11β-hydroxy-16α-methyl-3-oxo-17α-propionyloxy-androsta-1,4-diene-17β-carbothioic acid S-(2-oxo-tetrahydrofuran-3S-yl) ester, 6α, 9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α, 9α-difluoro-1β-hydroxy-16α-methyl-17α-(1-ethycyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α, 17-[[(cis)-cyclohexylmethylene]bis(oxy)]-11β,21-dihydroxypregna-1,4-diene-3,20-dione), butixocort propionate, RPR-106541, and ST-126. Preferred corticosteroids include fluticasone propionate, 6α, 9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methyl cyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

In another aspect, provided herein is a combination comprising a compound disclosed herein together with non-steroidal GR agonist. Non-steroidal compounds having glucocorticoid agonism that may possess selectivity for transrepression over transactivation and that may be useful in combination therapy include those covered in the following patents: WO 03/082827, WO 98/54159, WO 04/005229, WO 04/009017, WO 04/018429, WO 03/104195, WO 03/082787, WO 03/082280, WO 03/059899, WO 03/101932, WO 02/02565, WO 01/16128, WO 00/66590, WO 03/086294, WO 04/026248, WO 03/061651 and WO 03/08277. Further non-steroidal compounds are covered in: WO 2006/000401, WO 2006/000398 and WO 2006/015870.

In another aspect, provided herein is a combination comprising a compound disclosed herein together with non-steroidal anti-inflammatory drugs (NSAID's). Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Examples of iNOS inhibitors include those disclosed in WO 93/13055, WO 98/30537, WO 02/50021, WO 95/34534 and WO 99/62875. Examples of CCR3 inhibitors include those disclosed in WO 02/26722.

In one embodiment, the invention provides the use of the compounds disclosed herein in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4. Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl) cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep. 1996; this patent and the compounds it discloses are incorporated herein in full by reference.

In another aspect, provided herein is a combination comprising a compound disclosed herein together with an anticholinergic agent. Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide, CAS 22254-24-6, sold under the name ATROVENT®), oxitropium (for example, as the bromide, CAS 30286-75-0) and tiotropium (for example, as the bromide, CAS 136310-93-5, sold under the name SPIRIVA®). Also of interest are revatropate (for example, as the hydrobromide, CAS 262586-79-8) and LAS-34273 which is disclosed in WO 01/04118. Exemplary compounds for oral administration include pirenzepine (CAS 28797-61-7), darifenacin (CAS 133099-04-4, or CAS 133099-07-7 for the hydrobromide sold under the name ENABLEX®), oxybutynin (CAS 5633-20-5, sold under the name DITROPAN®), terodiline (CAS 15793-40-5), tolterodine (CAS 124937-51-5, or CAS 124937-52-6 for the tartrate, sold under the name DETROL®), otilonium (for example, as the bromide, CAS 26095-59-0, sold under the name SPASMOMEN®), trospium chloride (CAS 10405-02-4) and solifenacin (CAS 242478-37-1, or CAS 242478-38-2 for the succinate also known as YM-905 and sold under the name VESICARE®).

In another aspect, provided herein is a combination comprising a compound disclosed herein together with an H1 antagonist. Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In a further embodiment the invention provides a combination comprising a compound disclosed herein together with an H3 antagonist (and/or inverse agonist). Examples of H3 antagonists include, for example, those compounds disclosed in WO 2004/035556 and in WO 2006/045416. Other histamine receptor antagonists which may be used in combination with the compounds disclosed herein include antagonists (and/or inverse agonists) of the H4 receptor, for example, the compounds disclosed in Jablonowski et al., *J. Med. Chem.* 46:3957-3960 (2003).

In still another aspect, provided herein is a combination comprising a compound disclosed herein together with a PDE4 inhibitor and a $\beta_2$-adrenoreceptor agonist.

In yet another aspect, provided herein is a combination comprising a compound disclosed herein together with an anticholinergic and a PDE-4 inhibitor.

The combinations referred to above may conveniently be presented for use in the form of a pharmaceutical composition and thus pharmaceutical compositions comprising a combination as defined above together with a pharmaceutically acceptable excipient or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of a compound disclosed herein together with another therapeutically active agent.

In one embodiment, the pharmaceutical composition comprises a combination of a compound disclosed herein together with a PDE4 inhibitor.

In another embodiment, the pharmaceutical composition comprises a combination of a compound disclosed herein together with a $\beta_2$-adrenoreceptor agonist.

In another embodiment, the pharmaceutical composition comprises a combination of a compound disclosed herein together with a corticosteroid.

In another embodiment, the pharmaceutical composition comprises a combination of a compound disclosed herein together with a non-steroidal GR agonist.

In another embodiment, the pharmaceutical composition comprises a combination of a compound disclosed herein together with an anticholinergic agent.

In still another embodiment, the pharmaceutical composition comprises a combination of a compound disclosed herein together with an antihistamine.

In the field of medical oncology it is normal practice to use a combination of different forms of treatment to treat each patient with cancer. In medical oncology the other component(s) of such conjoint treatment in addition to compositions disclosed herein may be, for example, surgery, radiotherapy, chemotherapy, signal transduction inhibitors or modulators (e.g. kinase inhibitors or modulators) and/or monoclonoal antibodies.

A compound disclosed herein may also be used to advantage in combination with each other or in combination with other therapeutic agents, especially other antiproliferative agents. Such antiproliferative agents include, but are not limited to, aromatase inhibitors; antiestrogens; topoisomerase I inhibitors; topoisomerase II inhibitors; microtubule active agents; alkylating agents; histone deacetylase inhibitors; compounds that induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; agents used in the treatment of hematologic malignancies; compounds which target, decrease or inhibit the activity of Flt-3; Hsp90 inhibitors; temozolomide (TEMODAL®); and leucovorin.

The term "aromatase inhibitor", as used herein, relates to a compound which inhibits the estrogen production, i.e., the conversion of the substrates androstenedione and testosterone to estrone and estradiol, respectively. The term includes, but is not limited to, steroids, especially atamestane, exemestane and formestane; and, in particular, nonsteroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g., under the trademark AROMASIN®. Formestane can be administered, e.g., in the form as it is marketed, e.g., under the trademark LENTARON®. Fadrozole can be administered, e.g., in the form as it is marketed, e.g., under the trademark AFEMA®. Anastrozole can be administered, e.g., in the form as it is marketed, e.g., under the trademark ARIMIDEX®. Letrozole can be administered, e.g., in the form as it is marketed, e.g., under the trademark FEMARA® or FEMAR®. Aminoglutethimide can be administered, e.g., in the form as it is marketed, e.g., under the trademark ORIMETEN®. A combination of the invention comprising a chemotherapeutic agent which is an aromatase inhibitor is particularly useful for the treatment of hormone receptor positive tumors, e.g., breast tumors.

The term "anti-estrogen", as used herein, relates to a compound which antagonizes the effect of estrogens at the estrogen receptor level. The term includes, but is not limited to, tamoxifen, fulvestrant, raloxifene and raloxifene hydrochloride. Tamoxifen can be administered, e.g., in the form as it is marketed, e.g., under the trademark NOLVADEX®. Raloxifene hydrochloride can be administered, e.g., in the form as it is marketed, e.g., under the trademark EVISTA®. Fulvestrant can be formulated as disclosed in U.S. Pat. No. 4,659,516 or it can be administered, e.g., in the form as it is marketed, e.g., under the trademark FASLODEX®. A combination of the invention comprising a chemotherapeutic agent which is an antiestrogen is particularly useful for the treatment of estrogen receptor positive tumors, e.g., breast tumors.

The term "anti-androgen", as used herein, relates to any substance which is capable of inhibiting the biological effects of androgenic hormones and includes, but is not limited to, bicalutamide (CASODEX®), which can be formulated, e.g., as disclosed in U.S. Pat. No. 4,636,505.

The term "gonadorelin agonist", as used herein, includes, but is not limited to, abarelix, goserelin and goserelin acetate. Goserelin is disclosed in U.S. Pat. No. 4,100,274 and can be administered, e.g., in the form as it is marketed, e.g., under the trademark ZOLADEX®. Abarelix can be formulated, e.g., as disclosed in U.S. Pat. No. 5,843,901. The term "topoisomerase I inhibitor", as used herein, includes, but is not limited to, topotecan, gimatecan, irinotecan, camptothecian and its analogues, 9-nitrocamptothecin and the macromolecular camptothecin conjugate PNU-166148 (compound A1 in WO 99/17804). Irinotecan can be administered, e.g., in the form as it is marketed, e.g., under the trademark CAMPTOSAR®. Topotecan can be administered, e.g., in the form as it is marketed, e.g., under the trademark HYCAMTIN®.

The term "topoisomerase II inhibitor", as used herein, includes, but is not limited to, the anthracyclines, such as doxorubicin, including liposomal formulation, e.g., CAELYX®; daunorubicin; epirubicin; idarubicin; nemorubicin; the anthraquinones mitoxantrone and losoxantrone; and the podophillotoxines etoposide and teniposide. Etoposide can be administered, e.g., in the form as it is marketed, e.g., under the trademark ETOPOPHOS®. Teniposide can be administered, e.g., in the form as it is marketed, e.g., under the trademark VM 26-BRISTOL®. Doxorubicin can be administered, e.g., in the form as it is marketed, e.g., under the trademark ADRIBLASTIN® or ADRIAMYCIN®.

Epirubicin can be administered, e.g., in the form as it is marketed, e.g., under the trademark FARMORUBICIN®. Idarubicin can be administered, e.g., in the form as it is marketed, e.g., under the trademark ZAVEDOS®. Mitoxantrone can be administered, e.g., in the form as it is marketed, e.g., under the trademark NOVANTRON®.

The term "microtubule active agent" relates to microtubule stabilizing, microtubule destabilizing agents and microtublin polymerization inhibitors including, but not limited to, taxanes, e.g., paclitaxel and docetaxel; vinca alkaloids, e.g., vinblastine, especially vinblastine sulfate; vincristine, especially vincristine sulfate and vinorelbine; discodermolides; cochicine; and epothilones and derivatives thereof, e.g., epothilone B or D or derivatives thereof. Paclitaxel may be administered, e.g., in the form as it is marketed, e.g., TAXOL®. Docetaxel can be administered, e.g., in the form as it is marketed, e.g., under the trademark TAXOTERE®. Vinblastine sulfate can be administered, e.g., in the form as it is marketed, e.g., under the trademark VINBLASTIN R.P®. Vincristine sulfate can be administered, e.g., in the form as it is marketed, e.g., under the trademark FARMISTIN®. Discodermolide can be obtained, e.g., as disclosed in U.S. Pat. No. 5,010,099. Also included are epothilone derivatives which are disclosed in WO 98/10121, U.S. Pat. No. 6,194,181, WO 98/25929, WO 98/08849, WO 99/43653, WO 98/22461 and WO 00/31247. Especially preferred are epothilone A and/or B.

The term "alkylating agent", as used herein, includes, but is not limited to, cyclophosphamide, ifosfamide, melphalan or nitrosourea (BCNU or Gliadel). Cyclophosphamide can be administered, e.g., in the form as it is marketed, e.g., under the trademark CYCLOSTIN®. Ifosfamide can be administered, e.g., in the form as it is marketed, e.g., under the trademark HOLOXAN®.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl) ethyl]-amino]methyl]phenyl]-2E-2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further especially includes suberoylanilide hydroxamic acid (SAHA).

The term "antineoplastic antimetabolite" includes, but is not limited to, 5-fluorouracil or 5-FU; capecitabine; gemcitabine; DNA demethylating agents, such as 5-azacytidine and decitabine; methotrexate and edatrexate; and folic acid antagonists, such as pemetrexed. Capecitabine can be administered, e.g., in the form as it is marketed, e.g., under the trademark XELODA®. Gemcitabine can be administered, e.g., in the form as it is marketed, e.g., under the trademark GEMZAR®. Also included is the monoclonal antibody trastuzumab which can be administered, e.g., in the form as it is marketed, e.g., under the trademark HERCEPTIN®.

The term "platin compound", as used herein, includes, but is not limited to, carboplatin, cis-platin, cisplatinum and oxaliplatin. Carboplatin can be administered, e.g., in the form as it is marketed, e.g., under the trademark CARBOPLAT®. Oxaliplatin can be administered, e.g., in the form as it is marketed, e.g., under the trademark ELOXATIN®.

The term "compounds targeting/decreasing a protein or lipid kinase activity; or a protein or lipid phosphatase activity; or further anti-angiogenic compounds", as used herein, includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g., a N-phenyl-2-pyrimidine-amine derivative, e.g., imatinib, SU101, SU6668 and GFB-111;
b) compounds targeting, decreasing or inhibiting the activity of the fibroblast growth factor-receptors (FGFR);
c) compounds targeting, decreasing or inhibiting the activity of the insulin-like growth factor receptor I (IGF-IR), such as compounds which target, decrease or inhibit the activity of IGF-IR, especially compounds which inhibit the IGF-IR receptor, such as those compounds disclosed in WO 02/092599;
d) compounds targeting, decreasing or inhibiting the activity of the Trk receptor tyrosine kinase family;
e) compounds targeting, decreasing or inhibiting the activity of the Axl receptor tyrosine kinase family;
f) compounds targeting, decreasing or inhibiting the activity of the c-Met receptor;
g) compounds targeting, decreasing or inhibiting the activity of the Kit/SCFR receptor tyrosine kinase;
h) compounds targeting, decreasing or inhibiting the activity of the c-kit receptor tyrosine kinases—(part of the PDGFR family), such as compounds which target, decrease or inhibit the activity of the c-Kit receptor tyrosine kinase family, especially compounds which inhibit the c-Kit receptor, e.g., imatinib;
i) compounds targeting, decreasing or inhibiting the activity of members of the c-Abl family and their gene-fusion products, e.g., BCR-Abl kinase, such as compounds which target decrease or inhibit the activity of c-Abl family members and their gene fusion products, e.g., a N-phenyl-2-pyrimidine-amine derivative, e.g., imatinib, PD180970, AG957, NSC 680410 or PD173955 from ParkeDavis;
j) compounds targeting, decreasing or inhibiting the activity of members of the protein kinase C (PKC) and Raf family of serine/threonine kinases, members of the MEK, SRC, JAK, FAK, PDK and Ras/MAPK family members, or PI(3) kinase family, or of the PI(3)-kinase-related kinase family, and/or members of the cyclin-dependent kinase family (CDK) and are especially those staurosporine derivatives disclosed in U.S. Pat. No. 5,093,330, e.g., midostaurin; examples of further compounds include, e.g., UCN-01; safingol; BAY 43-9006; Bryostatin 1; Perifosine; Ilmofosine; RO 318220 and RO 320432; GO 6976; Isis 3521; LY333531/LY379196; isochinoline compounds, such as those disclosed in WO 00/09495; FTIs; PD184352; or QAN697 (a PI3K inhibitor);
k) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC®) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810, AG 99, Tyrphostin AG 213, Tyrphostin AG 1748, Tyrphostin AG 490, Tyrphostin B44, Tyrphostin B44 (+) enantiomer, Tyrphostin AG 555, AG 494, Tyrphostin AG 556, AG957 and adaphostin (4-{[(2,5-dihydroxyphenyl)methyl]amino}-benzoic acid adamantyl ester, NSC 680410, adaphostin; and 1) compounds targeting, decreasing or inhibiting the activity of the epidermal growth factor family of receptor tyrosine kinases (EGFR, ErbB2, ErbB3, ErbB4 as homo- or hetero-dimers), such as compounds which target, decrease or inhibit the activity of the epidermal growth factor receptor family are especially compounds, proteins or antibodies which inhibit members of the EGF receptor tyrosine kinase family, e.g., EGF receptor, ErbB2, ErbB3 and ErbB4 or bind to EGF or EGF related ligands, and are in particular those compounds, proteins or monoclonal antibodies generically and specifically disclosed in WO 97/02266, e.g., the compound of Example 39, or in EP 0564409; WO 99/03854; EP 0520722; EP 0566226; EP 0787722; EP 0837063; U.S. Pat. No. 5,747,498; WO 98/10767; WO 97/30034; WO 97/49688; WO 97/38983 and, especially, WO 96/30347, e.g., compound known as CP 358774; WO 96/33980, e.g., compound ZD 1839; and WO 95/03283, e.g., compound ZM1105180, e.g., trastuzumab (HERCEPTIN), cetuximab, Iressa, Tarceva, OSI-774, CI-1033, EKB-569, GW-2016, E1.1, E2.4, E2.5, E6.2, E6.4, E2.11, E6.3 or E7.6.3; and 7H-pyrrolo-[2,3-d]pyrimidine derivatives which are disclosed in WO 03/013541.

Further anti-angiogenic compounds include compounds having another mechanism for their activity, e.g., unrelated to protein or lipid kinase inhibition, e.g., thalidomide (THALOMID®) and TNP-470.

Compounds which target, decrease or inhibit the activity of a protein or lipid phosphatase are, e.g., inhibitors of phosphatase 1, phosphatase 2A, PTEN or CDC25, e.g., okadaic acid or a derivative thereof.

Compounds that induce cell differentiation processes are e.g. retinoic acid, α-, γ- or δ-tocopherol or α-, γ- or δ-tocotrienol.

The term cyclooxygenase inhibitor, as used herein, includes, but is not limited to, e.g., Cox-2 inhibitors, 5-alkyl substituted 2-arylaminophenylacetic acid and derivatives, such as celecoxib (CELEBREX®), rofecoxib (VIOXX®), etoricoxib, valdecoxib or a 5-alkyl-2-arylaminophenylacetic acid, e.g., 5-methyl-2-(2'-chloro-6'-fluoroanilino)phenyl acetic acid or lumiracoxib.

The term "bisphosphonates", as used herein, includes, but is not limited to, etridonic, clodronic, tiludronic, pamidronic, alendronic, ibandronic, risedronic and zoledronic acid. "Etridonic acid" can be administered, e.g., in the form as it is marketed, e.g., under the trademark DIDRONEL®. "Clodronic acid" can be administered, e.g., in the form as it is marketed, e.g., under the trademark BONEFOS®. "Tiludronic acid" can be administered, e.g., in the form as it is marketed, e.g., under the trademark SKELID®. "Pamidronic acid" can be administered, e.g., in the form as it is marketed, e.g., under the trademark AREDIA™. "Alendronic acid" can be administered, e.g., in the form as it is marketed, e.g., under the trademark FOSAMAX®. "Ibandronic acid" can be administered, e.g., in the form as it is marketed, e.g., under the trademark BONDRANAT®. "Risedronic acid" can be administered, e.g., in the form as it is marketed, e.g., under the trademark ACTONEL®. "Zoledronic acid" can be administered, e.g., in the form as it is marketed, e.g., under the trademark ZOMETA®.

The term "mTOR inhibitors" relates to compounds which inhibit the mammalian target of rapamycin (mTOR) and which possess antiproliferative activity, such as sirolimus (Rapamune®), everolimus (Certican™), CCI-779 and ABT578.

The term "heparanase inhibitor", as used herein, refers to compounds which target, decrease or inhibit heparin sulphate degradation. The term includes, but is not limited to, PI-88.

The term "biological response modifier", as used herein, refers to a lymphokine or interferons, e.g., interferon γ.

The term "inhibitor of Ras oncogenic isoforms", e.g., H-Ras, K-Ras or N-Ras, as used herein, refers to compounds which target, decrease or inhibit the oncogenic activity of Ras, e.g., a "farnesyl transferase inhibitor", e.g., L-744832, DK8G557 or R1 15777 (Zarnestra).

The term "telomerase inhibitor", as used herein, refers to compounds which target, decrease or inhibit the activity of telomerase. Compounds which target, decrease or inhibit the activity of telomerase are especially compounds which inhibit the telomerase receptor, e.g., telomestatin.

The term "methionine aminopeptidase inhibitor", as used herein, refers to compounds which target, decrease or inhibit the activity of methionine aminopeptidase. Compounds which target, decrease or inhibit the activity of methionine aminopeptidase are, e.g., bengamide or a derivative thereof.

The term "proteasome inhibitor", as used herein, refers to compounds which target, decrease or inhibit the activity of the proteasome. Compounds which target, decrease or inhibit the activity of the proteasome include, e.g., PS-341 and MLN 341.

The term "matrix metalloproteinase inhibitor" or "MMP inhibitor", as used herein, includes, but is not limited to, collagen peptidomimetic and nonpeptidomimetic inhibitors, tetracycline derivatives, e.g., hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "agents used in the treatment of hematologic malignancies", as used herein, includes, but is not limited to, FMS-like tyrosine kinase inhibitors, e.g., compounds targeting, decreasing or inhibiting the activity of FMS-like tyrosine kinase receptors (Flt-3R); interferon, 1-b-D-arabinofuransyl-cytosine (ara-c) and bisulfan; and ALK inhibitors, e.g., compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g., PKC412, midostaurin, a staurosporine derivative, SU1 1248 and MLN518.

The term "HSP90 inhibitors", as used herein, includes, but is not limited to, compounds targeting, decreasing or inhibiting the intrinsic ATPase activity of HSP90; degrading, targeting, decreasing or inhibiting the HSP90 client proteins via the ubiquitin proteasome pathway. Compounds targeting, decreasing or inhibiting the intrinsic ATPase activity of HSP90 are especially compounds, proteins or antibodies which inhibit the ATPase activity of HSP90, e.g., 17-allylamino, 17-demethoxygeldanamycin (17AAG), a geldanamycin derivative, other geldanamycin related compounds, radicicol and HDAC inhibitors.

The term "antiproliferative antibodies", as used herein, includes, but is not limited to, trastuzumab (HERCEPTIN™), Trastuzumab-DM1, erlotinib (TARCEVA™), bevacizumab (AVASTIN™), rituximab (RITUXAN®), PRO64553 (anti-CD40) and 2C4 antibody. By antibodies is meant, e.g., intact monoclonal antibodies, polyclonal antibodies, multispecific antibodies formed from at least two intact antibodies, and antibodies fragments so long as they exhibit the desired biological activity. For the treatment of acute myeloid leukemia (AML), compounds disclosed herein can be used in combination with standard leukemia therapies, especially in combination with therapies used for the treatment of AML. In particular, compounds disclosed herein can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

A compound disclosed herein may also be used to advantage in combination with each other or in combination with other therapeutic agents, especially other anti-malarial agents. Such anti-malarial agents include, but are not limited to proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, inhaled NO, L-arginine, Dipropylenetri-amine NONOate (NO donor), Rosiglitzone (PPAR-γ agonist), activated charcoal, Erythropoietin, Levamisole, and pyronaridine.

A compound disclosed herein may also be used to advantage in combination with each other or in combination with other therapeutic agents, such as used for the treatment of Leishmaniosis, Trypanosomiasis, Toxoplasmosis and Neurocysticercosis. Such agents include, but are not limited to chloroquine sulfate, atovaquone-proguanil, artemether-lumefantrine, quinine-sulfate, artesunate, quinine, doxycycline, clindamycin, meglumine antimoniate, sodium stibogluconate, miltefosine, ketoconazole, pentamidine, amphotericin B (AmB), liposomal-AmB, paromomycine, eflornithine, nifurtimox, suramin, melarsoprol, prednisolone, benznidazole, sulfadiazine, pyrimethamine, clindamycin, trimetropim, sulfamethoxazole, azitromycin, atovaquone, dexamethasone, praziquantel, albendazole, beta-lactams, fluoroquinolones, macrolides, aminoglycosides, sulfadiazine and pyrimethamine.

The structure of the active agents identified by code nos., generic or trade names may be taken from the actual edition of the standard compendium "The Merck Index" or from databases, e.g., Patents International, e.g., IMS World Publications.

The above-mentioned compounds, which can be used in combination with a compound disclosed herein, can be prepared and administered as described in the art, such as in the documents cited above.

A compound disclosed herein may also be used to advantage in combination with known therapeutic processes, e.g., the administration of hormones or especially radiation. A compound disclosed herein may in particular be used as a radiosensitizer, especially for the treatment of tumors which exhibit poor sensitivity to radiotherapy.

By "combination", there is meant either a fixed combination in one dosage unit form, or a kit of parts for the combined administration where a compound disclosed herein and a combination partner may be administered independently at the same time or separately within time intervals that especially allow that the combination partners show a cooperative, e.g., synergistic, effect or any combination thereof. The terms "coadministration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound disclosed herein and a combination partner, are both administered to a patient simultaneously in the form of a single entity or dosage. The term "non-fixed combination" means that the active ingredients, e.g. a compound disclosed herein and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

Methods of Treatment

In one embodiment, the methods of treatment disclosed herein comprise administering a safe and effective amount of a compound or a pharmaceutically composition disclosed herein to a patient in need thereof. Individual embodiments disclosed herein include methods of treating any one of the above-mentioned disorders by administering a safe and effective amount of a compound disclosed herein or a pharmaceutical composition containing a compound disclosed herein to a patient in need thereof.

In one embodiment, the compounds disclosed herein or pharmaceutically compositions containing the compounds disclosed herein may be administered by any suitable route of administration, including both systemic administration and topical administration. Systemic administration includes oral administration, parenteral administration, transdermal administration and rectal administration. Parenteral administration is typically by injection or infusion, including intravenous, intramuscular, and subcutaneous injection or infusion. Topical administration includes application to the skin as well as intraocular, otic, intravaginal, inhaled and intranasal administration. In one embodiment, the compounds disclosed herein or pharmaceutical compositions containing the compounds disclosed herein may be administered orally. In another embodiment, the compounds disclosed herein or pharmaceutically compositions containing the compounds disclosed herein may be administered by inhalation. In a further embodiment, the compounds disclosed herein or pharmaceutical compositions containing the compounds disclosed herein may be administered intranasally.

In another embodiment, the compounds disclosed herein or pharmaceutically compositions containing the compounds disclosed herein may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for a compound disclosed herein or a pharmaceutical composition containing a compound disclosed herein depend on the pharmacokinetic properties of that compound, such as absorption, distribution, and half-life, which can be determined by the skilled artisan. In addition, suitable dosing regimens, including the duration such regimens are administered, for a compound disclosed herein or a pharmaceutical composition containing a compound disclosed herein depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

The compound of the present invention may be administered either simultaneously with, or before or after, one or more other therapeutic agent. The compound of the present invention may be administered separately, by the same or different route of administration, or together in the same pharmaceutical composition as the other agents.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease. The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution.

In one embodiment, the therapeutically effective dose is from about 0.1 mg to about 2,000 mg per day of a compound provided herein. The pharmaceutical compositions therefore should provide a dosage of from about 0.1 mg to about 2000 mg of the compound. In certain embodiments, pharmaceutical dosage unit forms are prepared to provide from about 1 mg to about 2000 mg, from about 10 mg to about 1000 mg, from about 20 mg to about 500 mg or from about 25 mg to about 250 mg of the essential active ingredient or a combination of essential ingredients per dosage unit form. In certain embodiments, the pharmaceutical dosage unit forms are prepared to provide about 10 mg, 20 mg, 25 mg, 50 mg, 100 mg, 250 mg, 500 mg, 1000 mg or 2000 mg of the essential active ingredient.

Additionally, the compounds disclosed herein may be administered as prodrugs. As used herein, a "prodrug" of a compound disclosed herein is a functional derivative of the compound which, upon administration to a patient, eventually liberates the compound disclosed herein in vivo. Administration of a compound disclosed herein as a prodrug may enable the skilled artisan to do one or more of the following: (a) modify the onset of the activity of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleavable in vivo. Such modifications, which include the preparation of phosphates, amides, esters, thioesters, carbonates, and carbamates, are well known to those skilled in the art.

General Synthetic Procedures

In order to illustrate the invention, the following examples are included. However, it is to be understood that these examples do not limit the invention and are only meant to suggest a method of practicing the invention.

Generally, the compounds in this invention may be prepared by methods described herein, wherein the substituents are as defined for Formula (I), above, except where further noted. The following non-limiting schemes and examples are presented to further exemplify the invention. Persons skilled in the art will recognize that the chemical reactions described herein may be readily adapted to prepare a number of other compounds of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Arco Chemical Company and Alfa Chemical Company, Shanghai Medpep. Co Ltd, Aladdin-Shanghai Jinchun Reagents, Ltd, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tainjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexanes, DMA and DMF were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory.

$^1H$ NMR spectra were recorded with a Bruker 400 MHz or 600 MHz spectrometer at ambient temperature. $^1H$ NMR spectra were obtained as $CDCl_3$, DMSO-$d_6$, $CD_3OD$ or acetone-$d_6$ solutions (reported in ppm), using TMS (0 ppm) or chloroform (7.26 ppm) as the reference standard. When peak multiplicities are reported, the following abbreviations are used: s (singlet), d (doublet), t (triplet), m (multiplet), br (broadened), dd (doublet of doublets), dt (doublet of triplets), td (triplet of doublets). Coupling constants, when given, are reported in Hertz (Hz).

Low-resolution mass spectral (MS) data were generally determined on an Agilent 6120 quadrupole HPLC-MS (Zorbax SB-C18, 2.1×30 mm, 3.5 micron, 6 minutes run, 0.6 mL/min flow rate, 5% to 95% (0.1% formic acid in $CH_3CN$) in (0.1% formic acid in $H_2O$)) with UV detection at 210/254 nm and electrospray ionization (ESI).

Purities of compounds were assessed by Agilent 1260 pre-HPLC or Calesep pump 250 pre-HPLC (column: NOVASEP 50/80 mm DAC) with UV detection at 210 nm and 254 nm.

The following abbreviations are used throughout the specification:

AcOH, HAc, $CH_3COOH$ acetic acid
$Ac_2O$ acetic anhydride
BnBr benzyl bromide
BOC, Boc butyloxycarbony
$(Boc)_2O$ di-tert-butyl dicarbonate
$BH_3$.DMS borane-methyl sulfide complex
BINAP 2,2'-bis(diphenylphosphino)-1,1'-binaphthyl
n-BuOH n-butyl alcohol
$CH_2Cl_2$, DCM methylene chloride
$CDCl_3$ chloroform deuterated
$CH_3I$ iodomethane
DIEA, DIPEA, i-$Pr_2NEt$ N,N-diisopropylethylamine
DMF dimethylformamide
DMP dimethyl phthalate
DMAP 4-dimethylaminopyridine
DMSO dimethylsulfoxide
DHP dihydropyran
PPTs pyridinium toluene-4-sulphonate
$Et_3N$, TEA triethylamine
EtOAc, EA ethyl acetate
EtOH ethanol
$Et_2O$ diethyl ether
EDCI N-(3-dimethylaminopropyl)-N'-ethylcarbodiimide hydrochloride
g gram
h hour
HATU 2-(7-aza-1H-benzotriazole-1-yl)-1,1,3,3-tetramethyluronium hexafluorophosphate
HCl hydrochloric acid
HOAT 1-hydroxy-7-azabenzotriazole
KOH potassium hydroxide
$KMnO_4$ potassium permanganate
$K_2CO_3$ potassium carbonate
LiCl lithium chloride
LiHMDS, LHMDS lithium bis(trimethylsilyl)amide
LAH lithium aluminium hydride
MeCN, $CH_3CN$ acetonitrile
MsCl methanesulfonyl chloride
$(NH_4)_2SO_4$ ammonium sulfate
$NH_4Cl$ ammonium chloride
NaH sodium hydride
$NaBH_3CN$ sodium cyanoborohydride
$Na_2CO_3$ sodium carbonate
$NaHCO_3$ sodium bicarbonate
NaOH sodium hydroxide
$Na_2SO_4$ sodium sulfate
$Na_2S_2O_3$ sodium thiosulfate
NaOAc ammonium acetate
NBS bromosuccinimide
MeOH methanol
mL, ml milliliter
Pd/C palladium on carbon
PTSA p-toluenesulfonic acid
PE petroleum ether (60-90° C.)
PDC pyridinium dichromate
RT, rt, r.t. room temperature PTSA p-toluenesulfonamide
Pd(OAc)₂ palladium diacetate
Pd/C palladium on activated carbon
PDC pyridinium dichromate
Rt retention time
THF tetrahydrofuran
TBAF tetrabutylammonium fluoride
TFAA trifluoroacetic anhydride
TFA, CF₃COOH trifluoroacetic acid
Ti(Oi-Pr)₄ titanium tetraisopropanolate
TsCl tosyl chloride Representative synthetic procedures for the preparation of the compounds disclosed herein is outlined below in following Scheme 1 to Scheme 4. Unless otherwise indicated, each of Z, Z¹, R¹, R² and R⁴ carry the definitions set forth above in connection with Formula (I); p is 0, 1, 2, 3, or 4; q is 0, 1, 2 or 3; PG is a protecting group; W is an azolyl.

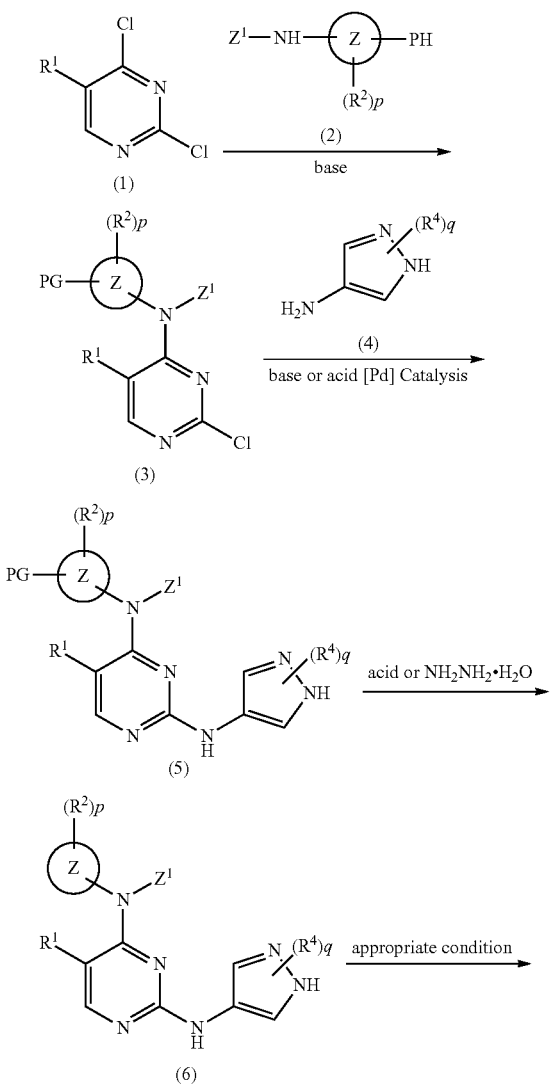

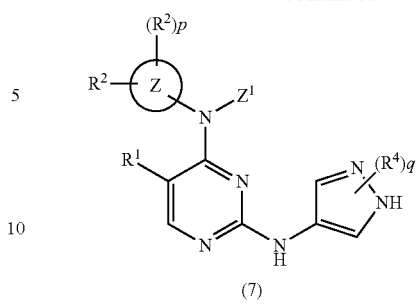

Some compounds having Formula (6) or Formula (7) can be prepared by a general method illustrated in Scheme 1 and described in details in the Examples. As showing in Scheme 1, optionally substituted dichloropyrimidine compound (1) is reacted with optionally substituted heterocyclic compound (2) with an aid of a base, such as Et₃N, to give optionally substituted heteroaryl compound (3). Compound (3) is then coupled with optionally substituted aminopyrazole (4) or a hydrochloride thereof in the presence of a base, such as DIPEA, Et₃N, or in the presence of an acid, such as trifluoroacetic acid, a solution of HCl in EtOAc, or in the presence of a suitable Pd catalyst, such as Pd(OAc)₂, to afford the compound (5). The protecting group of compound (5) is removed under acidic conditions, such as trifluoroacetic acid, a solution of HCl in EtOAc, or with an aid of hydrazine hydrate to give the desired protein kinase inhibitor (6). Other protein kinase inhibitor having Formula (7) is obtained by introducing various substituents to the compound (6) under appropriate conditions.

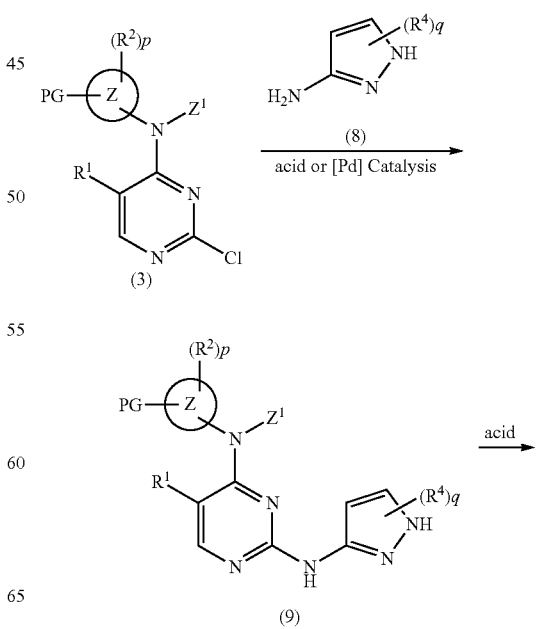

-continued

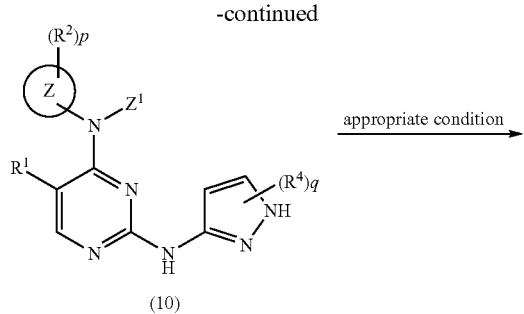

(10)

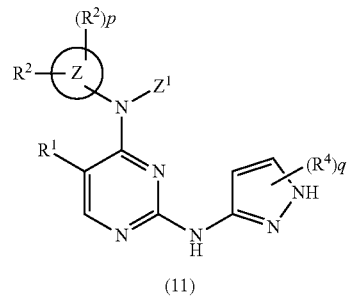

(11)

Some compounds having Formula (10) or Formula (11) can be prepared by a general method illustrated in Scheme 2 and described in details in the Examples. As showing in Scheme 2, Compound (3) is coupled with optionally substituted aminopyrazole (8) or a hydrochloride thereof in the presence of an acid, such as trifluoroacetic acid, a solution of HCl in EtOAc, or in the presence of a suitable Pd catalyst, such as Pd(OAc)$_2$, to afford the compound (9). The protecting group of compound (9) is removed under acidic conditions, such as trifluoroacetic acid, a solution of HCl in EtOAc, to give the desired protein kinase inhibitor (10). Other desired protein kinase inhibitor having Formula (11) is obtained by introducing various substituents to the compound (10) under appropriate conditions.

-continued

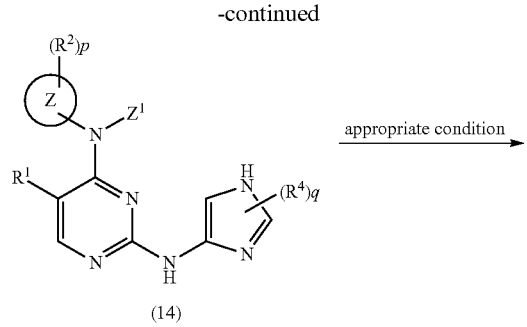

(14)

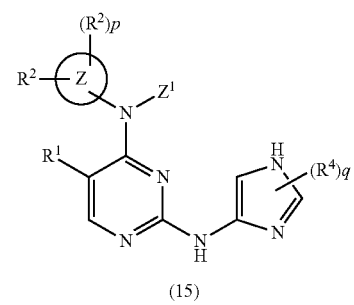

(15)

Some compounds having Formula (14) or Formula (15) can be prepared by a general method illustrated in Scheme 3 and described in details in the Examples. As showing in Scheme 3, Compound (3) is coupled with optionally substituted aminoimidazole (12) in the presence of a suitable Pd catalyst, such as Pd(OAc)$_2$, affords the compound (13). The protecting group of compound 13) is removed under acidic conditions, such as trifluoroacetic acid, a solution of HCl in EtOAc, to give the desired protein kinase inhibitor (14). Other desired protein kinase inhibitor having Formula (15) is obtained by introducing various substituents to the compound (14) under appropriate conditions.

Scheme 3:

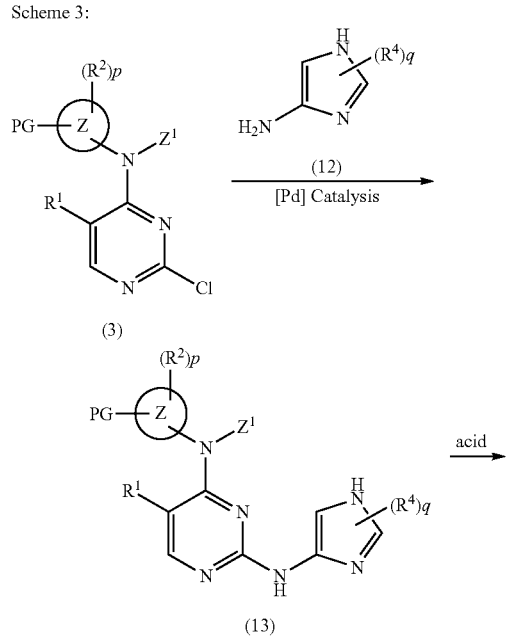

Scheme 4:

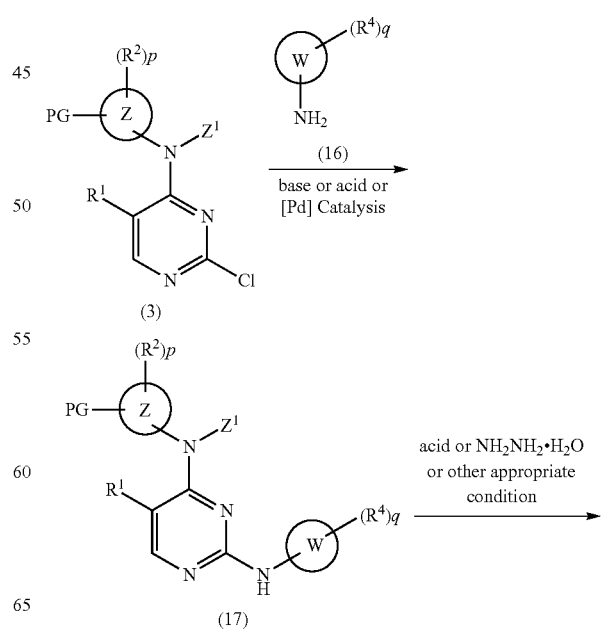

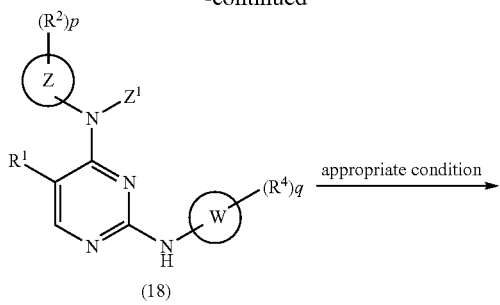

(18)

(19)

Some compounds having Formula (18) or Formula (19) can be prepared by a general method illustrated in Scheme 4 and described in details in the Examples. As showing in Scheme 4, Compound (3) is coupled with optionally substituted aminoazole compound (16) or a hydrochloride thereof in the presence of a base, such as DIPEA, Et₃N, or in the presence of an acid, such as trifluoroacetic acid, a solution of HCl in EtOAc, or in the presence of a suitable Pd catalyst, such as Pd(OAc)₂, to afford the compound (17). The protecting group of compound (17) is removed under acidic conditions, such as trifluoroacetic acid, a solution of HCl in EtOAc, or with an aid of hydrazine hydrate or any other appropriate condition to give the desired protein kinase inhibitor (18). Other desired protein kinase inhibitor having Formula (19) is obtained by introducing various substituents to the compound (18) under appropriate conditions.

EXAMPLES

Example 1

$N^4$-methyl-$N^2$-(1-methyl-1H-pyrazol-4-yl)-$N^4$-(2-azaspiro[4.4]nonan-4-yl) pyrimidine-2,4-diamine

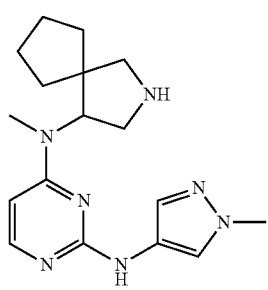 [SMILES: CN(c1ccnc(Nc2cnn(C)c2)n1)C1CNCC12CCCC2]

Step 1) N-benzyl-3-oxobutanamide

To a solution of 4-methyleneoxetan-2-one (60.00 g, 713.69 mmol) in DCM (600 mL) was added phenylmethanamine (91.76 g, 856.43 mmol) dropwise at 0° C. After addition, the reaction mixture was stirred at rt overnight and concentrated in vacuo. The residue was beaten with a mixture of PE and EtOAc (10/1 (v/v), 200 mL) for 1 h and filtered. The filter cake was washed with a mixture of PE and EtOAc (10/1 (v/v), 100 mL) to give the title compound as a yellow solid (136.38 g, 100%).

MS (ESI, pos. ion) m/z: 192.3 [M+H]⁺;
¹H NMR (400 MHz, CDCl₃): δ (ppm) 7.43 (s, 1H), 7.27 (m, 5H), 4.41 (d, J=5.8 Hz, 2H), 3.38 (s, 2H), 2.21 (s, 3H).

Step 2) 1-acetyl-N-benzylcyclopentane carboxamide

To a solution of N-benzyl-3-oxobutanamide (100.00 g, 522.93 mmol), K₂CO₃ (216.50 g, 1568.79 mmol) in DMF (1 L) was added 1,4-dibromobutane (169.36 g, 784.4 mmol) dropwise at rt. After addition, the reaction mixture was stirred at rt overnight and concentrated in vacuo. The residue was added water (500 mL) and extracted with EtOAc (500 mL×3). The combined organic phases were washed with brine (500 mL×3), dried over anhydrous Na₂SO₄, then filtered and concentrated in vacuo. The residue was purified by silica gel column chromatography (EtOAc/PE (v/v)=1/8) to give the product as a white solid (69.50 g, 54%).

MS (ESI, pos. ion) m/z: 246.3 [M+H]⁺;
¹H NMR (400 MHz, CDCl₃): δ (ppm) 7.24 (m, 5H), 6.12 (s, 1H), 4.40 (d, J=5.8 Hz, 2H), 2.23-2.03 (m, 7H), 1.60 (m, 4H).

Step 3) N-benzyl-1-(2-bromoacetyl)cyclopentane carboxamide

To a solution of 1-acetyl-N-benzylcyclopentane carboxamide (44 g, 179.36 mmol) in EtOH (700 mL) were added NBS (70.22 g, 394.59 mmol) and PTSA (3.5 g, 17.94 mmol). After addition, the reaction mixture was stirred at rt for 48 h and concentrated in vacuo. To the residue was added water (500 mL) and the resulting mixture was extracted with EtOAc (500 mL×3). Then the combined organic phases were washed with saturated Na₂S₂O₃ solution (500 mL×3) and brine (500 mL), dried over anhydrous Na₂SO₄, then filtered and concentrated in vacuo. The residue was purified by silica gel column chromatography (EtOAc/PE (v/v)=1/5) to give the product as a white solid (39.5 g, 68%).

MS (ESI, pos. ion) m/z: 324.2 [M+H]⁺;
¹H NMR (400 MHz, CDCl₃): δ (ppm) 7.28 (m, 5H), 6.29 (s, 1H), 4.41 (d, J=5.8 Hz, 2H), 4.13 (s, 2H), 2.20 (ddd, J=11.9, 8.2, 4.1 Hz, 4H), 1.66 (m, 4H).

Step 4) 2-benzyl-2-azaspiro[4.4]nonane-1,4-dione

To a suspension of NaH (60% mineral oil suspension, 7.40 g, 185.00 mmol) in DMF (450 mL) was added a solution of N-benzyl-1-(2-bromoacetyl)cyclopentanecarboxamide (50.00 g, 154.22 mmol) in DMF (100 mL) dropwise at 0° C. After addition, the reaction mixture was stirred at rt overnight and then quenched with water (200 mL) and extracted with EtOAc (300 mL×3). The combined organic phases were washed with brine (300 mL×3), dried over anhydrous Na₂SO₄, then filtered and concentrated in vacuo. The residue was purified by silica gel column chromatography (EtOAc/PE (v/v)=1/10) to give the product as yellow oil (21.00 g, 56.0%).

MS (ESI, pos. ion) m/z: 244.2 [M+H]⁺;
¹H NMR (400 MHz, CDCl₃): δ (ppm) 7.22 (m, 5H), 4.56 (s, 2H), 3.62 (s, 2H), 1.84 (m, 8H).

Step 5) 2-benzyl-2-azaspiro[4.4]nonan-4-ol

To a cooled to 0° C. solution of 2-benzyl-2-azaspiro[4.4]nonane-1,4-dione (20.00 g, 82.2 mmol) in THF (150 mL) was added LiAlH$_4$ (20.93 g, 550.8 mmol) portionwise. After addition, the reaction mixture was stirred at 80° C. overnight, cooled down to rt and quenched carefully with sequential addition of EtOAc (200 mL), 15% KOH aqueous solution (40 mL) and water (100 mL). After addition, the resulting mixture was stirred at rt for 3 h, and filtered through a Celite pad, then washed with EtOAc (1 L). The filtrate was concentrated in vacuo to give the product as yellow oil (19.02 g, 100%).

MS (ESI, pos. ion) m/z: 232.2 [M+H]$^+$;

$^1$H NMR (600 MHz, CDCl$_3$): δ (ppm) 7.35 (dt, J=14.9, 7.5 Hz, 4H), 7.28 (m, 1H), 3.81 (dd, J=4.4, 1.9 Hz, 1H), 3.73 (s, 2H), 2.96 (m, 1H), 2.78 (d, J=9.4 Hz, 1H), 2.74 (dd, J=10.4, 1.6 Hz, 1H), 2.46 (d, J=9.3 Hz, 1H), 1.96 (m, 1H), 1.64 (m, 3H), 1.56 (m, 3H), 1.45 (m, 1H).

Step 6) 2-azaspiro[4.4]nonan-4-ol

To a solution of 2-benzyl-2-azaspiro[4.4]nonan-4-ol (20.00 g, 86.5 mmol) in MeOH (200 mL) was added Pd/C (10% wt, 3.00 g). The suspension was stirred at 45° C. under a H$_2$ atmosphere overnight and filtered. The filtered cake was washed with EtOAc (50 mL×3). The filtrate was concentrated in vacuo to give the product as yellow oil (12.21 g, 100%).

MS (ESI, pos. ion) m/z: 142.2 [M+H]$^+$;

$^1$H NMR (600 MHz, CDCl$_3$): δ (ppm) 3.83 (d, J=2.8 Hz, 1H), 3.22 (dd, J=12.1, 4.3 Hz, 1H), 2.99 (m, 2H), 2.84 (m, 2H), 1.95 (m, 1H), 1.66 (m, 4H), 1.48 (m, 2H), 1.40 (m, 1H).

Step 7) tert-butyl 4-hydroxy-2-azaspiro[4.4]nonane-2-carboxylate

To a solution of 2-azaspiro[4.4]nonan-4-ol (12.45 g, 88.2 mmol) in THF (150 mL) was added a solution of Na$_2$CO$_3$ (18.70 g, 176.4 mmol) in water (50 mL) and Boc$_2$O (38.49 g, 176.4 mmol). After addition, the reaction mixture was stirred at rt for 4 h and concentrated in vacuo. The residue was diluted with water (100 mL) and the resulting mixture was extracted with EtOAc (250 mL×3). The combined organic phases were washed with brine (250 mL×3), dried over anhydrous Na$_2$SO$_4$, then filtered and concentrated in vacuo. The residue was purified by silica gel column chromatography (EtOAc/PE (v/v)=1/5) to give the product as yellow oil (12.07 g, 56.7%).

MS (ESI, pos. ion) m/z: 186.2 [(M−C$_4$H$_8$)+H]$^+$;

$^1$H NMR (400 MHz, CDCl$_3$): δ (ppm) 3.87 (dd, J=4.3, 1.6 Hz, 1H), 3.53 (dd, J=12.0, 4.3 Hz, 1H), 3.36 (dd, J=12.0, 1.6 Hz, 1H), 3.27 (q, J=10.4 Hz, 2H), 1.87 (m, 3H), 1.67 (m, 4H), 1.47 (s, 10H).

Step 8) tert-butyl 4-oxo-2-azaspiro[4.4]nonane-2-carboxylate

To a solution of tert-butyl 4-hydroxy-2-azaspiro[4.4]nonane-2-carboxylate (10.82 g, 44.8 mmol) in DCM (225 mL) was added 4 Å molecular sieve (22.00 g), then added PDC (42.17 g, 112.1 mmol) slowly. After addition, the reaction mixture was stirred at rt overnight and filtered. The filter cake was washed with EtOAc (50 mL×3) and the filtrate was concentrated in vacuo. The residue was purified by silica gel column chromatography (EtOAc/PE (v/v)=1/15) to give the product as colorless oil (5.92 g, 55.2%).

MS (ESI, pos. ion) m/z: 184.1 [(M−C$_4$H$_8$)+H]$^+$;

$^1$H NMR (600 MHz, CDCl$_3$): δ (ppm) 3.84 (br. s, 2H), 3.58 (br. s, 2H), 1.90 (br. s, 2H), 1.80 (m, 2H), 1.71 (m, 2H), 1.62 (br. s, 2H), 1.50 (s, 9H).

Step 9) tert-butyl 4-(methylamino)-2-azaspiro[4.4]nonane-2-carboxylate

To a solution of CH$_3$NH$_2$ (33% [w/w] in EtOH, 11.70 g, 124.3 mmol) was added tert-butyl 4-oxo-2-azaspiro[4.4]nonane-2-carboxylate (5.92 g, 24.7 mmol). After addition, the reaction mixture was stirred at rt overnight, and then NaBH$_3$CN (4.69 g, 74.6 mmol) was added portionwise. The resulting mixture was stirred at rt for 2 h and concentrated in vacuo. The residue was purified by silica gel column chromatography (EtOAc, 100%) to give the product as colorless oil (6.28 g, 100%).

MS (ESI, pos. ion) m/z: 255.2 [M+H]$^+$;

$^1$H NMR (600 MHz, DMSO-d$_6$): δ (ppm) 3.13 (dd, J=10.1, 4.5 Hz, 1H), 3.02 (m, 2H), 2.72 (dt, J=20.9, 5.2 Hz, 1H), 2.51 (m, 1H), 2.27 (s, 3H), 1.72 (m, 1H), 1.54 (m, 5H), 1.39 (dd, J=12.7, 4.5 Hz, 10H), 1.26 (m, 1H).

Step 10) tert-butyl 4-((2-chloropyrimidin-4-yl)(methyl)amino)-2-azaspiro[4.4]nonane-2-carboxylate To a suspension of 4,5-dichloropyrimidine (0.40 g, 2.68 mmol) in EtOH (10 mL) was added tert-butyl 4-(methylamino)-2-azaspiro[4.4]nonane-2-carboxylate (0.78 g, 2.68 mmol) and Et$_3$N (0.75 mL, 5.37 mmol). The mixture was stirred at rt overnight and then concentrated in vacuo. The residue was purified by silica gel column chromatography (EtOAc 100%) to give the product as a light yellow solid (0.34 g, 34%).

MS (ESI, pos. ion) m/z: 367.2 [M+H]$^+$;

$^1$H NMR (600 MHz, CDCl$_3$): δ (ppm) 8.09 (d, J=6.0 Hz, 1H), 6.35 (m, 1H), 5.34 (m, 1H), 3.87-3.76 (m, 1H), 3.63-3.36 (m, 2H), 3.29 (m, 1H), 2.93 (s, 3H), 1.80-1.68 (m, 2H), 1.65-1.54 (m, 4H), 1.54 (s, 9H), 1.41 (m, 2H).

Step 11) tert-butyl 4-(methyl(2-((1-methyl-1H-pyrazol-4-yl)amino)pyrimidin-4-yl)amino)-2-azaspiro[4.4]nonane-2-carboxylate To a suspension of tert-butyl 4-((2-chloropyrimidin-4-yl)(methyl)amino)-2-azaspiro[4.4]nonane-2-carboxylate (0.34 g, 0.93 mmol) in n-BuOH (5.0 mL) was added 1-methyl-1H-pyrazol-4-amine hydrochloride (0.25 g, 1.85 mmol) and DIPEA (0.48 g, 3.71 mmol). The mixture was stirred in a sealed tube and heated to 150° C. overnight, then concentrated in vacuo. The residue was purified by silica gel column chromatography (EA) to give the product as a yellow solid (0.22 g, 55%).

MS (ESI, pos. ion) m/z: 428.3 [M+H]$^+$;

$^1$H NMR (600 MHz, CDCl$_3$): δ (ppm) 7.98 (d, J=6.0 Hz, 1H), 7.71 (s, 1H), 7.48 (s, 1H), 6.91 (br, 1H), 5.92 (d, J=5.6 Hz, 1H), 5.51-5.06 (m, 1H), 3.88 (s, 3H), 3.83-3.74 (m, 1H), 3.62-3.49 (m, 1H), 3.49-3.34 (m, 1H), 3.32-3.23 (m, 1H), 2.91 (s, 3H), 1.75-1.62 (m, 4H), 1.60-1.48 (m, 4H), 1.50 (s, 9H).

Step 12) N$^4$-methyl-N$^2$-(1-methyl-H-pyrazol-4-yl)-N$^4$-(2-azaspiro[4.4]nonan-4-yl)pyrimidine-2,4-diamine To a suspension of tert-butyl 4-(methyl(2-((1-methyl-1H-pyrazol-4-yl)amino)pyrimidin-4-yl)amino)-2-azaspiro[4.4]nonane-2-carboxylate (0.22 g, 0.51 mmol) in DCM (10 mL) was added a solution of HCl in EtOAc (10 mL, 3.5 M). The mixture was stirred at room temperature for 3 h, then concentrated in vacuo. The residue was diluted with DCM (10 mL) and saturated Na$_2$CO$_3$ (10 mL) and the resulting mixture was extracted with a mixture of DCM and MeOH (10/1 (v/v), 30 mL×5). The combined organic layers was dried over anhydrous Na₂SO₄, then filtered and concentrated in vacuo. The residue was purified by silica gel column chromatography (DCM/2M NH₃ in MeOH (v/v)=5/1) to give the product as a light yellow solid (0.16 g, 95%).

MS (ESI, pos. ion) m/z: 328.2 [M+H]⁺;

¹H NMR (400 MHz, DMSO-$d_6$): δ (ppm) 8.73 (s, 1H), 7.87 (d, J=5.8 Hz, 1H), 7.76 (s, 1H), 7.44 (s, 1H), 5.98 (s, 1H), 5.38-6.01 (m, 1H), 3.77 (s, 3H), 3.28-3.22 (m, 1H), 2.91 (m, 4H), 2.74-2.65 (m, 2H), 1.67-1.42 (m, 6H), 1.37-1.31 (m, 2H).

Example 2

1-(4-(methyl(2-((1-methyl-1H-pyrazol-4-yl)amino) pyrimidin-4-yl)amino)-2-azaspiro[4.4]nonan-2-yl) prop-2-en-1-one

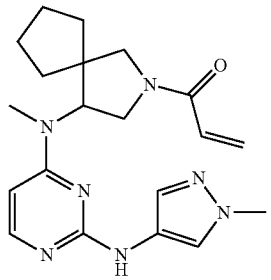 [SMILES: C=CC(=O)N1CC(N(C)c2ccnc(Nc3cnn(C)c3)n2)C2(CCCC2)C1]

To a suspension of $N^4$-methyl-$N^2$-(1-methyl-1H-pyrazol-4-yl)-$N^4$-(2-azaspiro[4.4]nonan-4-yl)pyrimidine-2,4-diamine (0.10 g, 0.31 mmol) in DCM (8.0 mL) was added acrylic acid (55 mg, 0.76 mmol), HATU (0.14 g, 0.37 mmol) and Et₃N (62 mg, 0.61 mmol). The mixture was stirred at room temperature for 4 h, then diluted with DCM (50 mL), and washed with water (20 mL) followed by brine (20 mL), dried over anhydrous Na₂SO₄, then filtered and concentrated in vacuo. The residue was purified by preparative-TLC (DCM/MeOH (v/v)=12/1) to give the product as a light yellow solid (25 mg, 21%).

MS (ESI, pos. ion) m/z: 382.3 [M+H]⁺;

¹H NMR (400 MHz, CDCl₃): δ (ppm) 7.93 (m, 1H), 7.63 (s, 1H), 7.55 (m, 1H), 6.47 (m, 2H), 5.97 (m, 1H), 5.77 (m, 1H), 5.37 (m, 1H), 4.08-3.92 (m, 1H), 3.89 (s, 3H), 3.75 (d, J=12.5 Hz, 1H), 3.61-3.41 (m, 2H), 2.94 (m, 3H), 1.78-1.38 (m, 8H).

Example 3

5-chloro-$N^4$-methyl-$N^2$-(1-methyl-1H-pyrazol-4-yl)-$N^4$-(2-azaspiro[4.5]decan-8-yl)pyrimidine-2,4-diamine (3.10 A and 3.10B)

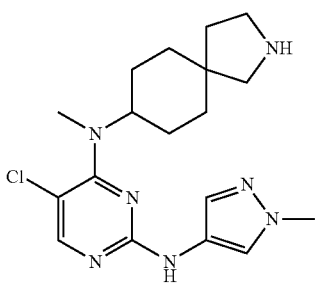 [SMILES: CN(c1nc(Nc2cnn(C)c2)ncc1Cl)C1CCC2(CCNC2)CC1]

Step 1) ethyl 2-(1,4-dioxaspiro[4.5]decan-8-ylidene)acetate

To a suspension of NaH (60% mineral oil suspension, 33.3 g, 832.38 mmol) in anhydrous THF (1 L) was added a solution of 1,4-dioxaspiro[4.5]decan-8-one (100 g, 640.29 mmol) in anhydrous THF (500 mL) dropwise at 0° C. for 1 h and continued to stir for 1 h. Then triethyl phosphonoacetate (203.23 g, 832.38 mmol) was added to the above suspension dropwise at −20° C. in 1 h. The resulting mixture was allowed to warm to rt, stirred for 2 h, quenched with H₂O (1 L) and extracted with EtOAC (1 L×3). The combined organic phases were washed with brine (1 L), dried over anhydrous Na₂SO₄, then filtered and concentrated in vacuo. The residue was purified by silica gel column chromatography (EtOAc/PE (v/v)=1/10) to give the title compound as pale yellow oil (157 g, 100%).

¹H NMR (600 MHz, CDCl₃): δ (ppm) 5.64 (s, 1H), 4.12 (q, J=7.1 Hz, 2H), 3.95 (s, 4H), 2.97 (m, 2H), 2.36 (m, 2H), 1.74 (m, 4H), 1.25 (t, J=7.2 Hz, 4H).

Step 2) ethyl 2-(8-(nitromethyl)-1,4-dioxaspiro[4.5] decan-8-yl)acetate

To a solution of ethyl 2-(1,4-dioxaspiro[4.5]decan-8-ylidene)acetate (157 g, 693.86 mmol) in THF (800 mL) was added nitromethane (55.8 mL, 1.04 mmol) at rt followed by 1M solution of TBAF in THF (763.25 mL, 763.25 mmol) which was added dropwise at rt. The reaction mixture was heated to reflux for 20 h and then concentrated in vacuo. The residue was diluted with H₂O (800 mL) and extracted with EtOAc (800 mL×3). The combined organic phases were washed with brine (1 L), dried over anhydrous Na₂SO₄, then filtered and concentrated in vacuo. The residue was purified by silica gel column chromatography (EtOAc/PE (v/v)=1/10) to give the title compound as pale yellow oil (165 g, 82.9%).

¹H NMR (600 MHz, CDCl₃): δ (ppm) 4.66 (s, 2H), 4.09 (q, J=7.1 Hz, 2H), 3.88 (s, 4H), 2.49 (s, 2H), 1.64 (m, 8H), 1.21 (t, J=7.2 Hz, 4H).

Step 3) 1,4-dioxa-10-aza-dispiro[4.2.4.2]tetradecan-9-one

To a solution of ethyl 2-(8-(nitromethyl)-1,4-dioxaspiro [4.5]decan-8-yl)acetate (109 g, 379.38 mmol) in EtOH (600 mL) was added Raney Ni (10 g). The reaction mixture was stirred under H₂ atmosphere at rt for 72 h and filtered. The filter cake was washed with a mixture of DCM and MeOH (1/1 (v/v), 500 mL). The filtrate was concentrated in vacuo and the residue was washed with a mixture of PE and EtOAc (10/1 (v/v), 800 mL) and filtered to give the product as a white solid (67 g, 83.8%).

MS (ESI, pos. ion) m/z: 212.1 [M+H]⁺;

¹H NMR (600 MHz, CDCl₃): δ (ppm) 6.60 (s, 1H), 3.95 (s, 4H), 3.20 (s, 2H), 2.23 (s, 2H), 1.72 (m, 4H), 1.65 (m, 4H).

Step 4) 1,4-dioxa-10-aza-dispiro[4.2.4.2]tetradecane

To a suspension of LiAlH₄ (21 g, 558.56 mmol) in anhydrous THF (500 mL) was added a solution of 1,4-dioxa-10-aza-dispiro[4.2.4.2]tetradecan-9-one (59 g, 279.28 mmol) in anhydrous THF (400 mL) dropwise at 0° C. in 1 h. The reaction mixture was heated to reflux and stirred for 2 h, then quenched with water at 0° C. until no bubble escaped and filtered. The filter cake was washed with a mixture of DCM and MeOH (1/1 (v/v), 500 mL). The filtrate was concentrated in vacuo and the residue was purified by silica gel column chromatography (MeOH/DCM (v/v)=1/10) to give the product as a yellow solid (52 g, 94%).

MS (ESI, pos. ion) m/z: 198.2 [M+H]+;
1H NMR (600 MHz, CDCl3): δ (ppm) 3.88 (s, 4H), 2.90 (t, J=7.1 Hz, 2H), 2.65 (s, 3H), 1.56 (ddd, J=29.3, 13.4, 6.9 Hz, 10H).

Step 5) 2-azaspiro[4.5]decan-8-one

To a solution of 1,4-dioxa-10-aza-dispiro[4.2.4.2]tetradecane (10 g, 50.69 mmol) in MeOH (100 mL) was added HCl aqueous solution (2 M, 30 mL, 60 mmol). The reaction mixture was stirred at rt overnight and concentrated in vacuo. The residue was dissolved in water (100 mL) and adjusted to pH=10 with a saturated Na2CO3 aqueous solution, then extracted with DCM (200 mL×3). The combined organic phases were washed with brine (200 mL), dried over anhydrous Na2SO4, then filtered and concentrated in vacuo. The residue was purified by silica gel column chromatography (MeOH/DCM (v/v)=1/7) to give the title compound as a yellow solid (10 g, 100%).

MS (ESI, pos. ion) m/z: 154.2 [M+H]+.

Step 6) tert-butyl 8-oxo-2-azaspiro[4.5]decane-2-carboxylate

To a solution of 2-azaspiro[4.5]decan-8-one (10 g, 65.26 mmol) in a mixture of THF and H2O (3/1 (v/v), 200 mL) were added (Boc)2O (28.48 g, 130.53 mmol) and Na2CO3 (13.83 g, 130.53 mmol). The reaction mixture was stirred at rt for 2 h, then quenched with H2O (200 mL) and extracted with EtOAc (300 mL×3). The combined organic phases were washed with brine (500 mL), dried over Na2SO4, concentrated in vacuo. The residue was purified by silica gel column chromatography (EtOAc/PE (v/v)=1/10) to give the product as colorless oil (9 g, 54.5%).

MS (ESI, pos. ion) m/z: 198.1 [(M–C4H8)+H]+.

Step 7) tert-butyl 8-(methylamino)-2-azaspiro[4.5]decane-2-carboxylate

To a solution of methylamine (33% [w/w] in EtOH, 7.42 g, 79.0 mmol) was added tert-butyl 8-oxo-2-azaspiro[4.5]decane-2-carboxylate (4 g, 15.80 mmol), the reaction mixture was stirred at rt overnight. To the mixture was added NaBH3CN (2.98 g, 47.4 mmol), and the reaction mixture was stirred at rt for another 2 h and concentrated in vacuo. The residue was diluted with H2O (50 mL) and the resulting mixture was extracted with DCM (80 mL×3). The combined organic phases were washed with brine (100 mL), dried over Na2SO4, filtered and concentrated in vacuo. The residue was purified by silica gel column chromatography (DCM/MeOH (v/v)=10/1) to give the product as yellow oil (3.2 g, 75.7%).

MS (ESI, pos. ion) m/z: 269.2 [M+H]+.

Step 8) tert-butyl 8-((2,5-dichloropyrimidin-4-yl)(methyl)amino)-2-azaspiro[4.5]decane-2-carboxylate (3.8 A and 3.8 B)

To a suspension of 2,4,5-trichloropyrimidine (0.50 g, 2.73 mmol) in EtOH (10 mL) was added tert-butyl 8-(methylamino)-2-azaspiro[4.5]decane-2-carboxylate (0.73 g, 2.73 mmol) and Et3N (0.75 mL, 5.45 mmol). The mixture was stirred at room temperature overnight, and then concentrated in vacuo. The residue was diluted with EtOAc (80 mL), washed with water (30 mL) and brine (30 mL×2), dried over anhydrous Na2SO4, then filtered and concentrated in vacuo. The residue was purified by silica gel column chromatography (EA/PE (v/v)=1/5) to afford isomer 3.8 A (Rf=0.5, EtOAc/PE (v/v)=1/5) as light yellow liquid (0.22 g) and isomer 3.8 B (Rf=0.4, EtOAc/PE (v/v)=1/5) as a light yellow solid (0.35 g) (yield 50% for 3.8 A and 3.8 B).

3.8 A:
MS (ESI, pos. ion) m/z: 359.1 [(M–56)+H]+;
1H NMR (400 MHz, CDCl3): δ (ppm) 8.02 and 8.01 (s, 1H), 4.42-4.26 (m, 1H), 3.44-3.31 (m, 2H), 3.27 and 3.18 (s, 2H), 3.07 and 3.03 (s, 3H), 1.81-1.50 (m, 10H), 1.47 and 1.46 (s, 9H).

3.8 B:
MS (ESI, pos. ion) m/z: 415.2 [M+H]+;
1H NMR (400 MHz, CDCl3): δ (ppm) 8.04 (s, 1H), 4.39-4.27 (m, 1H), 3.47-3.35 (m, 2H), 3.14 (s, 1H), 3.08 (s, 1H), 3.07 (s, 3H), 1.83-1.69 (m, 8H), 1.52 (m, 2H), 1.46 (s, 9H).

Step 9) tert-butyl 8-((5-chloro-2-((1-methyl-1H-pyrazol-4-yl)amino)pyrimidin-4-yl)(methyl)amino)-2-azaspiro[4.5]decane-2-carboxylate (3.9A)

To a suspension of tert-butyl 8-((2,5-dichloropyrimidin-4-yl)(methyl)amino)-2-azaspiro[4.5]decane-2-carboxylate (3.8 A: 0.14 g, 0.34 mmol) in n-BuOH (2.0 mL) was added 1-methyl-1H-pyrazol-4-amine hydrochloride (89 mg, 0.67 mmol) and DIPEA (0.17 g, 1.35 mmol). The mixture was stirred in a sealed tube and heated to 150° C. for 12 h and then concentrated in vacuo. The residue was purified by silica gel column chromatography (EA/PE (v/v)=4/1) to afford 3.9A as a light yellow solid (0.15 g, 93%).

MS (ESI, pos. ion) m/z: 476.2 [M+H]+;
1H NMR (400 MHz, CDCl3): δ (ppm) 7.94 (s, 1H), 7.69 (s, 1H), 7.49 (s, 1H), 6.66 (br, 1H), 4.29 (m, 1H), 3.90 (s, 3H), 3.40 (m, 2H), 3.31 and 3.22 (s, 2H), 3.04 and 3.00 (s, 3H), 1.76 (m, 4H), 1.68 (m, 6H), 1.50 (s, 9H).

Step 10) 5-chloro-N4-methyl-N2-(1-methyl-1H-pyrazol-4-yl)-N4-(2-azaspiro[4.5]decan-8-yl)pyrimidine-2,4-diamine (3.10 A)

To a suspension of tert-butyl 8-((5-chloro-2-((1-methyl-1H-pyrazol-4-yl)amino)pyrimidin-4-yl)(methyl)amino)-2-azaspiro[4.5]decane-2-carboxylate (3.9 A: 0.15 g, 0.32 mmol) in DCM (10 mL) was added a solution of HCl in EtOAc (10 mL, 3.5 M). The mixture was stirred at room temperature for 2 h, then concentrated in vacuo. The residue was diluted with DCM (20 mL) and saturated Na2CO3 solution (20 mL). The organic layer was separated and the aqueous layer was extracted with a mixture of DCM and MeOH (10/1 (v/v), 20 mL×5). The combined organic layers was washed with brine (30 mL), dried over anhydrous Na2SO4, then filtered and concentrated in vacuo. The residue was purified by silica gel column chromatography (DCM/2N NH3 in MeOH (v/v)=5/1) to afford 3.10 A as a brown solid (0.10 g, 84%).

MS (ESI, pos. ion) m/z: 188.7 [(M+2H)/2]+;
1H NMR (400 MHz, DMSO): δ (ppm) 9.11 (s, 1H), 7.95 (s, 1H), 7.74 (s, 1H), 7.46 (s, 1H), 4.19 (m, 1H), 3.79 and 3.77 (s, 3H), 3.18 (m, 1H), 2.98 (s, 3H), 2.85 (m, 2H), 2.74 (m, 2H), 1.65 (m, 6H), 1.49 (m, 4H).

Step 11) tert-butyl 8-((5-chloro-2-((1-methyl-1H-pyrazol-4-yl)amino)pyrimidin-4-yl)(methyl)amino)-2-azaspiro[4.5]decane-2-carboxylate (3.9 B)

To a suspension of tert-butyl 8-((2,5-dichloropyrimidin-4-yl)(methyl)amino)-2-azaspiro[4.5]decane-2-carboxylate (3.8 B: 0.30 g, 0.72 mmol) in n-BuOH (4.0 mL) was added 1-methyl-1H-pyrazol-4-amine hydrochloride (0.19 g, 1.44 mmol) and DIPEA (0.37 g, 2.89 mmol). The mixture was stirred in a sealed tube and heated to 150° C. for 12 h and then concentrated in vacuo. The residue was purified by silica gel column chromatography (EA/PE (v/v)=4/1) to afford 3.9 B as a light yellow solid (0.19 g, 55%).

MS (ESI, pos. ion) m/z: 476.3 [M+H]$^+$;

$^1$H NMR (600 MHz, CDCl$_3$): δ (ppm) 7.94 (s, 1H), 7.68 (m, 1H), 7.50 (m, 1H), 6.58 (br, 1H), 4.29 (m, 1H), 3.90 (s, 3H), 3.44 (m, 2H), 3.13 (m, 2H), 3.04 (s, 3H), 1.86-1.74 (m, 5H), 1.74-1.68 (m, 5H), 1.48 (s, 9H).

Step 12) 5-chloro-$N^4$-methyl-$N^2$-(1-methyl-1H-pyrazol-4-yl)-$N^4$-(2-azaspiro[4.5]decan-8-yl)pyrimidine-2,4-diamine (3.10 B)

To a suspension of tert-butyl 8-((5-chloro-2-((1-methyl-1H-pyrazol-4-yl)amino)pyrimidin-4-yl)(methyl)amino)-2-azaspiro[4.5]decane-2-carboxylate (3.9 B: 0.19 g, 0.40 mmol) in DCM (10 mL) was added a solution of HCl in EtOAc (10 mL, 3.5 M). The mixture was stirred at room temperature for 2 h, then concentrated in vacuo. The residue was diluted with DCM (10 mL) and saturated Na$_2$CO$_3$ aqueous solution (10 mL) and then the mixture was extracted with DCM/MeOH (v/v)=10/1 (30 mL×5). The combined organic layer was dried over anhydrous Na$_2$SO$_4$, then filtered and concentrated in vacuo. The residue was purified by silica gel column chromatography (DCM/2N NH$_3$ in MeOH (v/v)=5/1) to give 3.10 B as a light yellow solid (0.14 g, 93%).

MS (ESI, pos. ion) m/z: 188.7 [(M+2H)/2]$^+$;

$^1$H NMR (400 MHz, DMSO): δ (ppm) 9.12 (brs, 1H), 7.95 (s, 1H), 7.73 (s, 1H), 7.45 (s, 1H), 4.16 (m, 1H), 3.79 (s, 3H), 3.00-2.92 (m, 5H), 2.61 (s, 2H), 1.73-1.60 (m, 8H), 1.47-1.39 (m, 2H).

Example 4

3-(8-((5-chloro-2-((1-methyl-1H-pyrazol-4-yl)amino)pyrimidin-4-yl)(methyl)amino)-2-azaspiro[4.5]decan-2-yl)-3-oxopropanenitrile (4A and 4B)

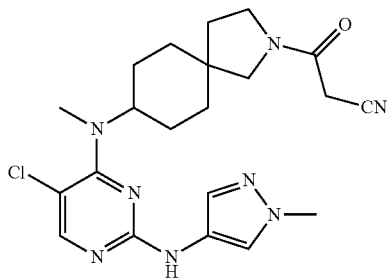 [SMILES: CN(c1nc(Nc2cnn(C)c2)ncc1Cl)C1CCC2(CC1)CCN(C(=O)CC#N)C2]

4A:
To a suspension of 5-chloro-$N^4$-methyl-$N^2$-(1-methyl-1H-pyrazol-4-yl)-$N^4$-(2-azaspiro[4.5]decan-8-yl)pyrimidine-2,4-diamine (3.10 A: 0.10 g, 0.27 mmol) in DCM (15 mL) was added 2-cyanoacetic acid (57 mg, 0.67 mmol), HATU (0.12 g, 0.32 mmol) and Et$_3$N (54 mg, 0.53 mmol). The mixture was stirred at room temperature overnight, and then diluted with DCM (50 mL), washed with water (20 mL) and brine (50 mL×2), then dried over anhydrous Na$_2$SO$_4$, filtered and concentrated in vacuo. The residue was purified by silica gel column chromatography (DCM/MeOH (v/v)=20/1) to afford 4A as a light yellow solid (72 mg, 61%).

MS (ESI, pos. ion) m/z: 443.3 [M+H]$^+$;

$^1$H NMR (400 MHz, CDCl$_3$): δ (ppm) 7.94 (m, 1H), 7.65 (s, 1H), 7.53 (s, 1H), 6.98 (br, 1H), 4.30 (m, 1H), 3.90 (s, 3H), 3.59 (t, J=7.1 Hz, 2H), 3.49 (s, 2H), 3.45 (m, 2H), 3.04 and 3.02 (s, 3H), 1.91-1.72 (m, 6H), 1.71-1.49 (m, 4H).

4B:
To a suspension of 5-chloro-$N^4$-methyl-$N^2$-(1-methyl-1H-pyrazol-4-yl)-$N^4$-(2-azaspiro[4.5]decan-8-yl)pyrimidine-2,4-diamine (3.10B: 0.10 g, 0.27 mmol) in DCM (5 mL) was added 2-cyanoacetic acid (57 mg, 0.67 mmol), HATU (0.12 g, 0.32 mmol) and Et$_3$N (54 mg, 0.53 mmol). The mixture was stirred at room temperature for 3 h, and then diluted with DCM (50 mL), washed with water (20 mL) followed by brine (20 mL×2), dried over anhydrous Na$_2$SO$_4$, then filtered and concentrated in vacuo. The residue was purified by silica gel column chromatography (DCM/MeOH (v/v)=20/1) to afford 4B as a white solid (82 mg, 69%).

MS (ESI, pos. ion) m/z: 443.3 [M+H]$^+$;

$^1$H NMR (600 MHz, CDCl$_3$): δ (ppm) 7.95 (s, 1H), 7.65 (m, 1H), 7.52 (m, 1H), 6.68 (br, 1H), 4.29 (m, 1H), 3.89 (s, 3H), 3.63 (t, J=7.0 Hz, 2H), 3.43 (m, 2H), 3.31 (m, 2H), 3.04 (s, 3H), 2.02 (t, J=7.1 Hz, 1H), 1.91 (t, J=7.2 Hz, 1H), 1.86-1.82 (m, 2H), 1.79-1.71 (m, 4H), 1.61-1.55 (m, 2H).

Example 5

$N^2$-(1-methyl-1H-pyrazol-4-yl)-$N^4$-(2-azaspiro[4.5]decan-8-yl)pyrimidine-2,4-diamine

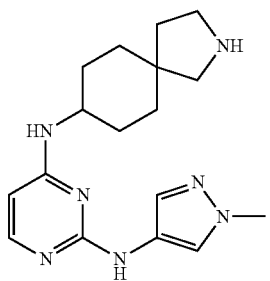 [SMILES: Cn1cc(Nc2nccc(NC3CCC4(CCNC4)CC3)n2)cn1]

Step 1) ethyl 2-(1,4-dioxaspiro[4.5]decan-8-ylidene)acetate

To a suspension of NaH (60% mineral oil suspension, 33.3 g, 832.38 mmol) in anhydrous THF (1 L) was added a solution of 1,4-dioxaspiro[4.5]decan-8-one (100 g, 640.29 mmol) in anhydrous THF (500 mL) dropwise at 0° C. in 1 h and the reaction mixture was stirred for another 1 h. Then triethyl phosphonoacetate (203.23 g, 832.38 mmol) was added dropwise to the above suspension at −20° C. in 1 h. The resulting mixture was allowed to warm to rt, stirred for another 2 h, then quenched with H$_2$O (1 L) and extracted with EtOAC (1 L×3). The combined organic phases were washed with brine (1 L), dried over anhydrous Na$_2$SO$_4$, then filtered and concentrated in vacuo. The residue was purified by silica gel column chromatography (EtOAc/PE (v/v)=1/10) to give the title compound as pale yellow oil (157 g, 100%).

$^1$H NMR (600 MHz, CDCl$_3$): δ (ppm) 5.64 (s, 1H), 4.12 (q, J=7.1 Hz, 2H), 3.95 (s, 4H), 2.97 (m, 2H), 2.36 (m, 2H), 1.74 (m, 4H), 1.25 (t, J=7.2 Hz, 4H).

Step 2) ethyl 2-(8-(nitromethyl)-1,4-dioxaspiro[4.5]decan-8-yl)acetate

To a solution of ethyl 2-(1,4-dioxaspiro[4.5]decan-8-ylidene)acetate (157 g, 693.86 mmol) in THF (800 mL) was added nitromethane (55.8 mL, 1.04 mmol) at rt followed by addition of 1M solution of TBAF in THF (763.25 mL, 763.25 mmol) which was added dropwise at rt. The reaction mixture was heated to reflux and stirred for 20 h and then concentrated in vacuo. The residue was diluted in $H_2O$ (800 mL) and extracted with EtOAc (800 mL×3). The combined organic phases were washed with brine (1 L), dried over anhydrous $Na_2SO_4$, filtered and concentrated in vacuo. The residue was purified by silica gel column chromatography (EtOAc/PE (v/v)=1/10) to give the title compound as pale yellow oil (165 g, 82.9%).

$^1$H NMR (600 MHz, $CDCl_3$): δ (ppm) 4.66 (s, 2H), 4.09 (q, J=7.1 Hz, 2H), 3.88 (s, 4H), 2.49 (s, 2H), 1.64 (m, 8H), 1.21 (t, J=7.2 Hz, 4H).

Step 3) 1,4-dioxa-10-aza-dispiro[4.2.4.2]tetradecan-9-one

To a solution of ethyl 2-(8-(nitromethyl)-1,4-dioxaspiro[4.5]decan-8-yl)acetate (109 g, 379.38 mmol) in EtOH (600 mL) was added Raney Ni (10 g). The reaction mixture was stirred at rt under $H_2$ atmosphere for 72 h and filtered. The filter cake was washed with a mixture of DCM and MeOH (1/1 (v/v), 500 mL). The filtrated was concentrated in vacuo and the residue was washed with a mixture of PE and EtOAc (10/1 (v/v), 800 mL) and filtered to give the product as a white solid (67 g, 83.8%).

MS (ESI, pos. ion) m/z: 212.1 [M+H]$^+$;
$^1$H NMR (600 MHz, $CDCl_3$): δ (ppm) 6.60 (s, 1H), 3.95 (s, 4H), 3.20 (s, 2H), 2.23 (s, 2H), 1.72 (m, 4H), 1.65 (m, 4H).

Step 4) 1,4-dioxa-10-aza-dispiro[4.2.4.2]tetradecane

To a suspension of $LiAlH_4$ (21 g, 558.56 mmol) in anhydrous THF (500 mL) was added a solution of 1,4-dioxa-10-aza-dispiro[4.2.4.2]tetradecan-9-one (59 g, 279.28 mmol) in anhydrous THF (400 mL) dropwise at 0° C. for 1 h. The reaction mixture was stirred at reflux for another 2 h, then quenched with water at 0° C. until no bubble escaped and filtered. The filter cake was washed with a mixture of DCM and MeOH (1/1 (v/v), 500 mL). The filtrate was concentrated in vacuo and the residue was purified by silica gel column chromatography (MeOH/DCM (v/v)=1/10) to give the product as a yellow solid (52 g, 94%).

MS (ESI, pos. ion) m/z: 198.2 [M+H]$^+$;
$^1$H NMR (600 MHz, $CDCl_3$): δ (ppm) 3.88 (s, 4H), 2.90 (t, J=7.1 Hz, 2H), 2.65 (s, 3H), 1.56 (ddd, J=29.3, 13.4, 6.9 Hz, 10H).

Step 5) 2-azaspiro[4.5]decan-8-one

To a solution of 1,4-dioxa-10-aza-dispiro[4.2.4.2]tetradecane (10 g, 50.69 mmol) in MeOH (100 mL) was added HCl aqueous solution (2 M, 30 mL, 60 mmol). The reaction mixture was stirred at rt overnight and then concentrated in vacuo. The residue was dissolved in water (100 mL) and adjusted to pH=8 with a saturated $Na_2CO_3$ aqueous solution, then extracted with DCM (200 mL×3). The combined organic phases were washed with brine (200 mL), dried over anhydrous $Na_2SO_4$, then filtered and concentrated in vacuo. The residue was purified by silica gel column chromatography (MeOH/DCM (v/v)=1/7) to give the title compound as a yellow solid (10 g, 100%).

MS (ESI, pos. ion) m/z: 154.2 [M+H]$^+$.

Step 6) tert-butyl 8-oxo-2-azaspiro[4.5]decane-2-carboxylate

To a solution of 2-azaspiro[4.5]decan-8-one (10 g, 65.26 mmol) in a mixture of THF and $H_2O$ (3/1 (v/v), 200 mL) were added $(Boc)_2O$ (28.48 g, 130.53 mmol) and $Na_2CO_3$ (13.83 g, 130.53 mmol). The reaction mixture was stirred at rt for 2 h, quenched with $H_2O$ (200 mL) and extracted with EtOAc (300 mL×3). The combined organic phases were washed with brine (500 mL), dried over $Na_2SO_4$, concentrated in vacuo. The residue was purified by silica gel column chromatography (EtOAc/PE (v/v)=1/10) to give the product as colorless oil (9 g, 54.5%).

MS (ESI, pos. ion) m/z: 198.1 [(M–$C_4H_8$)+H]$^+$.

Step 7) tert-butyl 8-amino-2-azaspiro[4.5]decane-2-carboxylate

To a solution of tert-butyl 5-oxohexahydro-1H-isoindole-2(3H)-carboxylate (9.20 g, 36.31 mmol) in EtOH (290 mL) were added a solution of $NH_3$ in MeOH (7 M, 290 mL, 2030 mmol) and Ti(Oi-Pr)$_4$ (20.64 g, 72.62 mmol). After addition, the reaction mixture was stirred at rt for 6 h and $NaBH_4$ (2.06 g, 54.47 mmol) was added portionwise. After addition, the resulting mixture was stirred at rt for 2 h, quenched with saturated ammonium hydroxide aqueous solution (150 mL), stirred at rt for 15 min and filtered. The filter cake was washed with DCM (150 mL) and the filtrate was concentrated in vacuo. The residue was dissolved in DCM (200 mL) and extracted with water (150 mL×2). The organic phase was washed with brine (100 mL), dried over anhydrous $Na_2SO_4$, concentrated in vacuo. The residue was purified by silica gel column chromatography (EtOAc/PE (v/v)=1/1) to give the product as yellow oil (7.34 g, 79.5%).

MS (ESI, pos. ion) m/z: 255.2 [M+H]$^+$.

Step 8) tert-butyl 8-((2-chloropyrimidin-4-yl)amino)-2-azaspiro[4.5]decane-2-carboxylate To a solution of 2,4-dichloropyrimidine (0.5 g, 3.4 mmol) and tert-butyl 8-amino-2-azaspiro[4.5]decane-2-carboxylate (0.89 g, 3.5 mmol) in EtOH (20 mL) was added $Et_3N$ (0.5 g, 5 mmol). The mixture was stirred at rt for 24 h, then the reaction mixture was concentrated in vacuo and the residue was purified by silica gel column chromatography (EtOAc/PE (v/v)=1/2) to give the product as a white solid (0.4 g, 33%).

MS (ESI, pos. ion) m/z: 367.2 [M+H]$^+$;
$^1$H NMR (600 MHz, $CDCl_3$): δ (ppm) 8.10 (s, 1H), 6.52 (d, J=5.1 Hz, 1H), 5.37 (s, 1H), 3.83 (s, 1H), 3.60-3.29 (m, 2H), 3.14 (m, 2H), 1.94 (m, 2H), 1.73 (m, 2H), 1.70-1.56 (m, 4H), 1.42 (s, 9H), 1.27 (m, 2H).

Step 9) tert-butyl 8-((2-((1-methyl-1H-pyrazol-4-yl)amino)pyrimidin-4-yl)amino)-2-azaspiro[4.5]decane-2-carboxylate To a solution of tert-butyl 8-((2-chloropyrimidin-4-yl)amino)-2-azaspiro[4.5]decane-2-carboxylate (0.4 g, 1.09 mmol) and 1-methyl-1H-pyrazol-4-amine (0.16 g, 1.64 mmol) in n-BuOH (5 mL) was added DIPEA (0.28 g, 2.18 mmol). The mixture was stirred at 150° C. for 16 h then concentrated in vacuo and the residue was purified by silica gel column chromatography (DCM/MeOH (v/v)=10/1) to give the product as a red solid (0.51 g, 98%).

MS (ESI, pos. ion) m/z: 428.1 [M+H]$^+$;

$^1$H NMR (400 MHz, CDCl$_3$): δ (ppm) 7.62 (m, 2H), 6.15 (s, 1H), 4.11 (m, 1H), 3.87 (s, 3H), 3.38 (m, 2H), 3.21-3.05 (m, 2H), 1.98 (m, 2H), 1.73 (m, 4H), 1.54 (m, 4H), 1.46 (s, 9H).

Step 10) N$^2$-(1-methyl-1H-pyrazol-4-yl)-N$^4$-(2-azaspiro[4.5]decan-8-yl)pyrimidine-2,4-diamine To a solution of tert-butyl 8-((2-((1-methyl-1H-pyrazol-4-yl)amino)pyrimidin-4-yl)amino)-2-azaspiro[4.5]decane-2-carboxylate (0.51 g, 1.19 mmol) in DCM (10 mL) was added a solution of HCl in EtOAc (5 mL, 2.83 M) and the mixture was stirred at rt for 16 h. The reaction mixture was diluted with water (10 mL) and adjusted to pH=8 with saturated Na$_2$CO$_3$ solution, then extracted with DCM (20 mL×3), dried over anhydrous Na$_2$SO$_4$, filtered and concentrated in vacuo. The residue was purified by silica gel column chromatography (DCM/MeOH (v/v)=10/1) to give the product as a yellow solid (0.17 g, 44%).

MS (ESI, pos. ion) m/z: 328.2 [M+H]$^+$;

$^1$H NMR (400 MHz, DMSO-d$_6$): δ (ppm) 8.72 (s, 1H), 7.74 (d, J=19.2 Hz, 2H), 6.96 (s, 1H), 5.81 (d, J=5.8 Hz, 1H), 4.52 (m, 2H), 3.77 (s, 3H), 3.17 (m, 2H), 3.00 (m, 2H), 1.87 (m, 2H), 1.73-1.56 (m, 4H), 1.43 (m, 2H), 1.37-1.19 (m, 2H).

Example 6

3-(8-((2-((1-methyl-1H-pyrazol-4-yl)amino)pyrimidin-4-yl)amino)-2-azaspiro[4.5]decan-2-yl)-3-oxo-propanenitrile

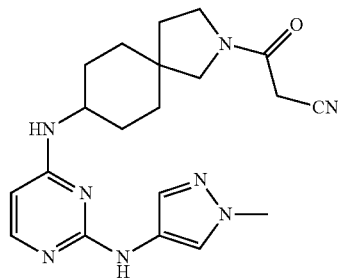 [SMILES: Cn1cc(Nc2nccc(NC3CCC4(CC3)CCN(C(=O)CC#N)C4)n2)cn1]

To a solution of N$^2$-(1-methyl-1H-pyrazol-4-yl)-N$^4$-(2-azaspiro[4.5]decan-8-yl)pyrimidine-2,4-diamine (80 mg, 0.24 mmol) and 2-cyanoacetic acid (22 mg, 0.26 mmol) in DCM (3 mL) and DMF (2 mL) were added EDCI (49 mg, 0.26 mmol) and HOAT (17 mg, 0.12 mmol). The mixture was stirred at 45° C. for 1 h then concentrated in vacuo. The residue was purified by silica gel column chromatography (DCM/MeOH (v/v)=10/1) to give the product as a yellow solid (13 mg, 13%).

MS (ESI, pos. ion) m/z: 395.1 [M+H]$^+$;

$^1$H NMR (400 MHz, CDCl$_3$): δ (ppm) 7.87 (s, 1H), 7.69 (s, 1H), 7.51 (s, 1H), 6.91 (s, 1H), 5.76 (d, J=5.6 Hz, 1H), 4.67 (s, 1H), 3.87 (s, 3H), 3.73 (s, 1H), 3.58 (m, 2H), 3.49-3.31 (m, 4H), 2.04 (m, 2H), 1.88 (m, 4H), 1.69 (m, 2H), 1.53 (m, 2H).

Example 7

5-methyl-N$^2$-(1-methyl-1H-pyrazol-4-yl)-N$^4$-(2-azaspiro[4.4]nonan-4-yl)pyrimidine-2,4-diamine

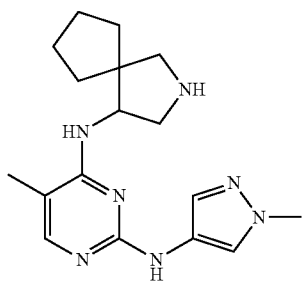

Step 1) 2-benzyl-2-azaspiro[4.4]nonan-4-ol

To a solution of 2-benzyl-2-azaspiro[4.4]nonane-1,4-dione (10.00 g, 41.10 mmol) in THF (240 mL) was added LiAlH$_4$ (3.12 g, 80.20 mmol) portionwise at 0° C. After addition, the reaction mixture was stirred at 85° C. for 1 hour, then cooled down to 0° C. and quenched carefully with water (3.12 mL) and 15% KOH aqueous solution (3.12 mL) followed by another water (9.36 mL). After that, anhydrous MgSO$_4$ (20 g) was added to the above mixture and stirred at rt for 15 min, then filtered through a pad of Celite. The filtrate was extracted with DCM (100 mL×3) and then the separated organic layer was concentrated in vacuo. The residue was purified by silica gel column chromatography (DCM/MeOH (v/v)=100/1 to 5/1) to give the title compound as yellow oil (8.89 g, 93.5%).

MS (ESI, pos. ion) m/z: 232.2 [M+H]$^+$;

$^1$H NMR (600 MHz, CDCl$_3$): δ (ppm) 7.35 (dt, J=14.9, 7.5 Hz, 4H), 7.28 (m, 1H), 3.81 (dd, J=4.4, 1.9 Hz, 1H), 3.73 (s, 2H), 2.96 (m, 1H), 2.78 (d, J=9.4 Hz, 1H), 2.74 (dd, J=10.4, 1.6 Hz, 1H), 2.46 (d, J=9.3 Hz, 1H), 1.96 (m, 1H), 1.64 (m, 3H), 1.56 (m, 3H), 1.45 (m, 1H).

Step 2) 2-azaspiro[4.4]nonan-4-ol

To a solution of 2-benzyl-2-azaspiro[4.4]nonan-4-ol (10.37 g, 44.83 mmol) in MeOH (150 mL) was added Pd/C (10%, 1.1 g) and the suspension was stirred at 45° C. under a H$_2$ atmosphere overnight. The resulting reaction mixture was filtered and the filter cake was washed with EtOAc (50 mL×3). The filtrate was concentrated in vacuo to give the product as yellow oil (7.12 g, 100%).

MS (ESI, pos. ion) m/z: 142.2 [M+H]$^+$;

$^1$H NMR (600 MHz, CDCl$_3$): δ (ppm) 3.83 (d, J=2.8 Hz, 1H), 3.22 (dd, J=12.1, 4.3 Hz, 1H), 2.99 (m, 2H), 2.84 (m, 2H), 1.951 (m, 1H), 1.66 (m, 4H), 1.48 (m, 2H), 1.40 (m, 1H).

Step 3) tert-butyl 4-hydroxy-2-azaspiro[4.4]nonane-2-carboxylate

To a solution of 2-azaspiro[4.4]nonan-4-ol (7.12 g, 50.42 mmol) in THF (100 mL) were added a solution of Na$_2$CO$_3$ (10.69 g, 100.84 mmol) in water (30 mL) and (Boc)$_2$O (22 g, 100.84 mmol). After addition, the reaction mixture was stirred at rt for 4 h and then concentrated in vacuo. The residue was diluted with water (200 mL) and extracted with EtOAc (300 mL×3). The combined organic phases were washed with brine (300 mL), dried over anhydrous $Na_2SO_4$, then filtered and concentrated in vacuo. The residue was purified by silica gel column chromatography (EtOAc/PE (v/v)=1/20 to 1/2) to give the product as colorless oil (11.37 g, 93.4%).

MS (ESI, pos. ion) m/z: 186.2 $[(M-C_4H_8)+H]^+$;
$^1$H NMR (400 MHz, $CDCl_3$): δ (ppm) 3.87 (dd, J=4.3, 1.6 Hz, 1H), 3.53 (dd, J=12.0, 4.3 Hz, 1H), 3.36 (dd, J=12.0, 1.6 Hz, 1H), 3.27 (q, J=10.4 Hz, 2H), 1.87 (m, 3H), 1.67 (m, 4H), 1.47 (s, 10H).

Step 4) tert-butyl 4-oxo-2-azaspiro[4.4]nonane-2-carboxylate

To a solution of tert-butyl 4-hydroxy-2-azaspiro[4.4]nonane-2-carboxylate (10.87 g, 45.04 mmol) in DCM (200 mL) were added 4 Å molecular sieve (20.00 g) followed by PCC (24.27 g, 112.6 mmol) slowly and the mixture was stirred at rt overnight. The resulting mixture was filtered and the filter cake was washed with EtOAc (50 mL×3). The filtrate was concentrated in vacuo and the residue was purified by silica gel column chromatography (EtOAc/PE (v/v)=1/50 to 1/10) to give the product as a white solid (8.56 g, 79.4%).

MS (ESI, pos. ion) m/z: 184.1 $[M-C_4H_8+H]^+$;
$^1$H NMR (600 MHz, $CDCl_3$): δ (ppm) 3.84 (br. s, 2H), 3.58 (br. s, 2H), 1.90 (br. s, 2H), 1.80 (m, 2H), 1.71 (m, 2H), 1.62 (br. s, 2H), 1.50 (s, 9H).

Step 5) tert-butyl 4-amino-2-azaspiro[4.4]nonane-2-carboxylate

To a solution of tert-butyl 4-oxo-2-azaspiro[4.4]nonane-2-carboxylate (8.56 g, 35.77 mmol) in ammonia (7M in methanol, 100 mL) was added $Ti(Oi-Pr)_4$ (22.37 g, 78.6 mmol) and the reaction mixture was stirred at rt overnight. Then $NaBH_4$ (2.71 g, 71.54 mmol) was added portion-wise and the resulting mixture was stirred at rt for another 2 h and concentrated in vacuo. The residue was purified by silica gel column chromatography (DCM/MeOH (v/v)=10/1) to give the product as yellow oil (5 g, 58%).

MS (ESI, pos. ion) m/z: 185.2 $[(M-C_4H_8)+H]^+$;
$^1$H NMR (600 MHz, DMSO-$d_6$): δ (ppm) 3.13 (dd, J=10.1, 4.5 Hz, 1H), 3.02 (m, 2H), 2.72 (dt, J=20.9, 5.2 Hz, 1H), 2.51 (m, 1H), 2.27 (s, 3H), 1.72 (m, 1H), 1.54 (m, 5H), 1.39 (dd, J=12.7, 4.5 Hz, 10H), 1.26 (m, 1H).

Step 6) tert-butyl 4-((2-chloro-5-methylpyrimidin-4-yl)amino)-2-azaspiro[4.4]nonane-2-carboxylate To a solution of 2,4-dichloro-5-methylpyrimidine (0.5 g, 3.07 mmol) and tert-butyl 4-amino-2-azaspiro[4.4]nonane-2-carboxylate (0.77 g, 3.22 mmol) in EtOH (15 mL) was added $Et_3N$ (0.62 g, 6.13 mmol) and the mixture was stirred at rt for 24 h, then concentrated in vacuo. The residue was purified by silica gel column chromatography (PE/EtOAc (v/v)=2/1) to give the product as colourless oil (0.23 g, 21%).

MS (ESI, pos. ion) m/z: 367.3 $[M+H]^+$;
$^1$H NMR (400 MHz, $CDCl_3$) δ (ppm) 7.85 (s, 1H), 4.62 (d, J=11.7 Hz, 2H), 3.75 (s, 1H), 3.30 (d, J=10.8 Hz, 2H), 2.01 (s, 3H), 1.75-1.58 (m, 8H), 1.47 (s, 9H).

Step 7) tert-butyl 4-((5-methyl-2-((1-methyl-1H-pyrazol-4-yl)amino)pyrimidin-4-yl)amino)-2-azaspiro[4.4]nonane-2-carboxylate To a solution of tert-butyl 4-((2-chloro-5-methylpyrimidin-4-yl)amino)-2-azaspiro[4.4]nonane-2-carboxylate (0.35 g, 0.95 mmol) and 1-methyl-1H-pyrazol-4-amine (0.14 g, 1.43 mmol) in n-BuOH (5 mL) was added DIPEA (0.25 g, 1.9 mmol). The reaction mixture was stirred at 150° C. for 16 h then concentrated in vacuo. The residue was purified by silica gel column chromatography (DCM/MeOH (v/v)=10/1) to give the product as black oil (0.45 g, 86%).

MS (ESI, pos. ion) m/z: 428.4 $[M+H]^+$;
$^1$H NMR (400 MHz, $CDCl_3$): δ (ppm) 7.64 (s, 1H), 7.49 (s, 1H), 7.11 (s, 1H), 6.96 (s, 1H), 4.73 (s, 1H), 4.54 (m, 2H), 3.76 (s, 3H), 3.70 (s, 1H), 3.38-3.29 (m, 2H), 1.94 (s, 3H), 1.71-1.58 (m, 8H), 1.47 (s, 9H).

Step 8) 5-methyl-$N^2$-(1-methyl-1H-pyrazol-4-yl)-$N^4$-(2-azaspiro[4.4]nonan-4-yl)pyrimidine-2,4-diamine To a solution of tert-butyl 4-((5-methyl-2-((1-methyl-1H-pyrazol-4-yl)amino)pyrimidin-4-yl)amino)-2-azaspiro[4.4]nonane-2-carboxylate (0.35 g, 0.82 mmol) in DCM (10 mL) was added a solution of HCl in EtOAc (2.83 M, 5 mL) and the reaction mixture was stirred at rt for 16 h then added water (10 mL). The resulting mixture was adjusted to pH=8 with a saturated $Na_2CO_3$ aqueous solution, then extracted with DCM (20 mL×3). The combined organic layers were washed with brine dried over anhydrous $Na_2SO_4$, filtered and concentrated in vacuo. The residue was purified by silica gel column chromatography (DCM/MeOH (v/v)=10/1) to give the product as a yellow solid (0.13 g, 48.5%).

MS (ESI, pos. ion) m/z: 328.3 $[M+H]^+$;
$^1$H NMR (400 MHz, $CDCl_3$): δ (ppm) 7.72 (s, 1H), 7.68 (s, 1H), 7.47 (s, 1H), 6.52 (s, 1H), 4.63 (m, 1H), 4.54-4.47 (m, 1H), 3.86 (s, 3H), 3.43 (dd, J=11.2, 6.2 Hz, 1H), 2.89 (d, J=5.1 Hz, 1H), 2.85 (m, 1H), 1.93 (s, 3H), 1.65 (m, 8H).

Example 8

3-(4-((5-methyl-2-((1-methyl-1H-pyrazol-4-yl)amino)pyrimidin-4-yl)amino)-2-azaspiro[4.4]nonan-2-yl)-3-oxopropanenitrile

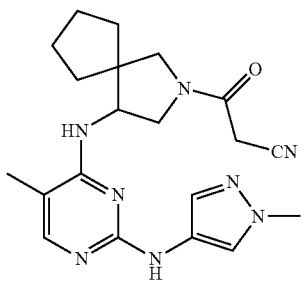

To a solution of 5-methyl-$N^2$-(1-methyl-1H-pyrazol-4-yl)-$N^4$-(2-azaspiro[4.4]nonan-4-yl)pyrimidine-2,4-diamine (130 mg, 0.39 mmol) and 2-cyanoacetic acid (36 mg, 0.42 mmol) in a mixture of DCM (5 mL) and DMF (2 mL) were added $Et_3N$ (80 mg, 0.79 mmol) and HATU (0.3 g, 0.79 mmol) and the reaction mixture was stirred at rt for 1 h, then concentrated in vacuo. The residue was purified by silica gel column chromatography (DCM/MeOH (v/v)=10/1) to give the product as a yellow solid (0.11 g, 70%).

MS (ESI, pos. ion) m/z: 395.3 $[M+H]^+$;
$^1$H NMR (400 MHz, DMSO): δ (ppm) 8.81 (s, 1H), 7.78 (d, J=4.0 Hz, 1H), 7.65 (s, 1H), 7.43 (s, 1H), 6.48 (s, 1H), 4.85-

4.72 (m, 1H), 4.11 (m, 1H), 3.93-3.87 (m, 1H), 3.78 (s, 3H), 3.44 (m, 2H), 3.17 (s, 2H), 1.95 (s, 3H), 1.76-1.42 (m, 8H).

Example 9

5-methyl-N²-(1-methyl-1H-pyrazol-4-yl)-N⁴-(2-azaspiro[4.5]decan-8-yl)pyrimidine-2,4-diamine

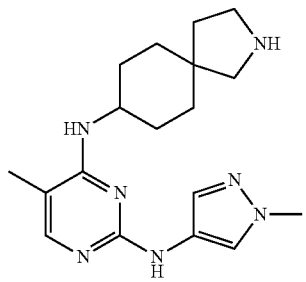

Step 1) tert-butyl 8-((2-chloro-5-methylpyrimidin-4-yl)amino)-2-azaspiro[4.5]decane-2-carboxylate To a solution of 2,4-dichloro-5-methylpyrimidine (585.5 g, 3.59 mmol) and tert-butyl 8-amino-2-azaspiro[4.5]decane-2-carboxylate (1.08 g, 4.24 mmol) in EtOH (10 mL) was added Et₃N (722.3 mg, 7.14 mmol) and the reaction mixture was stirred at rt for 48 h then concentrated in vacuo. The residue was purified by silica gel column chromatography (EtOAc/PE (v/v)=1/2) to give the title compound as yellow oil (1.04 g, 76.0%).

MS (ESI, pos. ion) m/z: 381.2 [M+H]⁺.

Step 2) tert-butyl 8-((5-methyl-2-((1-methyl-1H-pyrazol-4-yl)amino)pyrimidin-4-yl)amino)-2-azaspiro[4.5]decane-2-carboxylate To a suspension of tert-butyl 8-((2-chloro-5-methylpyrimidin-4-yl)amino)-2-azaspiro[4.5]decane-2-carboxylate (1.04 g, 2.73 mmol) and 1-methyl-1H-pyrazol-4-amine hydrochloride (365.4 mg, 2.73 mmol) in n-BuOH (8 mL) was added DIPEA (1.06 g, 8.20 mmol) and the reaction mixture was stirred in a sealed tube at 150° C. overnight then concentrated in vacuo. The residue was purified by silica gel column chromatography (MeOH/DCM (v/v)=1/100) to give the title compound as yellow oil (1.21 g, 100%).

MS (ESI, pos. ion) m/z: 442.4 [M+H]⁺.

Step 3) 5-methyl-N²-(1-methyl-1H-pyrazol-4-yl)-N⁴-(2-azaspiro[4.5]decan-8-yl) pyrimidine-2,4-diamine To a solution of tert-butyl 8-((5-methyl-2-((1-methyl-1H-pyrazol-4-yl)amino)pyrimidin-4-yl)amino)-2-azaspiro[4.5]decane-2-carboxylate (290 mg, 0.66 mmol) in DCM (10 mL) was added a solution of HCl in EtOAc (10 mL, 40 mmol) and the reaction mixture was stirred at rt overnight and then concentrated in vacuo. The residue was dissolved in water (30 mL) and adjusted to pH=10 with a saturated Na₂CO₃ aqueous solution, then extracted with DCM (100 mL×3). The combined organic phases were washed with brine (100 mL), dried over anhydrous Na₂SO₄, then filtered and concentrated in vacuo. The residue was purified by silica gel column chromatography (MeOH/DCM (v/v)=1/5) to give the title compound as a beige solid (210 mg, 93.2%).

MS (ESI, pos. ion) m/z: 342.2 [M+H]⁺;

¹H NMR (400 MHz, CDCl₃): δ (ppm) 7.74 (s, 1H), 7.69 (s, 1H), 7.52 (d, J=4.1 Hz, 1H), 7.37 (m, 1H), 6.54 (br. s, 1H), 4.34 (m, 1H), 4.03 (m, 2H), 3.90 and 3.89 (s, 3H), 3.00 (dt, J=16.1, 7.0 Hz, 2H), 2.10 (m, 2H), 1.94 (s, 3H), 1.69 (m, 2H), 1.63 (m, 3H), 1.56 (m, 2H), 1.45 (t, J=3.2 Hz, 1H).

Example 10

3-(8-((5-methyl-2-((1-methyl-1H-pyrazol-4-yl)amino)pyrimidin-4-yl)amino)-2-azaspiro[4.5]decan-2-yl)-3-oxopropanenitrile

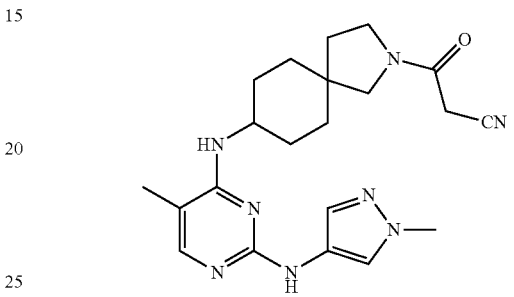

To a solution of 5-methyl-N²-(1-methyl-1H-pyrazol-4-yl)-N⁴-(2-azaspiro[4.5]decan-8-yl)pyrimidine-2,4-diamine (186 mg, 0.545 mmol), 2-cyanoacetic acid (48.4 mg, 0.569 mmol) in a mixture of DCM (32 mL) and DMF (8 mL) were added HATU (423.4 mg, 1.087 mmol) and Et₃N (0.21 g, 2.075 mmol). After addition, the reaction mixture was stirred at rt for 2 h, quenched with H₂O (30 mL) and extracted with DCM (100 mL×3). The combined organic phases were washed with brine (100 mL), dried over anhydrous Na₂SO₄ and concentrated in vacuo. The residue was purified by silica gel column chromatography (DCM/MeOH (v/v)=10/1) to give the title compound as a beige solid (170 mg, 76.4%).

MS (ESI, pos. ion) m/z: 409.2 [M+H]⁺;

¹H NMR (400 MHz, CDCl₃): δ (ppm) 7.71 (d, J=2.9 Hz, 1H), 7.67 (s, 1H), 7.57 (s, 1H), 6.50 (br. s, 1H), 4.32 (m, 1H), 4.04 (m, 2H), 3.89 (s, 3H), 3.63 (m, 3H), 3.48 (s, 1H), 3.45 (s, 3H), 2.14 (m, 2H), 2.04 (m, 2H), 1.95 (d, J=2.6 Hz, 2H), 1.73 (m, 4H).

Example 11

5-chloro-N²-(1-methyl-1H-pyrazol-4-yl)-N⁴-(octahydrocyclopenta[c]pyrrol-5-yl)pyrimidine-2,4-diamine

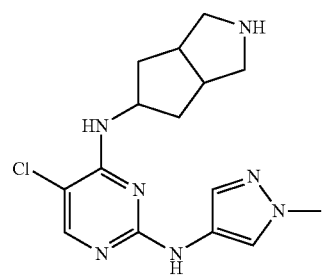 [SMILES: Cn1cc(Nc2ncc(Cl)c(NC3CC4CNCC4C3)n2)cn1]

Step 1) tert-butyl 3a,4,7,7a-tetrahydro-1H-isoindole-2(3H)-carboxylate

To a suspension of LAH (22.80 g, 600 mmol) in THF (600 mL) at 0° C. was added tetrahydrophthalimide (39.45 g, 260.9 mmol) portionwise. After addition, the reaction mixture was stirred at 60° C. for 18 h, then cooled down to 0° C. and quenched carefully with water (25 mL), followed by 15% KOH aqueous solution (25 mL) and another 75 mL of water. The resulting mixture was stirred at rt for 1 h and filtered through a pad of Celite, then washed with DCM (500 mL). The filtrate was concentrated in vacuo to give isoindole as yellow oil, which was used in the next step without purification.

Accordingly, the isoindole in DCM (300 mL) was treated with Et$_3$N (39.61 g, 391.4 mmol) and (Boc)$_2$O (68.32 g, 313.1 mmol) at 0° C. for 0.5 h and then warmed to rt and stirred for another 21 h. The resulting mixture was concentrated in vacuo and the residue was dissolved in EtOAc (600 mL), then washed with citric acid aqueous solution (1 M, 2×130 mL), followed by saturated NaHCO$_3$ (2×130 mL) and brine (250 mL). The combined organic layers were dried over anhydrous Na$_2$SO$_4$ then filtered and concentrated in vacuo. The residue was purified by silica gel column chromatography (EtOAc/PE (v/v)=1/5) to give the title compound as orange red oil (45.00 g, 77.3%).

MS (ESI, pos. ion) m/z: 168.2 [(M–C$_4$H$_8$)+H]$^+$;
$^1$H NMR (400 MHz, CDCl$_3$): δ (ppm) 5.64 (s, 2H), 3.40 (m, 2H), 3.16 (m, 1H), 3.07 (m, 1H), 2.25 (m, 4H), 1.90 (m, 2H), 1.46 (s, 9H).

Step 2) 2,2'-(1-(tert-butoxycarbonyl)pyrrolidine-3,4-diyl)diacetic acid

To a solution of tert-butyl 3a,4,7,7a-tetrahydro-1H-isoindole-2(3H)-carboxylate (4.91 g, 22 mmol) and (NH$_4$)$_2$SO$_4$ (1.55 g, 12 mmol) in H$_2$O (40 mL) was added KMnO$_4$ (8.20 g, 52 mmol) portionwise at 5° C. in 0.5 h. The reaction mixture was stirred for 6 h, then filtered and washed with H$_2$O (40 mL×3). The filtrate was extracted with CH$_2$Cl$_2$ (40 mL×3) and the aqueous layer was adjusted to pH=2-3 with 3 M HCl aqueous solution, then extracted with EtOAc (50 mL×3). The combined EtOAc phases were washed with brine (50 mL×3), dried over Na$_2$SO$_4$, filtered and concentrated in vacuo to give the title compound as a pale yellow solid (4.52 g, 71.5%).

MS (ESI, pos. ion) m/z: 232.2 [(M–C$_4$H$_8$)+H]$^+$;
$^1$H NMR (400 MHz, CDCl$_3$): δ (ppm) 3.53 (m, 2H), 3.04 (m, 2H), 2.80 (m, 2H), 2.44 (m, 4H), 1.43 (s, 9H).

Step 3) tert-butyl 5-oxohexahydrocyclopenta[c]pyrrole-2(1H)-carboxylate

To a suspension of 2,2'-(1-(tert-butoxycarbonyl)pyrrolidine-3,4-diyl)diacetic acid (3.40 g, 11.8 mmol) in Ac$_2$O (21 mL) was added NaOAc (0.78 g, 9.5 mmol) and the reaction mixture was stirred at 120° C. for 3 h. After that, the resulting mixture was cooled down to rt then filtered and washed with EtOAc (20 mL×2). The filtrate was concentrated in vacuo and the residue was purified by silica gel chromatography (EtOAc/PE (v/v)=1/4) to give the title compound as orange yellow oil (1.38 g, 55.0%).

MS (ESI, pos. ion) m/z: 170.2 [(M–C$_4$H$_8$)+H]$^+$;
$^1$H NMR (400 MHz, CDCl$_3$): δ (ppm) 3.69 (m, 2H), 3.00 (m, 4H), 2.61 (dd, J=8.2, 18.4 Hz, 2H), 2.29 (dd, J=5.8, 18.4 Hz, 2H), 1.43 (s, 9H).

Step 4) tert-butyl 5-(benzylamino)hexahydrocyclopenta[c]pyrrole-2(1H)-carboxylate To a solution of tert-butyl 5-oxohexahydrocyclopenta[c]pyrrole-2(1H)-carboxylate (9.57 g, 42.5 mmol) in DCM (170 mL) were added BnNH$_2$ (4.56 g, 42.5 mmol) and AcOH (2.55 g, 42.5 mmol) at 0° C. and the reaction mixture was stirred at 0° C. for 0.5 h. Then NaBH(OAc)$_3$ (18.00 g, 85.0 mmol) was added to the above mixture and the resulting mixture was stirred at rt for another 20 h, then quenched with saturated NaHCO$_3$ solution (142 mL), and extracted with DCM (250 mL×3). The combined organic phases were washed with brine (250 mL×3), dried over anhydrous Na$_2$SO$_4$, concentrated in vacuo. The residue was purified by silica gel column chromatography (EtOAc) to give the title compound as a yellow solid (7.44 g, 55.3%).

MS (ESI, pos. ion) m/z: 317.3 [M+H]$^+$;
$^1$H NMR (400 MHz, CDCl$_3$): δ (ppm) 7.31 (m, 4H), 7.26 (m, 1H), 3.79 (s, 2H), 3.46 (m, 2H), 3.28 (d, J=8.8 Hz, 1H), 3.16 (tt, J=9.6, 6.9 Hz, 1H), 2.55 (m, 2H), 2.28 (s, 2H), 2.22 (m, 2H), 1.45 (s, 9H), 1.31 (m, 2H).

Step 5) tert-butyl 5-aminohexahdrocyclopenta[c]pyrrole-2(1H)-carboxylate

To a solution of tert-butyl 5-(benzylamino)hexahydrocyclopenta[c]pyrrole-2(1H)-carboxylate (6.50 g, 20.5 mmol) and AcOH (1.23 g, 20.5 mmol) in MeOH (150 mL) was added Pd(OH)$_2$/C (10% wt, 1.00 g), and the suspension was stirred at 40° C. under H$_2$ atmosphere overnight. The mixture was filtered through a pad of Celite and then concentrated in vacuo. The residue was dissolved in saturated NaHCO$_3$ solution (70 mL) and extracted with DCM (100 mL×3). The combined organic phases were washed with brine (100 mL×3), dried over anhydrous Na$_2$SO$_4$, then filtered and concentrated in vacuo to give the title compound as a yellow solid (4.00 g, 86.2%).

MS (ESI, pos. ion) m/z: 227.2 [M+H]$^+$;
$^1$H NMR (400 MHz, CDCl$_3$): δ (ppm) 3.44 (m, 2H), 3.31 (m, 3H), 2.98 (br. s, 2H), 2.57 (m, 2H), 2.22 (dt, J=14.0, 7.2 Hz, 2H), 1.44 (s, 9H).

Step 6) tert-butyl 5-((2,5-dichloropyrimidin-4-yl)amino)hexahydrocyclopenta[c]pyrrole-2(1H)-carboxylate To a solution of 2,4,5-trichloropyrimidine (1.46 g, 7.96 mmol) and tert-butyl 5-aminohexahydrocyclopenta[c]pyrrole-2(1H)-carboxylate (3.11 g, 13.74 mmol) in EtOH (60 mL) was added Et$_3$N (2.21 g, 21.84 mmol) and the reaction mixture was stirred at rt overnight and then concentrated in vacuo. The residue was dissolved in a mixture of EtOAc (50 mL) and water (50 mL), and extracted with EtOAc (150 mL×3). The combined organic phases were washed with brine (150 mL), dried over anhydrous Na$_2$SO$_4$, then concentrated in vacuo. The residue was purified by silica gel column chromatography (EtOAc/PE (v/v)=1/5) to give the title compound as a pale yellow solid (2.97 g, 100%).

MS (ESI, pos. ion) m/z: 373.0 [M+H]$^+$.

Step 7) tert-butyl 5-((5-chloro-2-((1-methyl-1H-pyrazol-4-yl)amino)pyrimidin-4-yl)amino)hexahydrocyclopenta[c]pyrrole-2(1H)-carboxylate To a suspension of tert-butyl 5-((2,5-dichloropyrimidin-4-yl)amino)hexahydrocyclopenta[c]pyrrole-2(1H)-carboxylate (579.6 mg, 1.55 mmol) and 1-methyl-1H-pyrazol-4- amine hydrochloride (213.0 mg, 1.34 mmol) in n-BuOH (5 mL) was added N-ethyldiisopropylamine (668.2 mg, 5.17 mmol). The reaction mixture was stirred at 150° C. in a sealed tube overnight and concentrated in vacuo. The residue was purified by silica gel column chromatography (MeOH/DCM (v/v)=1/80) to give the title compound as a beige solid (672.6 mg, 100%).

MS (ESI, pos. ion) m/z: 434.3 [M+H]$^+$.

Step 8) 5-chloro-N$^2$-(1-methyl-1H-pyrazol-4-yl)-N$^4$-(octahydrocyclopenta[c]pyrrol-5-yl)pyrimidine-2,4-diamine To a solution of tert-butyl 5-((5-chloro-2-((1-methyl-1H-pyrazol-4-yl)amino)pyrimidin-4-yl)amino)hexahydrocyclopenta[c]pyrrole-2(1H)-carboxylate (672.6 mg, 1.55 mmol) in DCM (10 mL) was added a solution of HCl in EtOAc (10 mL, 40 mmol). The reaction mixture was stirred at rt overnight and concentrated in vacuo. The residue was dissolved in water (30 mL) and adjusted to pH=10 with saturated Na$_2$CO$_3$ aqueous solution, then extracted with DCM (250 mL×3). The combined organic phases were washed with brine (250 mL), dried over anhydrous Na$_2$SO$_4$, then filtered and concentrated in vacuo. The residue was purified by silica gel column chromatography (MeOH/DCM (v/v)=1/5) to give the title compound as a beige solid (410 mg, 79.2%).

MS (ESI, pos. ion) m/z: 334.2 [M+H]$^+$;
$^1$H NMR (400 MHz, DMSO-d$_6$): δ (ppm) 10.01 (s, 1H), 7.88 (s, 1H), 7.66 (s, 1H), 7.55 (s, 1H), 6.70 (s, 1H), 5.54 (s, 1H), 4.40 (m, 1H), 3.89 (s, 3H), 3.39 (d, J=11.6 Hz, 2H), 3.29 (m, 2H), 2.94 (m, 2H), 2.51 (m, 2H), 1.83 (m, 2H).

Example 12

3-(5-((5-chloro-2-((1-methyl-1H-pyrazol-4-yl)amino)pyrimidin-4-yl)amino)hexahydrocyclopenta[c]pyrrol-2(1H)-yl)-3-oxopropanenitrile

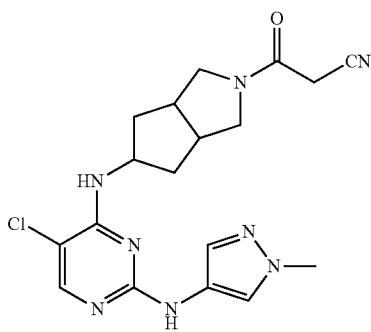 [SMILES: Cn1cc(Nc2ncc(Cl)c(NC3CC4CN(C(=O)CC#N)CC4C3)n2)cn1]

To a solution of 5-chloro-N$^2$-(1-methyl-1H-pyrazol-4-yl)-N$^4$-(octahydrocyclopenta[c]pyrrol-5-yl)pyrimidine-2,4-diamine (401.6 mg, 1.20 mmol), 2-cyanoacetic acid (110.3 mg, 1.30 mmol) in a mixture of DCM and DMF (4/1 (v/v)), 50 mL) were added HATU (555.6 mg, 1.46 mmol) and Et$_3$N (375.6 mg, 3.71 mmol). The reaction mixture was stirred at rt overnight, then quenched with H$_2$O (30 mL) and extracted with DCM (100 mL×3). The combined organic phases were washed with brine (100 mL), dried over anhydrous Na$_2$SO$_4$, concentrated in vacuo. The residue was purified by silica gel column chromatography (DCM/MeOH (v/v)=50/1) to give the title compound as a beige solid (350 mg, 72.8%).

MS (ESI, pos. ion) m/z: 401.2 [M+H]$^+$;
$^1$H NMR (400 MHz, CDCl$_3$): δ (ppm) 7.90 (s, 1H), 7.66 (s, 1H), 7.55 (s, 1H), 6.58 (s, 1H), 5.23 (d, J=6.9 Hz, 1H), 4.45 (m, 1H), 3.90 (s, 3H), 3.70 (m, 3H), 3.49 (dd, J=11.6, 7.9 Hz, 1H), 3.45 (s, 2H), 2.88 (m, 1H), 2.79 (m, 1H), 2.55 (m, 2H), 1.46 (m, 2H).

Example 13

5-chloro-N$^2$-(1-methyl-1H-pyrazol-4-yl)-N$^4$-(2-azaspiro[4.5]decan-8-yl)pyrimidine-2,4-diamine (13.3 A and 13.3 B)

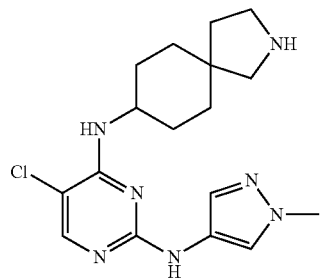 [SMILES: Cn1cc(Nc2ncc(Cl)c(NC3CCC4(CCNC4)CC3)n2)cn1]

Step 1) tert-butyl 8-((2,5-dichloropyrimidin-4-yl)amino)-2-azaspiro[4.5]decane-2-carboxylate To a suspension of 2,4,5-trichloropyrimidine (0.51 g, 2.78 mmol) in EtOH (15 mL) were added tert-butyl 8-amino-2-azaspiro[4.5]decane-2-carboxylate (0.71 g, 2.78 mmol) and Et$_3$N (0.80 mL, 5.56 mmol). The mixture was stirred at 25° C. overnight, and then concentrated in vacuo. The residue was purified by silica gel column chromatography (EA/PE (v/v)=1/1) to afford isomer 13.1 A (R$_f$=0.5, EtOAc/PE (v/v)=1/1) as a white solid 0.32 g and isomer 13.1B (R$_f$=0.4, EtOAc/PE (v/v)=1/1) as a white solid 0.33 g (yield 57% for 13.1 A and 13.1 B).

13.1 A:
MS (ESI, pos. ion) m/z: 345.1 [(M−C$_4$H$_8$)+H]$^+$;
$^1$H NMR (600 MHz, CDCl$_3$): δ (ppm) 8.03 (s, 1H), 5.35 (m, 1H), 4.11-4.02 (m, 1H), 3.43 (t, J=7.1 Hz, 1H), 3.38 (t, J=7.1 Hz, 1H), 3.28 (s, 1H), 3.21 (s, 1H), 2.08-2.00 (m, 2H), 1.73-1.68 (m, 4H), 1.55 (m, 2H), 1.49 and 1.48 (s, 9H), 1.38 (m, 2H).

13.1B:
MS (ESI, pos. ion) m/z: 401.2 [M+H]$^+$;
$^1$H NMR (600 MHz, CDCl$_3$): δ (ppm) 8.03 (s, 1H), 5.37 (d, J=7.7 Hz, 1H), 4.08 (m, 1H), 3.45 (t, J=7.0 Hz, 1H), 3.40 (t, J=7.0 Hz, 1H), 3.20 (s, 1H), 3.12 (s, 1H), 2.01 (m, 2H), 1.79 (m, 2H), 1.66 (m, 2H), 1.63-1.53 (m, 2H), 1.48 (s, 9H), 1.44 (m, 2H).

Step 2) tert-butyl 8-((5-chloro-2-((1-methyl-1H-pyrazol-4-yl)amino)pyrimidin-4-yl)amino)-2-azaspiro[4.5]decane-2-carboxylate (13.2 A)

To a suspension of tert-butyl 8-((2,5-dichloropyrimidin-4-yl)amino)-2-azaspiro[4.5]decane-2-carboxylate (13.1A: 0.16 g, 0.40 mmol) in n-BuOH (2.0 mL) were added 1-methyl-1H-pyrazol-4-amine hydrochloride (0.11 g, 0.80 mmol) and DIPEA (0.21 g, 1.59 mmol). The mixture was stirred in a sealed tube at 150° C. for 12 h and then concentrated in vacuo. The residue was purified by silica gel column chromatography (DCM/MeOH (v/v)=50/1) to afford 13.2A as a light yellow solid (0.14 g, 76%).

MS (ESI, pos. ion) m/z: 462.3 [M+H]$^+$;

$^1$H NMR (600 MHz, CDCl$_3$): δ (ppm) 7.88 (s, 1H), 7.68 (s, 1H), 7.53 (s, 1H), 6.74 (br, 1H), 5.18-5.06 (m, 1H), 4.03-3.93 (m, 1H), 3.90 (s, 3H), 3.44 (t, J=7.1 Hz, 1H), 3.38 (t, J=7.1 Hz, 1H), 3.29 (s, 1H), 3.22 (s, 1H), 2.14-2.05 (m, 2H), 1.73 (m, 4H), 1.49 (m, 11H), 1.42-1.38 (m, 2H).

Step 3) 5-chloro-N$^2$-(1-methyl-1H-pyrazol-4-yl)-N$^4$-(2-azaspiro[4.5]decan-8-yl)pyrimidine-2,4-diamine (13.3 A)

To a suspension of tert-butyl 8-((5-chloro-2-((1-methyl-1H-pyrazol-4-yl)amino) pyrimidin-4-yl)amino)-2-azaspiro[4.5]decane-2-carboxylate (13.2 A: 0.14 g, 0.30 mmol) in DCM (10 mL) was added a solution of HCl in EtOAc (10 mL, 3.5 M). The mixture was stirred at room temperature for 2 h, then concentrated in vacuo. The residue was diluted with DCM (10 mL) and saturated Na$_2$CO$_3$ (10 mL) aqueous solution and then extracted with DCM/MeOH (v/v)=10/1 (30 mL×4). The combined organic layer was dried over anhydrous Na$_2$SO$_4$, then filtered and concentrated in vacuo. The residue was purified by silica gel column chromatography (DCM/2M NH$_3$ in MeOH (v/v)=5/1) to afford 13.3 A as a yellow solid (94 mg, 85%).

MS (ESI, pos. ion) m/z: 362.2 [M+H]$^+$;

$^1$H NMR (600 MHz, DMSO-d$_6$): δ (ppm) 9.03 (br, 1H), 7.85 (s, 1H), 7.73 (s, 1H), 7.46 (s, 1H), 6.63 (s, 1H), 4.11 (br, 1H), 3.98-3.90 (m, 1H), 3.78 (s, 3H), 2.78 (t, J=7.1 Hz, 2H), 2.63 (s, 2H), 1.79 (m, 2H), 1.63 (m, 2H), 1.52-1.39 (m, 6H).

Step 4) tert-butyl 8-((5-chloro-2-((1-methyl-H-pyrazol-4-yl)amino)pyrimidin-4-yl)amino)-2-azaspiro[4.5]decane-2-carboxylate (13.2B)

To a suspension of tert-butyl 8-((2,5-dichloropyrimidin-4-yl)amino)-2-azaspiro[4.5]decane-2-carboxylate (13.1B: 0.16 g, 0.40 mmol) in n-BuOH (2.0 mL) was added 1-methyl-1H-pyrazol-4-amine hydrochloride (0.11 g, 0.80 mmol) and DIPEA (0.21 g, 1.59 mmol). The mixture was stirred in a sealed tube at 150° C. for 12 h then cooled down and concentrated in vacuo. The residue was purified by silica gel column chromatography (DCM/MeOH (v/v)=50/1) to afford 13.2B as a light yellow solid (0.13 g, 70%).

MS (ESI, pos. ion) m/z: 462.3 [M+H]$^+$;

$^1$H NMR (600 MHz, CDCl$_3$): δ (ppm) 7.88 (s, 1H), 7.74-7.63 (m, 1H), 7.57-7.45 (m, 1H), 6.73 (br, 1H), 5.14 (d, J=7.2 Hz, 1H), 3.98 (m, 1H), 3.90 and 3.89 (s, 3H), 3.45 (t, J=7.1 Hz, 1H), 3.41 (t, J=7.0 Hz, 1H), 3.21 (s, 1H), 3.13 (s, 1H), 2.10-2.02 (m, 2H), 1.84-1.77 (m, 2H), 1.74-1.66 (m, 2H), 1.57-1.52 (m, 2H), 1.47 (m, 11H).

Step 5) 5-chloro-N$^2$-(1-methyl-1H-pyrazol-4-yl)-N$^4$-(2-azaspiro[4.5]decan-8-yl) pyrimidine-2,4-diamine (13.3B)

To a suspension of tert-butyl 8-((5-chloro-2-((1-methyl-1H-pyrazol-4-yl)amino)pyrimidin-4-yl)amino)-2-azaspiro[4.5]decane-2-carboxylate (13.2B: 0.13 g, 0.28 mmol) in DCM (10 mL) was added a solution of HCl in EtOAc (10 mL, 3.5 M). The mixture was stirred at room temperature for 1.5 h, then concentrated in vacuo. The residue was diluted with DCM (10 mL) and saturated Na$_2$CO$_3$ (10 mL) and then extracted with DCM/MeOH (v/v)=10/1 (30 mL×3). The combined organic layer was dried over anhydrous Na$_2$SO$_4$, filtered and concentrated in vacuo. The residue was purified by silica gel column chromatography (DCM/2N NH$_3$ in MeOH (v/v)=5/1) to afford 13.3B as a yellow solid (90 mg, 88%).

MS (ESI, pos. ion) m/z: 362.3 [M+H]$^+$;

$^1$H NMR (600 MHz, DMSO-d$_6$): δ (ppm) 9.04 (br, 1H), 7.85 (s, 1H), 7.72 (s, 1H), 7.46 (s, 1H), 6.65 (s, 1H), 3.91 (m, 1H), 3.77 (s, 3H), 2.85 (t, J=7.1 Hz, 2H), 2.54 (s, 2H), 1.82 (m, 2H), 1.62-1.52 (m, 6H), 1.43-1.33 (m, 2H).

Example 14

3-(8-((5-chloro-2-((1-methyl-1H-pyrazol-4-yl)amino)pyrimidin-4-yl)amino)-2-azaspiro[4.5]decan-2-yl)-3-oxopropanenitrile (14A and 14B)

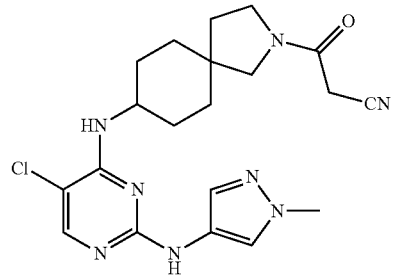 [SMILES: Cn1cc(Nc2ncc(Cl)c(NC3CCC4(CC3)CCN(C(=O)CC#N)C4)n2)cn1]

14A:

To a suspension of 5-chloro-N$^2$-(1-methyl-1H-pyrazol-4-yl)-N$^4$-(2-azaspiro[4.5]decan-8-yl)pyrimidine-2,4-diamine (13.3A: 84 mg, 0.23 mmol) in DCM (10 mL) were added 2-cyanoacetic acid (24 mg, 0.28 mmol), HATU (0.11 g, 0.28 mmol) and Et$_3$N (47 mg, 0.46 mmol). The mixture was stirred at rt for 2 h, and then diluted with DCM (50 mL), washed with water (20 mL) followed by brine (20 mL), dried over anhydrous Na$_2$SO$_4$, then filtered and concentrated in vacuo. The residue was purified by silica gel column chromatography (DCM/MeOH (v/v)=15/1) to afford 14A as a light yellow solid (57 mg, 57%).

MS (ESI, pos. ion) m/z: 429.3 [M+H]$^+$;

$^1$H NMR (600 MHz, CDCl$_3$): δ (ppm) 7.89 (m, 1H), 7.65 (s, 1H), 7.56 (s, 1H), 6.66 (br, 1H), 5.16-5.07 (m, 1H), 4.05-3.94 (m, 1H), 3.90 and 3.89 (s, 3H), 3.63-3.58 (m, 2H), 3.51 (s, 2H), 3.48 (s, 1H), 3.43 (s, 1H), 2.19-2.09 (m, 2H), 1.94-1.89 (m, 1H), 1.84-1.80 (m, 1H), 1.80-1.70 (m, 2H), 1.68-1.63 (m, 2H), 1.61-1.53 (m, 2H).

14B:

To a suspension of 5-chloro-N$^2$-(1-methyl-1H-pyrazol-4-yl)-N$^4$-(2-azaspiro[4.5]decan-8-yl)pyrimidine-2,4-diamine (13.3 B: 90 mg, 0.25 mmol) in DCM (10 mL) were added 2-cyanoacetic acid (25 mg, 0.30 mmol), HATU (0.12 g, 0.30 mmol) and Et$_3$N (50 mg, 0.50 mmol). The mixture was stirred at room temperature for 2 h, and then diluted with DCM (30 mL), and washed with brine (20 mL), dried over anhydrous Na$_2$SO$_4$, then filtered and concentrated in vacuo. The residue was purified by silica gel column chromatography (DCM/MeOH (v/v)=20/1) to afford 14B as a light yellow solid (77 mg, 72%).

MS (ESI, pos. ion) m/z: 429.3 [M+H]$^+$;

$^1$H NMR (600 MHz, CDCl$_3$): δ (ppm) 7.88 (s, 1H), 7.72-7.62 (m, 1H), 7.58-7.46 (m, 1H), 5.15 (s, 1H), 4.03-3.94 (m, 1H), 3.89 and 3.88 (s, 3H), 3.62-3.57 (m, 2H), 3.48 (m, 2H), 3.35 (s, 1H), 3.29 (s, 1H), 2.13-2.03 (m, 2H), 1.98 (t, J=7.1 Hz, 1H), 1.88 (t, J=7.3 Hz, 1H), 1.76-1.66 (m, 2H), 1.61-1.53 (m, 2H), 1.51-1.41 (m, 2H).

Example 15

N$^4$-methyl-N$^2$-(1-methyl-1H-pyrazol-4-yl)-N$^4$-(2-azaspiro[4.5]decan-8-yl)pyrimidine-2,4-diamine

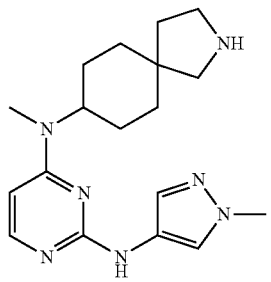 [SMILES: CN(c1ccnc(Nc2cnn(C)c2)n1)C1CCC2(CCNC2)CC1]

Step 1) tert-butyl 8-((2-chloropyrimidin-4-yl)(methyl)amino)-2-azaspiro[4.5]decane-2-carboxylate To a suspension of 4,5-dichloropyrimidine (0.80 g, 5.37 mmol) in EtOH (20 mL) were added tert-butyl 8-(methylamino)-2-azaspiro[4.5]decane-2-carboxylate (1.59 g, 5.91 mmol) and Et$_3$N (1.50 mL, 10.74 mmol). The mixture was stirred at 30° C. overnight and then concentrated in vacuo. The residue was purified by silica gel column chromatography (EA/PE (v/v)=1/1) to give the title compound as a light yellow solid (1.57 g, 76%).

MS (ESI, pos. ion) m/z: 381.3 [M+H]$^+$;
$^1$H NMR (400 MHz, CDCl$_3$): δ (ppm) 8.02 (d, J=6.2 Hz, 1H), 6.31 (d, J=5.5 Hz, 1H), 4.88-4.20 (m, 1H), 3.49-3.37 (m, 2H), 3.18-3.08 (m, 2H), 2.94 (s, 3H), 1.86-1.77 (m, 2H), 1.76-1.63 (m, 8H), 1.48 (s, 9H).

Step 2) tert-butyl 8-(methyl(2-((1-methyl-1H-pyrazol-4-yl)amino)pyrimidin-4-yl)amino)-2-azaspiro[4.5]decane-2-carboxylate To a suspension of tert-butyl 8-((2-chloropyrimidin-4-yl)(methyl)amino)-2-azaspiro[4.5]decane-2-carboxylate (0.30 g, 0.79 mmol) in n-BuOH (4.0 mL) were added 1-methyl-1H-pyrazol-4-amine hydrochloride (0.21 g, 1.58 mmol) and DIPEA (0.41 g, 3.15 mmol). The mixture was stirred in a sealed tube at 150° C. overnight. The mixture was concentrated in vacuo. The residue was purified by silica gel column chromatography (DCM/MeOH (v/v)=50/1) to give the title compound as a yellow solid (0.22 g, 63%).

MS (ESI, pos. ion) m/z: 442.4 [M+H]$^+$.

Step 3) N$^4$-methyl-N$^2$-(1-methyl-1H-pyrazol-4-yl)-N$^4$-(2-azaspiro[4.5]decan-8-yl)pyrimidine-2,4-diamine To a suspension of tert-butyl 8-(methyl(2-((1-methyl-1H-pyrazol-4-yl)amino)pyrimidin-4-yl)amino)-2-azaspiro[4.5]decane-2-carboxylate (0.22 g, 0.50 mmol) in DCM (10 mL) was added a solution of HCl in EtOAc (10 mL, 3.5 M). The mixture was stirred at room temperature for 1.5 h, then concentrated in vacuo. The residue was diluted with DCM (10 mL) and saturated Na$_2$CO$_3$ (10 mL) and then extracted with DCM/MeOH (v/v)=10/1 (30 mL×4). The combined organic layers was dried over anhydrous Na$_2$SO$_4$, then filtered and concentrated in vacuo. The residue was purified by silica gel column chromatography (DCM/2M NH$_3$ in MeOH (v/v)=5/1) to give the title compound as a yellow solid (0.12 g, 70%).

MS (ESI, pos. ion) m/z: 342.3 [M+H]$^+$;
$^1$H NMR (600 MHz, DMSO-d$_6$): δ (ppm) 8.78 (br, 1H), 7.86 (d, J=5.9 Hz, 1H), 7.75 (s, 1H), 7.45 (s, 1H), 5.99 (s, 1H), 4.70-4.35 (m, 1H), 3.78 and 3.77 (s, 3H), 2.92-2.78 (m, 5H), 2.71 (s, 1H), 2.54 (s, 1H), 1.72-1.39 (m, 10H).

Example 16

1-(8-(methyl(2-((1-methyl-1H-pyrazol-4-yl)amino)pyrimidin-4-yl)amino)-2-azaspiro[4.5]decan-2-yl)prop-2-en-1-one

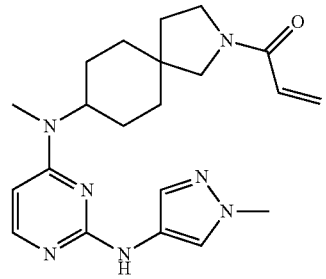 [SMILES: C=CC(=O)N1CCC2(CCC(N(C)c3ccnc(Nc4cnn(C)c4)n3)CC2)C1]

To a suspension of N$^4$-methyl-N$^2$-(1-methyl-1H-pyrazol-4-yl)-N$^4$-(2-azaspiro[4.4]nonan-4-yl)pyrimidine-2,4-diamine (0.10 g, 0.29 mmol) in DCM (10.0 mL) were added acrylic acid (21 mg, 0.29 mmol), HATU (0.13 g, 0.35 mmol) and Et$_3$N (59 mg, 0.59 mmol). The mixture was stirred at rt for 1.5 h, and then diluted with DCM (30 mL), washed with brine (20 mL), dried over anhydrous Na$_2$SO$_4$, filtered and concentrated in vacuo. The residue was purified by preparative-TLC (DCM/MeOH (v/v)=20/1) to give the title compound as a light yellow solid (27 mg, 21%).

MS (ESI, pos. ion) m/z: 396.3 [M+H]$^+$;
$^1$H NMR (600 MHz, CDCl$_3$): δ (ppm) 7.84 (s, 1H), 7.72-7.52 (m, 2H), 6.56-6.35 (m, 2H), 5.98 (s, 1H), 5.75-5.68 (m, 1H), 4.90-4.50 (m, 1H), 3.89 and 3.88 (s, 3H), 3.66 (m, 2H), 3.56-3.46 (m, 1H), 3.42-3.36 (m, 1H), 2.98 (s, 3H), 1.92-1.53 (m, 10H).

Example 17

3-(4-((2-((1-methyl-1H-pyrazol-4-yl)amino)pyrimidin-4-yl)amino)-2-azaspiro[4.4]nonan-2-yl)-3-oxopropanenitrile

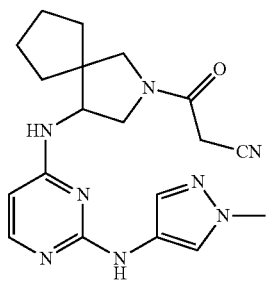 [SMILES: Cn1cc(Nc2nccc(NC3CN(C(=O)CC#N)CC34CCCC4)n2)cn1]

Step 1) tert-butyl 4-((2-chloropyrimidin-4-yl)amino)-2-azaspiro[4.4]nonane-2-carboxylate To a solution of 2,4-dichloropyrimidine (600 mg, 4.03 mmol) and tert-butyl 4-amino-2-azaspiro[4.4]nonane-2-carboxylate (1.07 g, 4.43 mmol) in EtOH (20 mL) was added Et$_3$N (815.6 mg, 8.06 mmol). After addition, the reaction mixture was stirred at rt overnight and then concentrated in vacuo. The residue was purified by silica gel column chromatography (PE/EtOAc (v/v)=10/1 to 1/1) to give the product as a white solid (528 mg, 37.2%).

MS (ESI, pos. ion) m/z: 353.2 [M+H]$^+$.

Step 2) tert-butyl 4-((2-((1-methyl-1H-pyrazol-4-yl)amino)pyrimidin-4-yl)amino)-2-azaspiro[4.4]nonane-2-carboxylate To a solution of tert-butyl 4-((2-chloropyrimidin-4-yl)amino)-2-azaspiro[4.4]nonane-2-carboxylate (528 mg, 1.50 mmol) and 1-methyl-1H-pyrazol-4-amine hydrochloride (240.52 mg, 1.8 mmol) in n-BuOH (8 mL) was added DIPEA (581.60 mg, 4.5 mmol). After addition, the reaction mixture was stirred at 150° C. overnight. The resulting mixture was concentrated in vacuo and purified by silica gel column chromatography (DCM/MeOH (v/v)=50/1 to 20/1) to give the product as a yellow oil (550 mg, 88.9%).

MS (ESI, pos. ion) m/z: 414.3 [M+H]$^+$.

Step 3) N$^2$-(1-methyl-1H-pyrazol-4-yl)-N$^4$-(2-azaspiro[4.4]nonan-4-yl)pyrimidine-2,4-diamine To a solution of tert-butyl 4-((2-((1-methyl-1H-pyrazol-4-yl)amino)pyrimidin-4-yl)amino)-2-azaspiro[4.4]nonane-2-carboxylate (550 mg, 1.33 mmol) in DCM (20 mL) was added CF$_3$COOH (5 mL) and the reaction mixture was stirred at rt for 2 h. The reaction mixture was concentrated in vacuo and adjust to pH=8~9 with the saturated NaHCO$_3$ aqueous solution, then diluted with H$_2$O (20 mL) and extracted withed EtOAc (50 mL×3). The combined organic phases were washed with brine (50 mL), then dried over Na$_2$SO$_4$, and concentrated in vacuo. The residue was purified by silica gel column chromatography (DCM/MeOH (v/v)=50/1 to 10/1) to give the product as a yellow solid (450 mg, 100%).

MS (ESI, pos. ion) m/z: 157.8 [(M+H)/2]$^+$;
$^1$H NMR (400 MHz, CDCl$_3$): δ (ppm) 11.54 (s, 1H), 9.60 (s, 1H), 7.64 (s, 1H), 7.51 (s, 1H), 7.45 (d, J=6.4 Hz, 1H), 7.28 (s, 1H), 6.14 (d, J=6.5 Hz, 1H), 4.68 (s, 1H), 3.82 (d, J=4.3 Hz, 3H), 3.60-3.47 (m, 1H), 3.34 (dd, J=21.6, 12.1 Hz, 2H), 3.11 (d, J=11.4 Hz, 1H), 1.83-1.61 (m, 4H), 1.52 (dt, J=19.3, 10.0 Hz, 4H).

Step 4) 3-(4-((2-((1-methyl-1H-pyrazol-4-yl)amino)pyrimidin-4-yl)amino)-2-azaspiro[4.4]nonan-2-yl)-3-oxopropanenitrile To a solution of N$^2$-(1-methyl-H-pyrazol-4-yl)-N$^4$-(2-azaspiro[4.4]nonan-4-yl)pyrimidine-2,4-diamine (310 mg, 0.99 mmol), 2-cyanoacetic acid (210.82 mg, 2.48 mmol), HATU (376.40 g, 0.99 mmol) in a mixture of DCM and DMF (4/1 (v/v), 25 mL) was added Et$_3$N (399.96 mg, 3.96 mmol) and the reaction mixture was stirred at rt for 1 hour. The reaction mixture was diluted with H$_2$O (20 mL) and extracted withed a mixture of DCM/MeOH (10/1 (v/v), 20 mL×3). The combined organic phases were washed with brine (50 mL×1), then dried over Na$_2$SO$_4$, and concentrated in vacuo. The residue was purified by silica gel column chromatography (DCM/MeOH (v/v)=100/1 to 20/1) to give the product as a light yellow solid (120 mg, 32%).

MS (ESI, pos. ion) m/z: 381.3 [M+H]$^+$;
HPLC: 98.83%;
$^1$H NMR (400 MHz, CDCl$_3$): δ (ppm) 10.75 (s, 1H), 8.52 (d, J=31.3 Hz, 1H), 7.44 (t, J=26.6 Hz, 3H), 5.99 (s, 1H), 4.41 (d, J=25.7 Hz, 1H), 3.74 (s, 3H), 3.61-3.42 (m, 2H), 3.40 (d, J=6.8 Hz, 2H), 3.27 (dd, J=56.2, 13.0 Hz, 2H), 1.66-1.29 (m, 8H).

Example 18

3-(4-((5-chloro-2-((1-methyl-1H-pyrazol-4-yl)amino)pyrimidin-4-yl)amino)-2-azaspiro[4.4]nonan-2-yl)-3-oxopropanenitrile

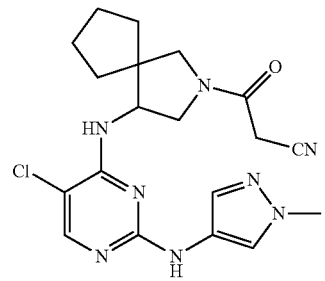 [SMILES: Cn1cc(Nc2ncc(Cl)c(NC3CN(C(=O)CC#N)CC34CCCC4)n2)cn1]

Step 1) tert-butyl 4-((2,5-dichloropyrimidin-4-yl)amino)-2-azaspiro[4.4]nonane-2-carboxylate To a solution of 2,4,5-trichloropyrimidine (500 mg, 2.73 mmol) and tert-butyl 4-amino-2-azaspiro[4.4]nonane-2-carboxylate (687.37 mg, 2.86 mmol) in EtOH (20 mL) was added Et$_3$N (552.50 mg, 5.46 mmol) and the reaction mixture was stirred at rt overnight. The resulting mixture was concentrated in vacuo and the residue was purified by silica gel column chromatography (PE/EtOAc (v/v)=10/1 to 5/1) to give the product as a white solid (930 mg, 88.2%).

MS (ESI, pos. ion) m/z: 387.2 [M+H]$^+$;
$^1$H NMR (400 MHz, CDCl$_3$): δ (ppm) 7.98 (s, 1H), 5.50 (d, J=8.5 Hz, 1H), 4.47 (s, 1H), 3.68 (d, J=5.6 Hz, 1H), 3.37-3.11 (m, 3H), 1.70-1.49 (m, 8H), 1.40 (s, 9H).

Step 2) tert-butyl 4-((5-chloro-2-((1-methyl-1H-pyrazol-4-yl)amino)pyrimidin-4-yl)amino)-2-azaspiro[4.4]nonane-2-carboxylate To a solution of tert-butyl 4-((2,5-dichloropyrimidin-4-yl)amino)-2-azaspiro[4.4]nonane-2-carboxylate (830 mg, 2.15 mmol) and 1-methyl-1H-pyrazol-4-amine hydrochloride (344.74 mg, 2.58 mmol) in n-BuOH (8 mL) was added DIPEA (833.60 mg, 6.45 mmol) and the reaction mixture was stirred at 150° C. overnight. The resulting mixture was concentrated in vacuo and the residue was purified by silica gel column chromatography (DCM/MeOH (v/v)=100/1) to give the product as a white solid (800 mg, 83%).

MS (ESI, pos. ion) m/z: 448.3 [M+H]$^+$;
$^1$H NMR (400 MHz, CDCl$_3$): δ (ppm) 7.89 (s, 1H), 7.67 (s, 1H), 7.46 (s, 1H), 6.94-6.61 (m, 1H), 5.30-5.12 (m, 1H), 4.55-4.34 (m, 1H), 3.87 (s, 3H), 3.81-3.63 (m, 1H), 3.35 (s, 1H), 3.28 (s, 1H), 3.28 (s, 1H), 1.68 (t, J=27.0 Hz, 8H), 1.47 (d, J=4.7 Hz, 9H).

Step 3) 5-chloro-$N^2$-(1-methyl-1H-pyrazol-4-yl)-$N^4$-(2-azaspiro[4.4]nonan-4-yl)pyrimidine-2,4-diamine To a solution of tert-butyl 4-((5-chloro-2-((1-methyl-1H-pyrazol-4-yl)amino)pyrimidin-4-yl)amino)-2-azaspiro[4.4]nonane-2-carboxylate (650 mg, 1.45 mmol) in DCM (20 mL) was added $CF_3COOH$ (5 mL) and the reaction mixture was stirred at rt for 2 hours. The reaction mixture was concentrated in vacuo and adjusted to pH=8-9 with a saturated $Na_2CO_3$ solution, then the mixture was diluted with $H_2O$ (20 mL) and extracted with EtOAc (50 mL×3). The combined organic phases were washed with brine (50 mL), then dried over $Na_2SO_4$, and concentrated in vacuo. The residue was purified by silica gel column chromatography (DCM/MeOH (v/v)=10/1 to 5/1) to give the product as a white solid (490 mg, 97%).

MS (ESI, pos. ion) m/z: 348.2[M+H]$^+$;
$^1$H NMR (400 MHz, CDCl$_3$): δ (ppm) 7.88 (s, 1H), 7.64 (s, 1H), 7.44 (d, J=11.9 Hz, 2H), 5.85 (s, 1H), 4.55 (s, 1H), 3.84 (s, 3H), 3.64 (dd, J=12.4, 6.4 Hz, 1H), 3.43 (dd, J=13.1, 3.6 Hz, 1H), 3.35 (d, J=11.6 Hz, 1H), 3.19 (d, J=11.6 Hz, 1H), 1.87-1.45 (m, 8H).

Step 4) 3-(4-((5-chloro-2-((1-methyl-1H-pyrazol-4-yl)amino)pyrimidin-4-yl)amino)-2-azaspiro[4.4]nonan-2-yl)-3-oxopropanenitrile To a solution of 5-chloro-$N^2$-(1-methyl-1H-pyrazol-4-yl)-$N^4$-(2-azaspiro[4.4]nonan-4-yl)pyrimidine-2,4-diamine (393 mg, 1.13 mmol), 2-cyanoacetic acid (240.83 mg, 2.83 mmol), HATU (429.63 g, 1.13 mmol) in a mixture of DCM and DMF (4/1 (v/v), 25 mL) was added Et$_3$N (456.52 mg, 4.52 mmol) and the reaction mixture was stirred at rt for 3 hours. The resulting mixture was diluted with $H_2O$ (20 mL) and extracted with a mixture of DCM and MeOH (10/1 (v/v), 20 mL×3). The combined organic phases were washed with brine (50 mL), and dried over anhydrous $Na_2SO_4$, then concentrated in vacuo. The residue was purified by silica gel column chromatography (DCM/MeOH=100/1 to 20/1) to give the product as a white solid (290 mg, 61.8%).

MS (ESI, pos. ion) m/z: 415.3 [M+H]$^+$;
HPLC: 99.83%;
$^1$H NMR (600 MHz, CDCl$_3$): δ (ppm) 12.22 (d, J=35.4 Hz, 1H), 7.97 (d, J=3.6 Hz, 1H), 7.81 (d, J=5.0 Hz, 1H), 7.58 (d, J=4.4 Hz, 1H), 6.47 (dd, J=26.5, 8.1 Hz, 1H), 4.72-4.59 (m, 1H), 4.05 (dd, J=11.0, 5.7 Hz, 1H), 3.93 (dd, J=13.6, 4.5 Hz, 3H), 3.68-3.62 (m, 1H), 3.62-3.54 (m, 1H), 3.55-3.47 (m, 2H), 3.44 (dd, J=18.0, 2.6 Hz, 1H), 1.83-1.53 (m, 8H).

Example 19

5-chloro-$N^4$-methyl-$N^2$-(1-methyl-1H-pyrazol-4-yl)-$N^4$-(7-azaspiro[4.5]decan-2-yl)pyrimidine-2,4-diamine

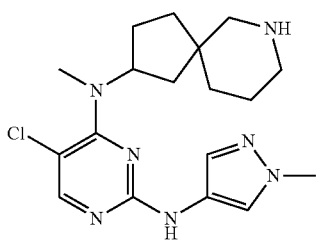 [SMILES: CN(c1nc(Nc2cnn(C)c2)ncc1Cl)C1CCC2(CCCNC2)C1]

Step 1) tert-butyl 2-oxopiperidine-1-carboxylate

To a solution of piperidin-2-one (0.97 g, 9.78 mmol) in DCM (20 mL) were added Et$_3$N (1.36 mL, 9.78 mmol), DMAP (0.12 g, 0.978 mmol) and Boc$_2$O (3.20 g, 14.7 mmol). The reaction mixture was stirred at rt for 3 h and concentrated in vacuo. The residue was purified by silica gel column chromatography (EtOAc/PE (v/v)=1/7) to give the title compound as pale yellow oil (1.78 g, 91%).

MS (ESI, pos. ion) m/z: 144.2 [(M−C$_4$H$_8$)+H]$^+$;
$^1$H NMR (600 MHz, CDCl$_3$): δ (ppm) 3.65 (t, J=6.1 Hz, 2H), 2.50 (t, J=9.6, 7.2 Hz, 2H), 1.82 (m, 4H), 1.52 (s, 9H).

Step 2) tert-butyl 3,3-diallyl-2-oxopiperidine-1-carboxylate

To a solution of tert-butyl 2-oxopiperidine-1-carboxylate (8.22 g, 41.3 mmol) in anhydrous THF (80 mL) was added LiHMDS (1.0 M in THF, 103 mL, 103 mmol) dropwise under nitrogen atmosphere at −78° C. and the reaction mixture was stirred for 20 min at the same temperature and then 3-bromoprop-1-ene (10.7 mL, 124 mmol) was added to. The resulting mixture was stirred for 15 min at −78° C. and warmed to rt, quenched with water (15 mL), and concentrated in vacuo. The residue was diluted with water (30 mL) and extracted with EtOAc (50 mL×3). The combined organic phases were washed with brine (50 mL), then dried over anhydrous Na$_2$SO$_4$, filtered and concentrated in vacuo. The residue was purified by silica gel column chromatography (EtOAc/PE (v/v)=1/50) to give the title compound as yellow oil (3.95 g, 35%).

MS (ESI, pos. ion) m/z: 224.2 [(M−C$_4$H$_8$)+H]$^+$;
$^1$H NMR (600 MHz, CDCl$_3$): δ (ppm) 5.72 (ddt, J=16.5, 10.5, 7.0 Hz, 2H), 5.06 (d, J=10.5 Hz, 2H), 5.03 (d, J=16.5 Hz, 2H), 3.55 (t, J=5.8 Hz, 2H), 2.46 (dd, J=13.6, 7.0 Hz, 2H), 2.21 (dd, J=13.6, 7.0 Hz, 2H), 1.75 (m, 4H), 1.48 (s, 9H).

Step 3) tert-butyl 6-oxo-7-azaspiro[4.5]dec-2-ene-7-carboxylate

To a solution of tert-butyl 3,3-diallyl-2-oxopiperidine-1-carboxylate (4.74 g, 16.9 mmol) in dichloromethane (20 mL) was added Grubbs first generation catalyst (711 mg, 0.85 mmol). The reaction mixture was stirred at rt for 4 h and concentrated in vacuo. The residue was purified by silica gel column chromatography (EtOAc/PE (v/v)=1/9) to give the title compound as a white solid (3.61 g, 85%).

MS (ESI, pos. ion) m/z: 196.2 ([M−C$_4$H$_8$+H]$^+$).
$^1$H NMR (600 MHz, CDCl$_3$): δ (ppm) 5.62 (s, 2H), 3.67 (t, J=6.0 Hz, 2H), 3.04 (d, J=14.0 Hz, 2H), 2.30 (d, J=14.2 Hz, 2H), 1.87 (m, 4H), 1.50 (m, 9H).

Step 4) tert-butyl 2-hydroxy-7-azaspiro[4.5]decane-7-carboxylate

To a solution of tert-butyl 6-oxo-7-azaspiro[4.5]dec-2-ene-7-carboxylate (0.61 g, 2.44 mmol) in anhydrous THF (5 mL) was added borane-methyl sulfide complex (10.0 M, 2.45 mL, 24.5 mmol) at 0° C. After stirring for 10 min, the reaction mixture was warmed to rt and stirred overnight, then cooled down to 0° C. and a mixture of NaOH aqueous solution (3 M, 3 mL, 9 mmol) and H$_2$O$_2$ (30% in water, 3 mL) was added. After stirring for 5 min, the reaction mixture was heated to reflux for 5 h, then cooled down to rt and concentrated in vacuo. The residue was dissolved in water (10 mL), and extracted with EtOAc (15 mL×3). The combined organic phases were washed with brine (50 mL), and dried over anhydrous Na$_2$SO$_4$, then concentrated in vacuo. The residue was purified by silica gel column chromatography (EtOAc/PE (v/v)=1/5) to give the title compound as colorless oil (252 mg, 41%).

MS (ESI, pos. ion) m/z: 200.1 [(M−C$_4$H$_8$)+H]$^+$.

Step 5) tert-butyl 2-oxo-7-azaspiro[4.5]decane-7-carboxylate

To a solution of tert-butyl 2-hydroxy-7-azaspiro[4.5]decane-7-carboxylate (252 mg, 1.0 mmol) in DCM (5 mL) was added Dess-Martin periodinane (0.84 g, 1.99 mmol). The reaction mixture was stirred at rt overnight and concentrated in vacuo. The residue was purified by silica gel column chromatography (EtOAc/PE (v/v)=1/5) to give the title compound as yellow oil (197 mg, 79%).

MS (ESI, pos. ion) m/z: 198.2 [(M−C$_4$H$_8$)+H]$^+$;
$^1$H NMR (600 MHz, CDCl$_3$): δ (ppm) 3.41 (s, 2H), 3.26 (s, 2H), 2.32 (s, 2H), 2.15 (s, 1H), 1.93 (d, J=6.6 Hz, 1H), 1.63 (m, 4H), 1.45 (s, 9H), 1.26 (s, 2H).

Step 6) tert-butyl 2-(methylamino)-7-azaspiro[4.5]decane-7-carboxylate

To a solution of CH$_3$NH$_2$ (33% [w/w] in EtOH, 2 mL) was added tert-butyl 2-oxo-7-azaspiro[4.5]decane-7-carboxylate (197 mg, 0.78 mmol) and the reaction mixture was stirred at rt overnight. Then NaBH$_3$CN (74 mg, 1.17 mmol) was added and the resulting mixture was stirred at rt for another 2 h and then concentrated in vacuo. The residue was purified by silica gel column chromatography (MeOH/DCM (v/v)=1/20) to give the title compound as colorless oil (208 mg, 100%).

MS (ESI, pos. ion) m/z: 269.3 [M+H]$^+$.

Step 7) tert-butyl 2-((2,5-dichloropyrimidin-4-yl)(methyl)amino)-7-azaspiro[4.5]decane-7-carboxylate To a solution of 2,4,5-trichloropyrimidine (355.7 g, 1.94 mmol) and tert-butyl 2-(methylamino)-7-azaspiro[4.5]decane-7-carboxylate (403.2 g, 1.50 mmol) in EtOH (10 mL) was added Et$_3$N (315.5 mg, 3.12 mmol). After addition, the reaction mixture was stirred at rt overnight and concentrated in vacuo. The residue was purified by silica gel column chromatography (EtOAc/PE (v/v)=1/8) to give the title compound as yellow oil (470 mg, 75.4%).

MS (ESI, pos. ion) m/z: 415.2 [M+H]$^+$;
$^1$H NMR (400 MHz, CDCl$_3$): δ (ppm) 8.06 (s, 1H), 4.95 (m, 1H), 3.27 (m, 4H), 3.11 (s, 2H), 3.07 (s, 1H), 1.74 (m, 5H), 1.56 (m, 5H), 1.48 (d, J=2.8 Hz, 9H).

Step 8) tert-butyl 2-((5-chloro-2-((1-methyl-1H-pyrazol-4-yl)amino)pyrimidin-4-yl)(methyl)amino)-7-azaspiro[4.5]decane-7-carboxylate To a suspension of tert-butyl 2-((2,5-dichloropyrimidin-4-yl)(methyl)amino)-7-azaspiro[4.5]decane-7-carboxylate (470 mg, 1.13 mmol) and 1-methyl-1H-pyrazol-4-amine hydrochloride (235.7 mg, 1.76 mmol) in n-BuOH (5 mL) was added DIPEA (482.6 g, 3.74 mmol). The reaction mixture was stirred at 150° C. in a sealed tube overnight and concentrated in vacuo. The residue was purified by silica gel column chromatography (EtOAc/PE (v/v)=1/1) to give the title compound as a white solid (280 mg, 52.0%).

MS (ESI, pos. ion) m/z: 476.3 [M+H]$^+$;
$^1$H NMR (400 MHz, CDCl$_3$): δ (ppm) 7.94 (m, 1H), 7.70 (s, 1H), 7.48 (d, J=5.0 Hz, 1H), 6.58 (m, 1H), 4.84 (m, 1H), 3.90 and 3.89 (s, 3H), 3.38 (s, 2H), 3.25 (s, 2H), 3.05 (s, 3H), 1.90 (m, 6H), 1.61 (s, 9H), 1.55 (s, 3H), 1.35 (m, 1H).

Step 9) 5-chloro-N$^4$-methyl-N$^2$-(1-methyl-1H-pyrazol-4-yl)-N$^4$-(7-azaspiro[4.5]decan-2-yl)pyrimidine-2,4-diamine To a solution of tert-butyl 2-((5-chloro-2-((1-methyl-1H-pyrazol-4-yl)amino)pyrimidin-4-yl)(methyl)amino)-7-azaspiro[4.5]decane-7-carboxylate (270 mg, 0.567 mmol) in DCM (10 mL) was added a solution of HCl in EtOAc (10 mL, 40 mmol). The reaction mixture was stirred at rt overnight and concentrated in vacuo. The residue was dissolved in water (30 mL) and adjusted to pH=10 with a saturated Na$_2$CO$_3$ aqueous solution, then extracted with DCM (100 mL×3). The combined organic phases were washed with brine (100 mL), then dried over anhydrous Na$_2$SO$_4$, filtered and concentrated in vacuo. The residue was purified by silica gel column chromatography (NH$_3$ in MeOH (7 M)/MeOH/DCM (v/v/v)=1/20/60) to give the title compound as a beige solid (0.20 g, 93.8%).

MS (ESI, pos. ion) m/z: 376.2 [M+H]$^+$;
$^1$H NMR (600 MHz, CDCl$_3$): δ (ppm) 7.96 and 7.93 (s, 1H), 7.74 and 7.65 (s, 1H), 7.58 and 7.52 (s, 1H), 6.87 (s, 1H), 4.86 and 4.69 (m, 1H), 3.89 and 3.87 (s, 3H), 3.33 and 3.20 (m, 1H), 3.04 (m, 6H), 1.98 (m, 2H), 1.90 (m, 2H), 1.64 (m, 6H).

Example 20

3-(8-((5-methyl-2-((1-methyl-1H-pyrazol-4-yl)amino)pyrimidin-4-yl)amino)-2-azaspiro[4.5]decan-2-yl)-3-oxopropanenitrile

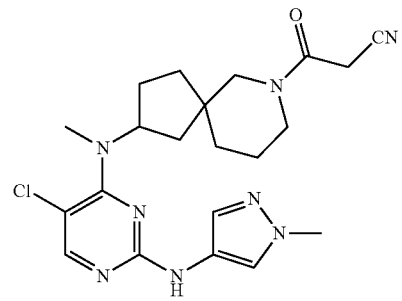 [SMILES: CN(c1nc(Nc2cnn(C)c2)ncc1Cl)C1CCC2(CCCN(C(=O)CC#N)C2)C1]

To a solution of 5-chloro-N$^4$-methyl-N$^2$-(1-methyl-1H-pyrazol-4-yl)-N$^4$-(7-azaspiro[4.5]decan-2-yl)pyrimidine-2,4-diamine (0.18 g, 0.479 mmol), 2-cyanoacetic acid (60.5 mg, 0.711 mmol) in a mixture of DCM (20 mL) and DMF (5 mL) were added HATU (335.2 mg, 0.882 mmol) and Et$_3$N (169.4 mg, 1.674 mmol). After addition, the reaction mixture was stirred at rt overnight, then quenched with H$_2$O (30 mL) and extracted with DCM (100 mL×3). The combined organic phases were washed with brine (100 mL), then dried over anhydrous Na$_2$SO$_4$, and concentrated in vacuo. The residue was purified by silica gel column chromatography (DCM/MeOH (v/v)=20/1) to give the title compound as a beige solid (83 mg, 39.1%).

MS (ESI, pos. ion) m/z: 443.3 [M+H]$^+$;
$^1$H NMR (400 MHz, CDCl$_3$): δ (ppm) 7.97 and 7.94 (s, 1H), 7.78 and 7.69 (s, 1H), 7.55 and 7.49 (s, 1H), 6.59 and 6.54 (s, 1H), 4.80 (m, 1H), 3.89 (s, 3H), 3.57 (t, J=12.6 Hz, 1H), 3.53 (t, J=3.3 Hz, 2H), 3.41 (m, 2H), 3.24 and 3.19 (d, J=5.0 Hz, 1H), 3.05 and 3.04 (s, 3H), 1.83 (m, 10H).

Example 21

5-chloro-N²-(1-methyl-1H-pyrazol-4-yl)-N⁴-(octahydro-1H-isoindol-5-yl) pyrimidine-2,4-diamine

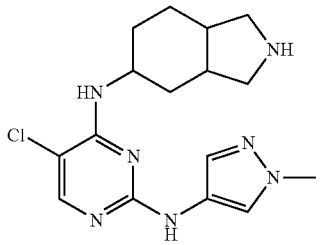 [SMILES: Cn1cc(Nc2ncc(Cl)c(NC3CCC4CNCC4C3)n2)cn1]

Step 1) tert-butyl 3a,4,7,7a-tetrahydro-1H-isoindole-2(3H)-carboxylate

To a suspension of LAH (22.80 g, 600 mmol) in THF (600 mL) at 0° C. was added tetrahydrophthalimide (39.45 g, 260.9 mmol) portionwise. After addition, the reaction mixture was stirred at 60° C. for 18 h, then cooled down to 0° C. and quenched carefully with water (25 mL) followed by 15% KOH aqueous solution (25 mL) and another 75 mL of water. The resulting mixture was stirred at rt for 1 h, and filtered through a pad of Celite, then washed with DCM (500 mL). The filtrate was concentrated in vacuo to give isoindole as yellow oil, which was used directly in the next reaction.

Accordingly, the crude isoindole in DCM (300 mL) was treated with Et₃N (39.61 g, 391.4 mmol) and (Boc)₂O (68.32 g, 313.1 mmol) at 0° C. for 0.5 h and then warmed to rt for another 21 h, then concentrated in vacuo. The residue was dissolved in EtOAc (600 mL), and washed with 1 M citric acid (2×130 mL), followed by saturated NaHCO₃ (2×130 mL) and brine (250 mL). The organic layer was dried over anhydrous Na₂SO₄, filtered and concentrated in vacuo. The residue was purified by silica gel column chromatography (EtOAc/PE (v/v)=1/5) to give the title compound as orange red oil (45.00 g, 77.3%).

MS (ESI, pos. ion) m/z: 168.2 [(M−C₄H₈)+H]⁺;
¹H NMR (400 MHz, CDCl₃): δ (ppm) 5.64 (s, 2H), 3.40 (m, 2H), 3.16 (m, 1H), 3.07 (m, 1H), 2.25 (m, 4H), 1.90 (m, 2H), 1.46 (s, 9H).

Step 2) tert-butyl 5-hydroxyhexahydro-1H-isoindole-2(3H)-carboxylate

To a solution of tert-butyl 3a,4,7,7a-tetrahydro-1H-isoindole-2(3H)-carboxylate (48.18 g, 215.8 mmol) in THF (500 mL) was added a solution of BH₃-DMS in THF (2 M in THF, 130 mL, 260.0 mmol) dropwise at 0° C. The reaction mixture was warmed slowly to rt and stirred overnight, then cooled down to 0° C. again. Methanol (120 mL) was added dropwise to the above mixture, and followed by a mixture of NaOH aqueous solution (3 M, 75 mL, 225 mmol) and H₂O₂ (30% in water, 75 mL). The resulting mixture was stirred at 60° C. for 1.5 h, then cooled down to rt, and diluted with Et₂O (500 mL) and water (450 mL), then extracted with EtOAc (450 mL×3). The combined organic phases were washed with brine (500 mL), then dried over anhydrous Na₂SO₄, filtered and concentrated in vacuo to give the title compound as orange oil (49.04 g, 94.2%), which was used in the next step without further purification.

MS (ESI, pos. ion) m/z: 186.2 [(M−C₄H₈)+H]⁺;
¹H NMR (400 MHz, CDCl₃): δ (ppm) 3.89 (m, 1H), 3.35 (m, 2H), 3.22 (m, 2H), 2.47 (m, 1H), 2.10 (m, 1H), 1.82 (m, 4H), 1.62 (m, 1H), 1.54 (m 2H), 1.46 (s, 9H).

Step 3) tert-butyl 5-oxohexahydro-1H-isoindole-2(3H)-carboxylate

To a solution of tert-butyl 5-hydroxyhexahydro-1H-isoindole-2(3H)-carboxylate (48.98 g, 203.0 mmol) in DCM (500 mL) at 0° C. was added DMP (103.31 g, 243.6 mmol) portionwise. After addition, the reaction mixture was stirred at 0° C. for 0.5 h and then moved to rt overnight, cooled down to 0° C. and washed with a mixture of NaHCO₃/Na₂S₂O₃ saturated solution (v/v, 1/1, 500 mL), then stirred at 0° C. for 0.5 h and filtered. The filter cake was washed with DCM (250 mL×3) and the filtrate was extracted with DCM (250 mL×3). The combined organic phases were washed with brine (500 mL), then dried over anhydrous Na₂SO₄, filtered and concentrated in vacuo. The residue was purified by silica gel column chromatography (EtOAc/PE (v/v)=1/5) to give the title compound as yellow oil (48.58 g, 100%).

MS (ESI, pos. ion) m/z: 184.2 [(M−C₄H₈)+H]⁺;
¹H NMR (600 MHz, CDCl₃): δ (ppm) 3.53 (m, 2H), 3.36 (m, 1H), 3.11 (m, 1H), 2.70 (m, 1H), 2.51 (s, 2H), 2.37 (m, 3H), 2.08 (s, 1H), 1.88 (br. s, 1H), 1.47 (s, 9H).

Step 4) tert-butyl 5-aminohexahydro-1H-isoindole-2(3H)-carboxylate

To a solution of tert-butyl 5-oxohexahydro-1H-isoindole-2(3H)-carboxylate (11.97 g, 50 mmol) in EtOH (100 mL) were added a solution of NH₃ in MeOH (7 M, 100 mL, 700 mmol) and Ti(OiPr)₄ (28.42 g, 100 mmol). After addition, the reaction mixture was stirred at rt overnight and NaBH₄ (3.78 g, 100 mmol) was added portionwise, then the resulting mixture was stirred at rt for another 5 h. The reaction was quenched with water (100 mL), stirred at rt for 1 h and filtered. The filter cake was washed with DCM (100 mL×3) and the filtrate was concentrated in vacuo. The residue was dissolved in a mixture of EtOAc (100 mL) and water (100 mL), and extracted with EtOAc (250 mL×3). The combined organic phases were washed with brine (250 mL), dried over anhydrous Na₂SO₄, filtered and concentrated in vacuo to give the title compound as brown oil (12.02 g, 100%).

MS (ESI, pos. ion) m/z: 185.2 [(M−C₄H₈)+H]⁺.

Step 5) tert-butyl 5-((2,5-dichloropyrimidin-4-yl)amino)hexahydro-1H-isoindole-2(3H)-carboxylate To a solution of 2,4,5-trichloropyrimidine (0.60 g, 3.27 mmol) and tert-butyl 5-aminohexahydro-1H-isoindole-2(3H)-carboxylate (2.79 g, 11.61 mmol) in EtOH (10 mL) was added Et₃N (1.30 g, 12.84 mmol). After addition, the reaction mixture was stirred at rt overnight and concentrated in vacuo. The residue was purified by silica gel column chromatography (EtOAc/PE (v/v)=1/5) to give the title compound as a pale yellow solid (1.60 g, 100%).

MS (ESI, pos. ion) m/z: 387.2 [M+H]⁺;
¹H NMR (600 MHz, CDCl₃): δ (ppm) 8.03 (s, 1H), 5.31 (m, 1H), 4.04 (m, 1H), 3.39 (m, 3H), 3.30 (m, 1H), 3.21 (m, 2H), 2.42 (m, 1H), 2.32 (m, 1H), 1.98 (m, 2H), 1.86 (m, 2H), 1.48 (d, J=3.2 Hz, 9H).

Step 6) tert-butyl 5-((5-chloro-2-((1-methyl-1H-pyrazol-4-yl)amino)pyrimidin-4-yl)amino)hexahydro-1H-isoindole-2(3H)-carboxylate To a suspension of tert-butyl 5-((2,5-dichloropyrimidin-4-yl)amino)hexahydro-1H-isoindole-2(3H)-carboxylate (767.3 mg, 1.98 mmol) and 1-methyl-1H-pyrazol-4-amine hydrochloride (411.5 mg, 3.08 mmol) in n-BuOH (5 mL) was added N-ethyldiisopropylamine (792.9 g, 6.14 mmol). The reaction mixture was stirred at 150° C. in a sealed tube overnight and concentrated in vacuo. The residue was purified by silica gel column chromatography ((EtOAc/PE (v/v)=1/1) to give the title compound as a pale yellow solid (493 mg, 55.6%).
MS (ESI, pos. ion) m/z: 448.2 [M+H]$^+$;
$^1$H NMR (400 MHz, CDCl$_3$): δ (ppm) 7.88 (s, 1H), 7.67 (s, 1H), 7.54 (s, 1H), 6.70 (s, 1H), 5.08 (d, J=7.5 Hz, 1H), 3.94 (m, 1H), 3.89 (s, 3H), 3.41 (m, 3H), 3.30 (m, 1H), 3.23 (m, 1H), 2.27 (m, 1H), 2.04 (m, 3H), 1.84 (m, 2H), 1.48 (d, J=7.3 Hz, 9H).

Step 7) 5-chloro-N$^2$-(1-methyl-H-pyrazol-4-yl)-N$^4$-(octahydro-1H-isoindol-5-yl)pyrimidine-2,4-diamine To a solution of tert-butyl 5-((5-chloro-2-((1-methyl-1H-pyrazol-4-yl)amino)pyrimidin-4-yl)amino)hexahydro-1H-isoindole-2(3H)-carboxylate (476.4 mg, 1.06 mmol) in DCM (10 mL) was added a solution of HCl in EtOAc (10 mL, 40 mmol). The reaction mixture was stirred at rt overnight and concentrated in vacuo. The residue was dissolved in water (30 mL) and adjusted to pH=10 with a saturated Na$_2$CO$_3$ aqueous solution, then extracted with DCM (250 mL×3). The combined organic phases were washed with brine (250 mL), dried over anhydrous Na$_2$SO$_4$, then filtered and concentrated in vacuo. The residue was purified by silica gel column chromatography (MeOH/DCM (v/v)=1/5) to give the title compound as a beige solid (333.9 mg, 96.0%).
MS (ESI, pos. ion) m/z: 348.3 [M+H]$^+$;
$^1$H NMR (400 MHz, CDCl$_3$): δ (ppm) 7.89 and 7.88 (s, 1H), 7.64 (s, 1H), 7.59 and 7.56 (s, 1H), 6.87 and 6.74 (s, 1H), 5.27 (d, J=7.6 Hz, 1H), 3.92 and 3.89 (s, 3H), 3.46 (m, 4H), 3.28 (m, 2H), 2.52 (m, 2H), 1.98 (m, 4H).

Example 22

3-(5-((5-chloro-2-((1-methyl-1H-pyrazol-4-yl)amino)pyrimidin-4-yl)amino)hexahydro-1H-isoindol-2(3H)-yl)-3-oxopropanenitrile

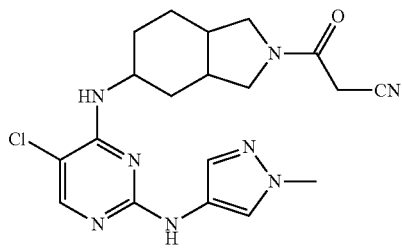 [SMILES: Cn1cc(Nc2ncc(Cl)c(NC3CCC4CN(C(=O)CC#N)CC4C3)n2)cn1]

To a solution of 5-chloro-N$^2$-(1-methyl-1H-pyrazol-4-yl)-N$^4$-(octahydro-1H-isoindol-5-yl)pyrimidine-2,4-diamine (470 mg, 1.35 mmol), 2-cyanoacetic acid (246.7 mg, 2.90 mmol) in a mixture of DCM (40 mL) and DMF (10 mL) were added EDCI (505.2 mg, 2.64 mmol) and HOAT (325.4 mg, 0.30 mmol). After addition, the reaction mixture was stirred at 45° C. for 3 h, quenched with H$_2$O (30 mL) and extracted with DCM (200 mL×3). The combined organic phases were washed with brine (200 mL), dried over anhydrous Na$_2$SO$_4$, then filtered and concentrated in vacuo. The residue was purified by silica gel column chromatography (DCM/MeOH (v/v)=50/1) to give the title compound as beige solid (228.4 mg, 40.8%).
MS (ESI, pos. ion) m/z: 415.1 [M+H]$^+$;
$^1$H NMR (400 MHz, CDCl$_3$): δ (ppm) 7.90 (s, 1H), 7.64 (s, 1H), 7.56 (s, 1H), 6.60 (s, 1H), 5.09 (m, 1H), 3.98 (m, 1H), 3.90 (s, 3H), 3.67 (m, 2H), 3.54 (m, 3H), 3.46 (s, 1H), 3.42 (s, 1H), 2.51 (m, 2H), 2.09 (m, 2H), 1.88 (m, 2H).

Example 23

3-(9-(methyl(5-methyl-2-((1-methyl-1H-pyrazol-4-yl)amino)pyrimidin-4-yl)amino)-3-azaspiro[5.5]undecan-3-yl)-3-oxopropanenitrile

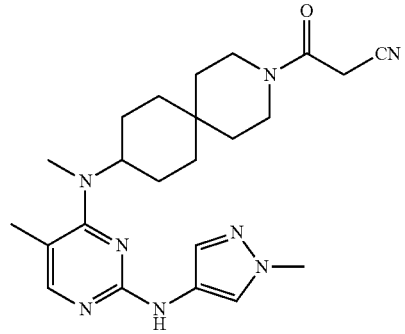 [SMILES: Cc1cnc(Nc2cnn(C)c2)nc1N(C)C1CCC2(CC1)CCN(C(=O)CC#N)CC2]

Step 1) tert-butyl 9-oxo-3-azaspiro[5.5]undec-7-ene-3-carboxylate

To a solution of tert-butyl 4-formylpiperidine-1-carboxylate (10.0 g, 46.9 mmol) and KOH (1.3 g, 23.5 mmol) in EtOH (200 mL) was added but-3-en-2-one (3.9 g, 56.3 mmol), the mixture was stirred at 70° C. for 16 h and concentrated in vacuo. The residue was purified by silica gel column chromatography (EtOAc/PE (v/v)=1/4) to give the product as brown oil (5.2 g, 41.8%).
MS (ESI, pos. ion) m/z: 210.2 [M−55]$^+$.

Step 2) tert-butyl 9-oxo-3-azaspiro[5.5]undecane-3-carboxylate

To a solution of tert-butyl 9-oxo-3-azaspiro[5.5]undec-7-ene-3-carboxylate (5.2 g, 19.6 mmol) in DCM (80 mL) was added 10% Pd/C (0.5 g) and the suspension was stirred under a H$_2$ atmosphere at room temperature overnight. The reaction mixture was filtered and concentrated in vacuo, then the residue was purified by silica gel column chromatography (EtOAc/PE (v/v)=1/4) to give the product as brown oil (3.1 g, 59.0%).
MS (ESI, pos. ion) m/z: 212.1 [M−55]$^+$.

Step 3) tert-butyl 9-(methylamino)-3-azaspiro[5.5]undecane-3-carboxylate

To a solution of tert-butyl 9-oxo-3-azaspiro[5.5]undecane-3-carboxylate (2.15 g, 8.05 mmol) in EtOH (20 mL) was added 33% methanamine in EtOH (3.7 g, 40.3 mmol), and the mixture was stirred at r.t for 1.5 h. Then NaBH$_3$CN (1.5 g, 24.2 mmol) was added to the mixture. After that the resulting mixture was stirred at r.t overnight and then concentrated in vacuo. The residue was purified by silica gel column chromatography (DCM/MeOH (v/v)=10/1) to give the product as brown oil (1.05 g, 46.2%).

MS (ESI, pos. ion) m/z: 283.3 [M+H]$^+$.

Step 4) tert-butyl 9-((2-chloro-5-methylpyrimidin-4-yl)(methyl)amino)-3-azaspiro[5.5]undecane-3-carboxylate To a solution of 2,4-dichloro-5-methylpyrimidine (300 mg, 1.84 mmol) and tert-butyl 9-(methylamino)-3-azaspiro[5.5]undecane-3-carboxylate (573.32 mg, 2.03 mmol) in ethanol (30 mL) was added N,N-diethylethanamine (372.38 mg, 3.68 mmol). The reaction mixture was stirred at 100° C. overnight and then concentrated in vacuo. The residue was purified by silica gel column chromatography (EtOAc/PE (v/v)=1/5) to give the title compound as yellow oil (165 mg, 22%).

MS (ESI, pos. ion) m/z: 409.4 [M+H]$^+$.
$^1$H NMR (400 MHz, CDCl$_3$): δ (ppm) 7.84 (s, 1H), 3.99 (t, J=11.4 Hz, 1H), 3.40-3.35 (m, 4H), 2.95 (s, 3H), 2.22 (s, 3H), 1.81 (s, 1H), 1.80-1.75 (m, 2H), 1.72 (d, J=15.2 Hz, 3H), 1.60 (d, J=10.7 Hz, 3H), 1.56-1.51 (m, 3H), 1.45 (s, 9H).

Step 5) tert-butyl 9-(methyl(5-methyl-2-((1-methyl-1H-pyrazol-4-yl)amino)pyrimidin-4-yl)amino)-3-azaspiro[5.5]undecane-3-carboxylate To a suspension of tert-butyl 9-((2-chloro-5-methylpyrimidin-4-yl)(methyl)amino)-3-azaspiro[5.5]undecane-3-carboxylate (211 mg, 0.52 mmol) and 1-methyl-1H-pyrazol-4-amine hydrochloride (160.3 mg, 1.20 mmol) in butan-1-ol (5 mL) was added DIPEA (201.63 mg, 1.56 mmol). The reaction mixture was stirred at 150° C. in a sealed tube overnight, then cooled down to rt, and concentrated in vacuo. The residue was purified by silica gel column chromatography (DCM/MeOH (v/v)=100/1 to 10/1) to give the title compound as a white solid (176.87 mg, 73%).

MS (ESI, pos. ion) m/z: 470.1 [M+H]$^+$.

Step 6) N$^4$,5-dimethyl-N$^2$-(1-methyl-1H-pyrazol-4-yl)-N$^4$-(3-azaspiro[5.5]undecan-9-yl)pyrimidine-2,4-diamine To a suspension of tert-butyl 9-(methyl(5-methyl-2-((1-methyl-1H-pyrazol-4-yl) amino)pyrimidin-4-yl)amino)-3-azaspiro[5.5]undecane-3-carboxylate (250 mg, 0.53 mmol) in dichloromethane (15 mL) was added the solution of HCl in EtOAc (3 mL, 12 mmol). The reaction mixture was stirred at rt for 2 h. The mixture was adjust to pH=8-9 with the saturated solution of NaHCO$_3$, then the mixture was diluted with 20 mL H$_2$O and exacted with DCM/MeOH (10/1, 10 mL×3). The combined organic layers were washed with brine (20 mL), dried over Na$_2$SO$_4$, filtered and concentrated in vacuo. The residue was purified by flash silica gel column chromatography (DCM/MeOH (v/v)=10/1 to 5/1) to give the title compound as a yellow solid (135 mg, 68.6%).

MS (ESI, pos. ion) m/z: 185.8 [(M+H)/2]$^+$.

Step 7) 3-(9-(methyl(5-methyl-2-((1-methyl-1H-pyrazol-4-yl)amino)pyrimidin-4-yl)amino)-3-azaspiro[5.5]undecan-3-yl)-3-oxopropanenitrile To a suspension of N$^4$,5-dimethyl-N$^2$-(1-methyl-1H-pyrazol-4-yl)-N$^4$-(3-azaspiro[5.5]undecan-9-yl)pyrimidine-2,4-diamine (93 mg, 0.25 mmol) and 2-cyanoacetic acid (63.8 mg, 0.75 mmol) in a mixture of dichloromethane and N,N-dimethylformamide (8 mL/2 mL) were added O-(7-aza-1H-benzotriazol-1-yl)-N,N,N',N'-tetramethyluronium-hexafluoro phosphate (51.72 mg, 0.38 mmol) and N,N-diethylethanamine (75.9 mg, 0.75 mmol). The mixture was stirred at rt overnight then concentrated in vacuo and the residue was purified by silica gel column chromatography (DCM/MeOH (v/v)=100/1 to 10/1) to give the title compound as a yellow solid (40 mg, 36.38%).

MS (ESI, pos. ion) m/z: 437.1 [M+H]$^+$.
$^1$H NMR (400 MHz, DMSO): δ (ppm) 8.88 (s, 1H), 7.75 (s, 1H), 7.72 (s, 1H), 7.44 (s, 1H), 5.37-5.27 (m, 1H), 4.01 (d, J=9.5 Hz, 4H), 3.78 (s, 3H), 3.45 (s, 2H), 2.93 (s, 3H), 2.13 (s, 3H), 1.99 (dd, J=10.6, 4.9 Hz, 2H), 1.76 (dd, J=26.4, 12.7 Hz, 5H), 1.55 (dd, J=24.1, 8.0 Hz, 5H).

Example 24

3-(9-((5-chloro-2-((1-methyl-1H-pyrazol-4-yl)amino)pyrimidin-4-yl)(methyl)amino)-3-azaspiro[5.5]undecan-3-yl)-3-oxopropanenitrile

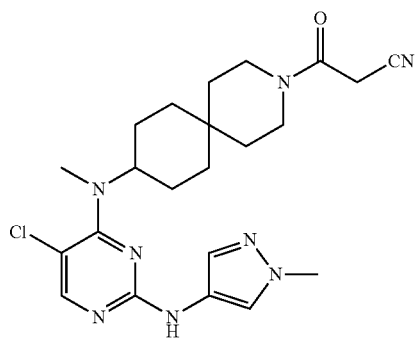 [SMILES: CN(c1nc(Nc2cnn(C)c2)ncc1Cl)C1CCC2(CC1)CCN(C(=O)CC#N)CC2]

Step 1) tert-butyl 9-((2,5-dichloropyrimidin-4-yl)(methyl)amino)-3-azaspiro[5.5]undecane-3-carboxylate To a solution of 2,4,5-trichloropyrimidine (300 mg, 1.64 mmol) and tert-butyl 9-(methylamino)-3-azaspiro[5.5]undecane-3-carboxylate (511.18 mg, 1.81 mmol) in ethanol (15 mL) was added N,N-diethylethanamine (331.90 mg, 3.28 mmol). The reaction mixture was stirred at rt overnight and then concentrated in vacuo. The residue was purified by silica gel column chromatography (EtOAc/PE (v/v)=1/10 to 1/5) to give the title compound as yellow oil (101.83 mg, 14.5%).

MS (ESI, pos. ion) m/z: 429.3 [M+H]$^+$.

Step 2) tert-butyl 9-((5-chloro-2-((1-methyl-1H-pyrazol-4-yl)amino)pyrimidin-4-yl)(methyl)amino)-3-azaspiro[5.5]undecane-3-carboxylate To a suspension of tert-butyl 9-((2,5-dichloropyrimidin-4-yl)(methyl)amino)-3-azaspiro[5.5]undecane-3-carboxylate (241 mg, 0.56 mmol) and 1-methyl-1H-pyrazol-4-amine hydrochloride (172.32 mg, 1.29 mmol) in butan-1-ol (5 mL) was added DIPEA (217.14 mg, 1.68 mmol). The reaction mixture was stirred at 150° C. in a sealed tube overnight, then cooled down to rt, and concentrated in vacuo. The residue was purified by silica gel column chromatography (DCM/MeOH (v/v)=100/1 to 10/1) to give the title compound as a white solid (198 mg, 72%).

MS (ESI, pos. ion) m/z: 490.4 [M+H]$^+$.

Step 3) 5-chloro-N⁴-methyl-N²-(1-methyl-1H-pyrazol-4-yl)-N⁴-(3-azaspiro[5.5]undecan-9-yl)pyrimidine-2,4-diamine To a suspension of tert-butyl 9-((5-chloro-2-((1-methyl-1H-pyrazol-4-yl)amino)pyrimidin-4-yl)(methyl)amino)-3-azaspiro[5.5]undecane-3-carboxylate (330 mg, 0.67 mmol) in dichloromethane (15 mL) was added the solution of HCl in EtOAc (3 mL, 12 mmol). The reaction mixture was stirred at rt for 2 h and then adjust to pH=8-9 with the solution of saturated NaHCO₃. The resulting mixture was diluted with 20 mL of H₂O and exacted with a mixture of DCM and MeOH (10/1, 10 mL×3). The combine organic layers were washed with brine (20 mL×1), then over Na₂SO₄, filtered and concentrated in vacuo. The residue was purified by flash silica gel column chromatography (DCM/MeOH (v/v)=10/1 to 5/1) to give the title compound as a yellow solid (170 mg, 64.8%).

MS (ESI, pos. ion) m/z: 195.8 [(M+H)/2]⁺

Step 4) 3-(9-((5-chloro-2-((1-methyl-1H-pyrazol-4-yl)amino)pyrimidin-4-yl)(methyl)amino)-3-azaspiro[5.5]undecan-3-yl)-3-oxopropanenitrile To a suspension 5-chloro-N⁴-methyl-N²-(1-methyl-1H-pyrazol-4-yl)-N⁴-(3-azaspiro [5.5]undecan-9-yl)pyrimidine-2,4-diamine (165 mg, 0.42 mmol) and 2-cyanoacetic acid (107.18 mg, 1.26 mmol) in a mixture of DCM and N,N-dimethylformamide (8 mL/2 mL) were added O-(7-aza-1H-benzotriazol-1-yl)-N,N,N',N'-tetramethyluronium hexafluorophosphate (85.75 mg, 0.63 mmol) and N,N-diethylethanamine (127.50 mg, 1.26 mmol). The mixture was stirred at rt overnight and then concentrated in vacuo. The residue was purified by silica gel column chromatography (DCM/MeOH (v/v)=100/1 to 10/1) to give the title compound as a yellow solid (30 mg, 15.54%).

MS (ESI, pos. ion) m/z: 457.4 [M+H]⁺.

¹H NMR (400 MHz, DMSO-d₆): δ (ppm) 9.08 (s, 1H), 7.93 (s, 1H), 7.72 (s, 1H), 7.44 (s, 1H), 4.15 (s, 1H), 4.01 (d, J=9.5 Hz, 4H), 3.77 (s, 3H), 3.44 (s, 2H), 2.98 (s, 3H), 2.03-1.93 (m, 1H), 1.76 (dd, J=25.8, 12.5 Hz, 4H), 1.51 (dd, J=35.9, 10.8 Hz, 5H), 1.34 (d, J=6.5 Hz, 2H).

Example 25

3-(9-((5-methyl-2-((1-methyl-1H-pyrazol-4-yl)amino)pyrimidin-4-yl)amino)-3-azaspiro[5.5]undecan-3-yl)-3-oxopropanenitrile

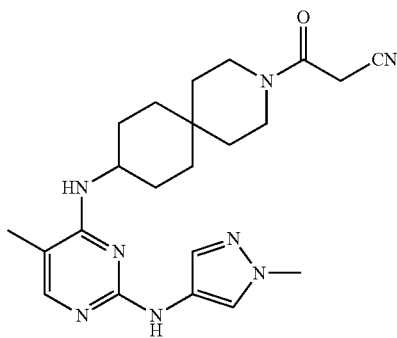 [SMILES: Cc1cnc(Nc2cnn(C)c2)nc1NC1CCC2(CC1)CCN(C(=O)CC#N)CC2]

Step 1) tert-butyl 9-amino-3-azaspiro[5.5]undecane-3-carboxylate

To a solution of tert-butyl 9-oxo-3-azaspiro[5.5]undecane-3-carboxylate (5.35 g, 20.0 mmol) in EtOH (40 mL) were added a solution of NH₃ in MeOH (7M, 40 mL, 280.0 mmol) and Ti(Oi-Pr)₄ (11.30 g, 40.0 mmol), the mixture was stirred at room temperature overnight. And then NaBH₄ (1.51 g, 40.0 mmol) was added portionwise. After addition, the resulting mixture was stirred at room temperature for another 5 h, then quenched with water (40 mL), stirred for 1 h and filtered. The filtrate was concentrated in vacuo, and the residue was purified by silica gel column chromatography (MeOH/DCM (v/v)=1/25) to give the product as a light yellow solid (1.20 g, 22.4%).

MS (ESI, pos. ion) m/z: 269.3 [M+H]⁺.

Step 2) tert-butyl 9-((2-chloro-5-methylpyrimidin-4-yl)amino)-3-azaspiro[5.5]undecane-3-carboxylate To a solution of 2,4-dichloro-5-methyl-pyrimidine (0.58 g, 3.60 mmol) and tert-butyl 3-amino-9-azaspiro[5.5]undecane-9-carboxylate (1.44 g, 5.37 mmol) in EtOH (25 mL) was added Et₃N (0.86 g, 8.50 mmol). After addition, the reaction mixture was stirred at 100° C. in a sealed tube for 25.5 h and concentrated in vacuo. The residue was purified by silica gel column chromatography (EtOAc/PE (v/v)=1/2) to give the title compound as a yellow solid (332.2 mg, 24%).

MS (ESI, pos. ion) m/z: 395.4 [M+H]⁺.

Step 3) tert-butyl 9-((5-methyl-2-((1-methyl-1H-pyrazol-4-yl)amino)pyrimidin-4-yl)amino)-3-azaspiro[5.5]undecane-3-carboxylate To a suspension of tert-butyl 9-((2-chloro-5-methylpyrimidin-4-yl)amino)-3-azaspiro[5.5]undecane-3-carboxylate (332.2 mg, 0.84 mmol) and 1-methyl-1H-pyrazol-4-amine hydrochloride (252.2 mg, 1.89 mmol) in n-BuOH (8 mL) was added DIPEA (445.9 mg, 3.45 mmol). The reaction mixture was stirred at 150° C. in a sealed tube for 16 h and concentrated in vacuo. The residue was purified by silica gel column chromatography (MeOH/DCM (v/v)=1/20) to give the title compound as yellow oil (0.38 g, 99%).

MS (ESI, pos. ion) m/z: 456.4 [M+H]⁺.

Step 4) 5-methyl-N²-(1-methyl-1H-pyrazol-4-yl)-N⁴-(3-azaspiro[5.5]undecan-9-yl)pyrimidine-2,4-diamine To a solution of tert-butyl 9-((5-methyl-2-((1-methyl-1H-pyrazol-4-yl)amino)pyrimidin-4-yl)amino)-3-azaspiro[5.5]undecane-3-carboxylate (400 mg, 0.88 mmol) in DCM (20 mL) was added a solution of HCl in EtOAc (20 mL, 80 mmol). The reaction mixture was stirred at rt overnight and concentrated in vacuo. The residue was dissolved in water (50 mL) and adjusted to pH=10 with a saturated Na₂CO₃ aqueous solution, then extracted with DCM (200 mL×3). The combined organic phases were washed with brine (200 mL), dried over anhydrous Na₂SO₄, then filtered and concentrated in vacuo. The residue was purified by silica gel column chromatography (a solution of NH₃ in MeOH (7 M)/MeOH/DCM (v/v/v)=1/20/60) to give the title compound as a beige solid (100.2 mg, 32%).

MS (ESI, pos. ion) m/z: 356.1 [M+H]⁺.

¹H NMR (600 MHz, CDCl₃): δ (ppm) 7.75 (s, 1H), 7.69 (s, 1H), 7.50 (s, 1H), 6.43 (br. s, 1H), 3.99 (m, 1H), 3.89 (s, 3H), 2.84 (m, 4H), 2.05 (m, 2H), 1.99 (m, 2H), 1.94 (s, 3H), 1.82 (d, J=12.4 Hz, 2H), 1.40 (m, 4H), 1.34 (m, 2H).

Step 5) 3-(9-((5-methyl-2-((1-methyl-1H-pyrazol-4-yl)amino)pyrimidin-4-yl)amino)-3-azaspiro[5.5]undecan-3-yl)-3-oxopropanenitrile To a solution of 5-methyl-$N^2$-(1-methyl-1H-pyrazol-4-yl)-$N^4$-(3-azaspiro[5.5]undecan-9-yl)pyrimidine-2,4-diamine (100 mg, 0.28 mmol), 2-cyanoacetic acid (43.3 mg, 0.51 mmol) in a mixture of DCM and DMF (20 mL/5 mL) were added HATU (241.9 mg, 0.64 mmol) and $Et_3N$ (85.8 mg, 0.85 mmol). After addition, the reaction mixture was stirred at rt overnight, then quenched with $H_2O$ (30 mL) and extracted with DCM (100 mL×3). The combined organic phases were washed with brine (100 mL), dried over anhydrous $Na_2SO_4$, then filtered and concentrated in vacuo. The residue was purified by silica gel column chromatography (DCM/MeOH (v/v)=10/1) to give the title compound as a beige solid (66.8 mg, 56%).

MS (ESI, pos. ion) m/z: 423.4 $[M+H]^+$;

$^1$H NMR (400 MHz, DMSO-$d_6$): δ (ppm) 8.54 (s, 1H), 8.32 (s, 1H), 7.74 (s, 1H), 7.57 (s, 1H), 7.42 (s, 1H), 3.95 (m, 1H), 3.76 (s, 3H), 3.23 (s, 6H), 1.99 (s, 3H), 1.75 (m, 4H), 1.52 (m, 4H), 1.28 (m, 4H).

Example 26

3-(9-((5-chloro-2-((1-methyl-1H-pyrazol-4-yl)amino)pyrimidin-4-yl)amino)-3-azaspiro[5.5]undecan-3-yl)-3-oxopropanenitrile

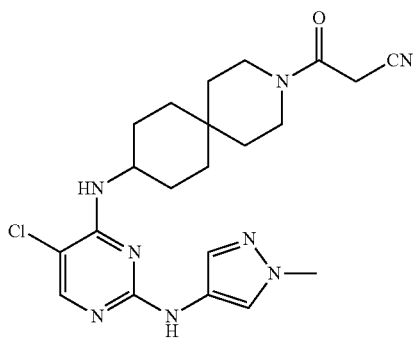 [SMILES: Cn1cc(Nc2ncc(Cl)c(NC3CCC4(CC3)CCN(C(=O)CC#N)CC4)n2)cn1]

Step 1) tert-butyl 9-((2,5-dichloropyrimidin-4-yl)amino)-3-azaspiro[5.5]undecane-3-carboxylate To a solution of 2,4,5-trichloropyrimidine (495.9 mg, 2.7 mmol) in ethanol (20 mL) were added tert-butyl 9-amino-3-azaspiro[5.5]undecane-3-carboxylate (1.08 g, 4.0 mmol) and $Et_3N$ (413.6 mg, 4.1 mmol). The mixture was stirred at room temperature for 12 h and then concentrated in vacuo. The residue was purified by silica gel column chromatography (EtOAc/PE (v/v)=1/10 to 1/7) to give the product as a light yellow solid (387.1 mg, 34.5%).

MS (ESI, pos. ion) m/z: 415.0 $[M+H]^+$.

Step 2) tert-butyl 9-((5-chloro-2-((1-methyl-1H-pyrazol-4-yl)amino)pyrimidin-4-yl)amino)-3-azaspiro[5.5]undecane-3-carboxylate To a solution of tert-butyl 9-((2,5-dichloropyrimidin-4-yl)amino)-3-azaspiro[5.5]undecane-3-carboxylate (230.0 mg, 0.55 mmol) and 1-methyl-1H-pyrazol-4-amine hydrochloride (185.4 mg, 1.39 mmol) in n-BuOH (3 mL) was added DIPEA (215.7 mg, 1.67 mmol). The mixture was stirred at 150° C. overnight and then concentrated in vacuo. The residue was purified by silica gel column chromatography (MeOH/DCM (v/v)=1/100 to 1/70) to give the product as a light yellow solid (87.0 mg, 33.0%).

MS (ESI, pos. ion) m/z: 476.1 $[M+H]^+$.

Step 3) 5-chloro-$N^2$-(1-methyl-1H-pyrazol-4-yl)-$N^4$-(3-azaspiro[5.5]undecan-9-yl)pyrimidine-2,4-diamine To a solution of tert-butyl 9-((5-chloro-2-((1-methyl-1H-pyrazol-4-yl)amino) pyrimidin-4-yl)amino)-3-azaspiro[5.5]undecane-3-carboxylate (87.0 mg, 0.18 mmol) in dichloromethane (5 mL) was added a solution of HCl in EtOAc (2 mL, 8 mmol). The mixture was stirred at room temperature for 5 h and then concentrated in vacuo. The residue was dissolved in MeOH (2 mL) and adjusted to pH=10 with a saturated $Na_2CO_3$ aqueous solution, then extracted with DCM (20 mL×3). The combined organic phases were washed with brine (20 mL), dried over anhydrous $Na_2SO_4$, then filtered and concentrated in vacuo. The residue was purified by preparative TLC (MeOH/DCM (v/v)=1/5) to give the product as a light yellow solid (54.0 mg, 78.6%).

MS (ESI, pos. ion) m/z: 376.1 $[M+H]^+$.

$^1$H NMR (400 MHz, DMSO-$d_6$): δ (ppm) 8.73 (s, 1H), 7.85 (s, 1H), 7.72 (s, 1H), 7.44 (s, 1H), 6.62 (s, 1H), 3.77 (s, 3H), 3.03 (m, 5H), 1.84-1.23 (m, 12H).

Step 4) 3-(9-((5-chloro-2-((1-methyl-1H-pyrazol-4-yl)amino)pyrimidin-4-yl)amino)-3-azaspiro[5.5]undecan-3-yl)-3-oxopropanenitrile To a solution of 5-chloro-$N^2$-(1-methyl-1H-pyrazol-4-yl)-$N^4$-(3-azaspiro[5.5]undecan-9-yl)pyrimidine-2,4-diamine (54.0 mg, 0.14 mmol) in a mixture of dichloromethane and DMF (8 mL/2 mL) were added 2-cyanoacetic acid (30.7 mg, 0.36 mmol), $Et_3N$ (52.1 mg, 0.52 mmol) and HATU (164.2 mg, 0.43 mmol). The mixture was stirred at room temperature overnight and then concentrated in vacuo. The residue was purified by preparative TLC (MeOH/DCM (V/V)=1/10) to give the title compound as a light yellow solid (53.0 mg, 83.3%).

MS (ESI, pos. ion) m/z: 443.1 $[M+H]^+$.

$^1$H NMR (400 MHz, DMSO): δ (ppm) 7.84 (s, 1H), 7.72 (s, 1H), 7.44 (s, 1H), 6.63 (s, 1H), 5.31 (s, 1H), 4.00 (s, 3H), 3.76 (s, 2H), 3.17-3.03 (m, 5H), 1.55-1.22 (m, 12H).

Example 27

6-(9-((5-chloro-2-((1-methyl-1H-pyrazol-4-yl)amino)pyrimidin-4-yl)amino)-3-azaspiro[5.5]undecan-3-yl)nicotinonitrile

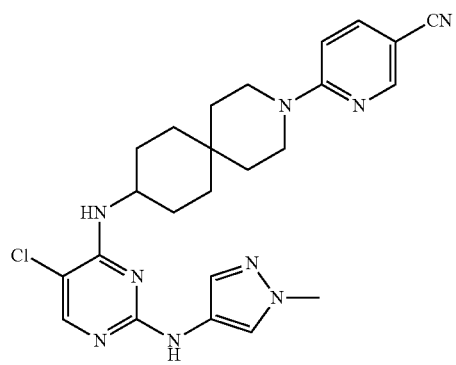 [SMILES: Cn1cc(Nc2ncc(Cl)c(NC3CCC4(CC3)CCN(c3ccc(C#N)cn3)CC4)n2)cn1]

To a suspension of 5-chloro-$N^2$-(1-methyl-1H-pyrazol-4-yl)-$N^4$-(3-azaspiro[5.5]undecan-9-yl) pyrimidine-2,4-diamine (0.11 g, 0.29 mmol) in a mixture of DCM and MeOH (5.0 mL/5.0 mL) were added 6-chloropyridine-3-carbonitrile (0.086 g, 0.62 mmol) and Et$_3$N (0.10 mL, 0.72 mmol). The mixture was heated to reflux overnight and then concentrated in vacuo. The residue was purified by silica gel column chromatography (DCM/MeOH (v/v)=50/1) to afford the product as a light yellow solid (55 mg, 39%).

MS (ESI, pos. ion) m/z: 478.4 [M+H]$^+$;

$^1$H NMR (400 MHz, CDCl$_3$): δ (ppm) 8.42 (d, J=2.0 Hz, 1H), 7.88 (s, 1H), 7.67 (s, 1H), 7.61 (dd, J=9.1, 2.3 Hz, 1H), 7.54 (s, 1H), 6.67 (s, br, 1H), 6.61 (d, J=9.1 Hz, 1H), 5.16 (d, J=7.3 Hz, 1H), 4.05-3.93 (m, 1H), 3.90 (s, 3H), 3.73-3.62 (m, 4H), 2.08-1.98 (m, 2H), 1.87-1.77 (m, 2H), 1.72-1.67 (m, 2H), 1.58-1.52 (m, 2H), 1.50-1.39 (m, 4H).

Example 28

1-(9-((5-chloro-2-((1-methyl-1H-pyrazol-4-yl)amino)pyrimidin-4-yl)amino)-3-azaspiro[5.5]undecan-3-yl)ethanone

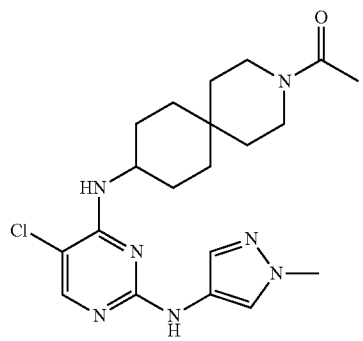 [SMILES: CC(=O)N1CCC2(CCC(Nc3nc(Nc4cnn(C)c4)ncc3Cl)CC2)CC1]

To a solution of 5-chloro-$N^2$-(1-methyl-1H-pyrazol-4-yl)-$N^4$-(3-azaspiro[5.5]undecan-9-yl)pyrimidine-2,4-diamine (150.3 mg, 0.3998 mmol) in dichloromethane (15 mL) were added acetyl acetate (81.5 mg, 0.798 mmol) and N,N-diethylethanamine (81.3 mg, 0.803 mmol). The mixture was stirred at room temperature for 2 h and concentrated in vacuo. The residue was purified by flash silica gel column chromatography (DCM/MeOH (v/v)=50/1 to 10/1) to give the product as a yellow solid (120.0 mg, 71.82%).

MS (ESI, pos. ion) m/z: 418.0 [M+H]$^+$ $^1$H NMR (400 MHz, CDCl$_3$): δ (ppm) 7.85 (s, 1H), 7.64 (d, J=8.4 Hz, 1H), 7.51 (d, J=11.2 Hz, 1H), 6.90 (s, 1H), 5.13 (d, J=4.3 Hz, 1H), 3.94 (dd, J=7.1, 3.4 Hz, 1H), 3.87 (s, 3H), 3.56 (dd, J=11.6, 5.9 Hz, 2H), 3.40 (dd, J=11.3, 5.5 Hz, 2H), 2.09 (t, J=3.3 Hz, 3H), 1.98 (dd, J=8.9, 3.9 Hz, 2H), 1.88 (s, 2H), 1.75 (s, 2H), 1.61-1.51 (m, 2H), 1.46 (d, J=12.8 Hz, 2H), 1.41-1.36 (m, 2H).

Example 29

5-chloro-$N^2$-(1-methyl-1H-pyrazol-4-yl)-$N^4$-(3-(methylsulfonyl)-3-azaspiro[5.5]undecan-9-yl)pyrimidine-2,4-diamine

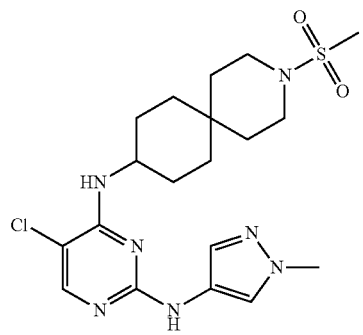 [SMILES: Cn1cc(Nc2ncc(Cl)c(NC3CCC4(CC3)CCN(S(C)(=O)=O)CC4)n2)cn1]

To a suspension of 5-chloro-$N^2$-(1-methyl-1H-pyrazol-4-yl)-$N^4$-(3-azaspiro[5.5]undecan-9-yl)pyrimidine-2,4-diamine (0.16 g, 0.43 mmol) in anhydrous DCM (10.0 mL) were added DMAP (0.011 g, 0.092 mmol) and Et$_3$N (0.15 mL, 1.10 mmol), followed by methanesulfonyl chloride (0.076 g, 0.66 mmol) at 0° C. The mixture was stirred at room temperature overnight and concentrated in vacuo. The residue was purified by silica gel column chromatography (DCM/MeOH (v/v)=10/1) to give the product as a light yellow solid (0.14 g, 72%).

MS (ESI, pos. ion) m/z: 454.2 [M+H]$^+$;

$^1$H NMR (400 MHz, CDCl$_3$): δ (ppm) 7.86 (s, 1H), 7.65 (s, 1H), 7.55 (s, 1H), 7.24-6.97 (m, 1H), 5.23 (d, J=6.5 Hz, 1H), 4.03-3.92 (m, 1H), 3.89 (s, 3H), 3.24 (m, 4H), 2.81 (s, 3H), 2.04-1.97 (m, 2H), 1.91 (m, 4H), 1.78 (m, 2H), 1.75-1.69 (m, 2H), 1.60-1.54 (m, 2H).

Example 30

1-(9-((5-chloro-2-((1-methyl-1H-pyrazol-4-yl)amino)pyrimidin-4-yl)amino)-3-azaspiro[5.5]undecan-3-yl)-2,2,2-trifluoroethanone

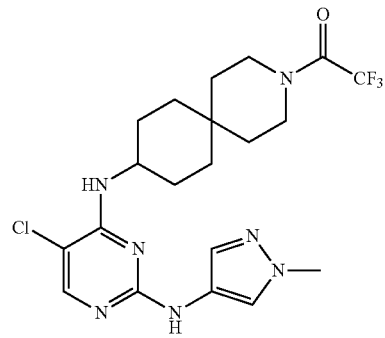 [SMILES: Cn1cc(Nc2ncc(Cl)c(NC3CCC4(CC3)CCN(C(=O)C(F)(F)F)CC4)n2)cn1]

To a suspension of 5-chloro-$N^2$-(1-methyl-1H-pyrazol-4-yl)-$N^4$-(3-azaspiro[5.5]undecan-9-yl)pyrimidine-2,4-diamine (0.30 g, 0.80 mmol) in anhydrous DCM (10.0 mL) were added N,N-diethylethanamine (0.25 mL, 1.80 mmol) and (2,2,2-trifluoroacetyl)2,2,2-trifluoroacetate (0.19 g, 0.89 mmol). The mixture was stirred at room temperature overnight, then concentrated in vacuo. The residue was purified by silica gel column chromatography (DCM/MeOH (v/v)=100/1 to 50/1) to afford the title compound as a white solid (0.27 g, 71%).

MS (ESI, pos. ion) m/z: 471.8 [M+H]$^+$;

$^1$H NMR (400 MHz, CDCl$_3$): δ (ppm) 7.89 (s, 1H), 7.66 (s, 1H), 7.54 (s, 1H), 6.60 (s, 1H), 5.13 (d, J=4.5 Hz, 1H), 4.04-3.92 (m, 1H), 3.90 (s, 3H), 3.70-3.62 m, 2H), 3.62-3.54 (m, 2H), 2.08-1.97 (m, 2H), 1.86-1.76 (m, 2H), 1.72-1.64 (m, 2H), 1.55-1.39 (m, 6H).

Example 31

5-chloro-N$^2$-(1-methyl-1H-pyrazol-4-yl)-N$^4$-(2-(methylsulfonyl)octahydrocyclopenta[c]pyrrol-5-yl)pyrimidine-2,4-diamine

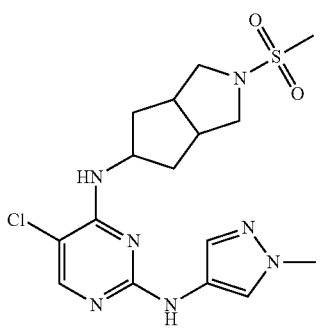 [SMILES: Cn1cc(Nc2ncc(Cl)c(NC3CC4CN(S(C)(=O)=O)CC4C3)n2)cn1]

Example 32

1-(5-((5-chloro-2-((1-methyl-1H-pyrazol-4-yl)amino)pyrimidin-4-yl)amino)hexahydrocyclopenta[c]pyrrol-2(1H)-yl)ethanone

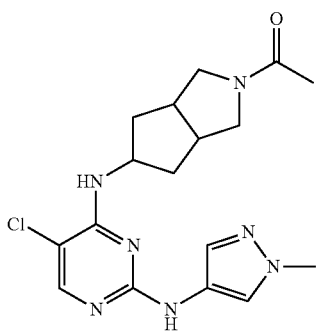 [SMILES: CC(=O)N1CC2CC(Nc3nc(Nc4cnn(C)c4)ncc3Cl)CC2C1]

To a suspension of 5-chloro-N$^2$-(1-methyl-1H-pyrazol-4-yl)-N$^4$-(octahydrocyclopenta[c]pyrrol-5-yl)pyrimidine-2,4-diamine (673.3 mg, 2.02 mmol) and DIPEA (0.52 g, 4.00 mmol) in DCM (10 mL) was added methanesulfonyl chloride (242.9 mg, 2.12 mmol). The reaction mixture was stirred at rt for 2 h, then quenched with H$_2$O (30 mL) and extracted with DCM (100 mL×3). The combined organic phases were washed with brine (100 mL), dried over anhydrous Na$_2$SO$_4$, filtered and concentrated in vacuo. The residue was purified by silica gel column chromatography (DCM/MeOH (v/v)=50/1) to give example 31 as a beige solid (166.5 mg, 20%) and another elution (DCM/MeOH (v/v)=30/1) to give example 32 as a beige solid (200.2 mg, 26.4%).

Example 31

MS (ESI, pos. ion) m/z: 412.3 [M+H]$^+$;

$^1$H NMR (400 MHz, DMSO-d$_6$): δ (ppm) 9.01 (s, 1H), 7.86 (s, 1H), 7.74 (s, 1H), 7.43 (s, 1H), 6.97 (d, J=7.7 Hz, 1H), 4.39 (m, 1H), 3.81 and 3.78 (s, 3H), 3.24 (m, 2H), 3.13 (d, J=8.3 Hz, 2H), 2.92 (s, 3H), 2.69 (br. s, 2H), 2.26 (m, 2H), 1.52 (m, 2H).

Example 32

MS (ESI, pos. ion) m/z: 376.3 [M+H]$^+$;

$^1$H NMR (400 MHz, CDCl$_3$): δ (ppm) 7.89 (s, 1H), 7.67 (s, 1H), 7.55 (s, 1H), 6.74 (s, 1H), 5.25 (d, J=7.0 Hz, 1H), 4.43 (m, 1H), 3.89 (s, 3H), 3.64 (m, 3H), 3.41 (dd, J=10.9, 3.5 Hz, 1H), 2.79 (m, 2H), 2.52 (m, 2H), 2.09 (s, 3H), 1.43 (m, 2H).

Example 33

6-(5-((5-chloro-2-((1-methyl-1H-pyrazol-4-yl)amino)pyrimidin-4-yl)amino)hexahydrocyclopenta[c]pyrrol-2(1H)-yl)nicotinonitrile

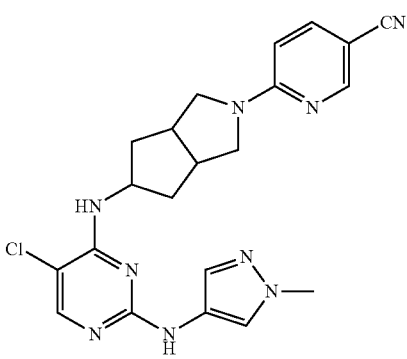 [SMILES: Cn1cc(Nc2ncc(Cl)c(NC3CC4CN(c5ccc(C#N)cn5)CC4C3)n2)cn1]

To a suspension of 5-chloro-N$^2$-(1-methyl-1H-pyrazol-4-yl)-N$^4$-(octahydrocyclopenta[c]pyrrol-5-yl)pyrimidine-2,4-diamine (377.4 mg, 1.13 mmol) and 6-chloronicotinonitrile (318.8 mg, 2.31 mmol) in a mixture of DCM and MeOH (10 mL/10 mL) was added Et$_3$N (235.0 mg, 2.32 mmol). The reaction mixture was stirred at 45° C. overnight and concentrated in vacuo. The residue was purified by silica gel column chromatography (MeOH/DCM (v/v)=1/80) to give the title compound as a beige solid (304.4 mg, 61.8%).

MS (ESI, pos. ion) m/z: 436.2 [M+H]$^+$;

$^1$H NMR (400 MHz, DMSO-d$_6$): δ (ppm) 8.44 (d, J=2.0 Hz, 1H), 7.87 (s, 1H), 7.67 (s, 1H), 7.62 (dd, J=8.9, 2.2 Hz, 1H), 7.55 (s, 1H), 6.56 (s, 1H), 6.40 (d, J=8.9 Hz, 1H), 5.29 (d, J=7.2 Hz, 1H), 4.52 (m, 1H), 3.90 (s, 3H), 3.70 (m, 2H), 3.58 (d, J=10.3 Hz, 2H), 2.93 (m, 2H), 2.57 (dt, J=14.7, 7.5 Hz, 2H), 1.53 (m, 2H).

Example 34

1-(5-((5-chloro-2-((1-methyl-1H-pyrazol-4-yl)amino)pyrimidin-4-yl)amino)hexahydrocyclopenta[c]pyrrol-2(1H)-yl)-2,2,2-trifluoroethanone

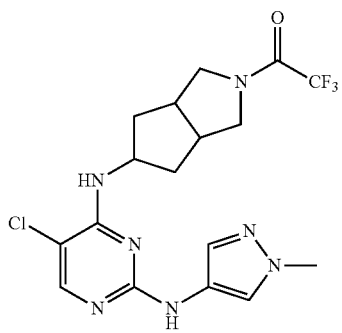 [SMILES: Cn1cc(Nc2ncc(Cl)c(NC3CC4CN(C(=O)C(F)(F)F)CC4C3)n2)cn1]

To a suspension of 5-chloro-$N^2$-(1-methyl-1H-pyrazol-4-yl)-$N^4$ (octahydrocyclopenta[c]pyrrol-5-yl)pyrimidine-2,4-diamine (0.38 g, 1.13 mmol) and Et$_3$N (0.35 g, 3.45 mmol) in DCM (10 mL) was added TFAA (376.6 mg, 1.79 mmol). The reaction mixture was stirred at rt overnight and concentrated in vacuo. The residue was purified by silica gel column chromatography (MeOH/DCM (v/v)=1/80) to give the title compound as a beige solid (0.20 g, 41%).

MS (ESI, pos. ion) m/z: 430.2 [M+H]$^+$;

$^1$H NMR (400 MHz, CDCl$_3$): δ (ppm) 7.88 (s, 1H), 7.64 (s, 1H), 7.58 (s, 1H), 7.09 (br. s, 1H), 5.28 (d, J=6.4 Hz, 1H), 4.44 (m, 1H), 3.89 (s, 3H), 3.74 (m, 4H), 2.83 (m, 2H), 2.57 (m, 2H), 1.36 (m, 2H).

Example 35

5-chloro-$N^2$-(1-methyl-1H-pyrazol-4-yl)-$N^4$-(2-(2,2,2-trifluoroethyl) octahydrocyclopenta[c]pyrrol-5-yl)pyrimidine-2,4-diamine

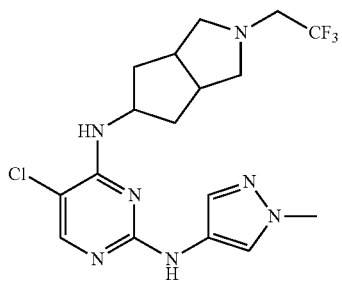 [SMILES: Cn1cc(Nc2ncc(Cl)c(NC3CC4CN(CC(F)(F)F)CC4C3)n2)cn1]

To a solution of 1-[5-[[5-chloro-2-[(1-methyl-1H-pyrazol-4-yl)amino]pyrimidin-4-yl]amino]-hexahydrocyclopenta[c]pyrrol-2(1H)-yl]-2,2,2-trifluoro-ethanone (0.89 g, 2.10 mmol) in THF (20 mL) was added a solution of borane dimethyl sulfide complex (1 mmol/L in THF, 6 mL, 6 mmol) at 0° C. After addition, the reaction mixture was stirred at 0° C. for 10 min and then heated to reflux overnight. The reaction was quenched with 6 M HCl aqueous solution (2 mL) then stirred at rt for 1 h and concentrated in vacuo. The residue was adjusted to pH=10 with a 50% NaOH solution, then diluted with water (50 mL), and extracted with EtOAc (100 mL×3). The combined organic phases were washed with brine (100 mL), dried over anhydrous Na$_2$SO$_4$, filtered and concentrated in vacuo. The residue was purified by silica gel column chromatography (MeOH/DCM (v/v)=1/50) to give the title compound as a beige solid (0.16 g, 19%).

MS (ESI, pos. ion) m/z: 415.8 [M+H]$^+$;

$^1$H NMR (400 MHz, CDCl$_3$): δ (ppm) 7.83 (s, 1H), 7.67 (s, 1H), 7.55 (s, 1H), 7.15 (br. s, 1H), 6.46 (d, J=7.3 Hz, 1H), 4.50 (m, 1H), 3.88 (s, 3H), 3.12 (q, J=9.7 Hz, 2H), 2.91 (d, J=9.2 Hz, 2H), 2.71 (s, 2H), 2.52 (m, 2H), 2.33 (m, 2H), 1.56 (m, 2H).

Example 36

5-chloro-$N^2$-(1,5-dimethyl-1H-pyrazol-3-yl)-$N^4$-(3-azaspiro[5.5]undecan-9-yl)pyrimidine-2,4-diamine

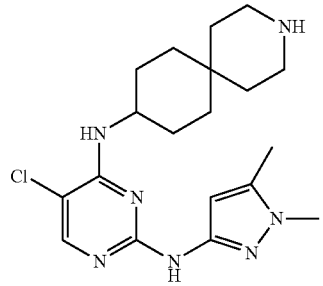 [SMILES: Cc1cc(Nc2ncc(Cl)c(NC3CCC4(CCNCC4)CC3)n2)nn1C]

To a solution of tert-butyl 9-((2,5-dichloropyrimidin-4-yl)amino)-3-azaspiro[5.5]undecane-3-carboxylate (1.52 g, 3.66 mmol) and 1,5-dimethyl-1H-pyrazol-3-amine (800.0 mg, 7.198 mmol in 1,4-dioxane (20 mL) was added trifluoroacetic acid (2.1 g, 18 mmol). The mixture was stirred at 100° C. overnight and concentrated in vacuo. The residue was dissolved in methanol (5 mL), and adjust to Ph=8~9 with the saturated aqueous solution of NaHCO$_3$. Then the mixture was exacted with DCM/MeOH (50 mL/10 mL) and the separated organic layer was washed with brine (100 mL), dried over anhydrous Na$_2$SO$_4$, filtered and concentrated in vacuo. The residue was purified by flash silica gel column chromatography (DCM/MeOH (v/v)=50/1 to 10/1) to give the product as a yellow white solid (1.36 g, 95.3%).

MS (ESI, pos. ion) m/z: 195.7 [(M+H)/2]⁺.
¹H NMR (400 MHz, DMSO): δ (ppm) 7.82 (s, 1H), 6.29 (s, 1H), 3.93 (s, 1H), 3.60 (s, 3H), 3.04 (s, 4H), 2.21 (s, 3H), 1.73 (d, J=11.6 Hz, 4H), 1.57 (d, J=12.5 Hz, 2H), 1.51 (d, J=5.2 Hz, 2H), 1.27-1.15 (m, 4H)

Example 37

3-(9-((5-chloro-2-((1,5-dimethyl-1H-pyrazol-3-yl)amino)pyrimidin-4-yl)amino)-3-azaspiro[5.5]undecan-3-yl)-3-oxopropanenitrile

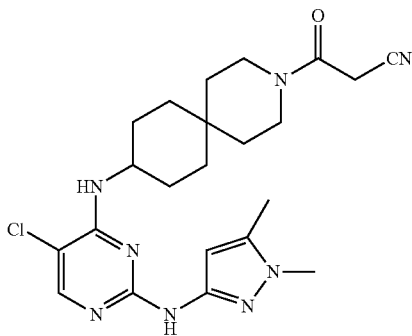 [SMILES: Cc1cc(Nc2ncc(Cl)c(NC3CCC4(CC3)CCN(C(=O)CC#N)CC4)n2)nn1C]

To a solution of 5-chloro-N²-(1,5-dimethyl-1H-pyrazol-3-yl)-N⁴-(3-azaspiro[5.5]undecan-9-yl)pyrimidine-2,4-diamine (200.5 mg, 0.5142 mmol) in dichloromethane (28 mL) and N,N-dimethylformamide (7 mL) were added 2-cyanoacetic acid (110.3 mg, 1.297 mmol), N,N-diethylethanamine (156.5 mg, 1.547 mmol) and HATU (585.4 mg, 1.540 mmol). The mixture was stirred at room temperature for 4 h and concentrated in vacuo. The residue was purified by flash silica gel column chromatography (DCM/MeOH (v/v)=50/1 to 10/1) to give the title compound as a white solid (128.5 mg, 54.68%).
MS (ESI, pos. ion) m/z: 457.2 [M+H]⁺.
¹H NMR (400 MHz, CD₃OD): δ (ppm) 7.87 (d, J=3.4 Hz, 2H), 6.05 (s, 1H), 4.54 (s, 1H), 4.10 (s, 1H), 3.83 (s, 1H), 3.79 (s, 3H), 3.59 (s, 2H), 3.44 (s, 2H), 2.31 (s, 3H), 2.03 (d, J=6.3 Hz, 1H), 1.85 (d, J=10.6 Hz, 4H), 1.76-1.69 (m, 1H), 1.63 (d, J=12.1 Hz, 4H), 1.51-1.44 (m, 1H), 1.41 (t, J=5.8 Hz, 1H).

Example 38

5-chloro-N²-(1,5-dimethyl-1H-pyrazol-3-yl)-N⁴-(octahydrocyclopenta[c]pyrrol-5-yl)pyrimidine-2,4-diamine

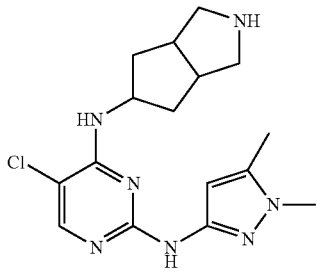 [SMILES: Cc1cc(Nc2ncc(Cl)c(NC3CC4CNCC4C3)n2)nn1C]

Step 1) tert-butyl 5-((5-chloro-2-((1,5-dimethyl-1H-pyrazol-3-yl)amino)pyrimidin-4-yl)amino)hexahydrocyclopenta[c]pyrrole-2(1H)-carboxylate To a solution of tert-butyl 5-[(2,5-dichloropyrimidin-4-yl)amino]-hexahydro-1H-cyclopenta[c]pyrrole-2-carboxylate (1.29 g, 3.46 mmol) and 1,5-dimethylpyrazol-3-amine (0.80 g, 7.20 mmol) in 1,4-dioxane (20 mL) was added trifluoroacetic acid (2.01 g, 17.60 mmol). The reaction mixture was stirred at 100° C. overnight and adjusted to pH=10 with a saturated Na₂CO₃ solution, then extracted with EtOAc (100 mL×3). The combined organic phases were washed with brine (50 mL), dried over anhydrous Na₂SO₄, filtered and concentrated in vacuo. The residue was purified by silica gel column chromatography (EtOAc/PE (v/v)=2/1) to give the title compound as a yellow solid (294.5 mg, 19%).
MS (ESI, pos. ion) m/z: 448.1 [M+H]⁺.

Step 2) 5-chloro-N²-(1,5-dimethyl-1H-pyrazol-3-yl)-N⁴-(octahydrocyclopenta[c]pyrrol-5-yl)pyrimidine-2,4-diamine To a solution of tert-butyl 5-((5-chloro-2-((1,5-dimethyl-1H-pyrazol-3-yl)amino)pyrimidin-4-yl)amino)hexahydrocyclopenta[c]pyrrole-2(1H)-carboxylate (256.3 mg, 0.57 mmol) in DCM (10 mL) was added a solution of HCl in EtOAc (10 mL, 40 mmol). The reaction mixture was stirred at rt for 1 h and concentrated in vacuo. The residue was dissolved in water (30 mL) and adjusted to pH=10 with a saturated Na₂CO₃ aqueous solution, then extracted with DCM (100 mL×3). The combined organic phases were washed with brine (100 mL), dried over anhydrous Na₂SO₄, filtered and concentrated in vacuo. The residue was purified by silica gel column chromatography (a solution of NH₃ in MeOH (7 M)/MeOH/DCM (v/v/v)=3/60/600) to give the title compound as a beige solid (199.0 mg, 100%).
MS (ESI, pos. ion) m/z: 348.3 [M+H]⁺;
¹H NMR (400 MHz, DMSO-d₆): δ (ppm) 8.97 (s, 1H), 8.03 (d, J=8.6 Hz, 1H), 7.81 (s, 1H), 6.33 (s, 1H), 4.41 (m, 1H), 3.58 (s, 3H), 2.68 (d, J=3.0 Hz, 4H), 2.54 (m, 2H), 2.19 (s, 4H), 2.14 (m, 2H), 1.39 (m, 2H).

Example 39

3-(5-((5-chloro-2-((1,5-dimethyl-1H-pyrazol-3-yl)amino)pyrimidin-4-yl)amino)hexahydrocyclopenta[c]pyrrol-2(1H)-yl)-3-oxopropanenitrile

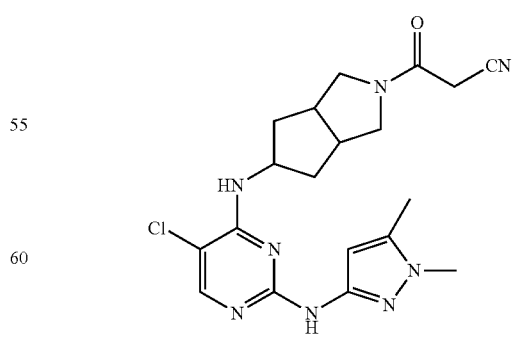

To a solution of 5-chloro-N²-(1,5-dimethyl-1H-pyrazol-3-yl)-N⁴-(octahydro cyclopenta[c]pyrrol-5-yl)pyrimidine-2,4-diamine (522.0 mg, 1.50 mmol) and 2-cyanoacetic acid (127.6 mg, 1.50 mmol) in a mixture of DCM (40 mL) and DMF (10 mL) were added HATU (690.2 mg, 1.82 mmol) and Et₃N (313.5 mg, 3.10 mmol). After addition, the reaction mixture was stirred at rt for 1.5 h, then quenched with H₂O (30 mL) and extracted with DCM (100 mL×3). The combined organic phases were washed with brine (100 mL), dried over anhydrous Na₂SO₄, filtered and concentrated in vacuo. The residue was purified by silica gel column chromatography (DCM/MeOH (v/v)=80/1) to give the title compound as a beige solid (455.2 mg, 73.1%).

MS (ESI, pos. ion) m/z: 415.2 [M+H]⁺;

¹H NMR (400 MHz, CDCl₃): δ (ppm) 7.92 (s, 1H), 7.12 (s, 1H), 6.41 (s, 1H), 5.21 (d, J=6.9 Hz, 1H), 4.47 (m, 1H), 3.74 (m, 2H), 3.69 (s, 3H), 3.62 (dd, J=12.7, 4.2 Hz, 1H), 3.49 (dd, J=13.9, 4.6 Hz, 1H), 3.45 (s, 2H), 2.84 (m, 2H), 2.58 (td, J=12.4, 7.1 Hz, 2H), 2.28 (s, 3H), 1.42 (m, 2H).

Example 40

5-chloro-N²-(1-methyl-1H-imidazol-4-yl)-N⁴-(octahydrocyclopenta[c]pyrrol-5-yl)pyrimidine-2,4-diamine

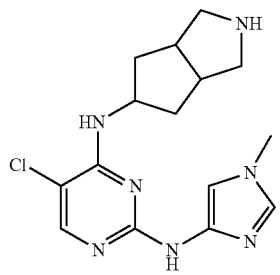 [SMILES: Cn1cnc(Nc2ncc(Cl)c(NC3CC4CNCC4C3)n2)c1]

Step 1) tert-butyl 5-((5-chloro-2-((1-methyl-1H-imidazol-4-yl)amino)pyrimidin-4-yl)amino)hexahydrocyclopenta[c]pyrrole-2(1H)-carboxylate To a suspension of tert-butyl 5-[(2,5-dichloropyrimidin-4-yl)amino]-hexahydrocyclopenta[c]pyrrole-2(1H)-carboxylate (373.0 mg, 1.00 mmol) and 1-methylimidazol-4-amine (341.8 mg, 3.52 mmol) in dioxane (10 mL) were added Pd(OAc)₂ (52.0 mg, 0.23 mmol), BINAP (125.0 mg, 0.19 mmol) and Cs₂CO₃ (647.2 mg, 1.99 mmol). The reaction mixture was stirred at 150° C. under microwave for 2 h and concentrated in vacuo. The residue was purified by silica gel column chromatography (MeOH/DCM (v/v)=1/50) to give the title compound as a pale yellow solid (0.21 g, 48%).

MS (ESI, pos. ion) m/z: 434.3 [M+H]⁺;

¹H NMR (400 MHz, CDCl₃): δ (ppm) 7.92 (s, 1H), 7.58 (br. s, 1H), 7.19 (d, J=8.9 Hz, 2H), 5.28 (d, J=7.3 Hz, 1H), 4.46 (m, 1H), 3.68 (s, 3H), 3.51 (m, 2H), 3.36 (d, J=10.0 Hz, 2H), 2.72 (m, 2H), 2.50 (dt, J=14.4, 7.3 Hz, 2H), 1.49 (s, 9H), 1.40 (m, 2H).

Step 2) 5-chloro-N²-(1-methyl-1H-imidazol-4-yl)-N⁴-(octahydrocyclopenta[c]pyrrol-5-yl)pyrimidine-2,4-diamine To a solution of tert-butyl 5-((5-chloro-2-((1-methyl-1H-imidazol-4-yl)amino)pyrimidin-4-yl)amino)hexahydrocyclopenta[c]pyrrole-2(1H)-carboxylate (398.3 mg, 0.92 mmol) in DCM (10 mL) was added a solution of HCl in EtOAc (10 mL, 40 mmol). The reaction mixture was stirred at rt for 1 h and concentrated in vacuo. The residue was dissolved in water (30 mL) and adjusted to pH=10 with a saturated Na₂CO₃ aqueous solution, then extracted with DCM (100 mL×3). The combined organic phases were washed with brine (100 mL), dried over anhydrous Na₂SO₄, filtered and concentrated in vacuo. The residue was purified by silica gel column chromatography (MeOH/DCM (v/v)=1/10) to give the title compound as a beige solid (0.29 mg, 95%).

MS (ESI, pos. ion) m/z: 334.2 [M+H]⁺;

¹H NMR (400 MHz, CDCl₃ and CD₃OD): δ (ppm) 7.84 (s, 1H), 7.46 (s, 1H), 7.07 (d, J=1.1 Hz, 1H), 4.45 (m, 1H), 3.71 (s, 3H), 3.33 (m, 4H), 2.92 (m, 2H), 2.42 (m, 2H), 1.70 (m, 2H).

Example 41

3-(5-((5-chloro-2-((1-methyl-1H-imidazol-4-yl)amino)pyrimidin-4-yl)amino)hexahydrocyclopenta[c]pyrrol-2(1H)-3-oxopropanenitrile

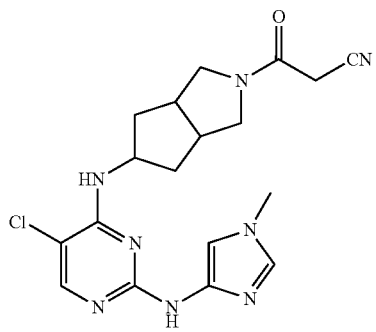 [SMILES: Cn1cnc(Nc2ncc(Cl)c(NC3CC4CN(C(=O)CC#N)CC4C3)n2)c1]

To a solution of 5-chloro-N²-(1-methyl-1H-imidazol-4-yl)-N⁴-(octahydrocyclopenta[c]pyrrol-5-yl)pyrimidine-2,4-diamine (276.4 mg, 0.83 mmol) and 2-cyanoacetic acid (159.9 mg, 1.88 mmol) in a mixture of DCM (20 mL) and DMF (5 mL) were added EDCI (342.0 mg, 1.77 mmol) and HOAT (215.1 mg, 1.58 mmol). After addition, the reaction mixture was stirred at 45° C. for 1 h, then quenched with H₂O (30 mL) and extracted with DCM (100 mL×3). The combined organic phases were washed with brine (100 mL), dried over anhydrous Na₂SO₄, filtered and concentrated in vacuo. The residue was purified by silica gel column chromatography (MeOH/DCM (v/v)=1/20) to give the title compound as a beige solid (84.1 mg, 25.3%).

MS (ESI, pos. ion) m/z: 400.8 [M+H]⁺;

¹H NMR (400 MHz, DMSO-d₆): δ (ppm) 9.00 (s, 1H), 7.87 (s, 1H), 7.37 (s, 1H), 7.11 (s, 1H), 6.94 (d, J=7.4 Hz, 1H), 4.49 (m, 1H), 3.95 (s, 2H), 3.63 (s, 3H), 3.57 (m, 2H), 3.48 (m, 2H), 2.65 (m, 2H), 2.28 (m, 2H), 1.51 (m, 2H).

Example 42

3-(9-((5-chloro-2-((1-methyl-1H-imidazol-4-yl)amino)pyrimidin-4-yl)amino)-3-azaspiro[5.5]undecan-3-yl)-3-oxopropanenitrile

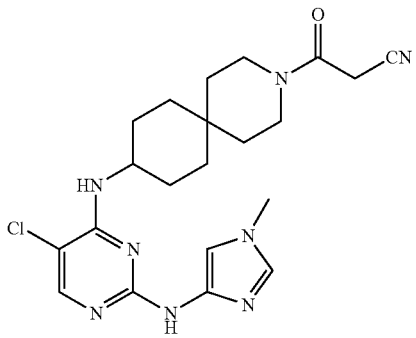 [SMILES: Cn1cnc(Nc2ncc(Cl)c(NC3CCC4(CC3)CCN(C(=O)CC#N)CC4)n2)c1]

Step 1) tert-butyl 9-((5-chloro-2-((1-methyl-1H-imidazol-4-yl)amino)pyrimidin-4-yl)amino)-3-azaspiro[5.5]undecane-3-carboxylate To a solution of tert-butyl 3-[(2,5-dichloropyrimidin-4-yl)amino]-9-azaspiro[5.5]undecane-9-carboxylate (500 mg, 1.204 mmol), 1-methylimidazol-4-amine (176.1 mg, 1.813 mmol) and cesium carbonate (1.19 g, 3.65 mmol) in anhydrous dioxane (10 mL) were added BINAP (148.6 mg, 0.2386 mmol) and Pd(OAc)$_2$ (54.1 mg, 0.241 mmol). The reaction was under an inert atmosphere and stirred at 150° C. under microwave irradiation for 2 h. The reaction solution was concentrated in vacuo and the residue was purified by silica gel column chromatography with (DCM/MeOH (v/v)=30/1) to give the title compound as a yellow solid (292 mg, 50.97%).

MS (ESI, pos. ion) m/z: 476.3 [M+H]$^+$.

Step 2) 5-chloro-N$^2$-(1-methyl-1H-imidazol-4-yl)-N$^4$-(3-azaspiro[5.5]undecan-9-yl)pyrimidine-2,4-diamine hydrochloride To a solution of tert-butyl 9-((5-chloro-2-((1-methyl-1H-imidazol-4-yl)amino)pyrimidin-4-yl)amino)-3-azaspiro[5.5]undecane-3-carboxylate (292 mg, 0.6134 mmol) in DCM (10 mL) was added a solution of HCl in EtOAc (8 mL, 3 mol/L). The reaction was stirred overnight at rt and concentrated in vacuo to give the title compound as a yellow solid (250 mg, 98.82%).

MS (ESI, pos. ion) m/z: 376.2 [M+H]$^+$.

Step 3) 3-(9-((5-chloro-2-((1-methyl-1H-imidazol-4-yl)amino)pyrimidin-4-yl)amino)-3-azaspiro[5.5]undecan-3-yl)-3-oxopropanenitrile To a solution of N$^4$-(9-azaspiro[5.5]undecan-3-yl)-5-chloro-N$^2$-(1-methylimidazol-4-yl)pyrimidine-2,4-diamine hydrochloride (200 mg, 0.4850 mmol), 2-cyanoacetic acid (41.6 mg, 0.489 mmol) and TEA (98.4 mg, 0.972 mmol) in a mixture of DCM and DMF (8 mL/2 mL) were added HOAT (99.6 mg, 0.732 mmol) and EDCI (138.7 mg, 0.724 mmol). The reaction was stirred for 2 h and concentrated in vacuo. The residue was purified by silica gel column chromatography (DCM/MeOH (v/v)=30/1) to give the title compound as a light yellow solid (61.8 mg, 28.8%).

MS (ESI, pos. ion) m/z: 443.3 [M+H]$^+$;

$^1$H NMR (400 MHz, CDCl$_3$): δ (ppm) 7.93 (s, 1H), 7.35 (s, 1H), 7.19 (d, J=14.8 Hz, 2H), 5.12 (d, J=7.0 Hz, 1H), 4.00 (s, 1H), 3.68 (s, 3H), 3.63 (dd, J=11.9, 6.5 Hz, 2H), 3.50 (d, J=2.5 Hz, 2H), 3.45 (dd, J=11.6, 7.1 Hz, 2H), 2.03 (d, J=4.4 Hz, 2H), 1.81 (d, J=10.0 Hz, 2H), 1.66-1.60 (m, 2H), 1.57-1.37 (m, 6H).

Example 43

2-(4-((5-chloro-4-((octahydrocyclopenta[c]pyrrol-5-yl)amino)pyrimidin-2-yl)amino)-1H-pyrazol-1-yl)ethanol

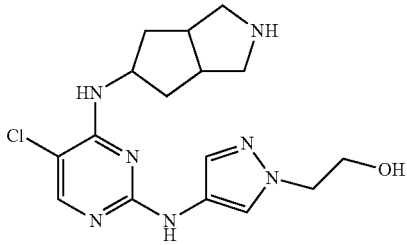 [SMILES: OCCn1cc(Nc2ncc(Cl)c(NC3CC4CNCC4C3)n2)cn1]

Step 1) tert-butyl 5-((5-chloro-2-((1-(2-hydroxyethyl)-1H-pyrazol-4-yl)amino)pyrimidin-4-yl)amino)hexahydrocyclopenta[c]pyrrole-2(1H)-carboxylate To a suspension of tert-butyl 5-((2,5-dichloropyrimidin-4-yl)amino)hexahydrocyclopenta[c]pyrrole-2(1H)-carboxylate (633.5 mg, 1.70 mmol) and 2-(4-amino-1H-pyrazol-1-yl)ethanol (249.1 mg, 1.99 mmol) in i-PrOH (8 mL) was added a solution of HCl in EtOAC ((1 mL, 4 mmol)). The reaction mixture was stirred at 140° C. under microwave radiation for 1 h and concentrated in vacuo. The residue was dissolved in water (30 mL) and adjusted to pH=10 with a saturated Na$_2$CO$_3$ aqueous solution, then extracted with DCM (100 mL×3). The combined organic phases were washed with brine (100 mL), dried over anhydrous Na$_2$SO$_4$, filtered and concentrated in vacuo. The residue was purified by silica gel column chromatography (MeOH/DCM (v/v)=1/30) to give the title compound as a yellow solid (0.50 g, 63%).

MS (ESI, pos. ion) m/z: 463.9 [M+H]$^+$.

Step 2) 2-(4-((5-chloro-4-((octahydrocyclopenta[c]pyrrol-5-yl)amino)pyrimidin-2-yl)amino)-1H-pyrazol-1-yl)ethanol To a solution of tert-butyl 5-((5-chloro-2-((1-(2-hydroxyethyl)-1H-pyrazol-4-yl)amino)pyrimidin-4-yl)amino)hexahydrocyclopenta[c]pyrrole-2(1H)-carboxylate (459.3 mg, 0.99 mmol) in DCM (10 mL) was added a solution of HCl in EtOAc (10 mL, 40 mmol). The reaction mixture was stirred at rt for 1 h and concentrated in vacuo. The residue was dissolved in water (30 mL) and adjusted to pH=10 with a saturated Na$_2$CO$_3$ aqueous solution, then extracted with DCM (250 mL×3). The combined organic phases were washed with brine (250 mL), dried over anhydrous Na$_2$SO$_4$, filtered and concentrated in vacuo. The residue was purified by silica gel column chromatography (MeOH/DCM (v/v)=1/5) to give the title compound as a beige solid (238.2 mg, 66.2%).

MS (ESI, pos. ion) m/z: 363.9 [M+H]⁺;

¹H NMR (400 MHz, CDCl₃): δ (ppm) 7.78 (s, 1H), 7.33 (s, 1H), 6.41 (s, 1H), 4.40 (m, 1H), 4.06 (t, J=4.9 Hz, 2H), 3.84 (t, J=4.8 Hz, 2H), 3.31 (s, 2H), 3.23 (d, J=4.0 Hz, 2H), 2.86 (br. s, 2H), 2.40 (m, 2H), 1.58 (m, 2H).

Example 44

3-(5-((5-chloro-2-((1-(2-hydroxyethyl)-1H-pyrazol-4-yl)amino)pyrimidin-4-yl)amino)hexahydrocyclopenta[c]pyrrol-2(1H)-yl)-3-oxopropanenitrile

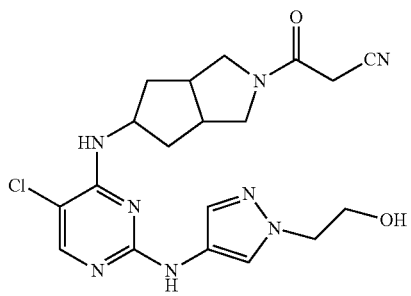 [SMILES: N#CCC(=O)N1CC2CC(Nc3nc(Nc4cnn(CCO)c4)ncc3Cl)CC2C1]

To a solution of 2-(4-((5-chloro-4-((octahydrocyclopenta[c]pyrrol-5-yl)amino)pyrimidin-2-yl)amino)-1H-pyrazol-1-yl)ethanol (0.29 g, 0.80 mmol) and 2-cyanoacetic acid (87.2 mg, 1.03 mmol) in a mixture of DCM (20 mL) and DMF (5 mL) were added HATU (462.4 mg, 1.22 mmol) and Et₃N (0.17 g, 1.68 mmol). After addition, the reaction mixture was stirred at rt for 1 h, then quenched with H₂O (30 mL) and extracted with DCM (100 mL×3). The combined organic phases were washed with brine (100 mL), dried over anhydrous Na₂SO₄, filtered and concentrated in vacuo. The residue was purified by silica gel column chromatography (MeOH/DCM (v/v)=1/20) to give the title compound as a beige solid (300.1 mg, 87%).

MS (ESI, pos. ion) m/z: 430.8 [M+H]⁺;

¹H NMR (400 MHz, DMSO-d₆): δ (ppm) 9.26 (s, 1H), 7.87 (s, 1H), 7.54 (d, J=1.6 Hz, 1H), 6.95 (d, J=7.7 Hz, 1H), 6.48 (d, J=1.8 Hz, 1H), 4.97 (t, J=5.1 Hz, 1H), 4.47 (m, 1H), 4.01 (t, J=5.5 Hz, 2H), 3.95 (s, 2H), 3.69 (dd, J=10.7, 5.3 Hz, 2H), 3.56 (dd, J=10.4, 7.8 Hz, 1H), 3.47 (dd, J=12.0, 8.1 Hz, 1H), 3.41 (d, J=4.1 Hz, 1H), 3.16 (d, J=5.1 Hz, 1H), 2.63 (m, 2H), 2.23 (m, 2H), 1.52 (m, 2H).

Example 45

5-chloro-N²-(1-(cyclopropylmethyl)-1H-pyrazol-4-yl)-N⁴-(octahydro cyclopenta[c]pyrrol-5-yl)pyrimidine-2,4-diamine

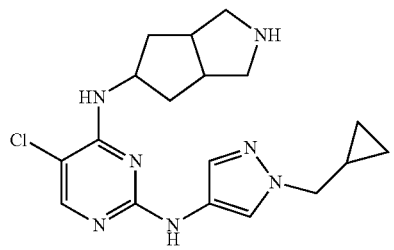 [SMILES: Clc1cnc(Nc2cnn(CC3CC3)c2)nc1NC1CC2CNCC2C1]

Step 1) 1-(cyclopropylmethyl)-4-nitro-1H-pyrazole

To a solution of 4-nitro-1H-pyrazole (5.05 g, 44.7 mmol) in N,N-dimethylformamide (250 mL) was added sodium hydride (2.7 g, 68 mmol, 60% mineral oil suspension) at 0° C. in portions and then followed by bromomethylcyclopropane (6.5 mL, 67 mmol) dropwise at same temperature. The mixture was stirred at room temperature for 4 h and diluted with water (300 mL) and extracted with EtOAc (300 mL×3). The combined organic phases were washed with brine (500 mL), dried over anhydrous Na₂SO₄, filtered and concentrated in vacuo. The residue was purified by silica gel column chromatography (EtOAc/PE (v/v)=1/50 to 1/20) to give the product as yellow oil (7.38 g, 98.9%).

MS (ESI, pos. ion) m/z: 168.2 [M+H]⁺;

¹H NMR (400 MHz, CDCl₃): δ (ppm) 8.25 (s, 1H), 8.0 (s, 1H), 3.97 (d, J=7.3 Hz, 2H), 1.26 (dtd, J=15.2, 7.6, 2.8 Hz, 1H), 0.72-0.63 (m, 2H), 0.38 (q, J=5.2 Hz, 2H)

Step 2) 1-(cyclopropylmethyl)-1H-pyrazol-4-amine

To a solution of 1-(cyclopropylmethyl)-4-nitro-1H-pyrazole (8.37 g, 50.1 mmol) in methanol (150 mL) was added 10% Pd/C (840.0 mg, 0.7893 mmol). The suspension was stirred at room temperature under a H₂ atmosphere for 2 h. Filtered and the filter cake was washed with MeOH (50 mL×3). The filtrate was concentrated in vacuo and the residue was purified by silica gel column chromatography (MeOH/DCM (v/v)=1/100 to 1/50) to give the title compound as purple oil (5.5 g, 80%).

MS (ESI, pos. ion) m/z: 138.2 [M+H]⁺;

¹H NMR (400 MHz, CDCl₃): δ (ppm) 7.12 (s, 1H), 7.09 (s, 1H), 3.83 (d, J=7.1 Hz, 2H), 2.71 (s, 2H), 1.26-1.14 (m, 1H), 0.62-0.53 (m, 2H), 0.34-0.26 (m, 2H)

Step 3) tert-butyl 5-((5-chloro-2-((1-(cyclopropylmethyl)-1H-pyrazol-4-yl)amino)pyrimidin-4-yl)amino)hexahydrocyclopenta[c]pyrrole-2(1H)-carboxylate To a solution of tert-butyl 5-[(2,5-dichloropyrimidin-4-yl)amino]-hexahydrocyclopenta[c]pyrrole-2(1H)-carboxylate (1.10 g, 2.95 mmol) and 1-(cyclopropylmethyl)pyrazol-4-amine (38.5 mg, 0.28 mmol) in dioxane (10 mL) was added 2,2,2-trifluoroacetic acid (61.8 mg, 0.54 mmol). The reaction mixture was stirred at 100° C. overnight, then adjusted to pH=10 with a saturated Na₂CO₃ solution, and extracted with EtOAc (100 mL×3). The combined organic phases were washed with brine (100 mL), dried over anhydrous Na₂SO₄, filtered and concentrated in vacuo. The residue was purified by silica gel column chromatography (EtOAc/PE (v/v)=1/2) to give the title compound as a pale yellow solid (0.36 g, 26%).

MS (ESI, pos. ion) m/z: 473.8 [M+H]⁺;

¹H NMR (400 MHz, CDCl₃): δ (ppm) 7.90 and 7.88 (s, 1H), 7.80 and 7.76 (s, 1H), 7.59 and 7.57 (s, 1H), 6.69 and 6.65 (s, 1H), 5.31 and 5.22 (d, J=7.1 Hz, 1H), 4.46 (d, J=5.8 Hz, 1H), 3.97 (d, J=7.0 Hz, 2H), 3.50 (m, 2H), 3.37 (d, J=9.1 Hz, 2H), 2.70 (m, 2H), 2.48 (m, 2H), 1.49 (s, 9H), 1.43 (m, 1H), 0.67 (q, J=5.7 Hz, 2H), 0.40 (q, J=5.0 Hz, 2H).

Step 4) 5-chloro-N²-(1-(cyclopropylmethyl)-1H-pyrazol-4-yl)-N⁴-(octahdrocyclopenta[c]pyrrol-5-yl)pyrimidine-2,4-diamine To a solution of tert-butyl 5-((5-chloro-2-((1-(cyclopropylmethyl)-1H-pyrazol-4-yl)amino)pyrimidin-4-yl)amino)

hexahydrocyclopenta[c]pyrrole-2(1H)-carboxylate (0.36 g, 0.76 mmol) in DCM (10 mL) was added a solution of HCl in EtOAc (10 mL, 40 mmol). The reaction mixture was stirred at rt for 1 h and concentrated in vacuo. The residue was dissolved in water (30 mL) and adjusted to pH=10 with a saturated Na$_2$CO$_3$ aqueous solution, then extracted with DCM (100 mL×3). The combined organic phases were washed with brine (100 mL), dried over anhydrous Na$_2$SO$_4$, filtered and concentrated in vacuo. The residue was purified by silica gel column chromatography (MeOH/DCM (v/v)=1/10) to give the title compound as a pale yellow solid (245.1 mg, 86%).

MS (ESI, pos. ion) m/z: 373.9 [M+H]$^+$;

$^1$H NMR (400 MHz, DMSO-d$_6$): δ (ppm) 9.07 and 8.98 (s, 1H), 8.12 and 6.95 (d, J=8.2 Hz, 1H), 7.84 (d, J=7.3 Hz, 2H), 7.42 (s, 1H), 4.46 and 4.37 (m, 1H), 3.90 (d, J=7.0 Hz, 2H), 3.21 (s, 2H), 3.17 (s, 1H), 2.68 (s, 2H), 2.55 (s, 2H), 2.15 (s, 2H), 1.45 (m, 2H), 1.17 (m, 1H), 0.52 (m, 2H), 0.33 (q, J=4.8 Hz, 2H).

Example 46

3-(5-((5-chloro-2-((1-(cyclopropylmethyl)-1H-pyrazol-4-yl)amino)pyrimidin-4-yl)amino)hexahydrocyclopenta[c]pyrrol-2(1H)-yl)-3-oxopropanenitrile

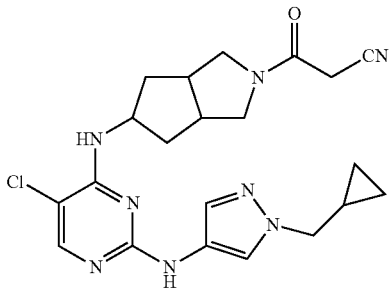 [SMILES: N#CCC(=O)N1CC2CC(Nc3nc(Nc4cnn(CC5CC5)c4)ncc3Cl)CC2C1]

To a solution of 5-chloro-N$^2$-(1-(cyclopropylmethyl)-1H-pyrazol-4-yl)-N$^4$-(octahydrocyclopenta[c]pyrrol-5-yl)pyrimidine-2,4-diamine (0.52 g, 1.40 mmol) and 2-cyanoacetic acid (136.9 mg, 1.61 mmol) in a mixture of DCM (40 mL) and DMF (10 mL) were added HATU (821.4 mg, 2.16 mmol) and Et$_3$N (0.33 g, 3.26 mmol). After addition, the reaction mixture was stirred at rt for 1 h, then quenched with H$_2$O (30 mL) and extracted with DCM (100 mL×3). The combined organic phases were washed with brine (100 mL), dried over anhydrous Na$_2$SO$_4$, filtered and concentrated in vacuo. The residue was purified by silica gel column chromatography (MeOH/DCM (v/v)=1/20) to give the title compound as a beige solid (357.2 mg, 58%).

MS (ESI, pos. ion) m/z: 441.1 [M+H]$^+$;

$^1$H NMR (400 MHz, DMSO-d$_6$): δ (ppm) 9.02 (s, 1H), 7.85 (d, J=13.7 Hz, 2H), 7.44 (s, 1H), 6.90 (d, J=7.7 Hz, 1H), 4.51 (m, 1H), 3.93 (s, 2H), 3.91 (d, J=7.1 Hz, 2H), 3.56 (dd, J=10.6, 7.6 Hz, 1H), 3.47 (d, J=7.9 Hz, 1H), 3.42 (dd, J=10.8, 3.7 Hz, 2H), 2.64 (m, 2H), 2.25 (m, 2H), 1.54 (m, 2H), 1.18 (m, 1H), 0.52 (q, J=5.6 Hz, 2H), 0.33 (q, J=4.9 Hz, 2H).

Example 47

5-chloro-N$^2$-(1-(cyclopropylmethyl)-1H-pyrazol-4-yl)-N$^4$-(3-azaspiro[5.5]undecan-9-yl)pyrimidine-2,4-diamine

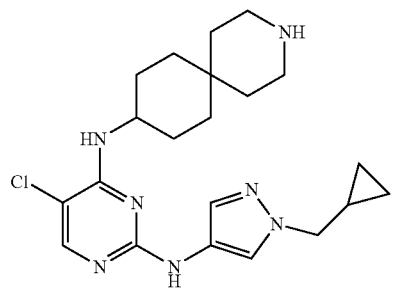 [SMILES: Clc1cnc(Nc2cnn(CC3CC3)c2)nc1NC1CCC2(CCNCC2)CC1]

Step 1) tert-butyl 9-((5-chloro-2-((1-(cyclopropylmethyl)-1H-pyrazol-4-yl)amino)pyrimidin-4-yl)amino)-3-azaspiro[5.5]undecane-3-carboxylate To a solution of tert-butyl 9-[(2,5-dichloropyrimidin-4-yl)amino]-3-azaspiro[5.5]undecane-3-carboxylate (500.5 mg, 1.21 mmol) and 1-(cyclopropylmethyl)-1H-pyrazol-4-amine (330.5 mg, 2.41 mmol) in 1,4-dioxane (50 mL) was added trifluoroacetic acid (686.5 mg, 6.02 mmol). The mixture was stirred at 100° C. overnight and concentrated in vacuo. The residue was purified with a silica gel column chromatography (PE/EtOAc (v/v)=1/1 to DCM/MeOH (v/v)=7/1) to give the product as a light yellow solid (550 mg, 88.45%).

MS (ESI, pos. ion) m/z: 515.8 [M+H]$^+$.

Step 2) 5-chloro-N$^2$-(1-(cycpropylmethyl)-1H-pyrazol-4-yl)-N$^4$-(3-azaspiro[5.5]undecan-9-yl)pyrimidine-2,4-diamine To a solution of tert-butyl 3-[[5-chloro-2-[[1-(cyclopropylmethyl)pyrazol-4-yl]amino]pyrimidin-4-yl]amino]-9-azaspiro[5.5]undecane-9-carboxylate (830 mg, 1.61 mmol) in dichloromethane (25 mL) was added a solution of HCl in EtOAc (5 mL, 20 mmol). The mixture was stirred at room temperature overnight and then concentrated in vacuo. The residue was dissolved in methanol (3 mL) and adjusted to pH=7-8 with the saturated solution of NaHCO$_3$ and extracted with DCM (100 mL×3) The combined organic phases were washed with brine (100 mL), dried over anhydrous Na$_2$SO$_4$, filtered and concentrated in vacuo. The residue was purified with a silica gel column chromatography (MeOH/DCM (v/v)=1/10 to 1/7) to give the product as a light yellow solid (665.2 mg, 99.43%).

MS (ESI, pos. ion) m/z: 208.6 [(M+H)/2]$^+$;

$^1$H NMR (400 MHz, DMSO-d$_6$): δ (ppm) 9.02 (s, 1H), 8.66 (s, 1H), 7.86 (s, 1H), 7.78 (s, 1H), 7.46 (s, 1H), 6.62 (d, J=8.1 Hz, 1H), 4.00-3.93 (m, 1H), 3.90 (d, J=7.0 Hz, 2H), 3.04 (s, 4H), 1.82-1.66 (m, 5H), 1.60 (dd, J=23.7, 11.2 Hz, 2H), 1.50 (s, 2H), 1.27-1.13 (m, 4H), 0.52 (q, J=5.5 Hz, 2H), 0.31 (q, J=4.9 Hz, 2H)

Example 48

3-(9-((5-chloro-2-((1-(cyclopropylmethyl)-1H-pyrazol-4-yl)amino)pyrimidin-4-yl)amino)-3-azaspiro[5.5]undecan-3-yl)-3-oxopropanenitrile

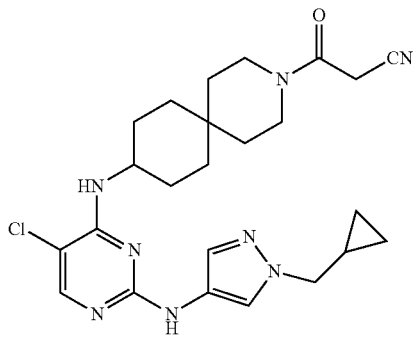 [SMILES: N#CCC(=O)N1CCC2(CCC(Nc3nc(Nc4cnn(CC5CC5)c4)ncc3Cl)CC2)CC1]

To a solution of 5-chloro-$N^2$-(1-(cyclopropylmethyl)-1H-pyrazol-4-yl)-$N^4$-(3-azaspiro[5.5]undecan-9-yl)pyrimidine-2,4-diamine (300.5 mg, 0.72 mmol), 2-cyanoacetic acid (92.2 mg, 1.08 mmol), HOAT (196.5 mg, 1.44 mmol) and EDCI (276.5 mg, 1.44 mmol) in a mixture of dichloromethane (20 mL) and N,N-dimethylformamide (5 mL) was added TEA (146.2 mg, 1.45 mmol). The mixture was stirred at room temperature for 1 h then diluted with water (50 mL), and extracted with DCM/MeOH (10/1, 50 mL×3). The combined organic layer was washed with brine, dried over anhydrous $Na_2SO_4$, filtered and concentrated in vacuo. The residue was purified by silica gel column chromatography (DCM/MeOH (v/v)=100/1) to give the product as a yellow solid (156.8 mg, 44.94%).

MS (ESI, pos. ion) m/z: 482.9 [M+H]$^+$;

$^1$H NMR (400 MHz, DMSO-$d_6$): δ (ppm) 9.02 (s, 1H), 7.85 (s, 1H), 7.79 (s, 1H), 7.45 (s, 1H), 6.63 (t, J=8.6 Hz, 1H), 4.01 (d, J=3.8 Hz, 4H), 3.95 (s, 1H), 3.90 (d, J=7.0 Hz, 2H), 3.45 (s, 2H), 1.72 (dd, J=30.9, 14.7 Hz, 4H), 1.59 (s, 2H), 1.51 (s, 1H), 1.35 (s, 1H), 1.31-1.13 (m, 5H), 0.51 (d, J=7.6 Hz, 2H), 0.31 (d, J=5.1 Hz, 2H).

Example 49

2-(4-((4-(3-azaspiro[5.5]undecan-9-ylamino)-5-chloropyrimidin-2-yl)amino)-1H-pyrazol-1-yl)ethanol

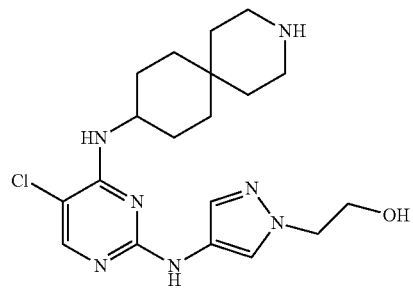 [SMILES: OCCn1cc(Nc2ncc(Cl)c(NC3CCC4(CCNCC4)CC3)n2)cn1]

Step 1) tert-butyl 9-((5-chloro-2-((1-(2-hydroxyethyl)-1H-pyrazol-4-yl)amino)pyrimidin-4-yl)amino)-3-azaspiro[5.5]undecane-3-carboxylate To a solution of tert-butyl 3-[(2,5-dichloropyrimidin-4-yl)amino]-9-azaspiro[5.5]undecane-9-carboxylate (501.5 mg, 1.21 mmol) and 2-(4-aminopyrazol-1-yl)ethanol (306.5 mg, 2.411 mmol) in propan-2-ol (6 mL) was added a solution of HCl in EtOAc (1 mL, 4 mmol). The mixture stirred in a sealed tube under the microwave radiation at 140° C. for 1 h and then concentrated in vacuo. The residue was purified by silica gel column chromatography (MeOH/DCM (v/v)=1/100 to 1/20 to 1/7) to give the product as a light yellow solid (500.0 mg, 0.9881 mmol, 81.85%).

MS (ESI, pos. ion) m/z: 506.3 [M+H]$^+$.

Step 2) 2-(4-((4-(3-azaspiro[5.5]undecan-9-ylamino)-5-chloropyrimidin-2-yl)amino)-1H-pyrazol-1-yl)ethanol To a solution of tert-butyl 9-((5-chloro-2-((1-(2-hydroxyethyl)-1H-pyrazol-4-yl)amino) pyrimidin-4-yl)amino)-3-azaspiro[5.5]undecane-3-carboxylate (500 mg, 0.99 mmol) in dichloromethane (20 mL) was added a solution of HCl in EtOAc (5 mL, 20 mmol). The mixture was stirred at room temperature for 2 h and then concentrated in vacuo. The residue was dissolved in methanol (2 mL) and adjust to pH=7-8 with the solution of $NaHCO_3$ and extracted with DCM (100 mL×3) The combined organic phases were washed with brine (100 mL), dried over anhydrous $Na_2SO_4$, filtered and concentrated in vacuo. The residue was purified with a silica gel column chromatography (MeOH/DCM (v/v)=1/10 to 1/7) to give the product as a light yellow solid (340 mg, 84.77%).

MS (ESI, pos. ion) m/z: 203.6 [(M+H)/2]$^+$:

$^1$H NMR (400 MHz, DMSO-$d_6$) δ (ppm) 9.27 (s, 1H), 8.60 (s, 1H), 7.87 (s, 1H), 7.54 (s, 1H), 6.65 (d, J=7.6 Hz, 1H), 6.48 (s, 1H), 4.86 (t, J=5.1 Hz, 1H), 4.00 (t, J=5.5 Hz, 2H), 3.92 (s, 1H), 3.76-3.64 (m, 2H), 3.03 (s, 4H), 2.00 (dd, J=15.1, 6.9 Hz, 1H), 1.82-1.64 (m, 6H), 1.57 (dd, J=28.1, 15.6 Hz, 5H).

Example 50

3-(9-((5-chloro-2-((1-(2-hydroxyethyl)-1H-pyrazol-4-yl)amino)pyrimidin-4-yl)amino)-3-azaspiro[5.5]undecan-3-yl)-3-oxopropanenitrile

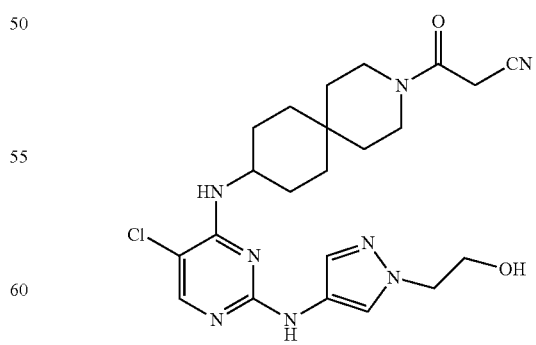

To a solution of 2-[4-[[4-(3-azaspiro[5.5]undecan-9-ylamino)-5-chloropyrimidin-2-yl]amino]-1H-pyrazol-1-yl]ethanol (200.5 mg, 0.4940 mmol) in a mixture of dichloromethane (40 mL) and DMF (10 mL) were added 2-cyanoacetic acid (46.5 mg, 0.547 mmol), HATU (375.2 mg, 0.9868 mmol) and TEA (100.5 mg, 0.9932 mmol). The mixture was stirred at room temperature for 2 h. The mixture was diluted with water (50 mL), and extracted with DCM/MeOH (10/1, 50 mL×3). The combined organic layer was dried over anhydrous Na$_2$SO$_4$, filtered and concentrated in vacuo. The residue was purified by silica gel column chromatography (DCM/MeOH (v/v)=100/1 to 10/1) to give the product as a yellow solid (105 mg, 44.94%).

MS (ESI, pos. ion) m/z: 472.9 [M+H]$^+$;
$^1$H NMR (400 MHz, DMSO-d$_6$) δ (ppm) 9.29 (s, 1H), 7.86 (s, 1H), 7.57 (s, 1H), 6.68 (s, 1H), 6.48 (s, 1H), 4.86 (s, 1H), 4.10-3.98 (m, 6H), 3.95 (s, 1H), 3.71 (dd, J=10.6, 5.2 Hz, 2H), 3.46 (s, 2H), 1.73 (t, J=13.2 Hz, 4H), 1.66-1.48 (m, 6H), 1.34 (d, J=7.5 Hz, 2H).

Example 51

5-chloro-N$^2$-(5-cyclopropyl-1H-pyrazol-3-yl)-N$^4$-(octahydrocyclopenta[c]pyrrol-5-yl)pyrimidine-2,4-diamine

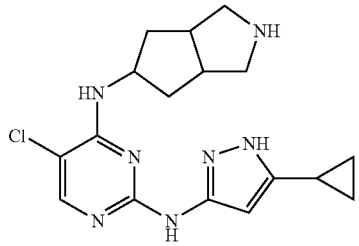 [SMILES: Clc1cnc(Nc2cc(C3CC3)[nH]n2)nc1NC1CC2CNCC2C1]

Step 1) tert-butyl 5-((5-chloro-2-((5-cyclopropyl-1H-pyrazol-3-yl)amino)pyrimidin-4-yl)amino)hexahydrocyclopenta[c]pyrrole-2(1H)-carboxylate To a suspension of tert-butyl 5-[(2,5-dichloropyrimidin-4-yl)amino]-hexahydrocyclopenta[c]pyrrole-2(1H)-carboxylate (373.3 mg, 1.00 mmol) and 5-cyclopropyl-1H-pyrazol-3-amine hydrochloride (376.4 mg, 2.36 mmol) in dioxane (10 mL) were added Pd(OAc)$_2$ (75.9 mg, 0.34 mmol), BINAP (164.0 mg, 0.25 mmol) and Cs$_2$CO$_3$ (1.08 g, 3.31 mmol). The reaction mixture was stirred at 150° C. under microwave radiation for 2 h and concentrated in vacuo. The residue was purified by silica gel column chromatography (EtOAc/PE (v/v)=2/1) to give the title compound as a pale yellow solid (0.29 g, 63%).

MS (ESI, pos. ion) m/z: 460.3 [M+H]$^+$.

Step 2) 5-chloro-N$^2$-(5-cyclopropyl-1H-pyrazol-3-yl)-N$^4$-(octahydrocyclopenta[c]pyrrol-5-yl)pyrimidine-2,4-diamine To a solution of tert-butyl 5-((5-chloro-2-((5-cyclopropyl-1H-pyrazol-3-yl)amino)pyrimidin-4-yl)amino)hexahydrocyclopenta[c]pyrrole-2(1H)-carboxylate (560.3 mg, 1.22 mmol) in DCM (15 mL) was added a solution of HCl in EtOAc (15 mL, 60 mmol). The reaction mixture was stirred at rt for 1 h and concentrated in vacuo. The residue was dissolved in water (30 mL) and adjusted to pH=10 with a saturated Na$_2$CO$_3$ aqueous solution, then extracted with DCM (100 mL×3). The combined organic phases were washed with brine (100 mL), dried over anhydrous Na$_2$SO$_4$, filtered and concentrated in vacuo. The residue was purified by silica gel column chromatography (MeOH/DCM (v/v)=1/5) to give the title compound as a pale yellow solid (0.31 g, 71%).

MS (ESI, pos. ion) m/z: 359.9 [M+H]$^+$;
$^1$H NMR (400 MHz, DMSO-d$_6$): δ (ppm) 11.86 (s, 1H), 9.31 (s, 1H), 7.89 (s, 1H), 7.26 (m, 1H), 6.77 (d, J=6.0 Hz, 1H), 6.10 (s, 1H), 4.35 (m, 1H), 3.27 (d, J=7.2 Hz, 1H), 3.17 (d, J=4.4 Hz, 1H), 3.05 (d, J=9.3 Hz, 2H), 2.74 (s, 2H), 2.30 (m, 2H), 1.85 (m, 1H), 1.59 (dd, J=19.1, 11.4 Hz, 2H), 0.90 (d, J=6.5 Hz, 2H), 0.63 (d, J=3.3 Hz, 2H).

Example 52

3-(5-((2-((5-cyclopropyl-1H-pyrazol-3-yl)amino)-5-methoxypyrimidin-4-yl)amino)hexahydrocyclopenta[c]pyrrol-2(1H)-yl)-3-oxopropanenitrile

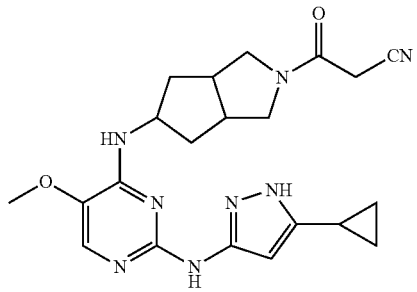 [SMILES: COc1cnc(Nc2cc(C3CC3)[nH]n2)nc1NC1CC2CN(C(=O)CC#N)CC2C1]

To a solution of 5-chloro-N$^2$-(5-cyclopropyl-1H-pyrazol-3-yl)-N$^4$-(octahydrocyclopenta[c]pyrrol-5-yl)pyrimidine-2,4-diamine (240.0 mg, 0.67 mmol) and 2-cyanoacetic acid (107.7 mg, 1.27 mmol) in a mixture of DCM (20 mL) and DMF (5 mL) were added EDCI (311.4 mg, 1.61 mmol) and HOAT (186.3 mg, 1.37 mmol). The reaction mixture was stirred at rt for 1 h and then quenched with H$_2$O (30 mL) and extracted with DCM (100 mL×3). The combined organic phases were washed with brine (100 mL), dried over anhydrous Na$_2$SO$_4$, filtered and concentrated in vacuo. The residue was purified by silica gel column chromatography (MeOH/DCM (v/v)=1/20) and a preparative HPLC to give the title compound as a beige solid (284.7 mg, 100%).

MS (ESI, pos. ion) m/z: 423.2 [M+H]$^+$;
$^1$H NMR (600 MHz, DMSO-d$_6$): δ (ppm) 9.12 (s, 1H), 7.87 (s, 1H), 6.95 (d, J=7.6 Hz, 1H), 6.10 (s, 1H), 4.44 (m, 1H), 3.93 (d, J=2.0 Hz, 2H), 3.57 (dd, J=10.7, 7.7 Hz, 2H), 3.49 (dd, J=12.2, 8.2 Hz, 2H), 3.18 (s, 3H), 2.67 (m, 1H), 2.60 (m, 1H), 2.25 (td, J=13.4, 7.0 Hz, 2H), 1.85 (m, 1H), 1.51 (m, 2H), 0.91 (m, 2H), 0.62 (m, 2H).

Example 53

1-(5-((5-chloro-2-((5-cyclopropyl-1H-pyrazol-3-yl)amino)pyrimidin-4-yl)amino)hexahydrocyclopenta[c]pyrrol-2(1H)-yl)ethanone

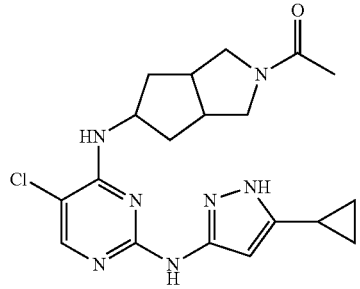 [SMILES: CC(=O)N1CC2CC(Nc3nc(Nc4cc(C5CC5)[nH]n4)ncc3Cl)CC2C1]

To a solution of 5-chloro-N²-(5-cyclopropyl-1H-pyrazol-3-yl)-N⁴-(octahydrocyclopenta[c]pyrrol-5-yl)pyrimidine-2,4-diamine (153.3 mg, 0.43 mmol) in DCM (10 mL) were added Et₃N (82.3 mg, 0.81 mmol) and acetyl acetate (62.5 mg, 0.61 mmol). The reaction mixture was stirred at rt for 15 min, then quenched with H₂O (30 mL) and extracted with DCM (100 mL×3). The combined organic phases were washed with brine (100 mL), then dried over anhydrous Na₂SO₄, filtered and concentrated in vacuo. The residue was purified by silica gel column chromatography (MeOH/DCM (v/v)=1/50) to give the title compound as a beige solid (79.0 mg, 46.1%).

MS (ESI, pos. ion) m/z: 401.9 [M+H]⁺;
¹H NMR (400 MHz, CDCl₃): δ (ppm) 7.85 (s, 1H), 5.67 (s, 1H), 4.34 (m, 1H), 3.58 (m, 2H), 3.45 (m, 2H), 2.66 (m, 2H), 2.37 (m, 2H), 1.99 (s, 3H), 1.78 (m, 1H), 1.42 (m, 2H), 0.94 (d, J=7.1 Hz, 2H), 0.69 (d, J=5.2 Hz, 2H).

Example 54

3-(9-((5-chloro-2-((5-cyclopropyl-1H-pyrazol-3-yl)amino)pyrimidin-4-yl)amino)-3-azaspiro[5.5]undecan-3-yl)-3-oxopropanenitrile

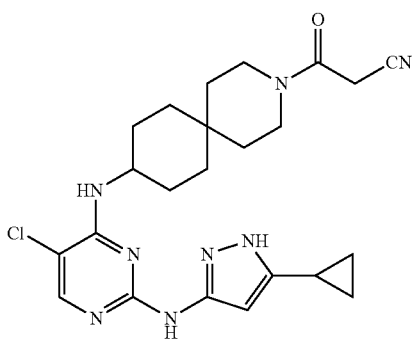 [SMILES: N#CCC(=O)N1CCC2(CCC(Nc3nc(Nc4cc(C5CC5)[nH]n4)ncc3Cl)CC2)CC1]

Step 1) tert-butyl 9-((5-chloro-2-((5-cyclopropyl-1H-pyrazol-3-yl)amino)pyrimidin-4-yl)amino)-3-azaspiro[5.5]undecane-3-carboxylate A solution of tert-butyl 9-((2,5-dichloropyrimidin-4-yl)amino)-3-azaspiro[5.5]undecane-3-carboxylate (506 mg, 1.22 mmol), 5-cyclopropyl-1H-pyrazol-3-amine hydrochloride (272 mg, 1.70 mmol), cesium carbonate (1.176 g, 3.609 mmol), [1-(2-diphenylphosphanyl-1-naphthyl)-2-naphthyl]-diphenyl-phosphane (147.6 mg, 0.2370 mmol) and diacetoxypalladium (53.8 mg, 0.240 mmol) in anhydrous dioxane (10 mL) stirred in a sealed tube under the microwave radiation at 150° C. for 2 h. Then the reaction mixture was concentrated in vacuo and the residue was purified by silica gel column chromatography (DCM/MeOH (v/v)=30/1) to give the title compound as a light yellow solid (364 mg, 59.5%).

MS (ESI, pos. ion) m/z: 502.3 [M+H]⁺.

Step 2) 5-chloro-N²-(5-cyclopropyl-1H-pyrazol-3-yl)-N⁴-(3-azaspiro[5.5]undecan-9-yl)pyrimidine-2,4-diamine hydrochloride To a solution of tert-butyl 9-((5-chloro-2-((5-cyclopropyl-1H-pyrazol-3-yl)amino)pyrimidin-4-yl)amino)-3-azaspiro[5.5]undecane-3-carboxylate (364 mg, 0.7251 mmol) in DCM (10 mL) was added a solution of HCl in ethyl acetate (20 mL, 60 mmol). The reaction was stirred overnight at rt and then concentrated in vacuo to give the title compound as a yellow solid (317 mg, 99%).

MS (ESI, pos. ion) m/z: 402.2 [M+H]⁺.

Step 3) 3-(9-((5-chloro-2-((5-cyclopropyl-1H-pyrazol-3-yl)amino)pyrimidin-4-yl)amino)-3-azaspiro[5.5]undecan-3-yl)-3-oxopropanenitrile To a solution of 5-chloro-N²-(5-cyclopropyl-1H-pyrazol-3-yl)-N⁴-(3-azaspiro[5.5]undecan-9-yl)pyrimidine-2,4-diamine hydrochloride (270 mg, 0.6159 mmol) in a mixture of DCM and DMF (6 mL/2 mL) were added TEA (253.2 mg, 2.502 mmol), cyanoacetic acid (52.1 mg, 0.733 mmol), HOAT (124.8 mg, 0.9169 mmol) and EDCI (177.5 mg, 0.9259 mmol). The reaction mixture was stirred at rt for 1.5 h then quenched with water (30 mL), and extracted with DCM/MeOH (10/1, 80 mL×3). The combined organic layers were dried over anhydrous Na₂SO₄, filtered and concentrated in vacuo and the residue was purified by silica gel column chromatography (DCM/MeOH (v/v)=30/1). The crude product was recrystallized from MeOH (10 mL) to give the title compound as a white solid (106.6 mg, 36.91%).

MS (ESI, pos. ion) m/z: 468.9 [M+H]⁺;
¹H NMR (400 MHz, DMSO-d₆): δ (ppm) 11.90 (s, 1H), 9.11 (s, 1H), 7.87 (d, J=10.6 Hz, 1H), 6.71 (s, 1H), 6.21 (s, 1H), 4.01 (d, J=5.2 Hz, 2H), 3.96 (s, 1H), 3.46 (s, 2H), 1.84 (s, 1H), 1.78 (d, J=12.9 Hz, 2H), 1.59 (dd, J=38.0, 25.2 Hz, 6H), 1.38-1.25 (m, 2H), 1.18 (t, J=12.0 Hz, 2H), 0.91 (s, 3H), 0.64 (s, 3H).

Example 55

5-chloro-N²-(3-cyclopropyl-1-methyl-1H-pyrazol-5-yl)-N⁴-(octahydro cyclopenta[c]pyrrol-5-yl)pyrimidine-2,4-diamine

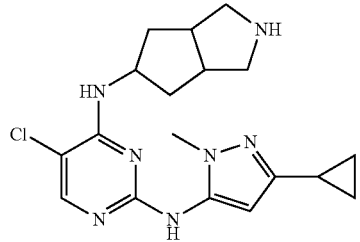 [SMILES: Cn1nc(C2CC2)cc1Nc1ncc(Cl)c(NC2CC3CNCC3C2)n1]

Step 1) 3-cyclopropyl-1-methyl-1H-pyrazol-5-amine

To a solution of 3-cyclopropyl-3-oxo-propanenitrile (2.22 g, 20.3 mmol) in HOAc (40 mL) was added methylhydrazine (40% [w/w] in water, 2.81 g, 24.4 mmol). The reaction mixture was stirred at 100° C. overnight and then concentrated in vacuo. The residue was purified by silica gel column chromatography (DCM) to give the title compound as yellow oil (2.80 g, 100%).

MS (ESI, pos. ion) m/z: 138.1 [M+H]⁺;
¹H NMR (400 MHz, CDCl₃): δ (ppm) 5.17 (s, 1H), 3.56 (s, 3H), 3.47 (s, 2H), 1.78 (m, 1H), 0.83 (m, 2H), 0.62 (m, 2H).

Step 2) tert-butyl 5-((5-chloro-2-((3-cyclopropyl-1-methyl-H-pyrazol-5-yl)amino)pyrimidin-4-yl)amino)hexahydrocyclopenta[c]pyrrole-2(1H)-carboxylate To a suspension of tert-butyl 5-[(2,5-dichloropyrimidin-4-yl)amino]-hexahydrocyclopenta[c]pyrrole-2(H)-carboxylate (403.7 mg, 1.08 mmol) and 3-cyclopropyl-1-methyl-1H-pyrazol-5-amine (809.2 mg, 5.90 mmol) in dioxane (10 mL) were added Pd(OAc)$_2$ (61.6 mg, 0.27 mmol), BINAP (158.8 mg, 0.24 mmol) and Cs$_2$CO$_3$ (713.4 mg, 2.19 mmol). The reaction mixture was stirred in a sealed tube at 150° C. under microwave radiation for 2 h and concentrated in vacuo. The residue was purified by silica gel column chromatography (EtOAc/PE (v/v)=1/1) to give the title compound as a pale yellow solid (387.0 mg, 75.5%).

MS (ESI, pos. ion) m/z: 474.3 [M+H]$^+$.

Step 3) 5-chloro-N$^2$-(3-cyclopropyl-1-methyl-1H-pyrazol-5-yl)-N$^4$-(octahydrocyclopenta[c]pyrrol-5-yl)pyrimidine-2,4-diamine To a solution of tert-butyl 5-((5-chloro-2-((3-cyclopropyl-1-methyl-1H-pyrazol-5-yl)amino)pyrimidin-4-yl)amino)hexahydrocyclopenta[c]pyrrole-2(1H)-carboxylate (751.2 mg, 1.58 mmol) in DCM (15 mL) was added a solution of HCl in EtOAc (15 mL, 60 mmol). The reaction mixture was stirred at rt for 1 h and concentrated in vacuo. The residue was dissolved in water (30 mL) and adjusted to pH=10 with a saturated Na$_2$CO$_3$ aqueous solution, then extracted with DCM (100 mL×3). The combined organic phases were washed with brine (100 mL), dried over anhydrous Na$_2$SO$_4$, filtered and concentrated in vacuo. The residue was purified by silica gel column chromatography (MeOH/DCM (v/v)=1/10) to give the title compound as a beige solid (0.29 g, 95%).

MS (ESI, pos. ion) m/z: 374.2 [M+H]$^+$;
$^1$H NMR (400 MHz, CDCl$_3$): δ (ppm) 7.83 (s, 1H), 7.32 (d, J=8.0 Hz, 1H), 6.53 (s, 1H), 5.92 (s, 1H), 4.41 (m, 1H), 3.69 (s, 3H), 3.02 (m, 4H), 2.75 (s, 2H), 2.29 (m, 2H), 1.90 (m, 1H), 1.56 (m, 2H), 0.90 (m, 2H), 0.70 (m, 2H).

Example 56

3-(5-((5-chloro-2-((3-cyclopropyl-1-methyl-1H-pyrazol-5-yl)amino)pyrimidin-4-yl)amino)hexahydrocyclopenta[c]pyrrol-2(1H)-yl)-3-oxopropanenitrile

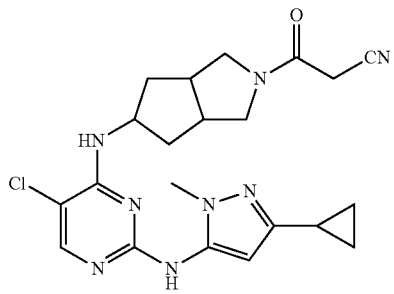 [SMILES: Cn1nc(C2CC2)cc1Nc1ncc(Cl)c(NC2CC3CN(C(=O)CC#N)CC3C2)n1]

To a solution of 5-chloro-N$^2$-(3-cyclopropyl-1-methyl-1H-pyrazol-5-yl)-N$^4$-(octahydrocyclopenta[c]pyrrol-5-yl) pyrimidine-2,4-diamine (251.7 mg, 0.67 mmol) and 2-cyanoacetic acid (107.2 mg, 1.26 mmol) in a mixture of DCM (20 mL) and DMF (5 mL) were added EDCI (292.5 mg, 1.51 mmol) and HOAT (205.3 mg, 1.51 mmol). After addition, the reaction mixture was stirred at 45° C. for 1 h, then quenched with H$_2$O (30 mL) and extracted with DCM (100 mL×3). The combined organic phases were washed with brine (100 mL), and dried over anhydrous Na$_2$SO$_4$, filtered and concentrated in vacuo. The residue was purified by silica gel column chromatography (MeOH/DCM (v/v)=1/40) to give the title compound as a beige solid (169.4 mg, 57.1%).

MS (ESI, pos. ion) m/z: 441.3 [M+H]$^+$;
$^1$H NMR (400 MHz, DMSO-d$_6$): δ (ppm) 7.90 (s, 1H), 6.59 and 6.56 (s, 1H), 5.92 (s, 1H), 5.31 (d, J=6.8 Hz, 1H), 4.32 (m, 1H), 3.74 (dd, J=10.7, 7.9 Hz, 1H), 3.69 (m, 4H), 3.62 and 3.60 (d, J=4.3 Hz, 1H), 3.46 (m, 3H), 2.85 (m, 1H), 2.76 (m, 1H), 2.49 (m, 2H), 1.91 (tt, J=8.5, 5.0 Hz, 1H), 1.39 (m, 2H), 0.91 (m, 2H), 0.70 (m, 2H).

Example 57

3-(9-((5-chloro-2-((1,3-dimethyl-1H-pyrazol-4-yl)amino)pyrimidin-4-yl)amino)-3-azaspiro[5.5]undecan-3-yl)-3-oxopropanenitrile

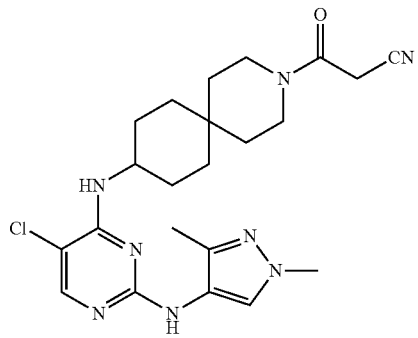 [SMILES: Cc1nn(C)cc1Nc1ncc(Cl)c(NC2CCC3(CC2)CCN(C(=O)CC#N)CC3)n1]

Step 1) 1,3-dimethyl-4-nitro-1H-pyrazole

To a solution of 3-methyl-4-nitro-1H-pyrazole (5.02 g, 39.5 mmol) in DMF (80 mL) were added CH$_3$I (10.01 mg, 70.52 mmol) and K$_2$CO$_3$ (9.97 g). The mixture was stirred at 60° C. for 2 h, quenched with water (100 mL), and extracted with EtOAc (250 mL×3). The combined organic phases were washed with brine (100 mL), dried over anhydrous Na$_2$SO$_4$, filtered and concentrated in vacuo to give the title compound as brown oil (10.01 g, 89.79%).

MS (ESI, pos. ion) m/z: 142.2 [M+H]$^+$.

Step 2) 1,3-dimethyl-1H-pyrazol-4-amine

To a solution of 1,3-dimethyl-4-nitro-1H-pyrazole (5.2 g, 19.6 mmol) in MeOH (30 mL) were added Pd/C (10%, 1.00 g) and conc. HCl (3 mL). The mixture was stirred at rt in a high pressure autoclave under 2 MPa H$_2$ overnight and filtered. The filtrate was concentrated in vacuo to give the title compound as brown oil (7.31 g, 92.6%).

MS (ESI, pos. ion) m/z: 112.2 [M+H]$^+$.

Step 3) 5-chloro-N$^2$-(1,3-dimethyl-1H-pyrazol-4-yl)-N$^4$-(3-azaspiro[5.5]undecan-9-yl) pyrimidine-2,4-diamine To a solution of tert-butyl 9-((2,5-dichloropyrimidin-4-yl)amino)-3-azaspiro[5.5]undecane-3-carboxylate (504.1 mg, 1.214 mmol) and 1,3-dimethyl-1H-pyrazol-4-amine hydrochloride (381.0 mg, 2.581 mmol) in n-BuOH (10 mL) was added trifluoroacetic acid (678.1 mg, 5.947 mmol). The mixture was stirred at 100° C. overnight, then quenched with water (30 mL), and adjusted to pH=9 with solid NaHCO$_3$, and then extracted with DCM (200 mL×3). The combined organic phases were washed with brine (100 mL), dried over anhydrous $Na_2SO_4$, filtered and concentrated in vacuo. The residue was purified by silica gel column chromatography (MeOH/DCM (v/v)=1/10) to give the title compound as brown oil (271 mg, 45.57%).

MS (ESI, pos. ion) m/z: 195.6 [(M+H)/2]$^+$.

Step 4) 3-(9-((5-chloro-2-((1,3-dimethyl-1H-pyrazol-4-yl)amino)pyrimidin-4-yl)amino)-3-azaspiro[5.5]undecan-3-yl)-3-oxopropanenitrile To a solution of 5-chloro-$N^2$-(1,3-dimethyl-1H-pyrazol-4-yl)-$N^4$-(3-azaspiro[5.5]undecan-9-yl)pyrimidine-2,4-diamine (238.1 mg, 0.6107 mmol) and 2-cyanoacetic acid (132.3 mg, 1555 mmol) in DCM (10 mL) and DMF (3 mL) were added HATU (703.4 mg, 17.94 mmol) and $Et_3N$ (225 mg, 2.201 mmol). The mixture was stirred at room temperature for 3 h and concentrated in vacuo. The residue was purified by silica gel column chromatography (MeOH/DCM (V/V)=1/5) to give the title compound as a light yellow solid (203.1 mg, 72.8%).

MS (ESI, pos. ion) m/z: 457.3 [M+H]$^+$;
$^1$H NMR (400 MHz, DMSO-$d_6$): δ (ppm) 8.72 (s, 1H), 7.87 (s, 1H), 7.48 (s, 1H), 4.03 (d, J=4.2 Hz, 2H), 3.90 (s, 1H), 3.69 (s, 3H), 3.44 (s, 5H), 2.16 (s, 3H), 1.99 (dt, J=11.5, 6.8 Hz, 1H), 1.73 (d, J=14.1 Hz, 2H), 1.62 (s, 4H), 1.59-1.44 (m, 3H), 1.37-1.31 (m, 1H), 1.17-1.04 (m, 2H).

Example 58

5-methyl-$N^2$-(1-methyl-1H-pyrazol-4-yl)-$N^4$-(octahydrocyclopenta[c]pyrrol-5-yl)pyrimidine-2,4-diamine

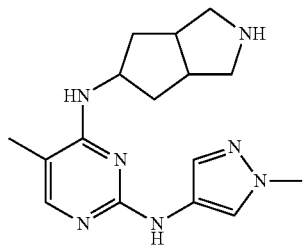

Step 1) tert-butyl 5-((2-chloro-5-methylpyrimidin-4-yl)amino)hexahydrocyclopenta[c]pyrrole-2(1H)-carboxylate To a solution of 2,4-dichloro-5-methyl-pyrimidine (2.00 g, 12.3 mmol) and tert-butyl 5-aminohexahydrocyclopenta[c]pyrrole-2(1H)-carboxylate (4.64 g, 20.5 mmol) in EtOH (25 mL) was added $Et_3N$ (2.62 g, 25.9 mmol). The reaction mixture was stirred at 50° C. overnight and concentrated in vacuo. The residue was purified by silica gel column chromatography (EtOAc/PE (v/v)=1/2) to give the title compound as yellow oil (2.42 g, 55.9%).

MS (ESI, pos. ion) m/z: 353.0 [M+H]$^+$;
$^1$H NMR (600 MHz, CDCl$_3$): δ (ppm) 7.68 (s, 1H), 5.25 (d, J=7.5 Hz, 1H), 4.48 (m, 1H), 3.42 (m, 2H), 3.26 (d, J=11.1 Hz, 2H), 2.63 (m, 2H), 2.38 (m, 2H), 1.92 (s, 3H), 1.41 (s, 9H), 1.33 (m, 2H).

Step 2) tert-butyl 5-((5-methyl-2-((1-methyl-1H-pyrazol-4-yl)amino)pyrimidin-4-yl)amino)hexahydrocyclopenta[c]pyrrole-2(1H)-carboxylate To a suspension of tert-butyl 5-((5-methyl-2-((1-methyl-1H-pyrazol-4-yl)amino)pyrimidin-4-yl)amino)hexahydrocyclopenta[c]pyrrole-2(1H)-carboxylate (1.41 g, 4.00 mmol) and 1-methylpyrazol-4-amine hydrochloride (1.60 g, 12.0 mmol) in n-BuOH (20 mL) was added DIPEA (2.61 g, 20.0 mmol). The reaction mixture was stirred in a sealed tube at 150° C. overnight and concentrated in vacuo. The residue was purified by silica gel column chromatography (EtOAc/PE (v/v)=4/1) to give the title compound as brown oil (1.66 g, 100%).

MS (ESI, pos. ion) m/z: 414.3 [M+H]$^+$.

Step 3) 5-methyl-$N^2$-(1-methyl-1H-pyrazol-4-yl)-$N^4$-(octahydrocyclopenta[c]pyrrol-5-yl)pyrimidine-2,4-diamine To a solution of tert-butyl 5-((5-methyl-2-((1-methyl-1H-pyrazol-4-yl)amino)pyrimidin-4-yl)amino)hexahydrocyclopenta[c]pyrrole-2(1H)-carboxylate (1.66 g, 4.01 mmol) in DCM (20 mL) was added a solution of HCl in EtOAc (20 mL, 80 mmol). The reaction mixture was stirred at rt for 1 h and concentrated in vacuo. The residue was dissolved in water (30 mL) and adjusted to pH=10 with saturated $Na_2CO_3$ aqueous solution, then extracted with DCM (250 mL×3). The combined organic phases were washed with brine (250 mL), dried over anhydrous $Na_2SO_4$, filtered and concentrated in vacuo. The residue was purified by silica gel column chromatography (MeOH/DCM (v/v)=1/5) to give the title compound as a beige solid (505.2 mg, 40.2%).

MS (ESI, pos. ion) m/z: 314.2 [M+H]$^+$;
$^1$H NMR (600 MHz, DMSO-$d_6$): δ (ppm) 7.84 (s, 1H), 7.62 (s, 1H), 7.54 (s, 1H), 7.24 (s, 1H), 7.16 (s, 1H), 4.44 (s, 1H), 3.84 (s, 3H), 3.29 (s, 2H), 3.08 (d, J=8.4 Hz, 2H), 2.78 (s, 2H), 2.31 (s, 2H), 2.00 (s, 3H), 1.67 (m, 2H).

Example 59

6-(5-((5-methyl-2-((1-methyl-1H-pyrazol-4-yl)amino)pyrimidin-4-yl)amino)hexahydrocyclopenta[c]pyrrol-2(1H)-yl)nicotinonitrile

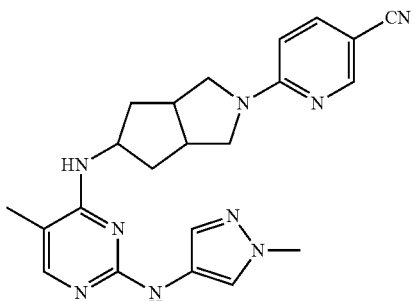

To a solution of 5-methyl-$N^2$-(1-methyl-1H-pyrazol-4-yl)-$N^4$-(octahydrocyclopenta[c]pyrrol-5-yl)pyrimidine-2,4-diamine (112.0 mg, 0.36 mmol) and 6-chloropyridine-3-carbonitrile (102.5 mg, 0.74 mmol) in a mixture of DCM (5 mL) and MeOH (5 mL) was added $Et_3N$ (200.7 mg, 1.98 mmol). The reaction mixture was stirred at 45° C. overnight and concentrated in vacuo. The residue was purified by silica gel column chromatography (MeOH/DCM (v/v)=1/40) to give the title compound as a beige solid (0.12 g, 81%).

MS (ESI, pos. ion) m/z: 416.3 [M+H]+;

$^1$H NMR (600 MHz, DMSO-$d_6$): δ (ppm) 10.00 (s, 1H), 8.48 (d, J=1.8 Hz, 1H), 7.98 (s, 1H), 7.85 (s, 1H), 7.83 (dd, J=9.0, 2.3 Hz, 1H), 7.61 (s, 1H), 7.55 (s, 1H), 6.62 (d, J=8.9 Hz, 1H), 4.61 (m, 1H), 3.85 (s, 3H), 3.61 (m, 4H), 2.81 (s, 2H), 2.33 (m, 2H), 1.95 (s, 3H), 1.63 (m, 2H).

Example 60

3-(5-((5-methyl-2-((1-methyl-1H-pyrazol-4-yl) amino)pyrimidin-4-yl)amino)hexahydrocyclopenta [c]pyrrol-2(1H)-yl)-3-oxopropanenitrile

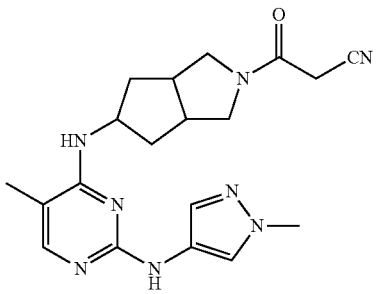 [SMILES: Cc1cnc(Nc2cnn(C)c2)nc1NC1CC2CN(C(=O)CC#N)CC2C1]

Example 61

1-(5-((5-methyl-2-((1-methyl-1H-pyrazol-4-yl) amino)pyrimidin-4-yl)amino)hexahydrocyclopenta [c]pyrrol-2(1H)-yl)ethanone

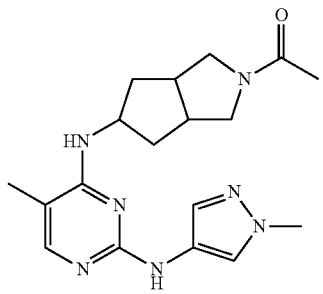 [SMILES: CC(=O)N1CC2CC(Nc3nc(Nc4cnn(C)c4)ncc3C)CC2C1]

To a solution of 5-methyl-N$^2$-(1-methyl-1H-pyrazol-4-yl)-N$^4$-(octahydrocyclopenta[c]pyrrol-5-yl)pyrimidine-2,4-diamine (291.8 mg, 0.93 mmol) and 2-cyanoacetic acid (153.0 mg, 1.80 mmol) in a mixture of DCM (20 mL) and DMF (5 mL) were added HOAT (263.4 mg, 1.94 mmol) and EDCI (406.0 mg, 2.10 mmol). After addition, the reaction mixture was stirred at 45° C. for 1 h, quenched with H$_2$O (30 mL) and extracted with DCM (100 mL×3). The combined organic phases were washed with brine (100 mL), dried over anhydrous Na$_2$SO$_4$, filtered and concentrated in vacuo. The residue was purified by silica gel column chromatography (MeOH/DCM (v/v)=1/10) to give example 60 as a beige solid (127.6 mg, 36.0%) and example 61 as a beige solid (29.6 mg, 9.0%).

Example 60

MS (ESI, pos. ion) m/z: 381.3 [M+H]+;

$^1$H NMR (600 MHz, CDCl$_3$): δ (ppm) 7.73 (s, 1H), 7.68 (s, 1H), 7.55 (s, 1H), 6.39 (s, 1H), 4.50 (m, 1H), 4.46 (d, J=6.9 Hz, 1H), 3.89 (s, 3H), 3.72 (m, 1H), 3.66 (m, 2H), 3.49 (dd, J=10.6, 3.8 Hz, 1H), 3.45 (d, J=3.7 Hz, 2H), 2.88 (m, 1H), 2.79 (m, 1H), 2.58 (m, 2H), 1.94 (s, 3H), 1.39 (m, 2H).

Example 61

MS (ESI, pos. ion) m/z: 356.3 [M+H]+;

$^1$H NMR (600 MHz, CDCl$_3$): δ (ppm) 7.71 (s, 1H), 7.70 (s, 1H), 7.54 (s, 1H), 6.41 (s, 1H), 4.51 (m, 1H), 4.47 (t, J=4.3 Hz, 1H), 3.89 (s, 3H), 3.62 (m, 3H), 3.42 (dd, J=10.9, 3.4 Hz, 1H), 2.78 (m, 2H), 2.55 (m, 2H), 2.09 (s, 3H), 1.93 (s, 3H), 1.38 (m, 2H).

Example 62

5-methyl-N$^2$-(1-methyl-1H-pyrazol-4-yl)-N$^4$-(2-(methylsulfonyl) octahydrocyclopenta[c]pyrrol-5-yl) pyrimidine-2,4-diamine

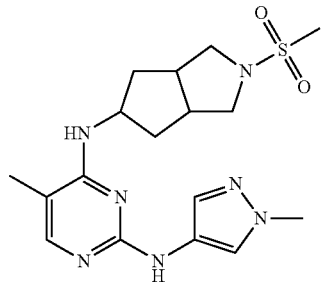

To a suspension of 5-methyl-N$^2$-(1-methyl-1H-pyrazol-4-yl)-N$^4$-(octahydrocyclopenta[c]pyrrol-5-yl)pyrimidine-2,4-diamine (122.4 mg, 0.39 mmol) and N,N-diethylethanamine (103.9 mg, 1.03 mmol) in DCM (10 mL) was added methanesulfonyl chloride (98.4 mg, 0.86 mmol). The reaction mixture was stirred at rt for 2 h, quenched with H$_2$O (30 mL) and extracted with DCM (100 mL×3). The combined organic phases were washed with brine (100 mL), dried over anhydrous Na$_2$SO$_4$, filtered and concentrated in vacuo. The residue was purified by silica gel column chromatography (MeOH/DCM (v/v)=1/20) to give the title compound as a beige solid (64.8 mg, 42.4%).

MS (ESI, pos. ion) m/z: 392.3 [M+H]+;

$^1$H NMR (400 MHz, CDCl$_3$): δ (ppm) 7.71 (s, 1H), 7.69 (s, 1H), 7.54 (s, 1H), 6.41 (s, 1H), 4.72 (d, J=7.6 Hz, 1H), 4.48 (m, 1H), 3.88 (s, 3H), 3.40 (d, J=9.6 Hz, 2H), 3.19 (m, 2H), 2.87 (s, 3H), 2.81 (m, 2H), 2.51 (m, 2H), 1.96 (s, 3H), 1.50 (m, 2H).

Example 63

5-chloro-$N^2$-(1,3-dimethyl-1H-pyrazol-4-yl)-$N^4$-(octahydrocyclopenta[c]pyrrol-5-yl) pyrimidine-2,4-diamine

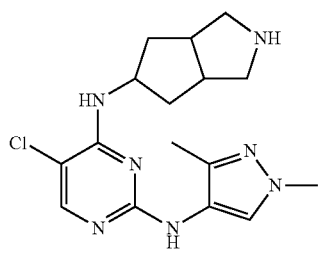 [SMILES: Cc1nn(C)cc1Nc1ncc(Cl)c(NC2CC3CNCC3C2)n1]

To a suspension of tert-butyl 5-((2,5-dichloropyrimidin-4-yl)amino)hexahydrocyclopenta[c]pyrrole2(1H)-carboxylate (573.1 mg, 1.54 mmol) and 1,3-dimethylpyrazol-4-amine hydrochloride (458.8 mg, 3.11 mmol) in dioxane (10 mL) was added trifluoroacetic acid (856.4 mg, 7.51 mmol). The reaction mixture was stirred at 100° C. overnight and adjusted to pH=10 with a saturated $Na_2CO_3$ solution, then extracted with DCM (100 mL×3). The combined organic phases were washed with brine (100 mL), dried over anhydrous $Na_2SO_4$, filtered and concentrated in vacuo. The residue was purified by silica gel column chromatography (MeOH/DCM=1/10) to give the title compound as a beige solid (256.8 mg, 48.1%).

MS (ESI, pos. ion) m/z: 348.2 [M+H]$^+$;
$^1$H NMR (400 MHz, $CDCl_3$): δ (ppm) 7.75 (s, 1H), 7.51 (s, 1H), 4.37 (m, 1H), 3.33 (m, 4H), 3.28 (s, 1H), 3.21 (m, 2H), 2.87 (m, 2H), 2.33 (m, 2H), 2.17 (s, 4H), 1.72 (m, 2H).

Example 64

3-(5-((5-chloro-2-((1,3-dimethyl-1H-pyrazol-4-yl)amino)pyrimidin-4-yl)amino)hexahydrocyclopenta[c]pyrrol-2(1H)-yl)-3-oxopropanenitrile

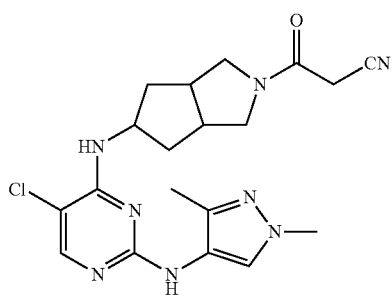 [SMILES: Cc1nn(C)cc1Nc1ncc(Cl)c(NC2CC3CN(C(=O)CC#N)CC3C2)n1]

To a solution of 5-chloro-$N^2$-(1,3-dimethyl-1H-pyrazol-4-yl)-$N^4$-(octahydrocyclopenta[c]pyrrol-5-yl)pyrimidine-2,4-diamine (186.6 mg, 0.54 mmol) and 2-cyanoacetic acid (64.8 mg, 0.76 mmol) in a mixture of DCM (20 mL) and DMF (5 mL) were added HATU (374.3 mg, 0.98 mmol) and $Et_3N$ (151.8 mg, 1.50 mmol). After addition, the reaction mixture was stirred at rt for 1 h, quenched with $H_2O$ (30 mL) and extracted with DCM (100 mL×3). The combined organic phases were washed with brine (100 mL), dried over anhydrous $Na_2SO_4$, filtered and concentrated in vacuo. The residue was purified by silica gel column chromatography (MeOH/DCM (v/v)=1/50) to give the title compound as a beige solid (124.5 mg, 55.9%).

MS (ESI, pos. ion) m/z: 415.2 [M+H]$^+$;
$^1$H NMR (400 MHz, $CDCl_3$): δ (ppm) 7.89 (s, 1H), 7.68 (s, 1H), 6.20 (s, 1H), 5.21 (d, J=7.1 Hz, 1H), 4.43 (m, 1H), 3.84 (s, 3H), 3.69 (m, 4H), 3.45 (s, 2H), 2.83 (m, 2H), 2.54 (m, 2H), 2.24 (s, 3H), 1.43 (m, 2H).

Example 65

5-chloro-$N^2$-(1,5-dimethyl-1H-pyrazol-4-yl)-$N^4$-(octahydrocyclopenta[c]pyrrol-5-yl)pyrimidine-2,4-diamine

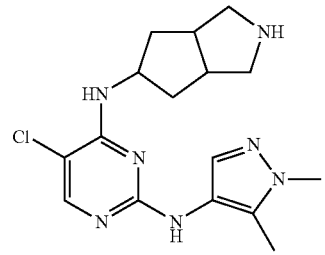 [SMILES: Cc1c(Nc2ncc(Cl)c(NC3CC4CNCC4C3)n2)cnn1C]

Step 1) 1,5-dimethyl-4-nitro-1H-pyrazole

To a solution of 3-methyl-4-nitro-1H-pyrazole (4.01 g, 31.6 mmol) in DMF (60 mL) were added $CH_3I$ (8.93 g, 63.0 mmol) and $K_2CO_3$ (8.73 g, 63.2 mmol). The reaction mixture was stirred at 60° C. in a sealed tube overnight and concentrated in vacuo. The residue was diluted with water (50 mL), and extracted with EtOAc (50 mL×3). The combined organic phases were washed with brine (50 mL), dried over anhydrous $Na_2SO_4$, filtered and concentrated in vacuo. The residue was purified by silica gel column chromatography (EtOAc/PE (v/v)=1/2) to give the title compound as a beige solid (1.01 g, 22.7%).

MS (ESI, pos. ion) m/z: 142.2 [M+H]$^+$.
$^1$H NMR (600 MHz, $CDCl_3$): δ (ppm) 8.05 (s, 1H), 3.85 (s, 3H), 2.65 (s, 3H).

Step 2) 1,5-dimethyl-1H-pyrazol-4-amine hydrochloride

To a solution of 1,5-dimethyl-4-nitro-1H-pyrazole (1.01 g, 7.2 mmol) in MeOH (15 mL) was added Pd/C (10%, 0.20 g) and concentrated HCl (1 mL, 12 mmol) in a high pressure autoclave under 2 MPa $H_2$. The reaction mixture was stirred at rt overnight and filtered. The filtrate was concentrated in vacuo to give the title compound as brown oil (763.0 mg, 95.9%).

MS (ESI, pos. ion) m/z: 112.2 [M+H]$^+$.

Step 3) 5-chloro-$N^2$-(1,5-dimethyl-1H-pyrazol-4-yl)-$N^4$-(octahydrocyclopenta[c]pyrrol-5-yl)pyrimidine-2,4-diamine To a suspension of tert-butyl 5-((2,5-dichloropyrimidin-4-yl)amino)hexahydrocyclopenta[c]pyrrole-2(1H)-carboxylate (579.1 mg, 1.55 mmol) and 1,5-dimethylpyrazol-4-amine hydrochloride (446.8 mg, 3.03 mmol) in dioxane (10 mL) was added trifluoroacetic acid (862.8 mg, 7.57 mmol). The reaction mixture was stirred at 100° C. overnight and adjusted to pH=10 with a saturated $Na_2CO_3$ solution, then extracted with DCM (100 mL×3). The combined organic phases were washed with brine (100 mL), dried over anhydrous $Na_2SO_4$, filtered and concentrated in vacuo. The residue was purified by silica gel column chromatography (MeOH/DCM=1/10) to give the title compound as a beige solid (105.6 mg, 19.6%).

MS (ESI, pos. ion) m/z: 348.2 [M+H]$^+$;

$^1$H NMR (600 MHz, CDCl$_3$): δ (ppm) 7.83 (s, 1H), 7.63 (s, 1H), 6.28 (br. s, 1H), 5.62 (br. s, 1H), 4.42 (m, 1H), 3.80 (s, 3H), 3.35 (d, J=11.3 Hz, 2H), 3.27 (dd, J=11.8, 7.3 Hz, 2H), 2.92 (m, 2H), 2.48 (dt, J=13.2, 7.6 Hz, 2H), 2.22 (s, 3H), 1.75 (m, 2H).

Example 66

3-(5-((5-chloro-2-((1,5-dimethyl-1H-pyrazol-4-yl)amino)pyrimidin-4-yl)amino)hexahydrocyclopenta[c]pyrrol-2(1H)-yl)-3-oxopropanenitrile

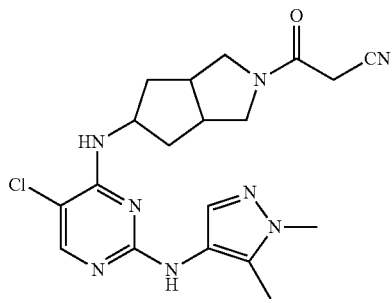 [SMILES: Cc1c(Nc2ncc(Cl)c(NC3CC4CN(C(=O)CC#N)CC4C3)n2)cnn1C]

To a solution of 5-chloro-N$^2$-(1,5-dimethyl-1H-pyrazol-4-yl)-N$^4$-(octahydrocyclopenta[c]pyrrol-5-yl)pyrimidine-2,4-diamine (58.4 mg, 0.17 mmol) and 2-cyanoacetic acid (23.1 mg, 0.27 mmol) in mixture of DCM (8 mL) and DMF (2 mL) were added HATU (109.8 mg, 0.29 mmol) and Et$_3$N (45.7 mg, 0.45 mmol). The reaction mixture was stirred at rt for 1 h, quenched with H$_2$O (30 mL) and extracted with DCM (100 mL×3). The combined organic phases were washed with brine (100 mL), dried over anhydrous Na$_2$SO$_4$, filtered and concentrated in vacuo. The residue was purified by silica gel column chromatography (MeOH/DCM (v/v)=1/50) to give the title compound as a beige solid (46.5 mg, 66.7%).

MS (ESI, pos. ion) m/z: 415.2 [M+H]$^+$;

$^1$H NMR (400 MHz, CDCl$_3$): δ (ppm) 7.85 (s, 1H), 7.64 (s, 1H), 6.26 (br. s, 1H), 5.22 (d, J=6.9 Hz, 1H), 4.42 (m, 1H), 3.80 (s, 3H), 3.71 (m, 2H), 3.60 (dd, J=12.7, 4.4 Hz, 1H), 3.45 (m, 3H), 2.82 (m, 2H), 2.52 (m, 2H), 2.22 (s, 3H), 1.41 (m, 2H).

Example 67

4-((2-(2-cyanoacetyl)octahydrocyclopenta[c]pyrrol-5-yl)amino)-2-((1-methyl-1H-pyrazol-4-yl)amino)pyrimidine-5-carbonitrile

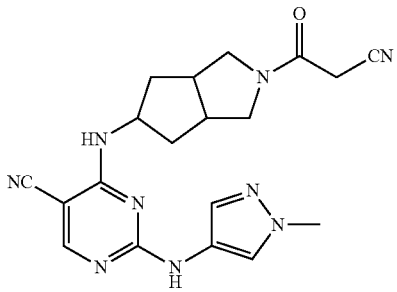 [SMILES: Cn1cc(Nc2ncc(C#N)c(NC3CC4CN(C(=O)CC#N)CC4C3)n2)cn1]

Step 1) tert-butyl 5-((2-chloro-5-cyanopyrimidin-4-yl)amino)hexahydrocyclopenta[c]pyrrole-2(1H)-carboxylate To a solution of 2,4-dichloropyrimidine-5-carbonitrile (600 mg, 3.4485 mmol) and tert-butyl 5-aminohexahydrocyclopenta[c]pyrrole-2(1H)-carboxylate (936.8 mg, 4.139 mmol) in ethanol (50 mL) was added N,N-diethylethanamine (698.5 mg, 6.903 mmol). The mixture was stirred at rt for 3 h. Then it was concentrated under vacuo, and the residue was purified by silica gel column chromatography (PE/EtOAc (v/v)=5/1) to give the title product as yellow oil (332.5 mg, 26.50%).

MS (ESI, pos. ion) m/z: 308.0 [M−55]$^+$.

Step 2) tert-butyl 5-((5-cyano-2-((1-methyl-1H-pyrazol-4-yl)amino)pyrimidin-4-yl)amino)hexahydrocyclopenta[c]pyrrole-2(1H)-carboxylate To a solution of tert-butyl 5-((2-chloro-5-cyanopyrimidin-4-yl)amino)hexahydrocyclopenta[c]pyrrole-2(1H)-carboxylate (377.2 mg, 1.037 mmol) and 1-methylpyrazol-3-amine hydrochloride (277.5 mg, 2.077 mmol) in butan-1-ol (15 mL) was added DIPEA (335.5 mg, 2.596 mmol). The mixture was stirred at 150° C. overnight, then concentrated in vacuo. The residue was purified by silica gel column chromatography (DCM/MeOH (v/v)=50/1) to give the title product as a yellow solid (425 mg, 96.56%).

MS (ESI, pos. ion) m/z: 425.3 [M+H]$^+$.

Step 3) 2-((1-methyl-1H-pyrazol-4-yl)amino)-4-((octahydrocyclopenta[c]pyrrol-5-yl)amino)pyrimidine-5-carbonitrile To a solution of tert-butyl 5-((5-cyano-2-((1-methyl-1H-pyrazol-4-yl)amino)pyrimidin-4-yl)amino)hexahydrocyclopenta[c]pyrrole-2(1H)-carboxylate (425 mg, 1.001 mmol) in dichloromethane (30 mL) was added the solution of HCl in EtOAc (10 mL, 40 mmol), and the mixture was stirred at rt for 1 h. The mixture was diluted with water (20 mL) and adjust to pH=8-9 with saturated NaHCO$_3$ solution and then extracted with DCM (30 mL×3). The combined organic phases were washed with brine (50 mL), dried with anhydrous Na$_2$SO$_4$, filtered and concentrated in vacuo. The residue was purified by silica gel column chromatography (DCM/MeOH (v/v)=5/1) to give the title product as a white solid (185.2 mg, 57.02%).

MS (ESI, pos. ion) m/z: 163.1 [(M+H)/2]$^+$

Step 4) 4-((2-(2-cyanoacetyl)octahydrocyclopenta[c]pyrrol-5-ylamino)-2-((1-methyl-1H-pyrazol-4-yl)amino)pyrimidine-5-carbonitrile To a suspension of 2-((1-methyl-1H-pyrazol-3-yl)amino)-4-((octahydrocyclopenta[c]pyrrol-5-yl)amino)pyrimidine-5-carbonitrile (165.2 mg, 0.5092 mmol) and 2-cyanoacetic acid (65 mg, 0.7642 mmol) in dichloromethane (20 mL) and N,N-dimethylformamide (5 mL) were added HATU (387.5 mg, 1.019 mmol) and N,N-diethylethanamine (103.5 mg, 1.023 mmol). The mixture was then stirred at rt for 1 h and then quenched with H$_2$O (20 mL), and the resulted mixture was extracted with DCM/MeOH (10/1, 20 mL×3). The combined organic phases were washed with brine (50 mL), dried over anhydrous Na$_2$SO$_4$, filtered and concentrated in vacuo. The residue was purified by silica gel column chromatography (DCM/MeOH (v/v)=10/1) to give the title compound as a white solid (36 mg, 18.06%).

MS (ESI, pos. ion) m/z: 391.9 [M+H]⁺;
¹H NMR (400 MHz, DMSO-d₆) δ 9.46 and 9.37 (s, 1H), 8.31 and 8.24 (s, 1H), 8.18 and 7.88 (s, 1H), 7.95 and 7.83 (d, J=7.3 Hz, 1H), 7.71 and 7.66 (s, 1H), 4.30 (ddd, J=23.6, 16.8, 8.9 Hz, 1H), 3.93 (dd, J=10.0, 5.5 Hz, 2H), 3.81 (s, 3H), 3.55 (dd, J=13.5, 9.7 Hz, 1H), 3.47 (ddd, J=12.1, 8.1, 4.2 Hz, 1H), 3.37 (d, J=12.7 Hz, 2H), 2.63 (tdd, J=20.5, 13.9, 8.0 Hz, 2H), 2.24 (dq, J=12.5, 7.2 Hz, 2H), 1.38 (dd, J=17.4, 9.2 Hz, 2H).

Example 68

5-chloro-N⁴-methyl-N²-(1-methyl-1H-pyrazol-4-yl)-N⁴-(octahydrocyclopenta[c]pyrrol-5-yl)pyrimidine-2,4-diamine

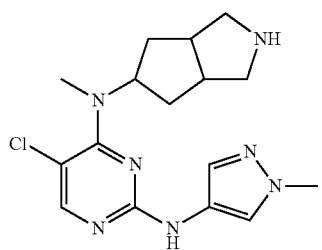 [SMILES: CN(c1nc(Nc2cnn(C)c2)ncc1Cl)C1CC2CNCC2C1]

Step 1) tert-butyl 5-((2,5-dichloropyrimidin-4-yl)(methyl)amino)hexahydrocyclopenta[c]pyrrole-2(1H)-carboxylate To a solution of 2,4,5-trichloropyrimidine (1.85 g, 10.1 mmol) and tert-butyl 5-(methylamino)hexahydrocyclopenta[c]pyrrole-2(1H)-carboxylate (3.66 g, 15.2 mmol) in EtOH (20 mL) was added Et₃N (2.08 g, 20.6 mmol). After addition, the reaction mixture was stirred at rt overnight and concentrated in vacuo. The residue was purified by silica gel column chromatography (EtOAc/PE (v/v)=1/12) to give the title compound as yellow oil (987.8 mg, 25.3%).
MS (ESI, pos. ion) m/z: 331.0 [(M–C₄H₈)+H]⁺.

Step 2) tert-butyl 5-((5-chloro-2-((1-methyl-1H-pyrazol-4-yl)amino)pyrimidin-4-yl)(methyl)amino)hexahydrocyclopenta[c]pyrrole-2(1H)-carboxylate To a suspension of tert-butyl 5-((2,5-dichloropyrimidin-4-yl)(methyl)amino)hexahydrocyclopenta[c]pyrrole-2(1H)-carboxylate (249.1 mg, 0.64 mmol) and 1-methylpyrazol-4-amine hydrochloride (333.1 mg, 2.49 mmol) in n-BuOH (10 mL) was added DIPEA (452.0 mg, 3.46 mmol). The reaction mixture was stirred at 150° C. in a sealed tube for 28 h and concentrated in vacuo. The residue was purified by silica gel column chromatography (EtOAc/PE (v/v)=2/1) to give the title compound as brown oil (230.8 mg, 80.1%).
MS (ESI, pos. ion) m/z: 447.9[M+H]⁺.

Step 3) 5-chloro-N⁴-methyl-N²-(1-methyl-1H-pyrazol-4-yl)-N⁴-(octahydrocyclopenta[c]pyrrol-5-yl)pyrimidine-2,4-diamine To a solution of tert-butyl 5-((5-chloro-2-((1-methyl-1H-pyrazol-4-yl)amino)pyrimidin-4-yl)(methyl)amino)hexahydrocyclopenta[c]pyrrole-2(1H)-carboxylate (217.4 mg, 0.48 mmol) in DCM (10 mL) was added a solution of HCl in EtOAc (10 mL, 40 mmol). The reaction mixture was stirred at rt overnight and concentrated in vacuo. The residue was dissolved in water (30 mL) and adjusted to pH=10 with a saturated Na₂CO₃ aqueous solution, then the resulting mixture was extracted with DCM (200 mL×3). The combined organic phases were washed with brine (200 mL), dried over anhydrous Na₂SO₄, filtered and concentrated in vacuo. The residue was purified by silica gel column chromatography (MeOH/DCM (v/v)=1/10) to give the title compound as a beige solid (100.3 mg, 59.4%).
MS (ESI, pos. ion) m/z: 348.3 [M+H]⁺;
¹H NMR (400 MHz, CDCl₃ and MeOH-d₄): δ (ppm) 7.80 (s, 1H), 7.55 (s, 1H), 7.47 (s, 1H), 4.55 (m, 1H), 3.79 (s, 3H), 3.30 (s, 2H), 3.21 (m, 2H), 3.06 (s, 3H), 2.81 (m, 2H), 2.13 (m, 2H), 1.74 (m, 2H).

Example 69

3-(5-((5-chloro-2-((1-methyl-1H-pyrazol-4-yl)amino)pyrimidin-4-yl)(methyl)amino)hexahydrocyclopenta[c]pyrrol-2(1H)-yl)-3-oxopropanenitrile

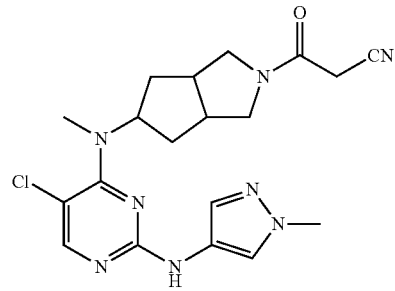 [SMILES: CN(c1nc(Nc2cnn(C)c2)ncc1Cl)C1CC2CN(C(=O)CC#N)CC2C1]

To a suspension of 5-chloro-N⁴-methyl-N²-(1-methyl-1H-pyrazol-4-yl)-N⁴-(octahydrocyclopenta[c]pyrrol-5-yl)pyrimidine-2,4-diamine (43.3 mg, 0.51 mmol) in DCM (15 mL) were added HOAT (71.6 mg, 0.53 mmol), EDCI (103.3 mg, 0.53 mmol) and Et₃N (111.1 mg, 1.10 mmol). The reaction mixture was stirred at rt for 1 h, then quenched with H₂O (30 mL) and extracted with DCM (100 mL×3). The combined organic phases were washed with brine (100 mL), dried over anhydrous Na₂SO₄, filtered and concentrated in vacuo. The residue was purified by silica gel column chromatography (MeOH/DCM (v/v)=1/30) to give the title compound as a beige solid (93.1 mg, 91.1%).
MS (ESI, pos. ion) m/z: 414.9 [M+H]⁺;
¹H NMR (400 MHz, CDCl₃): δ (ppm) 7.97 (s, 1H), 7.66 (s, 1H), 7.51 (s, 1H), 6.58 (s, 1H), 4.78 (m, 1H), 3.90 (s, 3H), 3.74 (m, 2H), 3.58 (dd, J=12.7, 4.5 Hz, 1H), 3.49 (m, 3H), 3.04 (s, 3H), 2.83 (m, 1H), 2.73 (m, 1H), 2.24 (td, J=12.9, 6.7 Hz, 2H), 1.61 (m, 2H).

Biological Testing

The LC/MS/MS system used in the analysis consists of an Agilent 1200 Series vacuum degasser, binary pump, well-plate autosampler, thermostatted column compartment, the Agilent G6430 Triple Quadrupole Mass Spectrometer with an electrosprayionization (ESI) source. Quantitative analysis was carried out using MRM mode. The parameters for MRM transitions are in the Table A.

TABLE A

| MRM | 490.2→383.1 |
|---|---|
| Fragmentor | 230 V |

TABLE A-continued

| CE | 55 V |
|---|---|
| Drying Gas Temp | 350° C. |
| Nebulize | 40 psi |
| Drying Gas Flow | 10 L/min |

An Agilent XDB-C18, 2.1×30 mm, 3.5 µM column was used for the analysis. 5 µL of the samples were injected. Analysis condition: The mobile phase was 0.1% formic acid in water (A) and 0.1% formic acid in methanol (B). The flow rate was 0.4 mL/min. And the gradient of Mobile phase was in the Table B.

TABLE B

| Time | Gradient of Mobile Phase B |
|---|---|
| 0.5 min | 5% |
| 1.0 min | 95% |
| 2.2 min | 95% |
| 2.3 min | 5% |
| 5.0 min | stop |

Alternatively, an Agilent 6330 series LC/MS/MS spectrometer equipped with G1312A binary pumps, a G1367A autosampler and a G1314C UV detector were used in the analysis. An ESI source was used on the LC/MS/MS spectrometer. The analysis was done in positive ion mode as appropriate and the MRM transition for each analyte was optimized using standard solution. A Capcell MP-C18 100×4.6 mm I.D., 5 µM column (Phenomenex, Torrance, Calif., USA) was used during the analysis. The mobile phase was 5 mM ammonia acetate, 0.1% MeOH in water (A): 5 mM ammonia acetate, 0.1% MeOH in acetonitrile (B) (70:30, v/v). The flow rate was 0.6 mL/min. Column was maintained at ambient temperature. 20 µL of the samples were injected.

Example A

Compound Stability in Human and Rat Liver Microsomes

Human or rat liver microsomes incubations were conducted in duplicate in polypropylene tubes. The typical incubation mixtures consisted of human or rat liver microsomes (0.5 mg protein/mL), compounds of interest (5 µM) and NADPH (1.0 mM) in a total volume of 200 µL potassium phosphate buffer (PBS, 100 mM, pH 7.4). Compounds were dissolved in DMSO and diluted with PBS such that the final concentration of DMSO was 0.05%. The enzymatic reactions were commenced with the addition of protein after a 3-min preincubation and incubated in a water bath open to the air at 37° C. Reactions were terminated at various time points (0, 5, 10, 15, 30, 60 min) by adding equal volume of ice-cold acetonitrile. The samples were stored at −80° C. until LC/MS/MS assays.

The concentrations of compounds in the incubation mixtures of human or rat liver microsomes were determined by a LC/MS/MS method. The ranges of the linearity in the concentration range were determined for each tested compounds. A parallel incubation was performed using denatured microsomes as the negative control, and reactions were terminated at various time points (0, 15, 60 min) after incubation at 37° C.

Dextromethorphan (70 µM) was selected as the positive control, and reactions were terminated at various time points (0, 5, 10, 15, 30, 60 min) after incubation at 37° C. Both positive and negative control samples were included in each assay to ensure the integrity of the microsomal incubation system.

Data Analysis

The concentrations of compounds in human or rat liver microsome incubations were plotted as a percentage of the relevant zero time point control for each reaction. The in vivo $CL_{int}$ were extrapolated (ref.: Naritomi, Y.; Terashita, S.; Kimura, S.; Suzuki, A.; Kagayama, A.; and Sugiyama, Y.; Prediction of human hepatic clearance from in vivo animal experiments and in vitro metabolic studies with liver microsomes from animals and humans. *Drug Metab. Dispos.*, 2001, 29: 1316-1324).

Exemplary results from selected compounds of the invention are listed in Table 2. The compounds disclosed herein exhibited desirable stability when the compounds were incubated in human and rat liver microsomes.

TABLE 2

Stability of selected compounds of the invention in human and rat liver microsomes

| Example # | Human $T_{1/2}$ (min) | Human $CL_{int}$ (mL/min/kg) | Rat $T_{1/2}$ (min) | Rat $CL_{int}$ (mL/min/kg) |
|---|---|---|---|---|
| Ex. 1 | 183.1 | 9.49 | 269.2 | 9.23 |
| Ex. 3.10A | 314.6 | 5.53 | 12.78 | 194.34 |
| Ex. 4A | 37.30 | 46.60 | 12.42 | 199.98 |
| Ex. 10 | 1508 | 1.15 | 52.65 | 47.17 |
| Ex. 11 | ∞ | ND | 17.74 | 140.01 |
| Ex. 12 | 186.9 | 9.30 | 11.96 | 207.67 |
| Ex. 14A | 203.2 | 8.55 | 10.60 | 234.31 |
| Ex. 14B | 171.8 | 10.12 | 71.63 | 34.67 |
| Ex. 22 | 157.5 | 11.04 | 12.19 | 203.75 |
| Ex. 23 | 125.3 | 13.87 | 4.50 | 551.94 |
| Ex. 25 | 521.5 | 3.33 | 16.80 | 147.84 |
| Ex. 27 | 21.80 | 79.74 | 9.20 | 269.97 |
| Ex. 28 | 268.0 | 6.49 | 73.57 | 33.76 |
| Ex. 29 | 83.77 | 20.75 | 40.32 | 61.60 |
| Ex. 30 | 38.05 | 45.69 | 24.18 | 102.72 |
| Ex. 31 | 67.23 | 25.86 | 13.20 | 188.16 |
| Ex. 32 | 202.2 | 8.60 | 27.17 | 91.41 |
| Ex. 34 | 18.97 | 91.64 | 2.31 | 1075.20 |
| Ex. 35 | 6.65 | 261.40 | 2.72 | 913.13 |
| Ex. 37 | 56.18 | 30.94 | 68.87 | 36.06 |
| Ex. 39 | 126.9 | 13.70 | 36.90 | 67.31 |
| Ex. 42 | 48.85 | 35.58 | 31.51 | 78.82 |
| Ex. 44 | 243.1 | 7.15 | 398.3 | 6.24 |
| Ex. 46 | 39.30 | 44.23 | 20.60 | 120.57 |
| Ex. 48 | 47.60 | 36.52 | 24.30 | 102.21 |
| Ex. 50 | 536.8 | 3.24 | 307.8 | 8.07 |
| Ex. 52 | 68.29 | 25.45 | 16.00 | 155.23 |
| Ex. 53 | 266.3 | 6.53 | 23.1 | 107.52 |
| Ex. 54 | 38.80 | 44.80 | 31.60 | 78.60 |
| Ex. 56 | 37.61 | 46.22 | 41.36 | 60.05 |
| Ex. 60 | 244.4 | 7.11 | 240.5 | 10.33 |
| Ex. 62 | 271.1 | 6.41 | 81.12 | 30.62 |
| Ex. 64 | 62.84 | 27.66 | 33.57 | 73.99 |
| Ex. 66 | 81.48 | 21.33 | 21.22 | 117.05 |
| Ex. 67 | 296.0 | 5.87 | 26.40 | 94.08 |
| Ex. 69 | 95.63 | 18.18 | 12.18 | 203.92 |

ND: not determined

Example B

Evaluation of Pharmacokinetics after Intravenous and Oral Administration of the Compounds Disclosed Herein in Mice, Rats, Dogs and Monkeys The compounds disclosed herein are assessed in pharmacokinetic studies in mice, rats, dogs or monkeys. The compounds are administered as a water solution, 2% HPMC+1% TWEEN®80 in water solution, 5% DMSO+5% solution in saline, 4% MC suspension or capsule. For the intravenous administration, the animals are generally given at 1 or 2 mg/kg dose. For the oral (p.o.) dosing, mice and rats are generally given 5 or 10 mg/kg dose, and dogs and monkeys are generally given 10 mg/kg dose. The blood samples (0.3 mL) are drawn at 0.25, 0.5, 1.0, 2.0, 3.0, 4.0, 6.0, 8.0, 12 and 24 h time points or 0.083, 0.25, 0.5, 1.0, 2.0, 4.0, 6.0, 8.0 and 24 h time points and centrifuged at 3,000 or 4000 rpm for 2 to 10 min. The plasma solutions are collected, and stored at −20° C. or −70° C. until analyzed by LC/MS/MS as described above.

Exemplary study results from examples disclosed herein are listed in Table 3. The compounds disclosed herein exhibited optimized pharmacokinetic properties with good absorption, desirable oral bioavailability (F) and half-life ($T_{1/2}$) when the compounds were administered orally or intravenously.

TABLE 3

Pharmacokinetic profiles of selected compounds of the invention in rats iv dosing

| Example # | dose (mg/kg) | $T_{1/2}$ (h) | $AUC_{last}$ (ng · h/ml) | Cl/F (L/h/kg) | Vss (L/kg) | F (%) |
|---|---|---|---|---|---|---|
| Ex. 1 | 1 | 3.77 | 103 | 9.42 | 40.3 | 44.39 |
| Ex. 3.10A | 1 | 2.72 | 216 | 4.21 | 13.5 | 19.06 |
| Ex. 4A | 1 | 0.86 | 345 | 2.93 | 1.38 | 21.81 |
| Ex. 8 | 1 | 0.88 | 272 | 3.70 | 2.85 | 17.5 |
| Ex. 11 | 1 | 2.51 | 146 | 6.30 | 18.6 | 18.13 |
| Ex. 12 | 1 | 0.24 | 143 | 7.26 | 1.75 | 39.2 |
| Ex. 14B | 1 | 0.49 | 193 | 5.21 | 2.41 | 12.7 |
| Ex. 18 | 1 | 2.26 | 731 | 2.75 | 4.32 | 55.9 |
| Ex. 22 | 1 | 0.43 | 176 | 5.69 | 2.02 | 22.6 |
| Ex. 27 | 0.72 | 0.77 | 452 | 1.67 | 1.74 | 15.0 |
| Ex. 28 | 1 | 0.65 | 251 | 4.26 | 3.06 | 63.6 |
| Ex. 29 | 1 | 0.82 | 382 | 2.74 | 2.05 | 19.1 |
| Ex. 30 | 1 | 1.15 | 370 | 2.74 | 4.77 | 26.1 |
| Ex. 31 | 1 | 0.66 | 272 | 3.67 | 2.06 | 25.7 |
| Ex. 32 | 1 | 0.59 | 264 | 3.77 | 1.65 | 41.3 |
| Ex. 33 | 1 | 2.45 | 702 | 1.49 | 3.33 | 60.4 |
| Ex. 37 | 1 | 1.19 | 381 | 2.66 | 2.97 | 31.3 |
| Ex. 39 | 1 | 0.69 | 422 | 2.39 | 1.19 | 83.1 |
| Ex. 44 | 1 | 0.55 | 343 | 2.96 | 1.09 | 12.0 |
| Ex. 46 | 1 | 0.48 | 244 | 4.13 | 1.53 | 26.0 |
| Ex. 48 | 1 | 0.73 | 252 | 3.97 | 3.41 | 13.6 |
| Ex. 50 | 1 | 0.99 | 384 | 2.59 | 1.93 | 17.3 |
| Ex. 52 | 1 | 0.32 | 197 | 5.05 | 1.60 | 16.5 |
| Ex. 53 | 1 | 1.02 | 296 | 3.31 | 2.46 | 33.0 |
| Ex. 56 | 1 | 0.54 | 459 | 2.18 | 0.95 | 31.3 |
| Ex. 59 | 1 | 0.97 | 648 | 1.61 | 1.76 | 36.9 |
| Ex. 62 | 1 | 0.81 | 184 | 4.97 | 5.43 | 29.6 |
| Ex. 64 | 1 | 0.41 | 315 | 3.19 | 1.31 | 48.1 |
| Ex. 66 | 1 | 0.27 | 201 | 4.91 | 2.28 | 21.0 |
| Ex. 69 | 1 | 0.47 | 281 | 3.91 | 1.19 | 56.2 |

Example C

Kinase Activity Assay

The efficacy of the compounds disclosed herein as inhibitors of protein kinases can be evaluated as follows.

General Description for Kinase Assays

Kinase assays can be performed by measurement of incorporation of γ-$^{33}$P ATP into immobilized myelin basic protein (MBP). High binding white 384 well plates (Greiner) are coated with MBP (Sigma #M-1891) by incubation of 60 μL/well of 20 μg/mL MBP in Tris-buffered saline (TBS; 50 mM Tris pH 8.0, 138 mM NaCl, 2.7 mM KCl) for 24 h at 4° C. Plates are washed 3× with 100 μL TBS. Kinase reactions are carried out in a total volume of 34 μL in kinase buffer (5 mM Hepes pH 7.6, 15 mM NaCl, 0.01% bovine gamma globulin (Sigma #I-5506), 10 mM MgCl$_2$, 1 mM DTT, 0.02% TritonX-100). Compound dilutions are performed in DMSO and added to assay wells to a final DMSO concentration of 1%. Each data point is measured in duplicate, and at least two duplicate assays are performed for each individual compound determination. Enzyme is added to final concentrations of 10 nM or 20 nM, for example. A mixture of unlabeled ATP and γ-$^{33}$P ATP is added to start the reaction (2×10$^6$ cpm of γ-$^{33}$P ATP per well (3000 Ci/mmole) and 10 μM unlabeled ATP, typically. The reactions are carried out for 1 h at room temperature with shaking. Plates are washed 7× with TBS, followed by the addition of 50 μL/well scintillation fluid (Wallac). Plates are read using a Wallac Trilux counter. This is only one format of such assays; various other formats are possible, as known to one skilled in the art.

The above assay procedure can be used to determine the IC$_{50}$ for inhibition and/or the inhibition constant, K$_i$. The IC$_{50}$ is defined as the concentration of compound required to reduce the enzyme activity by 50% under the condition of the assay. The IC$_{50}$ value is estimated by preparing a 10 point curve using a 1/2 log dilution series (for example, a typical curve may be prepared using the following compound concentrations: 3 μM, 1 μM, 0.3 μM, 0.1 μM, 0.03 μM, 0.01 μM, 0.003 μM, 0.001 μM, 0.0003 μM and 0 μM).

Kinase General Assay Protocol

JAK1 (h)

JAK1 (h) is incubated with 20 mM Tris/HCl pH 7.5, 0.2 mM EDTA, 500 μM GEEPLYWSFPAKKK, 10 mM MgAcetate and [γ-$^{33}$P-ATP](specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 μL of the reaction is then spotted onto a P30 filtermat and washed three times for 5 minutes in 75 mM phosphoric acid and once in methanol prior to drying and scintillation counting.

JAK2 (h)

JAK2 (h) is incubated with 8 mM MOPS pH 7.0, 0.2 mM EDTA, 100 μM KTFCGTPEYLAPEVRREPRILSEE-EQEMFRDFDYIADWC, 10 mM MgAcetate and [γ-$^{33}$P-ATP](specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 μL of the reaction is then spotted onto a P30 filtermat and washed three times for 5 minutes in 75 mM phosphoric acid and once in methanol prior to drying and scintillation counting.

JAK3 (h)

JAK3 (h) is incubated with 8 mM MOPS pH 7.0, 0.2 mM EDTA, 500 μM GGEEEEYFELVKKKK, 10 mM MgAcetate and [γ-$^{33}$P-ATP](specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 μL of the reaction is then spotted onto a P30 filtermat and washed three times for 5 minutes in 75 mM phosphoric acid and once in methanol prior to drying and scintillation counting.

TYK2 (h)

TYK2 (h) is incubated with 8 mM MOPS pH 7.0, 0.2 mM EDTA, 250 μM GGMEDIYFEFMGGKKK, 10 mM MgAcetate and [γ-$^{33}$P-ATP](specific activity approx. 500 cpm/ pmol, concentration as required). The reaction is initiated by the addition of the MgATP mix. After incubation for 40 minutes at room temperature, the reaction is stopped by the addition of 3% phosphoric acid solution. 10 μL of the reaction is then spotted onto a P30 filtermat and washed three times for 5 minutes in 75 mM phosphoric acid and once in methanol prior to drying and scintillation counting.

FLT3 (h)

FLT3 (h) is incubated with 8 mM MOPS pH 7.0, 0.2 mM EDTA, 50 μM EAIYAAPFAKKK, 10 mM MgAcetate and [γ-$^{33}$P-ATP](specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 μL of the reaction is then spotted onto a P30 filtermat and washed three times for 5 minutes in 75 mM phosphoric acid and once in methanol prior to drying and scintillation counting.

Aurora-A (h)

Aurora-A (h) is incubated with 8 mM MOPS pH 7.0, 0.2 mM EDTA, 200 μM LRRASLG (Kemptide), 10 mM MgAcetate and [γ-$^{33}$P-ATP](specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 μL of the reaction is then spotted onto a P30 filtermat and washed three times for 5 minutes in 75 mM phosphoric acid and once in methanol prior to drying and scintillation counting.

Aurora-B (h)

Aurora-B (h) is incubated with 8 mM MOPS pH 7.0, 0.2 mM EDTA, 30 μM AKRRRLSSLRA, 10 mM MgAcetate and [γ-$^{33}$PATP](specific activity approx. 500 cpm/pmol, concentration as required). The reaction is initiated by the addition of the MgATP mix. After incubation for 40 minutes at room temperature, the reaction is stopped by the addition of a 3% phosphoric acid solution. 10 μL of the reaction is then spotted onto a P30 filtermat and washed three times for 5 minutes in 75 mM phosphoric acid and once in methanol prior to drying and scintillation counting.

The kinase assays described herein were performed at Millipore UK Ltd, Dundee Technology Park, Dundee DD2 1SW, UK.

Alternatively, the kinase activities of the compounds can be measured using KINOMEscan™, which is based on a competition binding assay that quantitatively measures the ability of a compound to compete with an immobilized, active-site directed ligand. The assay was performed by combining three components: DNA-tagged kinase; immobilized ligand; and a test compound. The ability of the test compound to compete with the immobilized ligand was measured via quantitative PCR of the DNA tag.

For most assays, kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SEABLOCK™ (Pierce), 1% BSA, 0.05% TWEEN®20, 1 mM DTT) to remove unbound ligand and to reduce nonspecific binding. Binding reactions were assembled by combining kinases, liganded affinity beads, and test compounds in 1× binding buffer (20% SEABLOCK™, 0.17×PBS, 0.05% TWEEN®20, 6 mM DTT). All reactions were performed in polystyrene 96-well plates in a final volume of 0.135 mL. The assay plates were incubated at room temperature with shaking for 1 hour and the affinity beads were washed with wash buffer (lx PBS, 0.05% TWEEN®20). The beads were then re-suspended in elution buffer (lx PBS, 0.05% TWEEN®20, 0.5 μM non-biotinylated affinity ligand) and incubated at room temperature with shaking for 30 minutes. The kinase concentration in the eluates was measured by qPCR.

The kinase activity assays described herein can be performed using KINOMEscan™ Profiling Service at DiscoveRx Corporation, 42501 Albrae St. Fremont, Calif. 94538, USA.

Exemplary assay results from compounds disclosed herein are listed in Table 4 and Table 5. The compounds disclosed herein displayed potent inhibitory activities against JAK1, JAK2, JAK3, TYK2, Aurora-A and/or FLT3 kinase in the corresponding protein kinase assays.

Table 4 lised the $IC_{50}$s of some compounds described herein in the JAK1 and JAK2 kinase assays. Table 5 lised the $IC_{50}$s of some compounds described herein in the JAK3, TYK2, Aurora-A and FLT3 kinase assays.

TABLE 4

JAK1 and JAK2 Kinase inhibition data

| Example # | $IC_{50}$ (nM) | |
|---|---|---|
| | JAK1 | JAK2 |
| Ex. 4A | 20 | 83 |
| Ex. 6 | 55 | NT |
| Ex. 8 | 11 | NT |
| Ex. 10 | 7 | 129 |
| Ex. 11 | 27 | 176 |
| Ex. 12 | 1 | 18 |
| Ex. 13.3A | 2 | 55 |
| Ex. 13.3B | 2 | 14 |
| Ex. 14A | 0.8 | 5 |
| Ex. 14B | 2 | 15 |
| Ex. 18 | 7 | NT |
| Ex. 20 | 3 | 7 |
| Ex. 22 | 2 | 6 |
| Ex. 24 | 19 | 39 |
| Ex. 25 | 6 | 86 |
| Ex. 26 | 2 | 6 |
| Ex. 27 | 4 | 23 |
| Ex. 28 | 0.9 | 4 |
| Ex. 29 | 2 | 5 |
| Ex. 30 | 0.9 | 5 |
| Ex. 31 | 1 | 12 |
| Ex. 32 | 3 | 37 |
| Ex. 33 | 0.4 | 3 |
| Ex. 34 | 2 | 17 |
| Ex. 35 | 2 | 8 |
| Ex. 37 | 5 | 11 |
| Ex. 39 | 5 | 30 |
| Ex. 41 | 20 | 371 |
| Ex. 42 | 3 | 12 |
| Ex. 44 | 57 | NT |
| Ex. 46 | 0.5 | NT |
| Ex. 48 | 0.4 | NT |
| Ex. 50 | 14 | NT |
| Ex. 56 | 5 | NT |
| Ex. 57 | 16 | NT |
| Ex. 59 | 1 | NT |
| Ex. 60 | 5 | NT |
| Ex. 61 | 42 | NT |
| Ex. 62 | 4 | NT |
| Ex. 64 | 2 | NT |
| Ex. 66 | 7 | NT |
| Ex. 69 | 15 | 41 |

NT: not tested

TABLE 4

JAK3, TYK2, Aurora-A and FLT3 Kinase inhibition data

| Example # | JAK3 | TYK2 | Aurora-A | FLT3 |
|---|---|---|---|---|
| Ex. 12 | 359 | 7 | NT | NT |
| Ex. 14A | 39 | 1 | NT | NT |
| Ex. 28 | 47 | 4 | 22 | 16 |
| Ex. 31 | 178 | 18 | 4 | 134 |

NT: not tested

Finally, it should be noted that there are alternative ways of implementing the present invention. Accordingly, the present embodiments are to be considered as illustrative and not restrictive and the invention is not limited to the details given herein, but may be modified within the scope and equivalents of the appended claims. All publications and patents cited herein are incorporated by reference.

What is claimed is:

1. A compound having Formula (I):

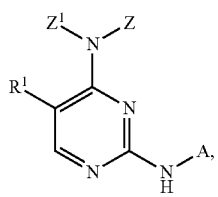

or a stereoisomer, a tautomer, an N-oxide, a solvate, or a pharmaceutically acceptable salt thereof, wherein:

Z is $C_7$-$C_{12}$ spiro bicycloalkyl, $C_7$-$C_{12}$ fused bicycloalkyl, 7-12 membered spiro heterobicyclyl or 7-12 membered fused heterobicycloalkyl, wherein Z is optionally substituted by 1, 2, 3, 4 or 5 $R^2$ groups;

$Z^1$ is H, $C_1$-$C_{12}$ alkyl, $C_3$-$C_{12}$ cycloalkyl or 3-12 membered heterocyclyl, wherein $Z^1$ is optionally substituted by 1, 2, 3, 4 or 5 $R^3$ groups;

A is pyrazolyl or imidazolyl, wherein A is optionally substituted by 1, 2, 3, 4 or 5 $R^4$ groups;

$R^1$ is H, F, Cl, Br, I, $NO_2$, $N_3$, CN, $C_1$-$C_{12}$ alkyl, $C_1$-$C_{12}$ haloalkyl, $C_1$-$C_{12}$ alkoxyl, $C_2$-$C_{12}$ alkenyl, $C_2$-$C_{12}$ alkynyl, $C_3$-$C_{12}$ cycloalkyl, 3-12 membered heterocyclyl, $C_6$-$C_{12}$ aryl, 5-12 membered heteroaryl, $-(CR^6R^7)_n-OR^c$, $-(CR^6R^7)_n-NR^aR^b$, $-C(=O)R^5$, $-OC(=O)R^5$, $-O(CR^6R^7)_n-R^5$, $-N(R^c)C(=O)R^5$, $-(CR^6R^7)_nC(=O)OR^c$, $-(CR^6R^7)_nC(=O)NR^aR^b$, $-C(=NR^c)NR^aR^b$, $-N(R^c)C(=O)NR^aR^b$, $-N(R^c)S(=O)_mR^5$ or $-S(=O)_2NR^aR^b$, wherein $R^1$ is optionally substituted by 1, 2, 3, 4 or 5 $R^8$ groups;

each $R^2$ is independently H, F, Cl, Br, I, $NO_2$, $N_3$, CN, OH, $NH_2$, $-C(=O)CH_2CN$, $C_1$-$C_{12}$ alkyl, $C_1$-$C_{12}$ haloalkyl, $C_1$-$C_{12}$ alkoxy, $C_2$-$C_{12}$ alkenyl, $C_2$-$C_{12}$ alkynyl, $C_3$-$C_{12}$ cycloalkyl, $C_6$-$C_{12}$ aryl, 3-12 membered heterocyclyl, 5-12 membered heteroaryl, $-(CR^6R^7)_n-OR^c$, $-(CR^6R^7)_n-NR^aR^b$, $-C(=O)R^5$, $-S(=O)_2R^5$, $-OC(=O)R^5$, $-O(CR^6R^7)_n-R^5$, $-O(CR^6R^7)_n-OR^c$, $-N(R^c)C(=O)R^5$, $-(CR^6R^7)_nC(=O)OR^c$, $-(CR^6R^7)_nC(=O)NR^aR^b$, $-C(=NR^c)NR^aR^b$, $-N(R^c)C(=O)NR^aR^b$, $-N(R^c)S(=O)_mR^5$ or $-S(=O)_2NR^aR^b$, or two adjacent $R^2$ taken together with the atoms to which they are attached form a $C_3$-$C_{12}$ cycloalkyl or 3-12 membered heterocycloalkyl group, wherein each of the above substituents is optionally independently substituted by 1, 2, 3, 4 or 5 $R^8$ groups;

each $R^3$ and $R^4$ is independently H, F, Cl, Br, I, $NO_2$, $N_3$, CN, $C_1$-$C_{12}$ alkyl, $C_2$-$C_{12}$ alkenyl, $C_2$-$C_{12}$ alkynyl, $C_3$-$C_{12}$ cycloalkyl, $-(C_1$-$C_4$ alkylene)-($C_3$-$C_{12}$ cycloalkyl), $C_6$-$C_{12}$ aryl, 3-12 membered heterocyclyl, $-(C_1$-$C_4$ alkylene)-(3-12 membered heterocyclyl), 5-12 membered heteroaryl, $-(CR^6R^7)_n-OR^c$, $-(CR^6R^7)_n-NR^aR^b$, $-C(=O)R^5$, $-OC(=O)R^5$, $-O(CR^6R^7)_n-R^5$, $-N(R^c)C(=O)R^5$, $-(CR^6R^7)_nC(=O)OR^c$, $-(CR^6R^7)_nC(=O)NR^aR^b$, $-C(=NR^c)NR^aR^b$, $-N(R^c)C(=O)NR^aR^b$, $-N(R^c)S(=O)_mR^5$ or $-S(=O)_2NR^aR^b$, wherein each $R^3$ and $R^4$ is optionally independently substituted by 1, 2, 3, 4 or 5 $R^8$ groups;

each $R^5$ is independently H, $C_1$-$C_{12}$ alkyl, $C_1$-$C_{12}$ haloalkyl, $C_2$-$C_{12}$ alkenyl, $C_2$-$C_{12}$ alkynyl, $C_3$-$C_{12}$ cycloalkyl, $C_6$-$C_{12}$ aryl, 3-12 membered heterocyclyl or 5-12 membered heteroaryl, wherein each $R^5$ is optionally independently substituted by 1, 2, 3, 4 or 5 $R^8$ groups;

each $R^6$ and $R^7$ is independently H, F, Cl, Br, I, $NO_2$, $N_3$, CN, $C_1$-$C_{12}$ alkyl, $C_2$-$C_{12}$ alkenyl, $C_2$-$C_{12}$ alkynyl, $C_3$-$C_{12}$ cycloalkyl, $C_6$-$C_{12}$ aryl, 3-12 membered heterocyclyl or 5-12 membered heteroaryl, or $R^6$ and $R^7$ taken together with the carbon atom to which they are attached form a $C_3$-$C_{12}$ cycloalkyl, $C_6$-$C_{12}$ aryl, 3-12 membered heterocyclyl or 5-12 membered heteroaryl group, wherein each of the above substituents is optionally independently substituted by 1, 2, 3, 4 or 5 $R^8$ groups;

each $R^8$ is independently F, Cl, Br, I, CN, $NO_2$, $N_3$, $C_1$-$C_{12}$ alkyl, $C_2$-$C_{12}$ alkenyl, $C_2$-$C_{12}$ alkynyl, $C_3$-$C_{12}$ cycloalkyl, $C_6$-$C_{12}$ aryl, 3-12 membered heterocyclyl, 5-12 membered heteroaryl, $NH_2$, $-NH(C_1$-$C_{12}$ alkyl), $-NH(CH_2)_n-(C_3$-$C_{12}$ cycloalkyl), $-NH(CH_2)_n-(C_6$-$C_{12}$ aryl), $-NH(CH_2)_n$-(3-12 membered heterocyclyl), $-NH(CH_2)_n$-(5-12 membered heteroaryl), $-N(C_1$-$C_{12}$ alkyl)$_2$, $-N[(CH_2)_n-(C_3$-$C_{12}$ cycloalkyl)]$_2$, $-N[(CH_2)_n-(C_6$-$C_{12}$ aryl)]$_2$, $-N[(CH_2)_n$-(3-12 membered heterocyclyl)]$_2$, $-N[(CH_2)_n$-(5-12 membered heteroaryl)]$_2$, OH, $-O(C_1$-$C_{12}$ alkyl), $-O(CH_2)_n-(C_3$-$C_{12}$cycloalkyl), $-O(CH_2)_n-(C_6$-$C_{12}$ aryl), $-O(CH_2)_n$-(3-12 membered heterocyclyl) or $-O(CH_2)_n$-(5-12 membered heteroaryl);

each $R^a$, $R^b$ and $R^c$ is independently H, $C_1$-$C_6$ alkyl, $C_2$-$C_6$ alkenyl, $C_2$-$C_6$ alkynyl, $C_3$-$C_6$ cycloalkyl, $-(C_1$-$C_4$ alkylene)-($C_3$-$C_6$ cycloalkyl), 3-6 membered heterocyclyl, $-(C_1$-$C_4$ alkylene)-(3-6 membered heterocyclyl), $C_6$-$C_{10}$ aryl, $-(C_1$-$C_4$ alkylene)-($C_6$-$C_{10}$ aryl), 5-10 membered heteroaryl or $-(C_1$-$C_4$ alkylene)-(5-10 membered heteroaryl), or $R^a$ and $R^b$ taken together with the nitrogen atom to which they are attached form a 3-8 membered heterocyclyl group, wherein each of the above substituents is optionally independently substituted by 1, 2, 3 or 4 substitutents independently selected from F, Cl, Br, CN, $N_3$, OH, $NH_2$, $C_1$-$C_6$ alkyl, $C_1$-$C_6$ haloalkyl, $C_1$-$C_6$ alkoxy and $C_1$-$C_6$ alkylamino;

each m is independently 1 or 2; and each n is independently 0, 1, 2, 3 or 4.

2. The compound of claim 1, wherein Z is $C_8$-$C_{11}$ spiro bicycloalkyl, $C_8$-$C_{10}$ fused bicycloalkyl, 8-11 membered spiro heterobicyclyl or 8-10 membered fused heterobicycloalkyl, wherein Z is optionally substituted by 1, 2, 3 or 4 $R^2$ groups.

3. The compound of claim 1, wherein $Z^1$ is H, $C_1$-$C_6$ alkyl, $C_3$-$C_6$ cycloalkyl or 3-6 membered heterocyclyl, wherein $Z^1$ is optionally substituted by 1, 2 or 3 $R^3$ groups.

4. The compound of claim 1, wherein $R^1$ is H, F, Cl, CN, $N_3$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_3$-$C_6$ cycloalkyl, 3-6 membered heterocyclyl, —$(CR^6R^7)_n$—$OR^c$, —$(CR^6R^7)_n$—$NR^aR^b$, —$C(=O)R^5$, —$(CR^6R^7)_nC(=O)NR^aR^b$ or —$S(=O)_2NR^aR^b$, wherein $R^1$ is optionally substituted by 1, 2 or 3 $R^8$ groups.

5. The compound of claim 1, wherein each $R^2$ is independently H, F, Cl, CN, $N_3$, $NO_2$, OH, $NH_2$, —$C(=O)CH_2CN$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_6$ cycloalkyl, phenyl, 3-6 membered heterocyclyl, 5-6 membered heteroaryl, —$(CR^6R^7)_n$—$OR^c$, —$(CR^6R^7)_n$—$NR^aR^b$, —$C(=O)R^5$, —$S(=O)_2R^5$, —$O(CR^6R^7)_n$—$R^5$, —$O(CR^6R^7)_n$—$OR^c$, —$N(R^c)C(=O)R^5$, —$(CR^6R^7)_nC(=O)NR^aR^b$, —$N(R^c)C(=O)NR^aR^b$, —$N(R^c)S(=O)_mR^5$ or —$S(=O)_2NR^aR^b$, or two adjacent $R^2$ taken together with the atoms to which they are attached form a $C_3$-$C_6$ cycloalkyl, or 3-6 membered heterocycloalkyl group, wherein each of the above substituents is optionally independently substituted by 1, 2 or 3 $R^8$ groups.

6. The compound of claim 1, wherein each $R^3$ and $R^4$ is independently H, F, Cl, Br, I, $NO_2$, $N_3$, CN, $C_1$-$C_6$ alkyl, $C_2$-$C_6$ alkenyl, $C_2$-$C_6$ alkynyl, $C_3$-$C_6$ cycloalkyl, —($C_1$-$C_2$ alkylene)-($C_3$-$C_6$ cycloalkyl), phenyl, 3-6 membered heterocyclyl, —($C_1$-$C_2$ alkylene)-(3-6 membered heterocyclyl), 5-6 membered heteroaryl, —$(CR^6R^7)_n$—$OR^c$, —$(CR^6R^7)_n$—$NR^aR^b$, —$C(=O)R^5$, —$OC(=O)R^5$, —$O(CR^6R^7)_n$—$R^5$, —$N(R^c)C(=O)R^5$, —$(CR^6R^7)_nC(=O)OR^c$, —$(CR^6R^7)_nC(=O)NR^aR^b$, —$N(R^c)S(=O)_mR^5$ or —$S(=O)_2NR^aR^b$, wherein each $R^3$ and $R^4$ is optionally independently substituted by 1, 2 or 3 $R^8$ groups.

7. The compound of claim 1, wherein each $R^5$ is independently H, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, phenyl, 3-6 membered heterocyclyl or 5-6 membered heteroaryl, wherein each $R^5$ is optionally independently substituted by 1, 2 or 3 $R^8$ groups.

8. The compound of claim 1, wherein each $R^6$ and $R^7$ is independently H, F, Cl, Br, I, CN, $N_3$, $NO_2$, $C_1$-$C_6$ alkyl, $C_2$-$C_6$ alkenyl, $C_2$-$C_6$ alkynyl, $C_3$-$C_6$ cycloalkyl, phenyl, 3-6 membered heterocyclyl or 5-6 membered heteroaryl, or $R^6$ and $R^7$ taken together with the carbon atom to which they are attached form a $C_3$-$C_6$ cycloalkyl, phenyl, 3-6 membered heterocyclyl or 5-6 membered heteroaryl group, wherein each of the above substituents is optionally independently substituted by 1, 2 or 3 $R^8$ groups.

9. The compound of claim 1, wherein each $R^8$ is independently F, Cl, CN, $N_3$, $C_1$-$C_6$ alkyl, $C_2$-$C_6$ alkenyl, $C_2$-$C_6$ alkynyl, $C_3$-$C_6$ cycloalkyl, phenyl, 3-6 membered heterocyclyl, 5-6 membered heteroaryl, $NH_2$, —$NH(C_1$-$C_6$ alkyl), —$NH(CH_2)_n$—($C_3$-$C_6$ cycloalkyl), —$NH(CH_2)_n$-phenyl, —$NH(CH_2)_n$-(3-6 membered heterocyclyl), —$NH(CH_2)_n$-(5-6 membered heteroaryl), —$N(C_1$-$C_4$ alkyl)$_2$, —$N[(CH_2)_n$—($C_3$-$C_6$cycloalkyl)]$_2$, —$N[(CH_2)_n$-phenyl]$_2$, —$N[(CH_2)_n$-(3-6 membered heterocyclyl)]$_2$, —$N[(CH_2)_n$-(5-6 membered heteroaryl)]$_2$, OH, —$O(C_1$-$C_6$ alkyl), —$O(CH_2)_n$—($C_3$-$C_6$ cycloalkyl), —$O(CH_2)_n$-phenyl, —$O(CH_2)_n$-(3-6 membered heterocyclyl) or —$O(CH_2)_n$-(5-6 membered heteroaryl).

10. The compound of claim 1, wherein each $R^a$, $R^b$ and $R^c$ is independently H, $C_1$-$C_4$ alkyl, $C_2$-$C_4$ alkenyl, $C_2$-$C_4$ alkynyl, $C_3$-$C_6$ cycloalkyl, —($C_1$-$C_2$ alkylene)-($C_3$-$C_6$ cycloalkyl), 3-6 membered heterocyclyl, —($C_1$-$C_2$ alkylene)-(3-6 membered heterocyclyl), phenyl, —($C_1$-$C_2$ alkylene)-phenyl, 5-6 membered heteroaryl or —($C_1$-$C_2$ alkylene)-(5-6 membered heteroaryl), or $R^a$ and $R^b$ taken together with the nitrogen atom to which they are attached form a 3-6 membered heterocyclyl group, wherein each of the above substituents is optionally independently substituted by 1, 2 or 3 substitutents independently selected from F, Cl, CN, $N_3$, OH, $NH_2$, $C_1$-$C_4$ alkyl, $C_1$-$C_4$ haloalkyl, $C_1$-$C_4$ alkoxy and $C_1$-$C_4$ alkylamino.

11. The compound of claim 1, wherein Z is:

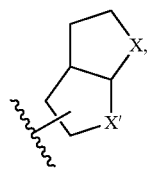

(Z-1)

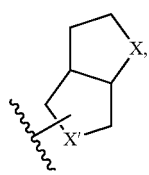

(Z-2)

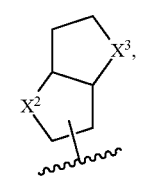

(Z-3)

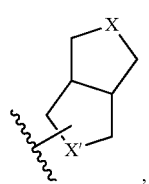

(Z-4)

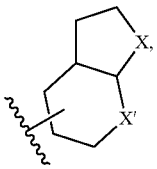

(Z-5)

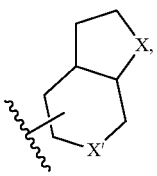

(Z-6)

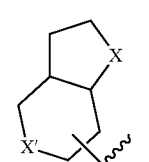

(Z-7)

,

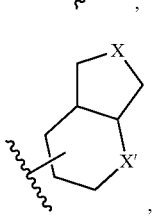

(Z-8)

,

-continued
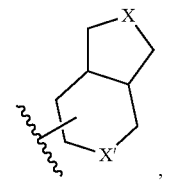 (Z-9)
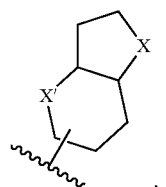 (Z-10)
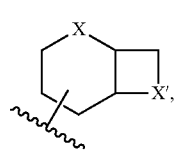 (Z-11)
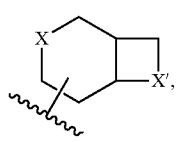 (Z-12)
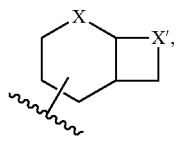 (Z-13)
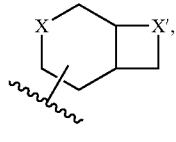 (Z-14)
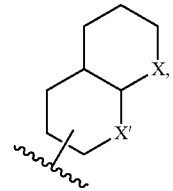 (Z-15)
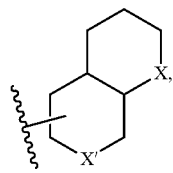 (Z-16)
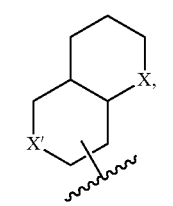 (Z-17)
-continued
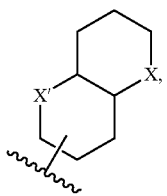 (Z-18)
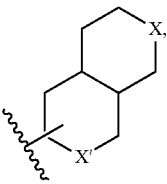 (Z-19)
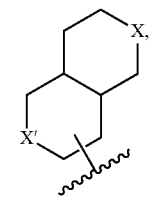 (Z-20)
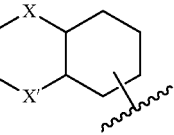 (Z-21)
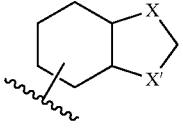 (Z-22)
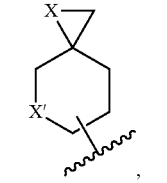 (Z-23)
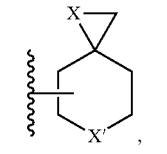 (Z-24)
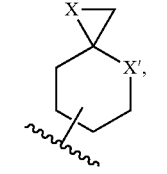 (Z-25)

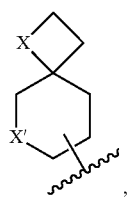(Z-26),
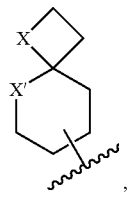(Z-27),
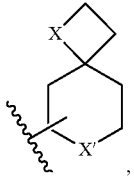(Z-28),
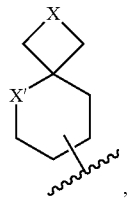(Z-29),
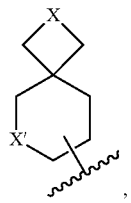(Z-30),
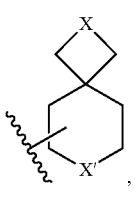(Z-31),
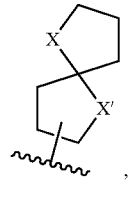(Z-32),
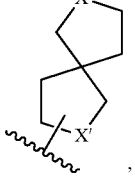(Z-33),
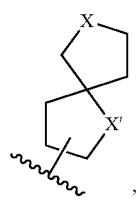(Z-34),
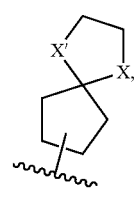(Z-35),
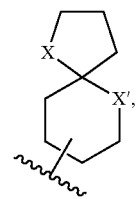(Z-36),
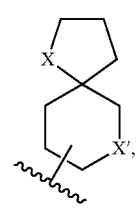(Z-37),
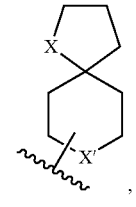(Z-38),
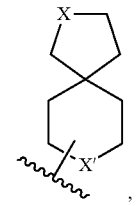(Z-39),
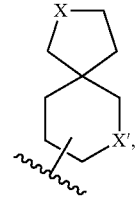(Z-40), (Z-41) 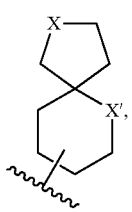
(Z-42) 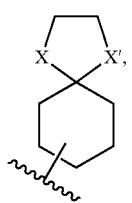
(Z-43) 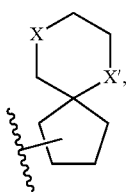
(Z-44) 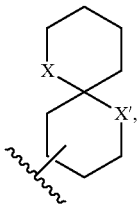
(Z-45) 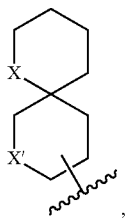
(Z-46) 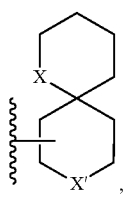
(Z-47) 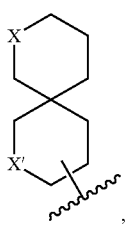
(Z-48) 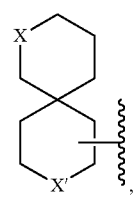
(Z-49) 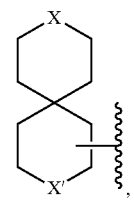
(Z-50) 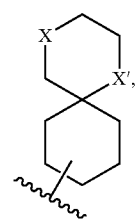
(Z-51) 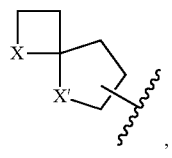
(Z-52) 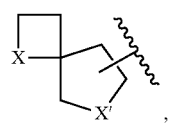
(Z-53) 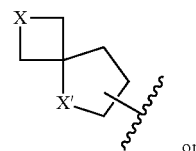
or
(Z-54) 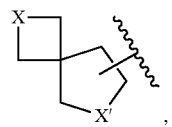
or a stereoisomer thereof, wherein each X, X', $X^2$ and $X^3$ is independently $CH_2$, NH or O, with the proviso that when $X^2$ is O, $X^3$ is not O; and wherein Z is optionally substituted by 1, 2 or 3 $R^2$ groups.
12. The compound of claim 1, wherein A is:
(L) 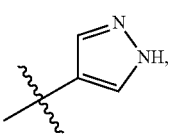

-continued

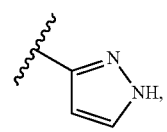
(M)

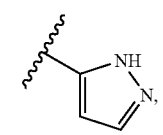
(N)

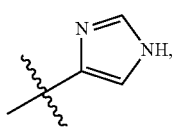
(O)

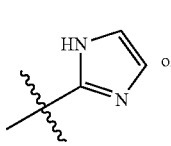
(P) or

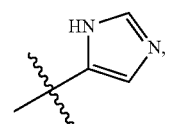
(Q)

wherein A is optionally substituted by 1, 2 or 3 $R^4$ groups.

13. The compound of claim 1, wherein $Z^1$ is H, methyl, ethyl, n-propyl, isopropyl or cyclopropyl.

14. The compound of claim 1, wherein $R^1$ is H, F, Cl, CN, $N_3$, $C_1$-$C_4$ alkyl, $C_2$-$C_4$ alkenyl, $C_2$-$C_4$ alkynyl, $C_1$-$C_4$ haloalkyl, $C_1$-$C_4$ alkoxyl, $C_3$-$C_6$ cycloalkyl, 3-6 membered heterocyclyl, —$(CR^6R^7)_n$—$OR^c$, —$(CR^6R^7)_n$—$NR^aR^b$, —$C(\!=\!O)R^5$, —$(CR^6R^7)_nC(\!=\!O)NR^aR^b$ or —$S(\!=\!O)_2NR^aR^b$, wherein $R^1$ is optionally substituted by 1, 2 or 3 $R^8$ groups.

15. The compound of claim 1, wherein each $R^2$ is independently H, F, Cl, CN, $N_3$, $NO_2$, OH, $NH_2$, —$C(\!=\!O)CH_2CN$, $C_1$-$C_4$ alkyl, $C_2$-$C_4$ alkenyl, $C_2$-$C_4$ alkynyl, $C_1$-$C_4$ haloalkyl, $C_1$-$C_4$ alkoxy, $C_3$-$C_6$ cycloalkyl, phenyl, 3-6 membered heterocyclyl, 5-6 membered heteroaryl, —$(CR^6R^7)_n$—$OR^c$, —$(CR^6R^7)_n$—$NR^aR^b$, —$C(\!=\!O)R^5$, —$S(\!=\!O)_2R^5$, —$O(CR^6R^7)_n$—$R^5$, —$O(CR^6R^7)_n$—$OR^c$, —$N(R^c)C(\!=\!O)R^5$, —$(CR^6R^7)_nC(\!=\!O)NR^aR^b$, —$N(R^c)S(\!=\!O)_mR^5$ or —$S(\!=\!O)_2NR^aR^b$, wherein each $R^2$ is optionally independently substituted by 1, 2 or 3 $R^8$ groups.

16. The compound of claim 1, wherein each $R^5$ is independently H, $C_1$-$C_4$ alkyl, $C_1$-$C_4$ haloalkyl, $C_2$-$C_4$ alkenyl, $C_2$-$C_4$ alkynyl, $C_3$-$C_6$ cycloalkyl, phenyl, 3-6 membered heterocyclyl or 5-6 membered heteroaryl, wherein each $R^5$ is optionally independently substituted by 1, 2 or 3 $R^8$ groups.

17. The compound of claim 1 having one of the following structures:

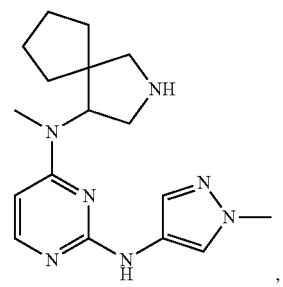
(1)

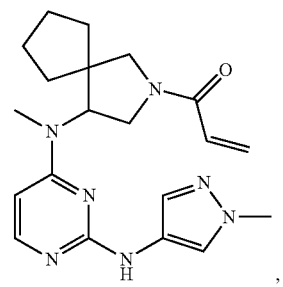
(2)

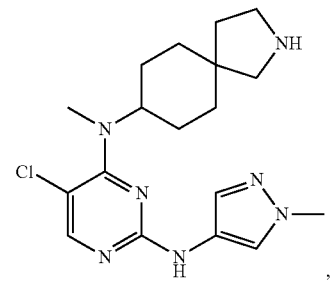
(3)

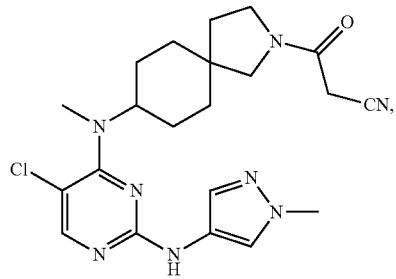
(4)

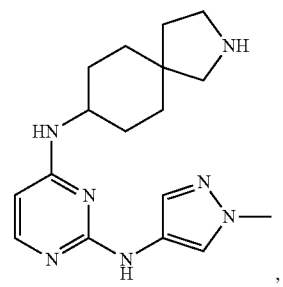
(5)

(6) 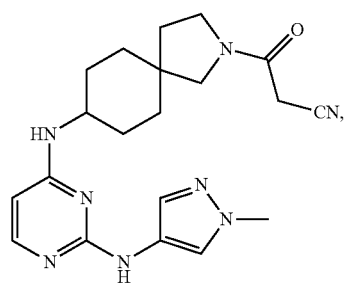
(7) 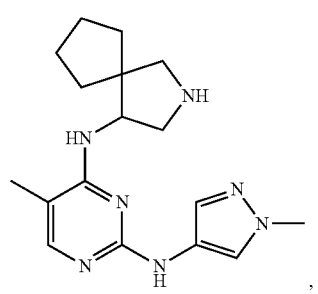
(8) 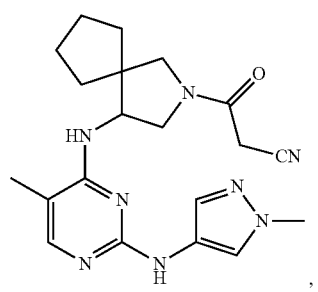
(9) 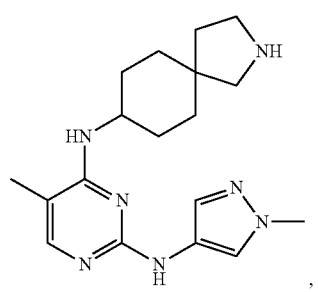
(10) 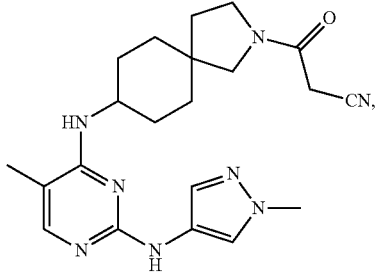
(11) 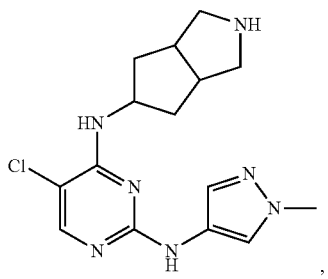
(12) 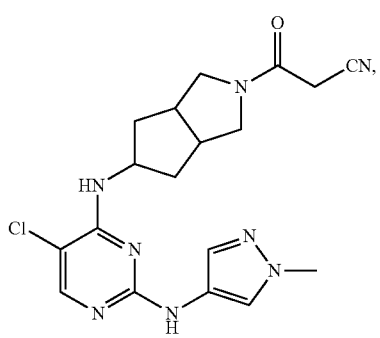
(13) 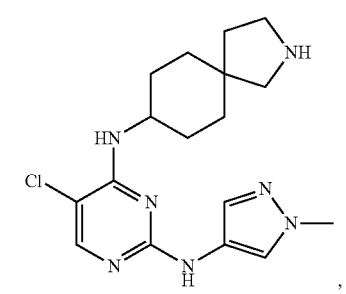
(14) 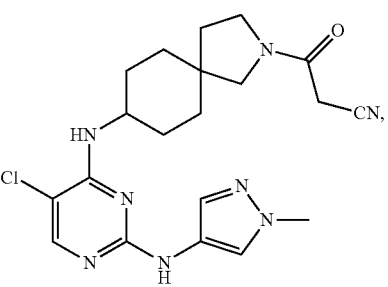
(15) 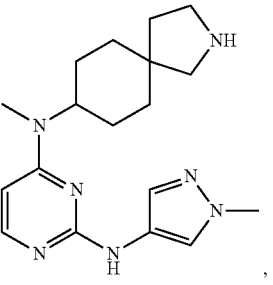

(16) 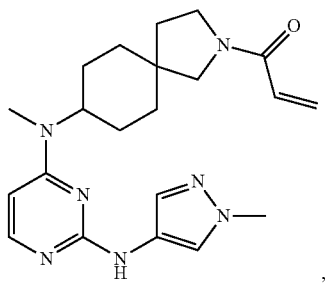
(17) 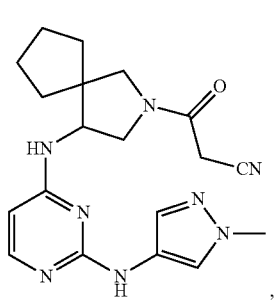
(18) 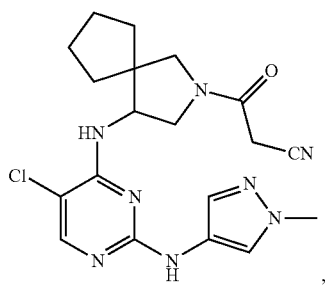
(19) 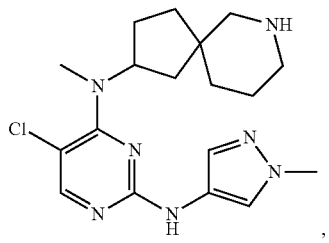
(20) 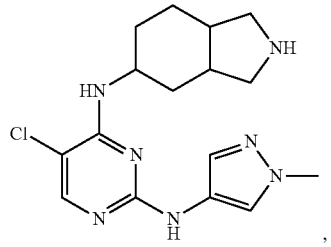
(21) 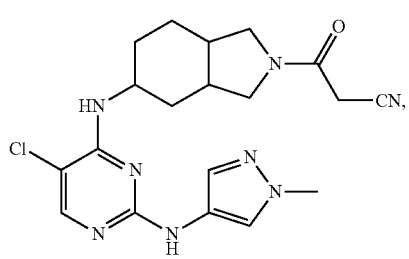
(22) 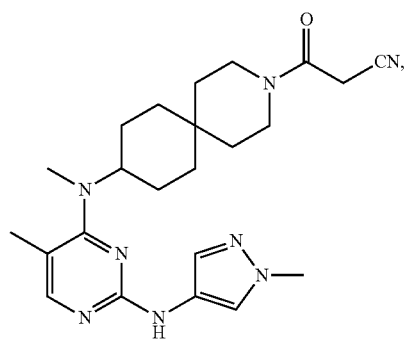
(23) 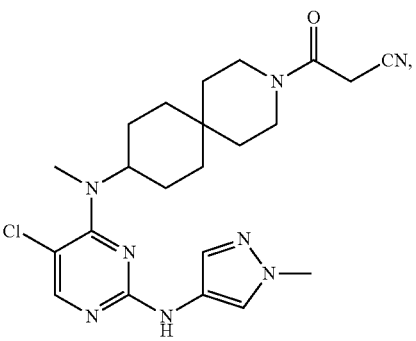
(24) 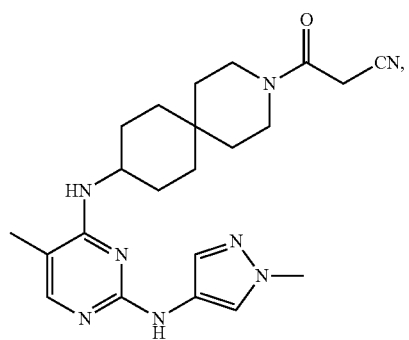
(25)

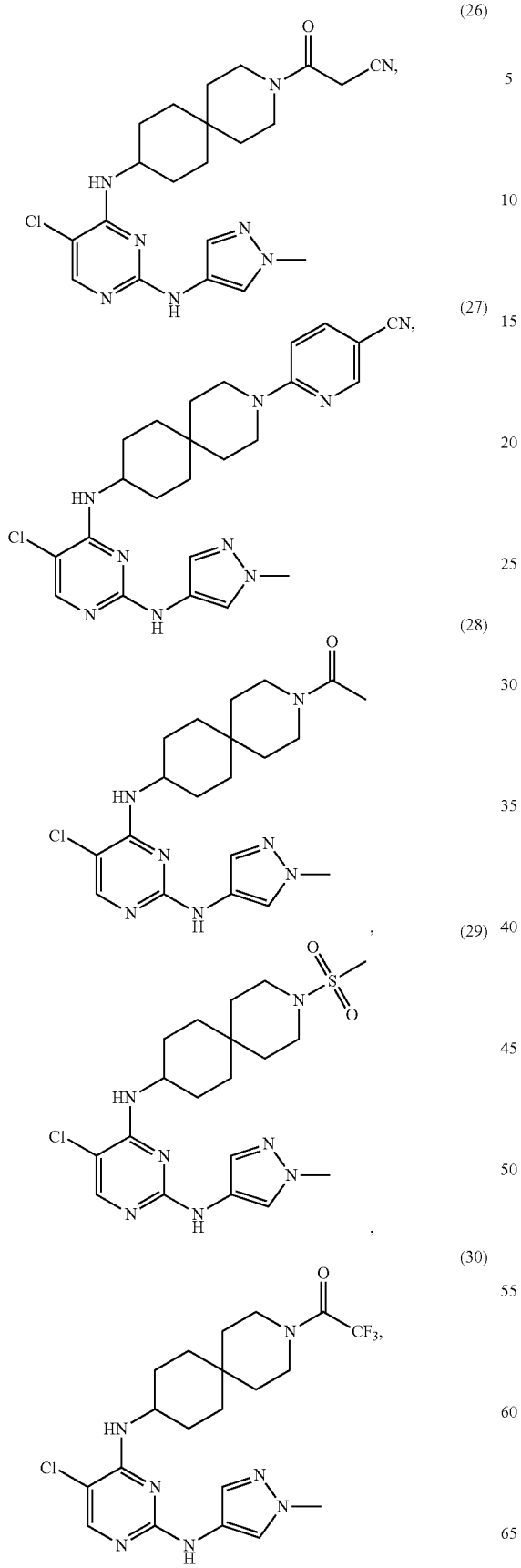
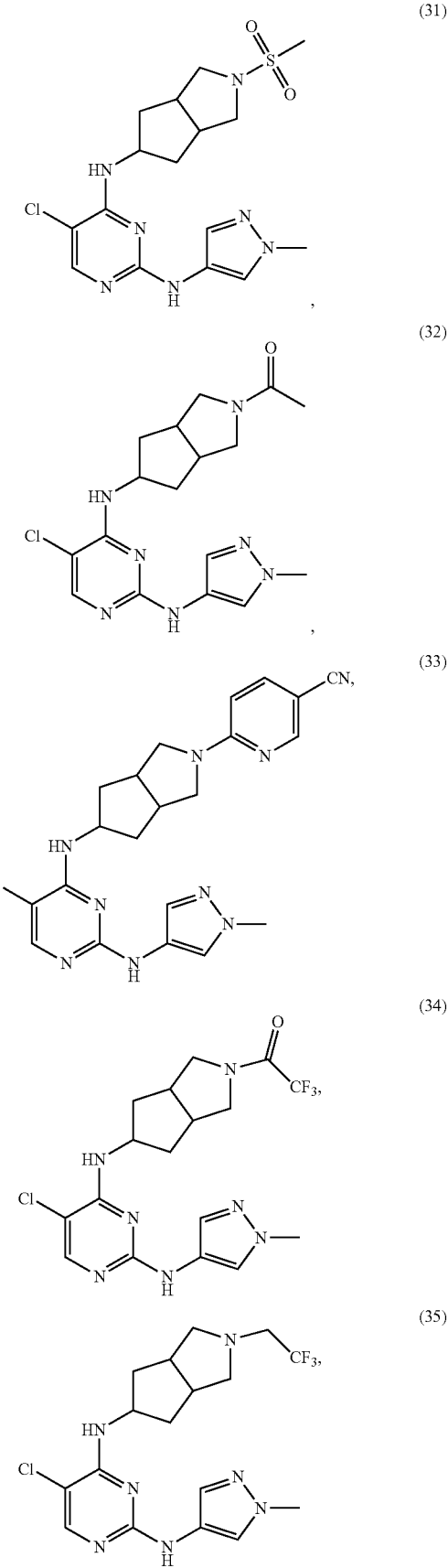

(36) 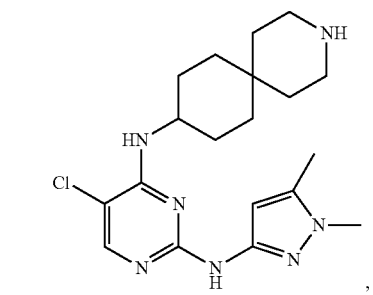
(37) 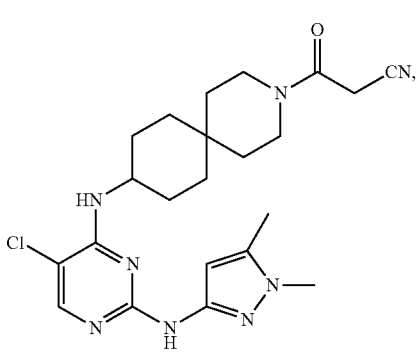
(38) 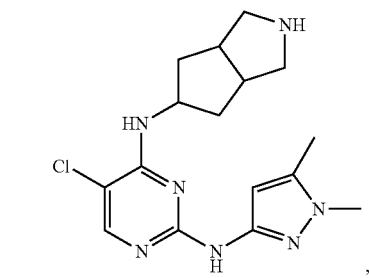
(39) 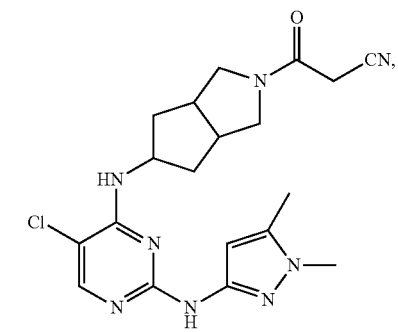
(40) 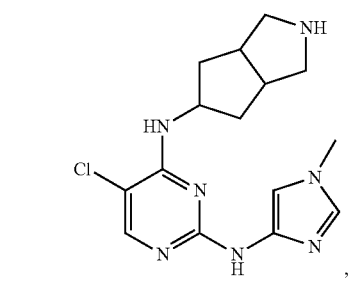
(41) 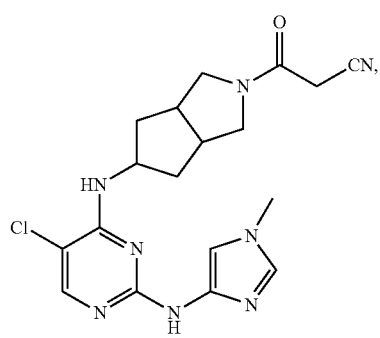
(42) 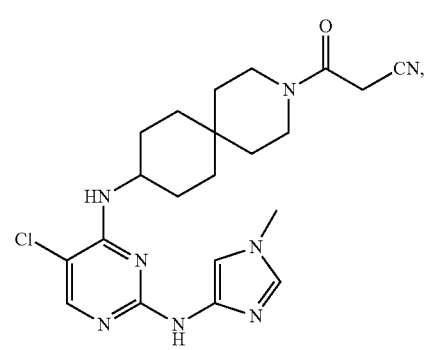
(43) 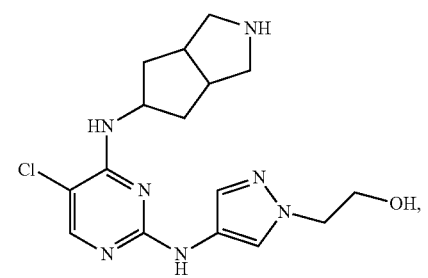
(44) 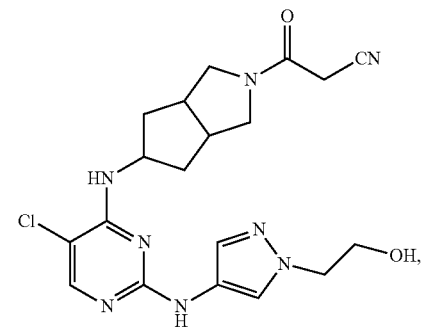
(45) 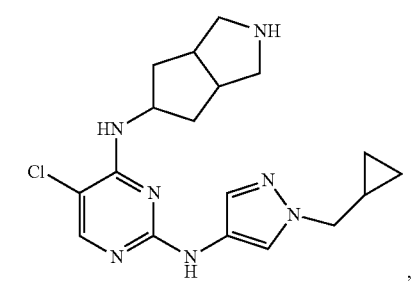

(46) 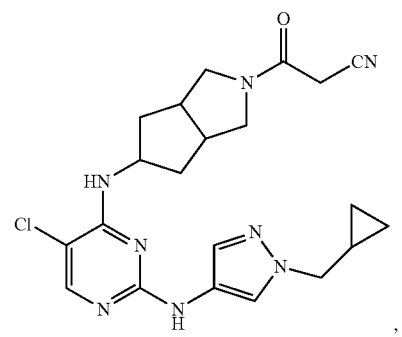
(47) 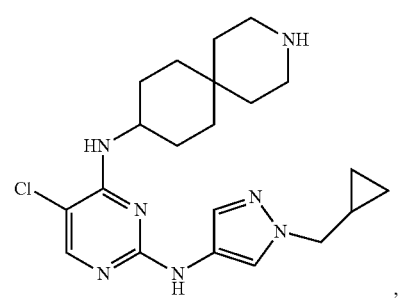
(48) 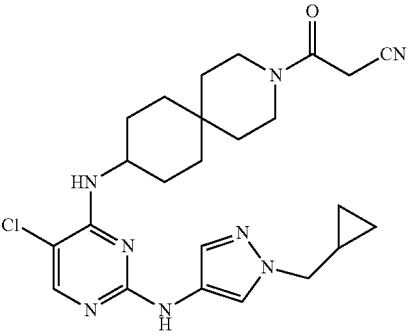
(49) 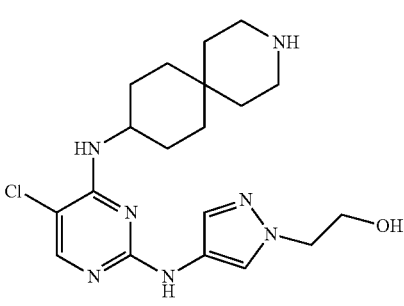
(50) 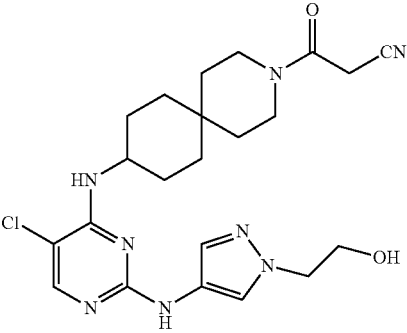
(51) 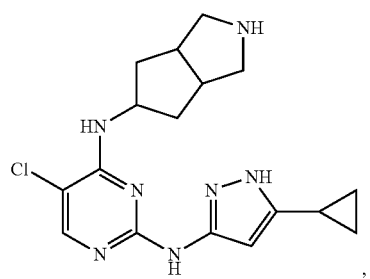
(52) 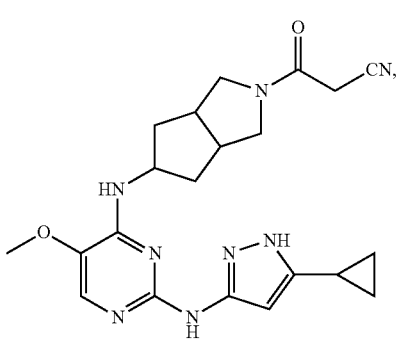
(53) 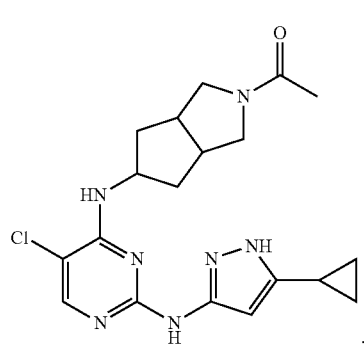
(54) 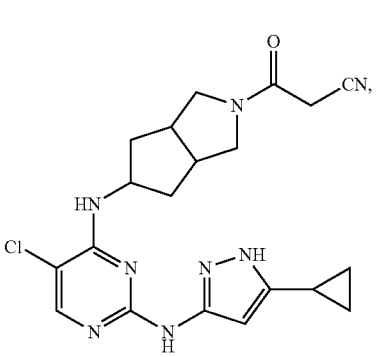
(55) 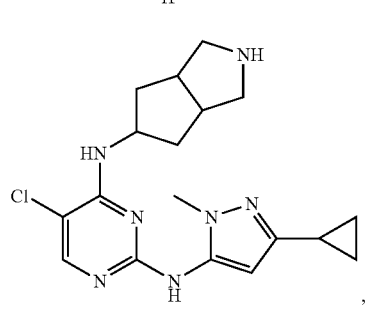

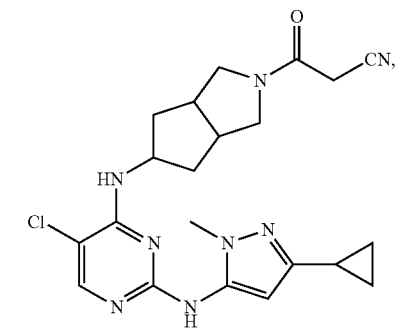
(56)
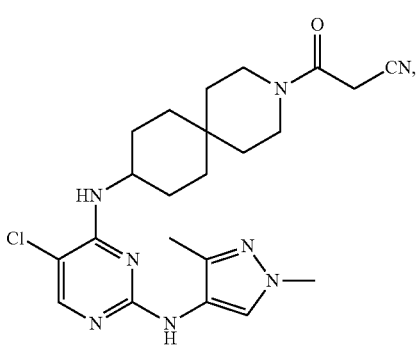
(57)
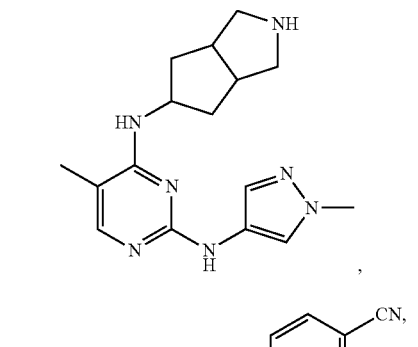
(58)
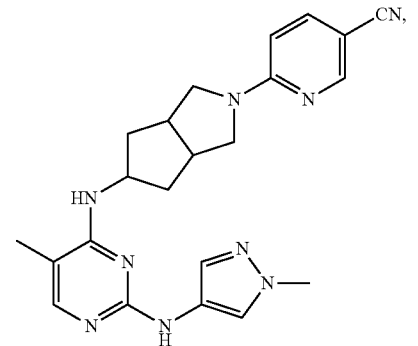
(59)
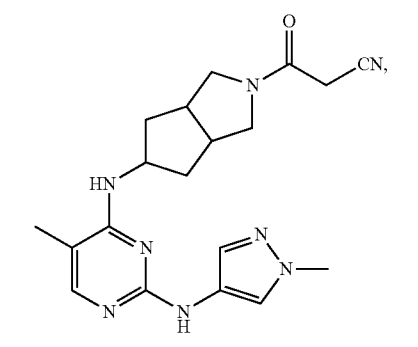
(60)
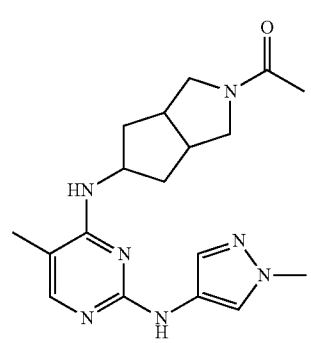
(61)
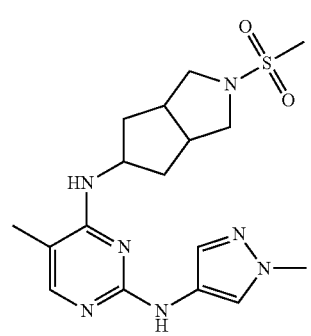
(62)
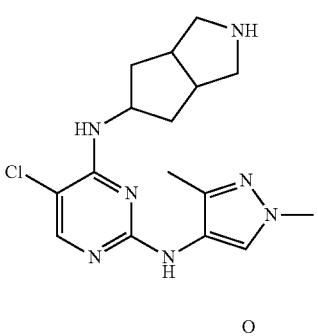
(63)
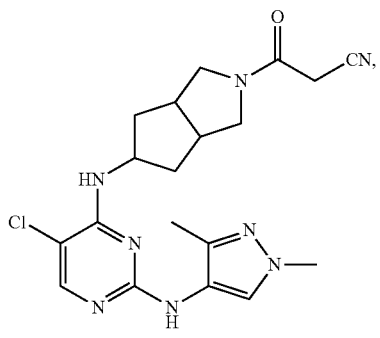
(64)
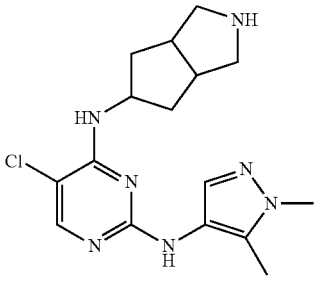
(65)

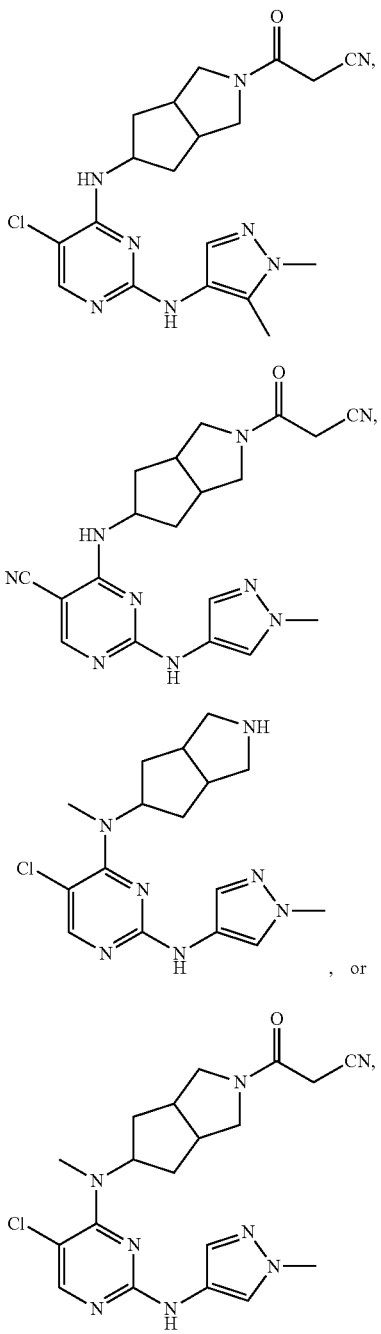

or a stereoisomer, a tautomer, an N-oxide, a solvate, or a pharmaceutically acceptable salt thereof.

18. A pharmaceutical composition comprising the compound of claim 1, and a pharmaceutically acceptable excipient, carrier, adjuvant, vehicle or a combination thereof.

19. The pharmaceutical composition of claim 18 further comprising a therapeutic agent selected from the group consisting of chemotherapeutic agents, anti-proliferative agents, phosphodiesterase 4 (PDE4) inhibitors, $\beta_2$-adrenoreceptor agonists, corticosteroids, non-steroidal GR agonists, anticholinergic agents, antihistamines, anti-inflammatory agents, immunosuppressants, immunomodulators, agents for treating atherosclerosis, agents for treating pulmonary fibrosis and combinations thereof.

20. A method of treating a disease in a patient comprising administering to the patient a compound of claim 1 or a stereoisomer, a tautomer, an N-oxide, a solvate, or pharmaceutically acceptable salt thereof, wherein the disease is selected from the group consisting of transplantation rejection, cancer, chronic obstructive pulmonary disease (COPD), asthma, systemic lupus erythematosis, cutaneous lupus erythematosis, lupus nephritis, dermatomyositis, Sjogren's syndrome, psoriasis, type I diabetes mellitus, allergic airway disease, sinusitis, eczema, hives, food allergies, allergies to insect venom, inflammatory bowel syndrome, Crohn's disease, rheumatoid arthritis, juvenile arthritis, and psoriatic arthritis.

21. The method of claim 20, wherein the cancer is selected from the group consisting of polycythemia vera, essential thrombocytosis, myelofibrosis, chronic myelogenous leukemia (CML), acute myeloid leukemia (AML), and acute lymphocytic leukemia (ALL).

22. The method of claim 20, wherein the transplantation rejection is organ transplant rejection, tissue transplant rejection or cell transplant rejection.

23. A method of treating a disease in a patient comprising administering to the patient the pharmaceutical composition of claim 18 or a stereoisomer, a tautomer, an N-oxide, a solvate, or pharmaceutically acceptable salt thereof, wherein the disease is selected from the group consisting of transplantation rejection, cancer, chronic obstructive pulmonary disease (COPD), asthma, systemic lupus erythematosis, cutaneous lupus erythematosis, lupus nephritis, dermatomyositis, Sjogren's syndrome, psoriasis, type I diabetes mellitus, allergic airway disease, sinusitis, eczema, hives, food allergies, allergies to insect venom, inflammatory bowel syndrome, Crohn's disease, rheumatoid arthritis, juvenile arthritis, and psoriatic arthritis.

24. A method of inhibiting the activity of a protein kinase selected from the group consisting of JAK kinase, FLT3 kinase, Aurora kinase or a combination thereof comprising contacting the kinase with a compound of claim 1 or a stereoisomer, a tautomer, an N-oxide, a solvate, or pharmaceutically acceptable salt thereof.

25. A method of inhibiting the activity of a protein kinase selected from the group consisting of JAK kinase, FLT3 kinase, Aurora kinase or a combination thereof comprising contacting the kinase with the pharmaceutical composition of claim 18.

26. The method of claim 23, wherein the cancer is selected from the group consisting of polycythemia vera, essential thrombocytosis, myelofibrosis, chronic myelogenous leukemia (CML), acute myeloid leukemia (AML), and acute lymphocytic leukemia (ALL).

27. The method of claim 23, wherein the transplantation rejection is organ transplant rejection, tissue-transplant rejection or cell-transplant rejection.

* * * * *